(12) United States Patent
Fantl et al.

(10) Patent No.: US 8,778,620 B2
(45) Date of Patent: Jul. 15, 2014

(54) METHODS FOR DIAGNOSIS, PROGNOSIS AND METHODS OF TREATMENT

(75) Inventors: Wendy J. Fantl, San Francisco, CA (US); David B. Rosen, San Francisco, CA (US); Alessandra Cesano, Redwood City, CA (US); Santosh K. Putta, Foster City, CA (US); Garry Nolan, San Francisco, CA (US); Aileen Cohen, Palo Alto, CA (US); Erik Evensen, Foster City, CA (US)

(73) Assignee: Nodality, Inc., South San Francisco, CA (US)

( * ) Notice: Subject to any disclaimer, the term of this patent is extended or adjusted under 35 U.S.C. 154(b) by 215 days.

(21) Appl. No.: 13/473,829

(22) Filed: May 17, 2012

(65) Prior Publication Data

US 2013/0130279 A1    May 23, 2013

Related U.S. Application Data

(62) Division of application No. 12/460,029, filed on Jul. 10, 2009, now Pat. No. 8,227,202.

(60) Provisional application No. 61/120,320, filed on Dec. 5, 2008, provisional application No. 61/104,666, filed on Oct. 10, 2008, provisional application No. 61/085,789, filed on Aug. 1, 2008, provisional application No. 61/079,766, filed on Jul. 10, 2008.

(51) Int. Cl.
G01N 33/53     (2006.01)
G01N 33/567    (2006.01)
G01N 33/00     (2006.01)

(52) U.S. Cl.
USPC ........ 435/7.21; 435/7.23; 435/7.24; 435/6.14

(58) Field of Classification Search
None
See application file for complete search history.

(56) References Cited

U.S. PATENT DOCUMENTS

| | | | |
|---|---|---|---|
| 4,568,649 A | 2/1986 | Bertoglio-Matte et al. |
| 4,979,824 A | 12/1990 | Mathies et al. |
| 5,137,809 A | 8/1992 | Loken et al. |
| 5,234,816 A | 8/1993 | Terstappen |
| 5,599,681 A | 2/1997 | Epstein et al. |
| 5,605,805 A | 2/1997 | Verwer et al. |
| 5,919,646 A | 7/1999 | Okun et al. |
| 5,968,738 A | 10/1999 | Anderson et al. |
| 6,232,299 B1 | 5/2001 | Jirousek et al. |
| 6,280,967 B1 | 8/2001 | Ransom et al. |
| 6,379,917 B1 | 4/2002 | Okun et al. |
| 6,495,333 B1 | 12/2002 | Willmann et al. |
| 6,506,551 B1 | 1/2003 | Chiorazzi et al. |
| 6,558,916 B2 | 5/2003 | Veerapandian et al. |
| 6,592,822 B1 | 7/2003 | Chandler |
| 6,673,554 B1 | 1/2004 | Kauvar |
| 6,733,743 B2 | 5/2004 | Jordan |
| 6,821,740 B2 | 11/2004 | Darzynkiewicz et al. |
| 6,872,574 B2 | 3/2005 | Cravatt et al. |
| 6,958,221 B2 | 10/2005 | Veerapandian et al. |
| 6,972,198 B2 | 12/2005 | Craig et al. |
| 7,001,725 B2 | 2/2006 | Singh et al. |
| 7,070,943 B2 | 7/2006 | Darzynkiewicz et al. |
| 7,102,005 B2 | 9/2006 | Agnew et al. |
| 7,183,385 B2 | 2/2007 | Comb et al. |
| 7,236,888 B2 | 6/2007 | Allbritton et al. |
| 7,316,897 B2 | 1/2008 | Bisconte de Saint Julien et al. |
| 7,316,906 B2 | 1/2008 | Chiorazzi et al. |
| 7,326,577 B2 | 2/2008 | Shults et al. |
| 7,329,502 B2 | 2/2008 | Staudt et al. |
| 7,381,535 B2 | 6/2008 | Perez et al. |
| 7,392,199 B2 | 6/2008 | Karlov et al. |
| 7,393,656 B2 | 7/2008 | Perez et al. |
| 7,419,777 B2 | 9/2008 | Bacus |
| 7,563,584 B2 | 7/2009 | Perez et al. |
| 7,695,924 B2 | 4/2010 | Perez et al. |
| 7,695,926 B2 | 4/2010 | Perez et al. |
| 7,939,278 B2 | 5/2011 | Perez et al. |
| 8,148,094 B2 | 4/2012 | Perez et al. |
| 8,187,885 B2 | 5/2012 | Purvis, Jr. |
| 8,198,037 B2 | 6/2012 | Perez et al. |
| 8,206,939 B2 | 6/2012 | Perez et al. |
| 8,214,157 B2 | 7/2012 | Moser et al. |
| 8,227,202 B2 | 7/2012 | Fantl et al. |
| 8,242,248 B2 | 8/2012 | Soper et al. |
| 8,273,544 B2 | 9/2012 | Fantl et al. |

(Continued)

FOREIGN PATENT DOCUMENTS

WO    WO 99/44067 A1    9/1999
WO    WO 03/067210 A2   8/2003

(Continued)

OTHER PUBLICATIONS

U.S. Appl. No. 14/045,548, filed Oct. 3, 2013, Fantl et al.
U.S. Appl. No. 14/072,623, filed Nov. 5, 2013, Longo.
U.S. Appl. No. 14/073,692, filed Nov. 6, 2013, Hawtin et al.
U.S. Appl. No. 14/086,922, filed Nov. 21, 2013, Cesano et al.
U.S. Appl. No. 13/083,156, filed Apr. 8, 2011, Fantl et al.
U.S. Appl. No. 13/094,735, filed Apr. 26, 2011, Perez et al.
U.S. Appl. No. 13/094,737, filed Apr. 26, 2011, Perez et al.
U.S. Appl. No. 13/384,181, filed Jan. 13, 2012, Cesano et al.
U.S. Appl. No. 13/453,636, filed Apr. 23, 2012, Purvis, Jr.

(Continued)

Primary Examiner — Daniel C Gamett
(74) Attorney, Agent, or Firm — Wilson, Sonsini, Goodrich & Rosati, PC

(57) ABSTRACT

The present invention provides an approach for the determination of the activation states of a plurality of proteins in single cells. This approach permits the rapid detection of heterogeneity in a complex cell population based on activation states, expression markers and other criteria, and the identification of cellular subsets that exhibit correlated changes in activation within the cell population. Moreover, this approach allows the correlation of cellular activities or properties. In addition, the use of modulators of cellular activation allows for characterization of pathways and cell populations. Several exemplary diseases that can be analyzed using the invention include AML, MDS, and MPN.

10 Claims, 42 Drawing Sheets

(56) References Cited

U.S. PATENT DOCUMENTS

| | | |
|---|---|---|
| 8,309,306 B2 | 11/2012 | Nolan et al. |
| 8,309,316 B2 | 11/2012 | Perez et al. |
| 8,394,599 B2 | 3/2013 | Perez et al. |
| 8,399,206 B2 | 3/2013 | Fantl et al. |
| 2002/0127604 A1 | 9/2002 | Albritton et al. |
| 2002/0177179 A1 | 11/2002 | Glickman et al. |
| 2002/0197658 A1 | 12/2002 | Delaney et al. |
| 2003/0148321 A1 | 8/2003 | Pecker et al. |
| 2003/0190688 A1 | 10/2003 | Crosby et al. |
| 2003/0190689 A1 | 10/2003 | Crosby et al. |
| 2003/0203416 A1 | 10/2003 | Staudt et al. |
| 2003/0219827 A1 | 11/2003 | Comb et al. |
| 2003/0232364 A1 | 12/2003 | Shaughnessy et al. |
| 2004/0063088 A1 | 4/2004 | Berg et al. |
| 2004/0072184 A1 | 4/2004 | Yoganathan et al. |
| 2004/0076984 A1 | 4/2004 | Eils |
| 2004/0106156 A1 | 6/2004 | Perez et al. |
| 2004/0126784 A1 | 7/2004 | Hitoshi et al. |
| 2004/0137539 A1 | 7/2004 | Bradford |
| 2004/0170995 A1 | 9/2004 | Lograsso et al. |
| 2004/0180380 A1 | 9/2004 | Lee et al. |
| 2004/0219592 A1 | 11/2004 | Berg et al. |
| 2004/0224371 A1 | 11/2004 | DeMatos et al. |
| 2004/0229284 A1 | 11/2004 | Luciw et al. |
| 2004/0241636 A1 | 12/2004 | Michnick et al. |
| 2004/0248151 A1 | 12/2004 | Bacus et al. |
| 2005/0009112 A1 | 1/2005 | Edgar et al. |
| 2005/0042694 A1 | 2/2005 | Darzynkiewicz et al. |
| 2005/0074834 A1 | 4/2005 | Chaplen et al. |
| 2005/0084924 A1 | 4/2005 | Shults et al. |
| 2005/0131006 A1 | 6/2005 | Mukherjee et al. |
| 2005/0202451 A1 | 9/2005 | Burczynski et al. |
| 2005/0216961 A1 | 9/2005 | Delaney |
| 2005/0250127 A1 | 11/2005 | Fisher et al. |
| 2005/0281743 A1 | 12/2005 | Delaney |
| 2006/0029944 A1 | 2/2006 | Huang et al. |
| 2006/0035211 A1 | 2/2006 | Levinson et al. |
| 2006/0040338 A1 | 2/2006 | Westwick et al. |
| 2006/0046249 A1 | 3/2006 | Huang et al. |
| 2006/0046272 A1 | 3/2006 | Chow et al. |
| 2006/0073474 A1 | 4/2006 | Perez et al. |
| 2007/0009923 A1 | 1/2007 | Nolan et al. |
| 2007/0105165 A1 | 5/2007 | Goolsby et al. |
| 2007/0172847 A1 | 7/2007 | Bonavida et al. |
| 2007/0196868 A1 | 8/2007 | Perez et al. |
| 2007/0196869 A1 | 8/2007 | Perez et al. |
| 2007/0196870 A1 | 8/2007 | Perez et al. |
| 2008/0026383 A1 | 1/2008 | Pepper et al. |
| 2008/0182262 A1 | 7/2008 | Perez et al. |
| 2008/0254489 A1 | 10/2008 | Perez et al. |
| 2008/0260754 A1 | 10/2008 | Li et al. |
| 2008/0275057 A1 | 11/2008 | Kawabe et al. |
| 2009/0068681 A1 | 3/2009 | Perez et al. |
| 2009/0081699 A1 | 3/2009 | Perez et al. |
| 2009/0098594 A1 | 4/2009 | Fantl et al. |
| 2009/0269773 A1 | 10/2009 | Fantl et al. |
| 2009/0269800 A1 | 10/2009 | Covey et al. |
| 2009/0291458 A1 | 11/2009 | Cohen et al. |
| 2009/0307248 A1 | 12/2009 | Moser et al. |
| 2010/0009364 A1 | 1/2010 | Fantl et al. |
| 2010/0014741 A1 | 1/2010 | Banville et al. |
| 2010/0030719 A1 | 2/2010 | Covey et al. |
| 2010/0042351 A1 | 2/2010 | Covey et al. |
| 2010/0086951 A1 | 4/2010 | Hedley et al. |
| 2010/0099109 A1 | 4/2010 | Fantl et al. |
| 2010/0105074 A1 | 4/2010 | Covey et al. |
| 2010/0151472 A1 | 6/2010 | Nolan et al. |
| 2010/0184092 A1 | 7/2010 | Perez et al. |
| 2010/0204973 A1 | 8/2010 | Parkinson et al. |
| 2010/0209929 A1 | 8/2010 | Fantl et al. |
| 2010/0215644 A1 | 8/2010 | Fantl et al. |
| 2010/0221750 A1 | 9/2010 | Perez et al. |
| 2010/0233733 A1 | 9/2010 | Fantl |
| 2010/0240542 A1 | 9/2010 | Soper et al. |
| 2010/0285594 A1 | 11/2010 | Purvis, Jr. |
| 2010/0297676 A1 | 11/2010 | Fantl et al. |
| 2011/0020839 A1 | 1/2011 | Perez et al. |
| 2011/0059861 A1 | 3/2011 | Nolan et al. |
| 2011/0104717 A1 | 5/2011 | Fantl et al. |
| 2011/0201018 A1 | 8/2011 | Perez et al. |
| 2011/0201019 A1 | 8/2011 | Perez et al. |
| 2011/0207145 A1 | 8/2011 | Perez et al. |
| 2011/0207146 A1 | 8/2011 | Perez et al. |
| 2011/0207149 A1 | 8/2011 | Perez et al. |
| 2011/0250614 A1 | 10/2011 | Perez et al. |
| 2011/0262468 A1 | 10/2011 | Fantl et al. |
| 2011/0269154 A1 | 11/2011 | Fantl et al. |
| 2011/0269634 A1 | 11/2011 | Perez et al. |
| 2012/0070849 A1 | 3/2012 | Perez et al. |
| 2012/0157340 A1 | 6/2012 | Cesano et al. |
| 2012/0215487 A1 | 8/2012 | Banville et al. |
| 2012/0276558 A1 | 11/2012 | Soper et al. |
| 2012/0309026 A1 | 12/2012 | Perez et al. |
| 2012/0309029 A1 | 12/2012 | Fantl et al. |
| 2013/0024177 A1 | 1/2013 | Nolan |
| 2013/0071860 A1 | 3/2013 | Hale et al. |
| 2013/0078621 A1 | 3/2013 | Nolan et al. |
| 2013/0096948 A1 | 4/2013 | Parkinson et al. |
| 2013/0109050 A1 | 5/2013 | Purvis, Jr. |
| 2013/0122524 A1 | 5/2013 | Fantl et al. |
| 2013/0123131 A1 | 5/2013 | Purvis et al. |
| 2013/0124522 A1 | 5/2013 | Moser et al. |
| 2013/0129681 A1 | 5/2013 | Covey et al. |
| 2014/0057865 A1 | 2/2014 | Fantl et al. |

FOREIGN PATENT DOCUMENTS

| | | |
|---|---|---|
| WO | WO 03/067210 A3 | 12/2003 |
| WO | WO 2006/012507 A2 | 2/2006 |
| WO | WO 2006/050333 A2 | 5/2006 |
| WO | WO 2006/079092 A2 | 7/2006 |
| WO | WO 2006/086111 A2 | 8/2006 |
| WO | WO 2006/012507 A3 | 10/2006 |
| WO | WO 2006/050333 A3 | 10/2006 |
| WO | WO 2006/128053 A1 | 11/2006 |
| WO | WO 2007/015886 A2 | 2/2007 |
| WO | WO 2007/027906 A2 | 3/2007 |
| WO | WO 2007/027957 A2 | 3/2007 |
| WO | WO 2007/056192 A2 | 5/2007 |
| WO | WO 2007/056192 A3 | 7/2007 |
| WO | WO 2007/117423 A2 | 10/2007 |
| WO | WO 2007/127335 A2 | 11/2007 |
| WO | WO 2007/140316 A1 | 12/2007 |
| WO | WO 2008/009004 A2 | 1/2008 |
| WO | WO 2007/127335 A3 | 6/2008 |
| WO | WO 2008/088857 A2 | 7/2008 |
| WO | WO 2007/015886 A3 | 10/2008 |
| WO | WO 2008/009004 A3 | 10/2008 |
| WO | WO 2007/027957 A3 | 1/2009 |
| WO | WO 2009/025847 A2 | 2/2009 |
| WO | WO 2006/086111 A3 | 4/2009 |
| WO | WO 2009/025847 A3 | 6/2009 |
| WO | WO 2009/134944 A2 | 11/2009 |
| WO | WO 2010/006291 A1 | 1/2010 |
| WO | WO 2010/006303 A2 | 1/2010 |
| WO | WO 2009/134944 A3 | 2/2010 |
| WO | WO 2010/028277 A1 | 3/2010 |
| WO | WO 2010/045651 A1 | 4/2010 |
| WO | WO 2007/027906 A3 | 11/2010 |
| WO | WO 2010/135608 A1 | 11/2010 |
| WO | WO 2011/031803 A1 | 3/2011 |
| WO | WO 2011/106558 A1 | 9/2011 |
| WO | WO 2011/119868 A2 | 9/2011 |
| WO | WO 2011/156654 A2 | 12/2011 |
| WO | WO 2012/024546 A2 | 2/2012 |
| WO | WO 2012/033537 A1 | 3/2012 |
| WO | WO 2012/083274 A2 | 6/2012 |
| WO | PCT/US2013/068815 | 11/2013 |
| WO | PCT/US2013/071354 | 11/2013 |

OTHER PUBLICATIONS

U.S. Appl. No. 13/464,254, filed May 4, 2012, Moser et al.
U.S. Appl. No. 13/493,857, filed Jun. 11, 2012, Fantl et al.

(56) References Cited

OTHER PUBLICATIONS

U.S. Appl. No. 13/544,053, filed Jul. 9, 2012, Soper et al.
U.S. Appl. No. 60/304,434, filed Jul. 10, 2001, Perez et al.
U.S. Appl. No. 60/310,141, filed Aug. 2, 2001, Nolan et al.
U.S. Appl. No. 61/048,657, filed Apr. 29, 2008, Covey et al.
U.S. Appl. No. 61/048,886, filed Apr. 29, 2008, Fantl et al.
U.S. Appl. No. 61/048,920, filed Apr. 29, 2008, Fantl et al.
U.S. Appl. No. 61/055,362, filed May 22, 2008, Cohen et al.
U.S. Appl. No. 61/079,537, filed Jul. 10, 2008, Putta.
U.S. Appl. No. 61/079,551, filed Jul. 10, 2008, Putta.
U.S. Appl. No. 61/079,579, filed Jul. 10, 2008, Banville et al.
U.S. Appl. No. 61/079,766, filed Jul. 10, 2008, Fantl et al.
U.S. Appl. No. 61/085,789, filed Apr. 1, 2008, Fantl et al.
U.S. Appl. No. 61/087,555, filed Apr. 8, 2008, Covey et al.
Allende, et al. A novel CD18 genomic deletion in a patient with severe leucocyte adhesion deficiency: a possible CD2/lymphocyte function-associated antigen-1 functional association in humans. Immunology. 2000; 99: 440-50.
Alvarez, et al. Signal Transducer and Activator of Transcription 3 Is Required for the Oncogenic Effects of Non-Small-Cell Lung Cancer-Associated Mutations of the Epidermal Growth Factor Receptor. Cancer Research. 2006;66:3162-3168.
Amendment, Request for continued examination (RCE), and response to notice to file corrected application papers dated Jan. 18, 2012 for U.S. Appl. No. 12/460,029.
Amico, et al. Differential response of human acute myeloid leukemia cells to gemtuzumab ozogamicin in vitro: role of Chk1 and Chk2 phosphorylation and caspase 3. Blood. Jun. 1, 2003;101(11):4589-97.
Anderson, et al. Simultaneous fluorescence-activated cell sorter analysis of two distinct transcriptional elements within a single cell using engineered green fluorescent proteins. Proc Natl Acad Sci USA. 1996; 93: 8508-11.
Apperley, et al. Bone marrow transplantation for chronic myeloid leukaemia in first chronic phase: importance of a graft-versus-leukaemia effect. Br J Haematol. Jun. 1988;69(2):239-45.
Aul, et al. Evaluating the prognosis of patients with myelodysplastic syndromes. Ann Hematol. 2002;81(9):485-97.
Bacon, et al. Interleukin 12 induces tyrosine phosphorylation and activation of STAT4 in human lymphocytes. Proc. Natl. Acad. Sci. USA. 1995;92:7307-7311.
Bagrintseva, et al. FLT3-ITD-TKD dual mutants associated with AML confer resistance to FLT3 PTK inhibitors and cytotoxic agents by overexpression of Bcl-x(L). Blood. May 1, 2005;105(9):3679-85.
Bai, et al. Dimerization of the extracellular calcium-sensing receptor (CaR) on the cell surface of CaR-transfected HEK293 cells. J Biol Chem. Sep. 4, 1998;273(36):23605-10.
Baldus, et al. Clinical outcome of de novo acute myeloid leukemia patients with normal cytogenetics is affected by molecular genetic alterations: a concise review. British J. Haematology. 2007;137:387-400.
Baldus, et al. BAALC expression predicts clinical outcome of de novo acute myeloid leukemia patients with normal cytogenetics: a Cancer and Leukemia Group B study. Blood. 2003;102:1613-18.
Bardet, et al. Single cell analysis of phosphoinositide 3-kinase/Akt and ERK activation in acute myeloid leukemia by flow cytometry. Haematologica. Jun. 2006;91(6):757-64.
Barrow, et al. You say ITAM and I say ITIM, let's call the whole thing off: the ambiguity of immunoreceptor signalling. Eur J Immunol. 2006;36(7):1646-53.
Bartram, et al. Translocation of c-abl oncogene correlates with the presence of a Philadelphia chromosome in chronic myelocytic leukaemia. Nature. Nov. 17-23, 1983;306(5940):277-80.
Baxter, et al. Acquired mutation of the tyrosine kinase JAK2 in human myeloproliferative disorders. The Lancet. 2005;365(9464):1054-1061.
Belloc, et al. Flow cytometry detection of caspase 3 activation in preapoptotic leukemic cells. Cytometry. Jun. 1, 2000;40(2):151-60.

Bene, et al. Detection of receptor clustering by flow cytometric fluorescence anisotropy measurements. Cytometry. 2000; 40: 292-306.
Benekli, et al. Signal transducer and activator of transcription proteins in leukemias. Blood. Apr. 15, 2003;101(8):2940-54.
Bernstein, et al. DNA repair/pro-apoptotic dual-role proteins in five major DNA repair pathways: fail-safe protection against carcinogenesis. Mutat Res. Jun. 2002;511(2):145-78.
Bienz. APC: the plot thickens. Curr Opin Genet Dev. 1999; 9(5): 595-603.
Bindoli, et al. Thiol chemistry in peroxidase catalysis and redox signaling. Antioxid Redox Signal. 2008. 10(9):1549-64.
Birkenkamp, et al. Regulation of constitutive STAT5 phosphorylation in acute myeloid leukemia blasts. Leukemia. 2001; 15(12):1923-31.
Bleijs, et al. A single amino acid in the cytoplasmic domain of the beta 2 integrin lymphocyte function-associated antigen-1 regulates avidity-dependent inside-out signaling. J Biol Chem. 2001; 276: 10338-46.
Boissel, et al. Incidence and prognostic impact of c-Kit, FLT3 Ligand, and Ras gene mutations in core binding factor acute myeloid leukemia (CBF-AML). Leukemia. 2006;20(6):965-970.
Broxmeyer, et al. The suppressive influences of human tumor necrosis factors on bone marrow hematopoietic progenitor cells from normal donors and patients with leukemia: synergism of tumor necrosis factor and interferon-gamma. Journal of Immunology. 1986;36:4487-4495.
Burks et al. IRS proteins and beta-cell function. Diabetes. 2001. S140-S145, Suppl 1:S140-5.
Cairo, et al. Contol of multivalent interactions by binding epitope density. J Am Chem Soc. 2002; 124(8): 1615-9.
Caligaris-Cappio, et al. Infrequent normal B lymphocytes express features of B-chronic lymphocytic leukemia. J Exp Med. Feb. 1, 1982;155(2):623-8.
Calo, et al. STAT proteins: from normal control of cellular events to tumorigenesis. J Cell Physiol. Nov. 2003;197(2):157-68.
Cantley, et al. Oncogenes and signal transduction. Cell. Jan. 25, 1991;64(2):281-302.
Castillo, et al. Proliferative response of mantle cell lymphoma cells stimulated by CD40 ligation and IL-4. Leukemia. Feb. 2000;14(2):292-8.
Cesano, et al. Single-cell network profiling as tool to identify AML chemotherapy resistant cell phenotypes under in vivo therapeutic pressure. Blood. Nov. 2009; 114(22):165. abstract #397.
Chang et al., Lymphocyte proliferation modulated by glutamine: involved in the endogenous redox reaction; Clin Exp Immunol. Sep. 1999; 117(3): 482-488.
Chen, et al. Down-regulation of the c-Jun N-terminal kinase (JNK) phosphatase M3/6 and activation of JNK by hydrogen peroxide and pyrrolidine dithiocarbamate. Oncogene. 2001. 20(3):367-74.
Chou, et al. Acute promyelocytic leukemia: recent advances in therapy and molecular basis of response to arsenic therapies. Curr Opin Hematol. 2005. 12(1):1-6.
Choudhary, et al. Activation mechanisms of STAT5 by oncogenic FLt3 ligand-ITD. Blood. 2007;110(1):370-4.
Choudhary, et al. AML-associated Flt3 kinase domain mutations show signal transduction differences compared with Flt3-ITD mutations. Blood. 2005;106:265-73.
Chow, et al. Constitutive phosphorylation of the S6 ribosomal protein via mTOR and ERK signaling in the peripheral blasts of acute leukemia patients. Experimental hematology. 2006; 34(9):1182-1190.
Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.
Chung, et al. The biology of Abl during hemopoietic stem cell differentiation and development. Oncogene. Apr. 6, 1995;10(7):1261-8.
Clark, et al. Regulation of human B-cell activation and adhesion. Annu Rev Immunol 1991;9:97-127.
Cochran, et al. Receptor clustering and transmembrane signaling in T cells. Trends in Biochemical Sciences. 2001; 26(5): 304-10.

(56) References Cited

OTHER PUBLICATIONS

Collins, et al. Multipotent hematopoietic cell lines derived from C/EBPa (−/−) knockout mice display granulocyte macrophage-colony-stimulating factor, granulocyte-colony-stimulating factor and retinoic acid-induced granulocytic differentiation. Blood. 2001;98:2382-8.

Colucci, et al. Redundant role of the Syk protein tyrosine kinase in muse NK cell differentiation. J Immunol. 1999; 163: 1769-74.

Corcoran, et al. Characterization of ligand binding by the human p55 tumour-necrosis-factor receptor. Involvement of individual cysteine-rich repeats. Eur J Biochem. 1994. 223(3):831-40.

Countouriotis, et al. Cell surface antigen and molecular targeting in the treatment of hematologic malignancies. Stem Cells. 2002;20(3):215-29.

Covey, et al. Modulated multiparametric phosphoflow cytometry in hematological malignancies: technological and clinical applications. Best Pract Res Clin Haematol. Sep. 2010;23(3):319-31. Epub Nov. 10, 2010.

Craig, et al. Flow cytometric immunophenotyping for hematologic neoplasms. Blood. Apr. 15, 2008;111(8):3941-67.

Crans-Vargas, et al. CREB as a prognostic marker in acute leukemia. Abstract. Blood. 2001; 98(11), part 1, p. 316a.

Czech, M. PIP3 and PIP2: Complex Roles at the Cell Surface. Cell, 2000; 100:603-606.

D'Ambrosio et al. Chemokine receptors in inflammation: an overview J Immunol Methods. 2003. 273(1-2):3-13.

Damle, et al. Differential regulatory effects of intercellular adhesion molecule-1 on costimulation by CD28 counter-receptor B7. J Immunol 1992; 149: 2541-8.

Danna, et al. Transcending the biomarker mindset: deciphering disease mechanisms at the single cell level. Curr Opin Chem Biol. Feb. 2006;10(1):20-7.

Dantuma, et al. Short-lived green fluorescent proteins for quantifying ubiquitin/proteasome-dependent proteolysis in living cells. Nat Biotechnol. 2000; 18: 538-43.

Davis, et al. Determination of CD4 antigen density on cells: role of antibody valency, avidity, clones, and conjugation. Cytometry. 1998; 33: 197-205.

De Fougerolles, et al. Characterization of ICAM-2 and evidence for a third counter-receptor for LFA-1. J Exp Med. 1991; 174: 253-67.

De Fougerolles, et al. Heterogenous glycosylation of ICAM-3 and lack of interaction with Mac-1 and p150,95. Eur J Immunol 1995; 25: 1008-12.

De Rosa, et al. 11-color, 13-parameter flow cytometry: Identification of human naive T cells by phenotype, function, and T-cell receptor diversity. Nat Med. 2001; 7: 245-8.

Deeths, et al. ICAM-1 and B7-1 provide similar but distinct costimulation for CD8+ T cells, while CD4+ T cells are poorly costimulated by ICAM-1. Eur J Immunol. 1999; 29: 45-53.

Devine, et al. Role of LFA-1, ICAM-1, VLA4 and VCAM-1 in lymphocyte migration across retinal pigment epithelial monolayers in vitro. Immunology. 1996; 88: 456-62.

Di Bacco, et al. Molecular abnormalities in chronic myeloid leukemia: deregulation of cell growth and apoptosis. Oncologist. 2000;5(5):405-15.

Diacovo, et al. A functional integrin ligand on the surface of platelets: intercellular adhesion molecule-2. J Clin Invest. 1994; 94: 1243-51.

Diaz-Flores, et al. Intracellular signals as molecular biomarkers for therapeutic responses in Kras mutant myeloid cells. Blood. Nov. 2007; 110(11)part1 :635a abstract #2196.

DiJoseph et al. Antitumor efficacy of a combination of CMC-544 (inotuzumab ozogamicin), a CD22-targeted cytotoxic immunoconjugate of calicheamicin, and rituximab against non-Hodgkin's B-cell lymphoma. Clin Cancer Res. 2006. 12(1):242-9.

DiJoseph F, Goad ME, Dougher MM, et al. Potent and specific antitumour efficacy of CMC-544, a CD22-targeted immunoconjugate of calicheamicin, against systemically disseminated B cell lymphoma. *Clin Cancer Res.* 2004;10:8620-8629.

Dikic, et al. A role for Pyk2 and Src in linking G-protein-coupled receptors with MAP kinase activation. Nature. 1996; 383: 547-50.

Doepfner, et al. Targeting receptor tyrosine kinase signaling in acute myeloid leukemia. Crit Rev Oncol Hematol. Sep. 2007;63(3):215-30.

Donskov, et al. Expression and function of LFA-1 on A-NK and T-LAK cells: role in tumor target killing and migration into tumor tissue. Nat Immun. 1996; 15: 134-46.

Ebert, et al. An Erythroid Differentiation Signature Predicts Response to Lenalidomide in Myelodysplastic Syndrome. PLoS Medicine. 2008;5(2):312-322.

Egger, et al. Epigenetics in human disease and prospects for epigenetic therapy. Nature. 2004. 429(6990):457-63.

Erlanson, et al. Flow cytometric quantification of cyclin E in human cell lines and hematopoietic malignancies. Cytometry. Jul. 1, 1998;32(3):214-22.

European search report Jul. 10, 2006 for Application No. 02805693.5.

European search report and search opinion dated Feb. 22, 2011 for Application No. 10180167.8.

European Search Report dated Nov. 2, 2010 for EP Application No. EP08795509.

Fantl, et al. High Level phosphatas activity revealed in chronic lymphocytic leukemia cells that use mutated ommunoglobulin heavy chain variable region genes and lack high-level expression of the zeta-assocaited protein(ZAP-70). Blood. 2007. 110(11): Part 1 pp. 228A-229A (Abstracts).

Fiering, et al. Improved FAGS-Gal: flow cytometric analysis and sorting of viable eukaryotic cells expressing reporter gene constructs. Cytometry. 1991; 12: 291-301.

Figueiredo-Pontes, et al. Determination of P-glycoprotein, MDR-related protein 1, breast cancer resistance protein, and lung-resistance protein expression in leukemic stem cells of acute myeloid leukemia. Clinical Cytometry. 2008;74B(3):163-168.

Fine, et al. The role of LFA-1/ICAM-1 interactions during murine T lymphocyte development. J Immunol. 1991; 147: 2852-9.

Frank, et al. Interleukin 2 signaling involves the phosphorylation of Stat proteins. Proc. Natl. Acad. Sci. USA. 1995;92:7779-7783.

Friedman, et al. Bayesian network classifiers. Machine Learning. 1997; 29:131-163.

Friedman, et al. Inferring cellular networks using probabilistic graphical models. Science. Feb. 6, 2004;303(5659):799-805.

Friedman, et al. Using Bayesian networks to analyze expression data. J Comput Biol. 2000;7(3-4):601-20.

Frohling, et al. Prognostic significance of activating FLT3 mutations in younger adults (16 to 60 years) with acute myeloid leukemia and normal cytogenetics: a study of the AML Study Group Ulm. Blood. 2002;100:4372-80.

Fujii, et al. Activation of Stat5 by interleukin 2 requires a carboxyl-terminal region of the interleukin 2 receptor beta chain but is not essential for the proliferative signal transmission. Proc. Natl. Acad. Sci USA. 1995;92:5482-5486.

Galaris, et al. Redox signaling and cancer: The role of "labile" iron. Cancer Letters. 2008;266(1):21-29.

Garrido, et al. Three-color versus four-color multiparameter cell cycle analyses of primary acute myeloid leukemia samples. Cytometry. Apr. 15, 2000;42(2):83-94.

Geiger, et al. Cytohesion-1 regulates beta-2 integrin-mediated adhesion through both ARF-GEF function and interaction with LFA-1. Embo J. 2000; 19: 2525-36.

Georgiou, et al. Serial determination of FLT3 mutations in myelodysplastic syndrome patients at diagnosis, follow up or acute myeloid leukaemia transformation: incidence and their prognostic significance. Br J Haematol. 2006;134(3):302-6.

Gert-Jan, et al. G-CSF receptor truncations found in SCN/AML relieve SOCS3-controlled inhibition of STAT5 but leave suppression of STAT3 intact. Blood. 2004;104:667-74.

Gery, et al. Adaptor protein Lnk negatively regulates the mutant MPL, MPLW515L associated with myeloproliferative neoplasms. Blood. 2007;110(9):3360-3364.

Gilliland, et al. The roles of FLT3 in hematopoiesis and leukemia. Blood. 2002;100:1532-1542.

Green DR. Apoptotic pathways: the roads to ruin. Cell. 1998. 94(6):695-8.

(56) References Cited

OTHER PUBLICATIONS

Grell et al. The transmembrane form of tumor necrosis factor is the prime activating ligand of the 80 kDa tumor necrosis factor receptor. Cell. 1995. 83(5):793-802.
Griffioen, et al. Endothelial intercellular adhesion molecule-1 expression is suppressed in human malignancies: the role of angiogenic factors. Cancer Res. 1996; 56: 1111-7.
Griffioen, et al. Tumor angiogenesis is accompanied by a decreased inflammatory response of tumor-associated endothelium. Blood. 1996; 88: 667-73.
Gueller, et al. Adaptor protein Lnk associates with Tyr(568) in c-Kit. Biochem J. 2008;415(2):241-5.
Hamblin, et al. Unmutated Ig V(H) genes are associated with a more aggressive form of chronic lymphocytic leukemia. Blood. Sep. 15, 1999;94(6):1848-54.
Hanahan, et al. The Hallmarks of Cancer. Cell. 2000;100(1):57-70.
Hartemink, et al. Using graphical models and genomic expression data to statistically validate models of genetic regulatory networks. Pac Symp Biocomput. 2001;:422-33.
Haswell, et al. Analysis of the oligomeric requirements for signaling by CD40 using soluble multimeric forms of its ligands, CD154. Eur J Immunol. 2001; 31(10): 3094-100.
Hayakawa, et al. SFK-STAT pathway: an alternative and important way to malignancies. Annals of the New York Academy of Sciences. 2006;1086:213-22.
Helander, et al. ICAM-2 redistributed by ezrin as a target for killer cells. Nature. 1996; 382: 265-8.
Hirai et al. A novel putative tyrosine kinase receptor encoded by the eph gene. Science. 1987. 238(4834):1717-20.
Ho, et al. MDR1 and BCRP1 expression in leukemic progenitors correlates with chemotherapy response in acute myeloid leukemia. Experimental Hematology. 2008;36:433-442.
Hofmann, et al. Mutation analysis of the DNA-damage checkpoint gene CHK2 in myelodysplastic syndromes and acute myeloid leukemias. Leukemia Research. 2001;25:333-338.
Hogg, et al. A novel leukocyte adhesion deficiency caused by expressed by nonfunctional beta2 integrins Mac-1 and LFA-1. J Clin Invest. 1999; 103: 97-106.
Hunter T. Signaling—2000 and beyond. Cell. 2000. 100(1):113-27.
Hunter. Cooperation between oncogenes. Cell. Jan. 25, 1991;64(2):249-70.
Igietseme, et al. The intercellular adhesion molecule type-1 is required for rapid activation of T helped type 1 lymphocytes that control early acute phase of genital chlamydial infection of mice. Immunology. 1999; 98: 510-8.
Ikezoe, et al. The antitumor effects of sunitinib (formerly SU11248) against a variety of human hematologic malignancies: enhancement of growth inhibition via inhibition of mammalian target of rapamycin signaling. Mol Cancer Ther. Oct. 2006;5(10):2522-30.
International preliminary report on patentability dated Mar. 4, 2010 for PCT/US2008/009975.
International preliminary report on patentability dated May 5, 2008 for PCT/US2006/043050.
International search report and written opinion dated Mar. 20, 2009 for PCT/US2008/009975.
International search report and written opinion dated May 2, 2007 for PCT/US2006/043050.
International search report dated Jul. 10, 2006 for PCT/US2005/026026.
International search report dated Sep. 21, 2010 for PCT/US2010/035690.
International search report dated Oct. 5, 2006 for PCT/US2006/002583.
International search report dated Oct. 15, 2003 for PCT/US2002/022328.
International search report dated Oct. 15, 2009 for PCT/US2008/000655.
International search report dated Nov. 24, 2009 for PCT/US2009/050295.
International search report dated Mar. 9, 2010 for PCT Application No. US2009/61195.
Irish, et al. Mapping normal and cancer cell signalling networks: towards single-cell proteomics. Nat. Rev. Cancer. 2006. 6:146-155.
Irish, et al. Altered B-cell receptor signaling kinetics distinguish human follicular lymphoma B cells from tumor-infiltrating nonmalignant B cells. Blood. Nov. 1, 2006;108(9):3135-42.
Irish, et al. Flt3 Y591 duplication and Bcl-2 overexpression are detected in acute myeloid leukemia cells with high levels of phosphorylated wild-type p53. Blood. 2007. 109(6):2589-96.
Irish, et al. Kinetics of B cell receptor signaling in human B cell subsets mapped by phosphospecific flow cytometry. J Immunol Aug. 1, 2006;177(3):1581-9.
Irish, et al. Single cell profiling of potentiated phospho-protein networks in cancer cells. Cell. Jul. 23, 2004;118(2):217-28.
Iyer, et al. Quantitation of CD38 expression using QuantiBRITE™ beads. Cytometry. 1998; 33: 206-12.
James, et al. A unique clonal JAK2 mutation leading to constitutive signalling causes polycythaemia vera. Nature. 2005;434:1144-1148.
Jiang, et al. Pivotal role of phosphoinositide-3 kinase in regulation of cytotoxicity in natural killer cells. Nat Immunol. 2000; 1: 419-25.
Johnson, et al. Effector caspases are dispensable for the early nuclear morphological changes during chemical-induced apoptosis. J Cell Sci. 2000; 113: 2941-53.
Karihtala et al. Reactive oxygen species and antioxidant mechanisms in human tissues and their relation to malignancies. APMIS. 2007. 115(2):81-103.
Karp, et al. Targeting Vascular Endothelial Growth Factor for Relapsed and Refractory Adult Acute Myelogenous Leukemias. Clinical Cancer Res. 2004;10:3577-85.
Kennedy, et al. Akt/Protein kinase B inhibits cell death by preventing the release of cytochrome c from mitochondria. Mol Cell Biol. 1999; 19: 5800-10.
Khalidi, et al. The immunophenotype of adult acute myeloid leukemia: high frequency of lymphoid antigen expression and comparison of immunophenotype, French-American-British classification, and karyotypic abnormalities. Am J Clin Pathol. Feb. 1998;109(2):211-20.
Kikukawa, et al. Study of p53 in elderly patients with myelodysplastic syndromes by immunohistochemistry and DNA analysis. American Journal of Pathology. 1999;155:717-721.
Kim, et al. Constitutively activated FLT3 phosphorylates BAD partially through pim-1. Br J Haematol. Sep. 2006;134(5):500-9.
Kindler, et al. Indentification of a novel activating mutation (Y842C) within the activation loop of FLT3 in a patient with AML. Abstract 4681. Blood. 2003; 102(11):239B-240B and 45th Annual Meeting of the American Society of Hematology. San Diego, CA, USA. Dec. 6-9, 2003.
Kishimoto, T. Signal transduction through homo- or heterodimers of gp130. Stem Cells. 1994;12(Suppl 1):37-44;discussion 44-5.
Kliche, et al. Signaling by human herpesvirus 8 kaposin A through direct membrane recruitment of cytohesin-1. Mol Cell. 2001; 7: 833-43.
Koester, et al. Intracellular markers. J Immunol Methods. Sep. 21, 2000;243(1-2):99-106.
Koretzky, et al. SLP76 and SLP65: complex regulation of signalling in lymphocytes and beyond. Nature Reviews Immunology. 2006;6:67-78.
Kornblau, et al. Dynamic single-cell network profiles in acute myelogenous leukemia are associated with patient response to standard induction therapy. Clin Cancer Res. Jul. 15, 2010;16(14):3721-33. (abstract).
Kovtun, Yelena V. et al., Antibody-Drug Conjugates Designed to Eradicate Tumors with Homogeneous and Heterogeneous Expression of the Target Antigen, *Cancer Research* 66, 3214-3221, Mar. 15, 2006.
Kralovics, et al. A Gain-of-Function Mutation of JAK2 in Myeloproliferative Disorders. N Engl J Med. 2005;352:1779.
Kralovics, et al. Altered gene expression in myeloproliferative neoplasms correlates with the activation of signaling by the V617F mutation of JAK2. Blood. 2005;106(10):3374-3376.

(56) References Cited

OTHER PUBLICATIONS

Kroeger et al. Constitutive and agonist-dependent homo-oligomerization of the thyrotropin-releasing hormone receptor. Detection in living cells using bioluminescence resonance energy transfer. J Biol Chem. 2001. 276(16):12736-43.

Krutzik, et al. High-content single-cell drug screening with phosphospecific flow cytometry. Natural Chemical Biology. 2008. 4(2):132-42.

Krutzik, et al. Intracellular phospho-protein staining techniques for flow cytometry: monitoring single cell signaling events. Cytometry A. 2003; 55(2): 61-70.

Krutzik, et al. Analysis of protein phosphorylation and cellular signaling events by flow cytometry: techniques and clinical applications. Clinical Immunology. 2004; 110: 206-21.

Krutzik, et al. Coordinate analysis of murine immune cell surface markers and intracellular phosphoproteins by flow cytometry. J Immunol 2005. 175(4):2357-65.

Krutzik, et al. Intracellular phospho-protein staining techniques for flow cytometry: monitoring single cell singaling events. Cytometry Part A. 2003; 55A:61-70.

Krutzik. Characterization of the murine immunological signaling network with phosphospecific flow cytometry. J Immunol. 2005. 175(4): 2366-73.

Kulik, et al. Antiapoptotic signaling by the insulin-like growth factor I receptor, phosphatidylinositol 3-kinase, and Akt. Mol Cell Biol. 1997; 17: 1595-606.

Kumar, et al. 2-methoxyestradiol blocks cell-cycle progression at G(2)/M phase and inhibits growth of human prostate cancer cells. Mol Carcinog. Jul. 2001;31(3):111-24.

Kurotaki, et al. Apoptosis, bcl-2 expression and p53 accumulation in MDS, MDS derived acute myeloid leukemia and de novo acute myeloid leukemia. Acta Haematologica. 2000;102:115-123.

Lecoeur, et al. A novel flow cytometric assay for quantitation and multiparametric characterization of cell-mediated cytotoxicity. J Immunol Methods. 2001; 253: 177-87.

Legrand, et al. Pgp and MRP Activities Using Calcein-AM Are Prognostic Factors in Adult Acute Myeloid Leukemia Patients. Blood. 1998;91:4480-4488.

Leith, et al. Acute Myeloid Leukemia in the Elderly: Assessment of Multidrug Resistance (MDR1) and Cytogenetics Distinguishes Biologic Subgroups With Remarkably Distinct Responses to Standard Chemotherapy. A Southwest Oncology Group Study. Blood. 1997;89:3323-3329.

Leith, et al. Frequency and Clinical Significance of the Expression of the Multidrug Resistance Proteins MDR1/P-Glycoprotein, MRP1, and LRP in Acute Myeloid Leukemia. A Southwest Oncology Group Study. Blood. 1999;94:1086-1099.

Lenkei, et al. Performance of calibration standards for antigen quantitation with flow cytometry. Cytometry. 1998; 33: 188-96.

Levine, et al. Activating mutation in the tyrosine kinase JAK2 in polycythemia vera, essential thrombocythemia, and myeloid metaplasia with myelofibrosis. Cancer Cell. 2005;7(4):387-397.

Leyval, D et al., Flow cytometry for the intracellular pH measurement of glutamate producing *Corynebacterium glutamicum*, Journal of Microbiological Methods, vol. 29, Issue 2, May 1, 1997, pp. 121-127.

Lindberg et al. cDNA cloning and characterization of eck, an epithelial cell receptor protein-tyrosine kinase in the eph/elk family of protein kinases. Mol Cell Biol. 1990. 10(12):6316-24.

Linenberger, et al. Multidrug-resistance phenotype and clinical responses to gemtuzumab ozogamicin. Blood. Aug. 15, 2001;98(4):988-94.

Liu, et al. Overexpression of cyclin D1 in accelerated-phase chronic myeloid leukemia. Leuk Lymphoma. Dec. 2004;45(12):2419-25.

Lub, et al. Dual role of the actin cytoskeleton in regulating cell adhesion mediated by the integrin lymphocyte function-associated molecule-1. Mol Biol Cell. 1997; 8: 341-51.

Mack, et al. Detection of caspase-activation in intact lymphoid cells using standard caspase substrates and inhibitors. J Immunol Methods. Jul. 31, 2000;241(1-2):19-31.

Mahmoud, et al. Induction of CD45 expression and proliferation in U-266 myeloma cell line by interleukin-6. Blood. 1998. 92(10):3887-97.

Malhotra et al. Molecular biology of protein kinase C signaling in cardiac myocytes. Mol Cell Biochem. 2001. 225(1-):97-107.

Mandler R, Kobayashi H, Hinson ER, et al. Herceptin-geldanamycin immunoconjugates: pharmacokinetics, biodistribution, and enhanced antitumor activity. *Cancer Res*. 2004;64:1460-1467.

Marcucci, et al. Overexpression of the ETS-related gene, ERG, predicts a worse outcome in acute myeloid leukemia with normal karyotype: a Cancer and Leukemia Goruop B study. J. Clinical Oncology. 2005;23:9234-42.

Marone, et al. Targeting phosphoinositide 3-kinase—Moving towards therapy. Biochimica et Biophysica Acta (BBA)—Proteins & Proteomics. 2008;1784:159-185.

Marvin et al. Normal bone marrow signal transduction profiles: a requisite for enhanced detection of signaling dysregulations in AML. Blood. Jan. 13, 2011. doi:10.1182/blood-2010-10-316026 [Epub ahead of print].

Mates, et al. Intracellular redox status and oxidative stress: implications for cell proliferation, apoptosis, and carcinogenesis. Arch Toxicol. May 2008;82(5):273-99.

Matsumoto, et al. Adhesion mediated by LFA-1 is required for efficient IL-12-induced NK and NKT cell cytotoxicity. Eur J Immunol 2000; 30: 3723-31.

McDowall, et al. The I domain of integrin leukocyte function-associated antigen-1 is involved in a conformational change leading to high affinity binding to ligand intercellular adhesion molecule 1 (ICAM-1). J Biol Chem. 1998; 273: 27396-403.

Melchert, et al. The role of lenalidomide in the treatment of patients with chromosome 5q deletion and other myelodysplastic syndromes. Current Opinion in Haematology. 2007;14:123-129.

Menard, et al. Biologic and therapeutic role of HER2 in cancer. Oncogene. 2003. 22(42): 6570-8.

Meshinchi et al. Structural and functional Alterations of FLT3 in Acute Myeloid Leukemia. Clin Cancer Res. 2009;15(13):4263-4269.

Miller, et al. Intercellular adhesion molecule-1 dimerization and its consequences for adhesion mediated by lymphocyte function associated-1. J Exp Med. 1995; 182: 1231-41.

Minami, et al. Different antiapoptotic pathways between wild-type and mutated FLT3: insights into therapeutic targets in leukemia. Blood. Oct. 15, 2003;102(8):2969-75.

Moon, et al. Molecular mechanisms of ZD1839 (Iressa)-induced apoptosis in human leukemic U937 cells. Acta Pharmacol Sin. Aug. 2007;28(8):1205-14.

Morgan, et al. Cell-cycle-dependent activation of mitogen-activated protein kinase kinase (MEK-1/2) in myeloid leukemia cell lines and induction of growth inhibition and apoptosis by inhibitors of RAS signaling. Blood. Mar. 15, 2001;97(6):1823-34.

Morgan, et al. Superantigen-induced T cell:B cell conjugation is mediated by LFA-1 and required signaling though Lck, but not ZAP-70. J Immunol. 2001; 167: 5708-18.

Morkve, et al. Quantitation of biological tumor markers (p53, c-myc, Ki-67 and DNA ploidy) by multiparameter flow cytometry in non-small-cell lung cancer. Int J Cancer. Dec. 2, 1992;52(6):851-5.

Moser, et al. Improved outcome of chronic *Pseudomonas aeruginosa* lung infection associated with induction of a Th1-dominated cytokine response. Clin Exp Immunol. 2002; 127: 206-13.

Mukai, et al. Critical role of CD1 la (LFA-1) in therapeutic efficacy of systemically transferred antitumor effector T cells. Cell Immunol 1999; 192: 122-32.

Musso, et al. Regulation of JAK3 expression in human monocytes: phosphorylation in response to interleukins 2, 4, and 7. J. Exp. Med. 1995;181:1425-1431.

Nam, et al. The PI3K-Akt mediates oncogenic Met-induced centrosome amplification and chromosome instability. Carcinogenesis. Sep. 2010;31(9):1531-40. Abstract only.

Neben, et al. Gene expression patterns in acute myeloid leukemia correlate with centrosome aberrations and numerical chromosome changes. Oncogene. Mar. 25, 2004;23(13):2379-84.

Neeson, et al. Characterization of activated lymphocyte-tumor cell adhesion. J Leukoc Biol. 2000; 67: 847-55.

(56) References Cited

OTHER PUBLICATIONS

Neote et al. Molecular cloning, functional expression, and signaling characteristics of a C-C chemokine receptor. Cell. 1993. 72(3):415-25.

Neubauer, et al. Mutations in the ras proto-oncogenes in patients with myelodysplastic syndromes. Leukemia. 1994;8:638-641.

Nielson, et al. Expression of the activation antigen CD69 predicts functionality of in vitro expanded peripheral blood mononuclear cells (PBMC) from healthy donors and HIV-infected patients. Clin Exp Immunol. 1998; 114: 66-72.

Nishimura, et al. Distinct role of antigen-specific T helper type 1 (Th1) and Th2 cells in tumor eradication in vivo. J Exp Med. 1999; 190: 617-27.

Nolan, et al. Fluorescence activated cell analysis and sorting of viable mammalian cells based on beta-D-galactosidase activity after transduction of *Escherichia coli* lacZ. Proc Natl Acad Sci USA. 1988; 85: 2603-7.

Norris. Multivariate analysis and reverse engineering of signal transduction pathways. Masters thesis. The University of British Columbia. Apr. 2002; pp. 152.

Notice of Allowance dated Nov. 1, 2011 for U.S. Appl. No. 12/460,029.

Nurse. Universal control mechanism regulating onset of M-phase. Nature. 1990; 344:503-508.

Okuda, et al. AML1, the target of multiple chromosomal translocations in human leukemia, is essential for normal fetal liver hematopoiesis. Cell. 1996;84:321-30.

Olsen, et al. Function-based isolation of novel enzymes from a large library. Nat Biotechnol. 2000; 18: 1071-4.

Onishi, et al. Applications of retrovirus-mediated expression cloning. Exp Hematol. 1996; 24: 324-9.

Padro, et al. Overexpression of vascular endothelial growth factor (VEGF) and its cellular receptor KDR (VEGFR-2) in the bone marrow of patients with acute myeloid leukemia. Leukemia. 2002;16:1302-1310.

Padua, et al. RAS, FMS and p53 mutations and poor clinical outcome in myelodysplasias: a 10-year follow-up. Leukemia. 1998;12:887-892.

Pallis, et al. Flow cytometric measurement of phosphorylated STAT5 in AML: lack of specific association with FLT3 internal tandem duplications. Leuk Res. Sep. 2003;27(9):803-5.

Papa, et al. Proapoptotic activity and chemosensitizing effect of the novel Akt inhibitor perifosine in acute myelogenous leukemia cells. Leukemia. Jan. 2008;22(1):147-60.

Pardanani, et al. MPL515 mutations in myeloproliferative and other myeloid disorders: a study of 1182 patients. Blood. 2006.108:3472-3476.

Parsons et al. An integrated genomic analysis of human glioblastoma multiforme. Science. 2008. 321(5897):1807-12.

Pascual, et al. Analysis of somatic mutation in five B cell subsets of human tonsil. J Exp Med. Jul. 1, 1994;180(1):329-39.

Paul, et al. Myeloid specific human CD33 is an inhibitory receptor with differential ITIM function in recruiting the phosphatases SHP-1 and SHP-2. Blood. 2000;96:483-490.

Pawson T. Regulation and targets of receptor tyrosine kinases. Eur J Cancer. 2002. 38 Suppl 5:S3-10.

Peer, et al. Inferring subnetworks from perturbed expression profiles. Bioinformatics. 2001;17 Suppl 1:S215-24.

Perez, et al. Activation of the PKB/AKT pathway by ICAM-2. Immunity 2002; 16: 51-65.

Perez, et al. Flow cytometric analysis of kinase signaling cascades. Methods Mol Biol. 2004;263:67-94.

Perez, et al. Leukocyte functional antigen 1 lowers T cell activation thresholds and signaling through cytohesin-1 and Jun-activating binding protein 1. Nat Immunol. Nov. 2003;4(11):1083-92.

Perez, et al. LFA-1 signaling through p44/42 is coupled to perforin degranulation in CD56+CD8+ natural killer cells. Blood. Aug. 15, 2004;104(4):1083-93.

Perez, et al. Phospho-proteomic immune analysis by flow cytometry: from mechanism to translational medicine at the single-cell level. Immunol Rev. Apr. 2006;210:208-28.

Perez, et al. Simultaneous measurement of multiple active kinase states using polychromatic flow cytometry. Nat Biotechnol. 2002; 20: 155-62.

Perfetto, et al. Seventeen-colour flow cytometry: unravelling the immune system. Nat Rev Immunol. Aug. 2004;4(8):648-55.

Perl, et al. Single-cell pharmacodynamic monitoring of S6 ribosomal protein in AML blasts during a clinical trial combining the mTOR inhibitor sirolimus with mitoxantrone, etoposide, and cytarabine chemotherapy. Blood. Nov. 2009; 114(22):172. abstract #413.

Peterson, et al. Coupling of the TCR to integrin activation by Slap-130/Fyb. Science. 2001; 293: 2263-5.

Pettersen, et al. CD47 signals T cell death. The American Association of Immunologists. 1999; 162: 7031-40.

Pikman, et al. MPLW515L Is a Novel Somatic Activating Mutation in Myelofibrosis with Myeloid Metaplasia. PLoS Med. 2006;3(7):e270.

Plasilova, et al. TRAIL (Apo2L) suppresses growth of primary human leukemia and myelodysplasia progenitors. Leukemia. 2002;16:67-73.

Poppe, et al. Expression analyses identify MEL as a prominent target of 11q23 amplification and support an etiologic role for MLL gain of function in myeloid malignancies. Blood. 2004;103:229-235.

Pruneri, et al. Angiogenesis in myelodysplastic syndromes. British Journal of Cancer. 1999;81:1398-1401.

Raaijmakers. ATP-binding-cassette transporters in hematopoietic stem cells and their utility as therapeutical targets in acute and chronic myeloid leukemia. Leukemia. 2007;21:2094-2102.

Radoja, et al. CD8+ tumor-infiltrating T cells are deficient in perforin-mediated cytolytic activity due to defective microtubule-organizing center mobilization and lytic granule exocytosis. J Immunol. 2001; 167: 5042-51.

Renneville et al, Cooperating gene mutations in acute myeloid leukemia: a review of the literature. Leukemia. 2008;22:915-31.

Rezaei, et al. Leukemia markers expression of peripheral blood vs bone marrow blasts using flow cytometry. Med Sci Monit. Aug. 2003;9(8):CR359-62.

Rice, et al. HOX deregulation in acute myeloid leukemia. Journal of Clinical Investigation. 2007;117(4):865-868.

Risso, et al. CD69 in resting and activated T lymphocytes. Its association with a GTP binding protein and biochemical requirements for its expression. J Immunol 1991; 146: 4105-14.

Rocheville et al. Subtypes of the somatostatin receptor assemble as functional homo- and heterodimers. J Biol Chem. 2000. 275(11):7862-9.

Rosen, et al. Functional characterization of FLT3 receptor signaling deregulation in acute myeloid leukemia by single cell network profiling (SCNP). PLoS One. Oct. 27, 2010;5(10):e13543.

Sachs, et al. Analysis of signaling pathways in human T-cells using bayesian network modeling of single cell data. Proceedings of the 2004 IEEE computational systems bioinformatics conferences. 2004; p. 644.

Sachs, et al. Bayesian network approach to cell signaling pathway modeling. Sci STKE. Sep. 3, 2002;2002(148):PE38.

Sachs, et al. Causal protein-signaling networks derived from multiparameter single-cell data. Science. Apr. 22, 2005;308(5721):523-9.

Sakatsume, et al. The Jak Kinases Differentially Associate with the α and β (Accessory Factor) Chains of the Interferon γ Receptor to Form a Functional Receptor Unit Capable of Activating STAT Transcription Factors. J. Biol. Chem. 1995;270:17528-17534.

Salomon, et al. LFA-1 interaction with ICAM-1 and ICAM-2 regulates Th2 cytokine production. J Immunol 1998; 161: 5138-42.

Sanderson RJ, Hering MA, James SF, et al. In vivo drug-linker stability of an anti-CD30 dipeptide-linked auristatin immunoconjugate. *Clin Cancer Res.* 2005;11:843-852.

Sawanobori, et al. Expression of TNF receptors and related signaling molecules in the bone marrow from patients with myelodysplastic syndromes. Leukemia Research. 2003;27:583-591.

Schaefer, et al. IGF-I and Prostate Cancer. Science. 1998; 282:199a.

(56) References Cited

OTHER PUBLICATIONS

Scharfe, et al. JAK3 protein tyrosine kinase mediates interleukin-7-induced activation of phosphatidylinositol-3' kinase. Blood. 1995;86:2077-2085.
Scharffetter-Kochanek, et al. Spontaneous skin ulceration and defective T cell function in CD18 null mice. J Exp Med. 1998; 188: 119-31.
Schepers, et al. STAT5 is required for long-term maintenance of normal and leukemic human stem/progenitor cells. Blood. 2007;110(8):2880-2888.
Schittenheim, et al. FLT3 K663Q is a novel AML-associated oncogenic kinase: determination of biochemical properties and sensitivity to sunitnib. Leukemia. 2006;20:2008-14.
Schlessinger, et al. Growth factor signaling by receptor tyrosine kinases. Neuron. Sep. 1992;9(3):383-91.
Schulz. Single-cell phospho-protein analysis by flow cytometry. Curr Protoc Immunol 2007; Chapter 8:Unit 8.17.
Seita, et al. Lnk negatively regulates self-renewal of hematopoietic stem cells by modifying thrombopoietin-mediated signal transduction. Proc Natl Acad Sci U S A. Feb. 13, 2007;104(7):2349-54.
Setsukinai et al. Development of novel fluorescence probes that can reliably detect reactive oxygen species and distinguish specific species. J Biol Chem. 2003. 278(5):3170-5.
Shankar, et al. ABT-869, a multitargeted receptor tyrosine kinase inhibitor: inhibition of FLT3 phosphorylation and signaling in acute myeloid leukemia. Blood. Apr. 15, 2007;109(8):3400-8. Epub Jan. 5, 2007.
Shankar, et al. CREB is amplified in AML blasts and is associated with an increased risk of relapse and decreased event-free survival. Abstract. Blood. 2004; 104(11), Part 1, p. 166A.
Shankar, et al. Role of cyclic AMP response element binding protein in human leukemias. Cancer. Nov. 1, 2005;104(9):1819-24.
Shankar, et al. The role of CREB as a proto-oncogene in hematopoiesis and in acute myeloid leukemia. Cancer Cell. Apr. 2005;7(4):351-62.
Shankaran, et al. IFNgamma and lymphocytes prevent primary tumour development and shape tumour immunogenicity. Nature. Apr. 26, 2001;410(6832):1107-11.
Shaw, R. Ras, PI(3)K and mTOR signaling controls tumor cell growth. Nature. 2006;441:424-430.
Shibuya, et al. Physical and functional association of LFA-1 with DNAM-1 adhesion molecule. Immunity 1999; 11: 615-23.
Shier, et al. Defective CD8+ T cell activation and cytolytic function in the absence of LFA-1 cannot be restored by increased TCR signaling. J Immunol. 1999; 163: 4826-32.
Shulz, et al. Single-Cell Phospho-Protein Analysis by Flow Cytometry. Current Protocols in Immunology. 2007;78:8.17.1-20.
Singh et al. Recent trends in targeted anticancer prodrug and conjugate design. Curr Med Chem. 2008. 15(18):1802-26.
Soede, et al. LFA-1 to LFA-1 signals invole zeta-associated protein-70 (ZAP-70) tyrosine kinase: relevance for invasion and migration of a T cell hybridoma. J Immunol 1999; 163: 4253-61.
Solling, et al. Free light chains of immunoglobulins in serum from patients with leukaemias and multiple myeloma. Scand J Haematol. Apr. 1982;28(4):309-18.
Somersalo, et al. Activation of natural killer cell migration by leukocyte integrin-binding peptide from intracellular adhesion molcule-2 (ICAM-2). J Biol Chem. 1995; 270: 8629-36.
Song, et al. Flow cytometry based biosensor for detection of multivalent proteins. Anal Biochem. 2000; 284: 35-41.
Spiekermann, et al. Overexpression and constitutive activation of FLT3 induces STAT5 activation in primary acute myeloid leukemia blast cells. Clinical Cancer Research. Jun. 2003; 9:2140-2150.
Staquet, et al. Expression of ICAM-3 on human epidermal dendritic cells. Immunobiology. 1995; 192: 249-61.
Starling, et al. Intercellular adhesion molecule-3 is the predominant co-stimulatory ligand for leukocyte function antigen-1 on human blood dendritic cells. Eur J Immunol. 1995; 25: 2528-32.
Steffen, et al. The molecular pathogenesis of acute myeloid leukemia. Critical Reviews in Oncology/Hematology. 2005;56:195-221.
Stelzer, et al. Use of Multiparameter Flow Cytometry and Immunophenotyping for the Diagnosis and Classfication of Acute Myeloid Leukemia. In Immunophenotyping. New York, NY: Wiley-Liss, 2000.
Stephenson, et al. Possible co-existence of RAS activation and monosomy 7 in the leukemic transformation of myelodysplastic syndromes. Leukemia Research. 1995;19:741-8.
Stirewalt, et al. Novel FLT3 point mutations within exon 14 found in patients with acute myeloid leukemia. Br. J. Haematol. 2004;124:481-84.
Sugai, et al. Allelic losses of 17p, 5q, and 18q loci in diploid and aneuploid populations of multiploid colorectal carcinomas. Hum Pathol. 2000; 31: 925-30.
Sugimoto, et al. Mutations of the p53 gene in MDS and MDS-derived leukemia. Blood. 1993;81:3022-6.
Szegedi, et al. A new method to localize acid phosphatase using the confocal laser-scanning microscope. Pathol Oncol Res. 1998;4(3):217-23.
Tanaka, et al. Intercellular adhesion molecule 1 underlies the functional heterogeneity of synovial cells in patients with rheumatoid arthritis: involvement of cell cycle machinery. Arthritis Rheum. 2000; 43(11): 2513-22.
Taylor, et al. Complement-opsonized IgG antibody/dsDNA immune complexes bind to CR1 clusters on isolated human erythrocytes. Clinical Immunology and Immunopathology. 1991; 61: 143-60.
Tefferi. JAK and MPL mutations in myeloid malignancies. Leukemia and Lymphoma. 2008;49(3):388-397.
Thomas, et al. Spontaneous activation and signaling by overexpressed epidermal growth factor receptors in glioblastoma cells. Int J Cancer. 2003; 104(1): 19-27.
Tobal, et al. Mutation of the human FMS gene (M-CSF receptor) in myelodysplastic syndromes and acute myeloid leukemia. Leukemia. 1990;4:486-489.
Tockman, et al. Considerations in bringing a cancer biomarker to clinical application. Cancer Res. May 1, 1992;52(9 Suppl):2711s-2718s.
Touw, et al. Granulocyte colony-stimulating factor: key factor or innocent bystander in the development of secondary myeloid malignancy? J. Natl. Cancer. Inst. 2007;99:183-186.
Trinchieri. Biology of natural killer cells. Adv Immunol. 1989;47:187-376.
Uesugi, et al. Inhibition of ATRA-induced myeloid differentiation in acute promyelocytic leukemia by a new protein tyrosine phosphatase inhibitor, 3,4-dephostatin. J Exp Clin Cancer Res. Sep. 2000;19(3):363-6.
UK office action and search report dated Feb. 22, 2011 for GB Application No. 1017857.2.
UK office action and search report dated Nov. 18, 2011 for GB Application No. 1017857.2.
UK search report Apr. 23, 2012 for GB Application No. 1017857.2.
Ushio-Fukai et al. Reactive oxygen species and angiogenesis: NADPH oxidase as target for cancer therapy. Cancer Lett. 2008. 266(1):37-52.
Valli, M, et al., Intracellular pH Distribution in *Saccharomyces cerevisiae* Cell Populations, Analyzed by Flow Cytometry, Applied and Environmental Microbiology, Mar. 2005, p. 1515-1521, vol. 71, No. 3.
Van Meter, et al. K-RasG12D expression induces hyperproliferation and aberrant signaling in primary hematopoietic stem/progenitor cells. Blood. May 1, 2007;109(9):3945-52.
Vivanco, I. The Phosphatidylinositol 3-Kinase-AKT Pathway in Human Cancer. Nature Reviews: Cancer. 2002;2:489-501.
Walter, et al. Tyrosine phosphorylation enhances ITIM-dependent internalization of CD33, the target for the anti-AML imunnoconjugate, gentuzumab ozogamicin. Part 1 2006. 108(11):Abstract 729A.
Walter, r. et al. ITIM-dependant endocytosis of CD33-related Siglecs: role of intracellular domain, tyrosine phosphorylation, and the tyrosine phosphatases, Shp1 and Shp, Journal. Leuk. Bio., 83:Jan. 2008, p. 200-211.
Walter, R., et al., Influence of CD33 expression levels and ITIM-dependent internalization on gemtuzumab ozogamicin-induced cytotoxicity, Blood 2005: 105: 1295-1302.

(56) References Cited

OTHER PUBLICATIONS

Walter, R., et al., Phosphorylated ITIMs enable ubiquitylation of an inhibitory cell surface receptor, Traffice 2008:9: 267-279.
Wang, et al. Decreased production of reactive oxygen intermediates is an early event during in vitro apoptosis of rat thymocytes. Free Radic Biol Med. 1996;20:533-42.
Wang, et al. The TEL/ETV6 gene is required specifically for hematopoiesis in the bone marrow. Genes and Development. 1998;12:2392-402.
Watanabe, et al. Poly(ADP-ribose) polymerase-1 inhibits ATM kinase activity in DNA damage response. Biochem Biophys Res Commun. Jun. 25, 2004;319(2):596-602.
Weber, et al. Cytohesin-1 is a dynamic regulator of distinct LFA-1 functions in leukocyte arrest and transmigration triggered by chemokines. Curr Biol. 2001; 11: 1969-74.
Weider, ED, et al., Measurement of intracellular pH using flow cytometry with carboxy-SNARF-1. Cytometry,Nov. 1993;14(8):916-21.
Whang, et al. Inactivation of the tumor suppressor PTEN/MMAC1 in advanced human prostate cancer through loss of expression. Proc Natl Acad Sci USA. 1998; 95(9): 5246-50.
Woolf, et al. Bayesian analysis of signaling networks governing embryonic stem cell fate decisions. Bioinformatics. Mar. 2005;21(6):741-53.
Yamamoto, et al. Activating mutation of D835 within the activation loop of FLT3 in human hematologic malignancies. Blood. 2001;97:2434-39.
Yang KD, Shaio MF. Hydroxyl radicals as an early signal involved in phorbol ester-induced monocyte differentiation of HL60 cells. Biochem Biophys Res Commun. 1994;200:1650-7.
Yu, et al. IL-2 activation of NK cells: involvement of MKK1/2/ERK but not p38 kinase pathway. J Immunol. 2000; 164: 6244-51.
Yunis, et al. Mechanisms of ras mutation in myelodysplastic syndrome. Oncogene. 1989;4:609-614.
Zhao, et al. Interferon-α-induced Expression of Phospholipid Scramblase 1 through STAT1 Requires the Sequential Activation of Protein Kinase Cδ and JNK. J. Biol. Chem. 2005;280:42707-42714.
Zheng, et al. Regulation of STAT3 and STAT5 in the differentiation of FLT3/ITD expressing 32Dcl3 cells induced by G-CSF and CEP-701. Abstract 2935.Blood. 2002; 100(11) and 44th Annual Meeting of the American Society of Hematology. Philadelphia, PA, USA. Dec. 6-10, 2002.
Zhou, et al. The ABC transporter Bcrp1/ABCG2 is expressed in a wide variety of stem cells and is a molecular determinant of the side-population phenotype. Nature Medicine. 2001;7:1028-1034.
Zupo, et al. CD38 expression distinguishes two groups of B-cell chronic lymphocytic leukemias with different responses to anti-IgM antibodies and propensity to apoptosis. Blood. Aug. 15, 1996;88(4):1365-74.
Zwaan, et al. FLT3 internal tandem duplication in 234 children with acute myeloid leukemia (AML): prognostic significance and relation to cellular drug resistance. Blood. 2003;102:2387-94.
Holleman, et al. Decreased PARP and procaspase-2 protein levels are associated with cellular drug resistance in childhood acute lymphoblastic leukemia. Blood. Sep. 1, 2005;106(5):1817-23. Epub May 17, 2005.
McCubrey, et al. Roles of the Raf/MEK/ERK pathway in cell growth, malignant transformation and drug resistance. Biochim Biophys Acta. Aug. 2007;1773(8):1263-84. Epub Oct. 7, 2006.
U.S. Appl. No. 61/120,320, filed Dec. 5, 2008, Fantl et al.
U.S. Appl. No. 61/181,211, filed May 26, 2009, Covey et al.
U.S. Appl. No. 13/750,700, filed Jan. 25, 2013, Longo.
U.S. Appl. No. 13/801,420, filed Mar. 13, 2013, Cesano et al.
U.S. Appl. No. 13/821,539, filed Mar. 7, 2013, Longo.
U.S. Appl. No. 13/900,170, filed May 22, 2013, Fantl.
U.S. Appl. No. 13/913,029, filed Jun. 7, 2013, Fantl et al.
Chanoux, et al. ATR and H2AX cooperate in maintaining genome stability under replication stress. J Biol Chem. Feb. 27, 2009;284(9):5994-6003. Epub Dec. 2, 2008.
Chim et al. SOCS1 and SHP1 hypermethylation in mantle cell lymphoma and follicular lymphoma: implications for epigenetic activation of the Jak/STAT pathway. Leukemia. 2004. 18(2): 356-8.
Cimmino et al. miR-15 and miR-16 induce apoptosis by targeting BCL2. Proc Natl Acad Sci U S A. 2005. 102(39):13944-9. Epub Sep. 15, 2005. Erratum in: Proc Natl Acad Sci U S A. 2006. 103(7):2464.
Danial et al., Cell Death: Critical Control Points, Cell. 2004. 116(2):205-219.
Dmitrieva, et al. Rapid activation of G2/M checkpoint after hypertonic stress in renal inner medullary epithelial (IME) cells is protective and requires p38 kinase. Proc Natl Acad Sci U S A. Jan. 8, 2002;99(1):184-9. Epub Dec. 26, 2001.
Esquela-Kerscher et al. Oncomirs—microRNAs with a role in cancer. Nat Rev Cancer. 2006. 6(4):259-69.
European office action dated Apr. 11, 2013 for Application No. 9790295.1.
Garzon et al. MicroRNAs in normal and malignant hematopoiesis, Current Opinion Hematology. 2008. 15:352-8.
Giancotti et al. Integrin signaling. Science. 1999. 285(5430):1028-32.
Griffiths et al. DNA Methyltransferase and Histone Deacetylase Inhibitors in the Treatment of Myelodysplastic Syndromes, Semin Hematol. 2008. 45(1) pp. 23-30.
Hanks, et al. The protein kinase family: conserved features and deduced phylogeny of the catalytic domains. Science. 1988. 241(4861):42-52.
Hopfer et al. Aberrant promotor methylation in MDS hematopoietic cells during in vitro lineage specific differentiation is differently associated with DNMT isoforms. Leuk Res. 2009. 33(3):434-42.
Huang, et al. Histone H2AX phosphorylation induced by selective photolysis of BrdU-labeled DNA with UV light: relation to cell cycle phase. Cytometry A. Nov. 2004;62(1):1-7.
Huang, et al. Sequential phosphorylation of Ser-10 on histone H3 and ser-139 on histone H2AX and ATM activation during premature chromosome condensation: relationship to cell-cycle phase and apoptosis. Cytometry A. Apr. 2006;69(4):222-9.
International search report and written opinion dated Mar. 12, 2012 for PCT Application No. US11/48332.
International search report and written opinion dated Jun. 20, 2012 for PCT/US2011/065675.
Itzykson et al., Meeting report: myelodysplastic syndromes at ASH 2007. Leukemia. 2008. 22(5): 893-7.
Jones et al., Core Signaling Pathways in Human Pancreatic Cancers Revealed by Global Genomic Analyses. Science. 2008. 321(5897):1801-1806.
Kolonics, et al. Unregulated activation of STAT-5, ERK1/2 and c-Fos may contribute to the phenotypic transformation from myelodysplastic syndrome to acute leukemia. Haematologia. 2001; 31(2):125-138.
Krutzik et al. Coordinate analysis of murine immune cell surface markers and intracellular phosphoproteins by flow cytometry, J. Immunol. 2005. 175(4): 2357-65.
Krutzik et al. High content single cell drug screening with phosphospecific flow cytometry. Nat. Chem. Biol. 2008. 4(2):132-42.
Krutzik et al. Intracellular phospho-protein staining techniques for flow cytometry: monitoring single cell signaling events, Cytometry A. 2003. 55(2): 61-70.
Krutzik et al., Characterization of the murine immunological signaling network with phosphospecific flow cytometry, J Immunol., Aug. 15, 2005, 175(4): 2366-73.
Länger et al. Up-regulation of DNA methyltransferases DNMT1, 3A, and 3B in myelodysplastic syndrome. Leuk Res. 2005. 29(3):325-9.
Marcos Malumbes & Mariano Barbacid, Cell Cycle, CDKs, and Cancer: A Changing Paradigm, 9 Nature Rev. Cancer 153 (2009).
Marcucci, et al. Prognostic significance of, and gene and microRNA expression signatures associated with, CEBPA mutations in cytogenetically normal acute myeloid leukemia with high-risk molecular features: a Cancer and Leukemia Group B Study. J Clin Oncol. 2008. 26(31):5078-87.
Mirnezami et al. Transhiatal oesophagectomy: treatment of choice for high-grade dysplasia. Eur J Cardiothorac Surg. 2009. 36(2):364-7.

(56) References Cited

OTHER PUBLICATIONS

Notice of Allowance dated May 13, 2012 for U.S. Appl. No. 12/460,029.
Notice of Allowance dated Jul. 9, 2012 for U.S. Appl. No. 13/083,156.
Notice of Allowance dated Dec. 18, 2012 for U.S. Appl. No. 12/910,769.
Office action dated Feb. 5, 2013 for U.S. Appl. No. 12/713,165.
Office action dated Apr. 5, 2011 for U.S. Appl. No. 12/460,029.
Office action dated Apr. 13, 2012 for U.S. Appl. No. 12/581,536.
Office action dated May 22, 2012 for U.S. Appl. No. 12/910,769.
Office action dated Jun. 4, 2012 for U.S. Appl. No. 13/083,156.
Office action dated Nov. 15, 2011 for U.S. Appl. No. 12/581,536.
Schwartz et al. Targeting the Cell Cycle: A New Approach to Cancer Therapy, 23 J. Clinical Oncol. 9408 (2005).
Tanner et al., Spectrochimica Acta Part B: Atomic Spectroscopy, Mar. 2007;62(3):188-195.
Tsvetkov et al. Phosphorylation of Plk1 at S137 and T210 is inhibited in response to DNA damage. Cell Cycle. 2005. 4(1):166-71.
Wood et al. The Genomic Landscapes of Human Breast and Colorectal Cancers. Science. 2007. 318:1108-1113.
Yarden et al. Growth factor receptor tyrosine kinases. Annu Rev Biochem. 1988. 57:443-78.
U.S. Appl. No. 13/566,991, filed Aug. 3, 2012, Rosen et al.
U.S. Appl. No. 13/596,579, filed Aug. 28, 2012, Fantl et al.
European office action dated Apr. 23, 2012 for Application No. 9790295.1.
U.S. Appl. No. 13/958,285, filed Aug. 2, 2013, Fantl et al.
U.S. Appl. No. 14/011,715, filed Aug. 27, 2013, Ptacek et al.
U.S. Appl. No. 14/013,567, filed Aug. 29, 2013, Purvis, Jr.
U.S. Appl. No. 14/014,110, filed Aug. 29, 2013, Moser et al.
U.S. Appl. No. 14/036,216, filed Sep. 25, 2013, Fantl et al.
Banath, et al. Expression of phosphorylated histone H2AX as a surrogate of cell killing by drugs that create DNA double-strand breaks. Cancer Res. Aug. 1, 2003;63(15):4347-50.
Damle, et al. Antibody-targeted chemotherapy with immunoconjugates of calicheamicin. Curr Opin Pharmacol. Aug. 2003;3(4):386-90.
Office action dated Oct. 7, 2013 for U.S. Appl. No. 12/581,536.
Office action dated Apr. 14, 2014 for U.S. Appl. No. 12/581,536.

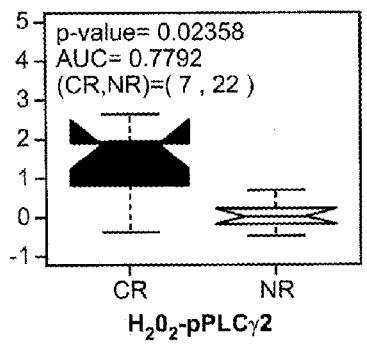
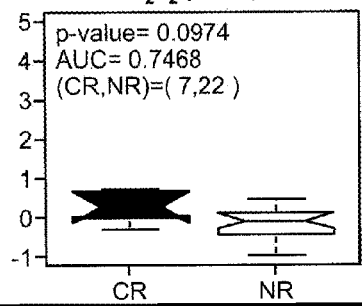
Fig. 4a
$H_2O_2$-pPLCγ2
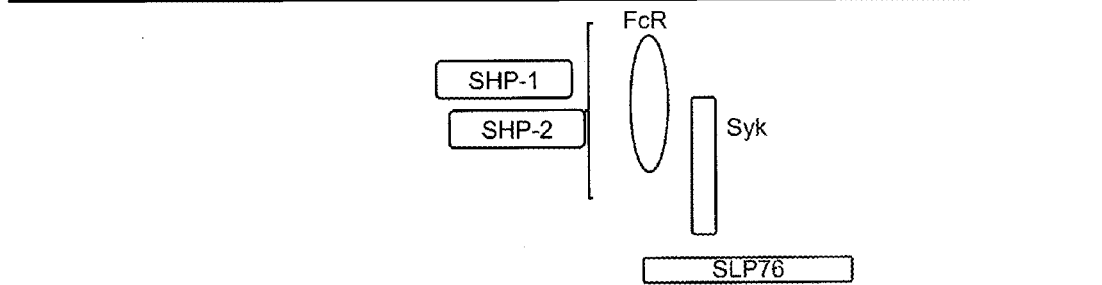
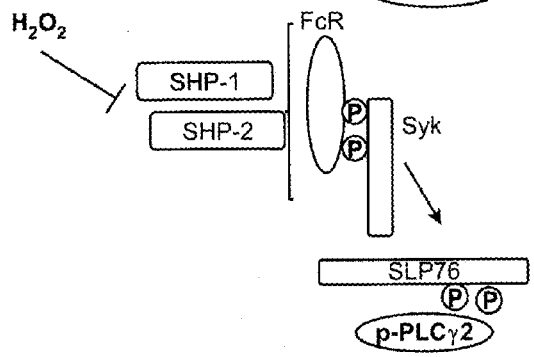
Fig. 4b

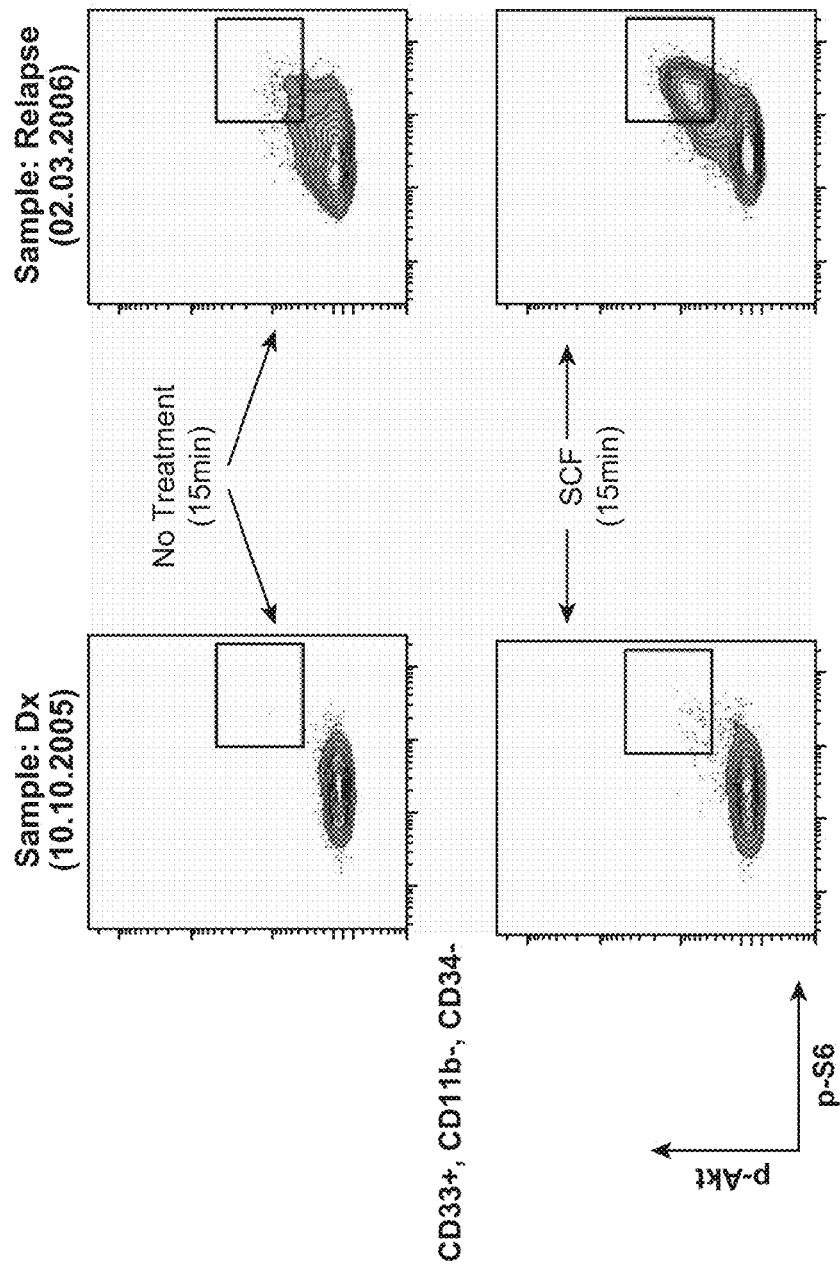

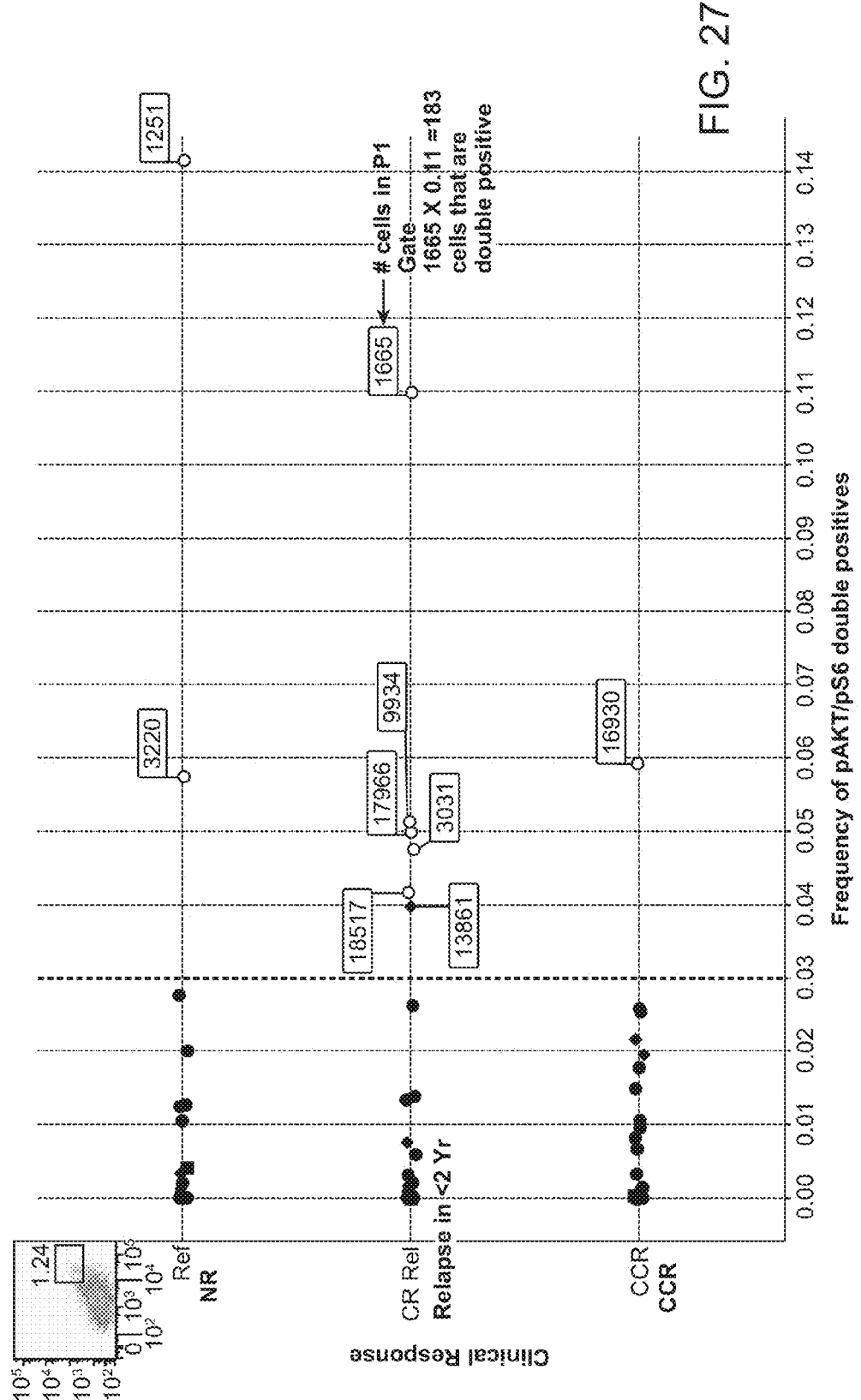

| Donor | UHN_0216 | UHN_0713 | UHN_8825 | UHN_5688 | UHN_8362 | UHN_8100 | UHN_29C1A | UHN_5717 | UHN_5684 | UHN_8451 | UHN_8303 | UHN_8402 | UHN_8001 |
|---|---|---|---|---|---|---|---|---|---|---|---|---|---|
| | | | | | | Apoptosis Competent | | | | | | | |
| Stauro.Apoptosis | 58.25 | 45.35 | 64 | 42.15 | 44.5 | 58.3 | 51.65 | 70.75 | 71.5 | 61.85 | 57.85 | 64.8 | 63.25 |
| Stauro.cPARP | 57.15 | 38.225 | 62.635 | 60.61 | 48.47 | 70.14 | 57.855 | 71.855 | 74.885 | 67.615 | 60.53 | 66.675 | 79.09 |
| Stauro.cCasp-3 | 60.61 | 37.43 | 62.6 | 69.68 | 42.21 | 71.8 | 56.55 | 74.3 | 75.61 | 67.08 | 59.5 | 66.14 | 78.11 |
| Stauro.cCasp-8 | 57.64 | 41.61 | 63.33 | 66.42 | 54.67 | 72.42 | 57.77 | 74.59 | 73.76 | 67.54 | 59.7 | 66.17 | 80.05 |
| Stauro.Zvad.Apoptosis | 11.05 | 20.3 | 30.75 | 23.95 | 27.95 | 49.6 | 47.25 | 66.4 | 67.35 | 59.4 | 57.65 | 64.7 | 53 |
| Stauro.Zvad.cPARP | 6.695 | 18.925 | 32.32 | 26.37 | 28.47 | 64.84 | 63.15 | 65.13 | 73.56 | 64.825 | 61.515 | 66.51 | 79.305 |
| Stauro.Zvad.cCasp-3 | 3.49 | 16.21 | 17.31 | 8.99 | 17.61 | 34.44 | 5.31 | 30.65 | 29.84 | 27.76 | 52.3 | 60.25 | 69.91 |
| Stauro.Zvad.cCasp-8 | 4.3 | 18.6 | 16.92 | 17.09 | 29.18 | 52.18 | 21.19 | 24.04 | 37.67 | 39.1 | 38.15 | 61.68 | 77.67 |
| Caspase-Independent Apoptosis | | | | | + | + | + | + | + | + | + | + | + |
| Etopo.Apoptosis | 31.45 | 26.45 | 45.75 | 32.5 | 46 | 24 | 27.3 | 31.6 | 49.7 | 40.5 | 46 | 58.5 | 28.4 |
| Etopo.cPARP | 23.195 | 20.81 | 51.8 | 41.43 | 50.39 | 30.66 | 35.3 | 20.07 | 55.675 | 47.87 | 47.955 | 52.365 | 38.445 |
| Etopo.cCasp-3 | 25.15 | 17.44 | 68.91 | 57.62 | 59.6 | 36.35 | 38.44 | 33.85 | 60.69 | 47.23 | 56.35 | 60.87 | 47.66 |
| p.CHK2 Upregulation | 2.32 | 1.81 | 0.43 | 1.08 | 2.55 | 1.32 | 1.06 | 1.75 | 1.48 | 2.07 | 2.66 | 2.07 | 1.35 |
| Etopo.Apoptosis Response | + | + | ++ | + | ++ | + | + | + | ++ | ++ | ++ | ++ | + |
| Etopo.DNA Damage Response | ++ | ++ | + | + | ++ | + | + | ++ | + | ++ | ++ | ++ | + |
| FLT3-ITD | NR | NR | ITD | NR | NR | NR | NR | NR | NR | NR | ITD | NR | ITD |
| | N.D. | ITD | ITD | WT | ITD | N.D. | ITD | ITD | ITD | ITD | ITD | N.D. | N.D. |

FIG. 28B

| | Etopo Resistant | | | | | | | | Stauro Resistant | | | | |
|---|---|---|---|---|---|---|---|---|---|---|---|---|---|
| | UHN_0521 | UHN_0577 | UHN_0401 | UHN_5643 | UHN_8093 | UHN_8665 | UHN_8165 | UHN_8789 | UHN_0341 | UHN_4353 | UHN_8190 | UHN_8314 | UHN_9172 |
| | 55.5 | 63.45 | 60.85 | 65.5 | 37.85 | 41.8 | 39 | 69.95 | 33.9 | 26.7 | 24.8 | 28.6 | 27.45 |
| | 35.48 | 72.765 | 59.51 | 55.925 | 30.79 | 40.4 | 26.82 | 73.5 | 27.05 | 27.525 | 27.875 | 20.545 | 28.275 |
| | 27.09 | 64.27 | 56.36 | 65.77 | 47.74 | 46.61 | 70.87 | 75.71 | 27.11 | 31.86 | 27.06 | 19.27 | 29.6 |
| | 31.31 | 42.85 | 55.1 | 63.4 | 42.8 | 57.53 | 69.86 | 70.77 | 35.05 | 31.58 | 26.81 | 20.91 | 28.56 |
| | 24 | 36.75 | 39.8 | 41.85 | 24.95 | 30.05 | 41.1 | 75.3 | 12.8 | 9.95 | 9.9 | 18.8 | 17.85 |
| | -8.465 | 8.755 | 37.495 | 32.765 | 18.81 | 28.075 | 14.98 | 80.735 | 4.905 | 6.535 | 13.065 | 15.78 | 20.03 |
| | -19.49 | -0.13 | 24.19 | -5.03 | 3.14 | -2.36 | -11.22 | 58.23 | 1.35 | -2.75 | 1.13 | -2.29 | 12.79 |
| | -26.43 | -4.35 | 20.07 | -6.82 | 13.52 | 8.8 | -21.03 | 60.95 | 0.78 | -0.18 | 5.86 | -0.83 | 5.74 |
| | 11.6 | 6.7 | 13.75 | 12.65 | 13.1 | 21.55 | 8.25 | 10 | 13.45 | 29.5 | 9.35 | 7.05 | 30.8 |
| | 9.8 | 6.99 | 6.335 | 7.28 | 6.98 | 21.53 | 1.065 | 5.62 | 5.745 | 23.75 | 8.095 | 4.17 | 30.695 |
| | 10.83 | 6.71 | 6.32 | 15.71 | 3.51 | 18.82 | 1.6 | 11.45 | 8.9 | 32.48 | 13.3 | 4.32 | 31.25 |
| | 1.31 | 1.6 | 1.5 | 1.29 | 1.46 | 1.52 | 1.37 | 1.64 | 1.34 | 1.26 | 1.52 | 1.07 | 1.04 |
| | - | - | - | - | - | - | - | - | - | + | - | - | + |
| | + | ++ | ++ | + | + | ++ | + | ++ | + | + | ++ | - | +/- |
| | NR | NR | NR | NR | NR | NR | NR | NR | NR | NR | NR | NR | NR |
| | WT | WT | WT | WT | ITD | ITD | WT | N.D. | WT | WT | WT | WT | N.D. |

FIG. 28B (Cont.)

| Donor | Apoptosis Competent | | | G-CSF_Stat3_Fold | G-CSF_Stat5_Fold | FLT3-ITD | Resp |
|---|---|---|---|---|---|---|---|
| | IL-27_Stat3_Total | IL-27_Stat1_Total | IL-6_Stat3_Total | | | | |
| UHN_0713 | 0.88 | 0.27 | 1.01 | -0.16 | -0.46 | ITD | CR |
| UHN_0216 | 1.01 | 0.30 | 0.42 | 2.19 | 1.40 | N.D. | NR |
| UHN_8303 | 1.03 | 0.26 | 0.85 | CR | 0.41 | ITD | CR |
| UHN_8825 | | 0.78 | | 0.99 | 0.40 | ITD | CR |
| UHN_8402 | 1.35 | 0.30 | | 0.57 | -0.02 | N.D. | NR |
| UHN_8362 | 1.41 | 0.81 | 1.19 | 0.61 | 0.31 | ITD | CR |
| UHN_29C1A | 1.45 | 0.67 | 1.61 | 1.02 | 0.44 | ITD | NR |
| UHN_8451 | 1.47 | 0.54 | 2.02 | 0.94 | 0.34 | ITD | NR |
| UHN_8001 | 1.52 | 0.56 | 1.11 | 2.53 | 1.61 | N.D. | CR |
| UHN_5688 | 1.56 | 0.76 | 1.63 | | 1.13 | | NR |
| UHN_8100 | 1.72 | 0.76 | 2.28 | 2.19 | 1.50 | N.D. | NR |
| UHN_5684 | 1.77 | 0.71 | 1.55 | 2.75 | 2.24 | ITD | NR |
| UHN_5717 | 2.24 | 0.91 | 1.42 | 1.48 | 0.51 | ITD | NR |

| Donor | UHN_8100 | UHN_5684 | UHN_8451 | UHN_8303 | UHN_5717 | UHN_0216 | UHN_8362 | UHN_0713 | UHN_5688 | UHN_29C1A | UHN_8825 | UHN_8402 | UHN_8001 |
|---|---|---|---|---|---|---|---|---|---|---|---|---|---|
| | | | | | Apoptosis Competent | | | | | | | | |
| p.Akt.FLT3L.Total | -0.470 | -0.186 | 0.088 | 0.288 | 0.405 | 0.511 | 0.752 | 0.903 | 0.935 | 0.964 | 1.141 | 1.174 | 1.212 |
| p.Akt.SCF.Total | -0.060 | 0.004 | 0.305 | 1.176 | 1.034 | | 0.804 | 0.635 | 0.574 | | 0.890 | 0.583 | 0.719 |
| p.Akt.SDF.1a.Total | -0.198 | 0.057 | 0.741 | 0.414 | | -0.316 | 1.281 | 0.540 | 0.834 | 1.291 | 0.898 | 0.978 | 0.969 |
| p.S6.FLT3L.Total | 0.195 | 0.191 | 0.017 | -0.133 | 0.157 | 0.318 | 0.750 | 0.142 | 0.467 | 0.455 | 0.925 | 0.103 | |
| p.S6.SCF.Total | 0.389 | 0.299 | 0.106 | 0.656 | 0.469 | 0.947 | 0.616 | -0.157 | 0.166 | 1.161 | 0.636 | -0.067 | 0.432 |
| p.S6.PMA.Total | 1.491 | | 0.959 | .963 | 2.784 | 1.325 | 1.640 | 2.797 | 0.935 | | 1.280 | 0.750 | |
| p.S6.G_CSF.Fold | 0.036 | 0.149 | -0.007 | 0.059 | 0.017 | 0.045 | -0.004 | -0.034 | 0.087 | 0.007 | 0.059 | 0.024 | 0.154 |
| p.S6.GM_CSF.Fold | 0.038 | 0.017 | -0.010 | | 0.162 | 0.029 | 0.021 | 0.003 | 0.197 | 0.083 | -0.057 | 0.045 | 0.094 |
| Resp | NR | NR | NR | | NR | NR | | | NR | NR | | NR | |
| FLT3_ITD | N.D. | ITD | ITD | ITD | ITD | N.D. | ITD | ITD | | ITD | ITD | N.D. | N.D. |

METHODS FOR DIAGNOSIS, PROGNOSIS AND METHODS OF TREATMENT

CROSS-REFERENCE

This application is a Divisional application which claims the benefit of U.S. application Ser. No. 12/460,029, filed Jul. 10, 2009; which claims the benefit of the filing date of U.S. Ser. No. 61/079,766 filed Jul. 10, 2008, U.S. Ser. No. 61/085,789 filed Aug. 1, 2008, U.S. Ser. No. 61/104,666 filed Oct. 10, 2008 and U.S. Ser. No. 61/120,320 filed Dec. 5, 2008; and each of these provisional applications are hereby expressly incorporated by reference in their entirety.

BACKGROUND OF THE INVENTION

Many conditions are characterized by disruptions in cellular pathways that lead, for example, to aberrant control of cellular processes, with uncontrolled growth and increased cell survival. These disruptions are often caused by changes in the activity of molecules participating in cellular pathways. For example, alterations in specific signaling pathways have been described for many cancers. Despite the increasing evidence that disruption in cellular pathways mediate the detrimental transformation, the precise molecular events underlying these transformations in diseases remain unclear. As a result, therapeutics may not be effective in treating conditions involving cellular pathways that are not well understood. Thus, the successful diagnosis of a condition and use of therapies will require knowledge of the cellular events that are responsible for the condition pathology.

Acute myeloid leukemia (AML), myelodysplastic syndrome (MDS), and myeloproliferative neoplasms (MPN) are examples of disorders that arise from defects of hematopoietic cells of myeloid origin. These hematopoietic disorders are recognized as clonal diseases, which are initiated by somatic and/or inherited mutations that cause dysregulated signaling in a progenitor cell. The wide range of possible mutations and accompanying signaling defects accounts for the diversity of disease phenotypes and response to therapy observed within this group of disorders. For example, some leukemia patients respond well to treatment and survive for prolonged periods, while others die rapidly despite aggressive treatment. Some patients with myelodysplastic syndrome suffer only from anemia while others transform to an acute myeloid leukemia that is difficult to treat. Despite the emergence of new therapies to treat these disorders the percentage of patients who do not benefit from current treatment is still high. Patients that are resistant to therapy experience significant toxicity and have very short survival times. While various staging systems have been developed to address this clinical heterogeneity, they cannot accurately predict at diagnosis the prognosis or predict response to a given therapy or the clinical course that a given patient will follow.

Despite this heterogeneity, it is recognized that these disorders share both biologic and clinical commonalities. The first commonality is the cell type affected by the disorders i.e. myeloid cell lineage. Second, all three disorders share cytogenetic abnormalities and have been shown to have defects in transcription factors common in myeloid cell development. Third, many of the same signaling pathways, including the RAS, JAK-STAT, and AKT, have been shown to be important for AML, MDS and MPN pathogenesis Although MDS and most MPNs are clinical chronic diseases while AML is an acute disease, all three have effects on cellular proliferation and apoptosis of myeloid progenitors and clinically approximately 30% of MDS and 5-10% of MPNs transform into AML.

Accordingly, there is a need for a biologically based clinically relevant re-classification of these disorders that can inform on disease management at the individual level. This classification, based upon the biologic commonalities of the disorders above, will aid clinicians in both prognosis and therapeutic selection at the individual patient level thus improving patient outcomes e.g. survival and quality of life.

There are also needs for a biologically based clinically relevant re-classification of these disorders to aid in new druggable target identification and drug screening for agents that may be active against myeloid malignancies.

SUMMARY OF THE INVENTION

In some embodiments, the invention provides methods of diagnosing, prognosing, or determining progression of acute leukemia, myelodysplastic syndrome or myeloproliferative neoplasms in an individual, the method comprising: A] classifying one or more hematopoietic cells associated with acute leukemia, myelodysplastic syndrome or myeloproliferative neoplasms in the individual by a method comprising: a) subjecting a cell population comprising the one or more hematopoietic cells from the individual to a plurality of modulators in plurality of cultures, b) characterizing a plurality of pathways in one or more cells from the plurality of cultures by determining an activation level of at least one activatable element within a plurality of pathways, where i) at least one of the pathways being characterized in at least one of the plurality of cultures is an apoptosis or a DNA damage pathway, ii) the modulators activate or inhibit one or more of the plurality of pathways being characterized, and c) classifying one or more hematopoietic cells based on the pathways characterization; and B] making a decision regarding diagnosis, prognosis or progression of acute leukemia, myelodysplastic syndrome or myeloproliferative neoplasms in the individual, where the decision is based on the classification of the cells. In some embodiments, the acute leukemia is acute myeloid leukemia. In some embodiments, the pathways are selected from the group consisting of apoptosis, cell cycle, signaling, or DNA damage pathways. In some embodiments, the methods further comprise determining whether the apoptosis, cell cycle, signaling, or DNA damage pathways are functional in the individual based on the activation levels of the activatable elements, wherein a pathway is functional if it is permissive for a response to the treatment, wherein if the apoptosis, cell cycle, signaling, and DNA damage pathways are functional the individual can respond to treatment, and wherein if at least one of the pathways is not functional the individual can not respond to treatment. In some embodiments, the methods further comprise determining whether the apoptosis, cell cycle, signaling, or DNA damage pathways are functional in the individual based on the activation levels of the activatable elements, wherein a pathway is functional if it is permissive for a response to the treatment, where if the apoptosis and DNA damage pathways are functional the individual can respond to treatment.

In some embodiments, the individual has a predefined clinical parameter. In some embodiments, the predefined clinical parameter is selected from the group consisting of age, de novo acute myeloid leukemia patient, secondary acute myeloid leukemia patient, or a biochemical/molecular marker. In some embodiments, a decision is made regarding diagnosis, prognosis or progression of acute leukemia, myelodysplastic syndrome or myeloproliferative neoplasms in the individual based on the classification of the cells in combination with the predefined clinical parameter.

In some embodiments, the methods of the invention further comprise determining the levels of a cytokine receptor, growth factor receptor and/or a drug transporter in one or more hematopoetic cells. In some embodiments, the cytokine receptor, growth factor receptor or drug transporters are selected from the group consisting of MDR1, ABCG2, MRP, P-Glycoprotein, CXCR4, FLT3, and c-kit. In some embodiments, the levels of the cytokine receptor and/or the drug transporter in combination with the cell classification and the clinical parameter are indicative of the diagnosis, prognosis or progression of acute myeloid leukemia, myelodysplastic syndrome or myeloproliferative neoplasms.

In some embodiments, the modulators are independently selected from the group consisting of growth factor, mitogen, cytokine, chemokine, adhesion molecule modulator, hormone, small molecule, polynucleotide, antibody, natural compound, lactone, chemotherapeutic agent, immune modulator, carbohydrate, protease, ion, reactive oxygen species, and radiation. In some embodiments, the modulators are independently selected from the group consisting of FLT3L, GM-CSF, SCF, G-CSF, SDF1a, LPS, PMA, Thapsigargin, IFNg, IFNa, IL-27, IL-3, IL-6, IL-10, ZVAD, H2O2, Staurosporine, Etoposide, Mylotarg, Daunorubicin, and AraC.

In some embodiments, the activatable element is a protein selected from the group consisting of p-Slp-76, p-Plcg2, p-Stat3, p-Stat5, p-Stat1, p-Stat6, p-Creb, cleaved Parp, p-Chk2, p65/Rel-A, p-Akt, p-S6, p-ERK, Cleaved Caspase 8, Cleaved Caspase 3, Cytoplasmic Cytochrome C, and p38.

In some embodiments, the methods further comprise determining the presence or absence of one or more cell surface markers, intracellular markers, or combination thereof. In some embodiments, the cell surface markers and the intracellular markers are independently selected from the group consisting of proteins, carbohydrates, lipids, nucleic acids and metabolites. In some embodiments, the presence or absence of one or more cell surface markers or intracellular markers comprises determining the presence or absence of an epitope in both activated and non-activated forms of the cell surface markers or the intracellular markers. In some embodiments, the diagnosing, prognosing or determining progression of acute leukemia, myelodysplastic syndrome or myeloproliferative neoplasms in the individual is based on both the activation levels of the activatable element and the presence or absence of the one or more cell surface markers, intracellular markers, or combination thereof.

In some embodiments, the activation level is determined by a process comprising the binding of a binding element which is specific to a particular activation state of the particular activatable element. In some embodiments, the binding element comprises an antibody.

In some embodiments, the methods further comprise predicting a response to a treatment or choosing a treatment for acute myeloid leukemia, myelodysplastic syndrome or myeloproliferative neoplasms in an individual. In some embodiments, the treatment is a chemotherapy agent. In some embodiments, the chemotherapy agent is selected from the group consisting of cytarabine (ara-C), daunorubicin, idarubicin, etoposide, mitoxantrone and 6-thioguanine. In some embodiments, the treatment is allogeneic stem cell transplant or autologous stem cell transplant.

In some embodiments, where the individual is under 60 years old the plurality of distinct modulators and activatable elements are selected from the modulators and activatable elements listed in table 6. In some embodiments, where the individual is over 60 years old the plurality of distinct modulators and activatable elements are selected from the modulators and activatable elements listed in table 7. In some embodiments, where the individual is a secondary acute myeloid leukemia patient the plurality of distinct modulators and activatable elements are selected from the modulators and activatable elements listed in table 8 and table 9. In some embodiments, where the individual is a de novo acute myeloid leukemia patient the plurality of distinct modulators and the activatable elements are selected from the modulators and activatable elements listed in table 10 and table 11. In some embodiments, where the individual has a wild type FLT3 the plurality of modulators and activatable elements are selected from the modulators and activatable elements listed in table 13.

In some embodiments, the invention provides methods of predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to at least three distinct modulators in separate cultures, wherein: i) a first modulator is a growth factor or a mitogen, ii) a second modulator is a cytokine, iii) a third modulator is a modulator that slows or stops the growth of cells, and/or induces apoptosis of cells, and/or is an inhibitor of a cellular function, b) determining an activation level of at least one activatable element in one or more cells from each of the separate cultures, wherein: i) a first activatable element is an activatable element within the PI3K/AKT, or MAPK pathways and the activation level is measured in response to the growth factor or mitogen, ii) a second activatable element is an activatable element within the STAT pathway and the activation level is measured in response to the cytokine, iii) a third activatable element is an activatable element within an apoptosis pathway and the activation level is measured in response to the modulator that slows or stops the growth of cells and/or induces apoptosis of cells, or the third activatable element is an activatable element within a phospholipase C pathway and the activation level is measured in response to the inhibitor, or the third activatable element is a phosphatase and the activation level is measured in response to the inhibitor, and c) classifying the one or more hematopoeitic cells based on the activation levels of the activatable elements; and (2) making a decision regarding a response to a treatment or a selection of treatment for acute leukemia, myelodysplastic syndrome or myeloproliferative neoplasms in the individual based on the classification of the one or more hematopoeitic cells. In some embodiments, the acute leukemia is acute myeloid leukemia. In some embodiments, the individual has a predefined clinical parameter. In some embodiments, the predefined clinical parameter is selected from the group consisting of age, de novo acute myeloid leukemia patient, secondary acute myeloid leukemia patient, or a biochemical/molecular marker.

In some embodiments, activation levels higher than a threshold level of the activatable element within the STAT pathway in response to the cytokine is indicative that individual can not respond to treatment. In some embodiments, the activatable element within the STAT pathway is selected from the group consisting of p-Stat3, p-Stat5, p-Stat1, and p-Stat6 and the cytokine is selected from the group consisting of IFNg, IFNa, IL-27, IL-3, IL-6, IL-10, and G-CSF. In some embodiments, the activatable element within the STAT pathway is Stat1 and the cytokine is IL-27 or G-CSF.

In some embodiments, activation levels higher than a threshold level of the activatable element within the PI3K/AKT, or MAPK pathway in response to the growth factor or mitogen is indicative that individual can not respond to treatment. In some embodiments, the activatable element within the PI3K/AKT, or MAPK pathway is selected from the group consisting of p-Akt, p-ERK, p38 and pS6 and the growth factor or mitogen is selected from the group consisting of FLT3L, SCF, G-CSF, SCF, G-CSF, SDF1a, LPS, PMA, Thapsigargin.

In some embodiments, activation levels higher than a threshold level of the activatable element within the phospholipase C pathway in response to the inhibitor is indicative that individual can respond to treatment. In some embodiments, the activatable element within the phospholipase C pathway is selected from the group consisting of p-Slp-76, and Plcg2 and the inhibitor is H2O2.

In some embodiments, activation levels higher than a threshold of an activatable element within the apoptosis pathway in response to a modulator that slows or stops the growth of cells and/or induces apoptosis of cells is indicative that the individual can respond to treatment. In some embodiments, the activatable element within the apoptosis pathway is selected from the group consisting of Parp+, Cleaved Caspase 3, Cleaved Caspase 8, and Cytochrome C, and the modulator that slows or stops the growth of cells and/or induces apoptosis of cells is selected from the group consisting of Staurosporine, Etoposide, Mylotarg, Daunorubicin, and AraC.

In some embodiments, the methods further comprise determining an activation level of an activatable element within a DNA damage pathway or a cell cycle pathway in response to a modulator that slows or stops the growth of cells and/or induces apoptosis of cells. In some embodiments, the activatable element within a DNA damage pathway is selected from the group consisting of Chk1, Chk2, ATR, ATM, and 14-3-3 and the modulator that slows or stops the growth of cells and/or induces apoptosis of cells is selected from the group consisting of Staurosporine, Etoposide, Mylotarg, Daunorubicin, and AraC.

In some embodiments, activation levels higher than a threshold of the activatable element within a DNA damage pathway and activation levels lower than a threshold of the activatable element within the apoptosis pathway in response to a modulator that slows or stops the growth of cells and/or induces apoptosis of cells is indicative of a communication breakdown between the DNA damage response pathway and the apoptotic machinery and that the individual can not respond to treatment. In some embodiments, the activatable element within a cell cycle pathway is selected from the group consisting of Cdc25, p53, CyclinA-Cdk2, CyclinE-Cdk2, CyclinB-Cdk1, p21, p-Histone H3 and Gadd45, and the modulator that slows or stops the growth of cells and/or induces apoptosis of cells is selected from the group consisting of Staurosporine, Etoposide, Mylotarg, Daunorubicin, and AraC.

In some embodiments, the methods further comprising determining the levels of a drug transporter, growth factor receptor and/or a cytokine receptor. In some embodiments, the cytokine receptor, growth factor receptor or drug transporter are selected from the group consisting of MDR1, ABCG2, MRP, P-Glycoprotein, CXCR4, FLT3, and c-kit. In some embodiments, levels higher than a threshold of the drug transporter, growth factor receptor and/or the cytokine receptor is indicative that the individual can not respond to treatment.

In some embodiments, the methods further comprising determining the activation levels of an activatable element within the Akt pathway in response to an inhibitor, wherein activation levels higher that a threshold of the activatable element within the Akt pathway in response to the inhibitor is indicative that the individual can not respond to treatment.

In some embodiments, activation levels higher than a threshold of the activatable element in the PI3K/AKT pathway in response to a growth factor is indicative that the individual can not respond to treatment. In some embodiments, the activatable element in the PI3K/Akt pathway is Akt and the growth factor is FLT3L.

In some embodiments, activation levels higher than a threshold of the activatable element in the apoptosis pathway in response to a modulator that slows or stops the growth of cells and/or induces apoptosis of cells is indicative that the individual can respond to treatment. In some embodiments, the activatable element within the apoptosis pathway is Parp+ and the modulator that slows or stops the growth of cells and/or induces apoptosis of cells is selected from the group consisting of Staurosporine, Etoposide, Mylotarg, Daunorubicin, and AraC.

In some embodiments, the cytokine is selected from the group consisting of G-CSF, IFNg, IFNa, IL-27, IL-3, IL-6, and IL-10. In some embodiments, the growth factor or mitogen is selected from the group consisting of FLT3L, SCF, G-CSF, SCF, G-CSF, SDF1a, LPS, PMA, and Thapsigargin. In some embodiments, the modulator that slows or stops the growth of cells and/or induces apoptosis of cells is selected from the group consisting of Staurosporine, Etoposide, Mylotarg, Daunorubicin, and AraC.

In some embodiments the inhibitor is selected from the group consisting of AG 490, AG 825, AG 957, AG 1024, aloisine A, alsterpaullone, aminogenistein, API-2, apigenin, arctigenin, AY-22989, BAY 61-3606, Azacitidine bisindolylmaleimide IX, chelerythrine, 10-[4'-(N,N-Diethylamino)butyl]-2-chlorophenoxazine hydrochloride, dasatinib, 2-Dimethylamino-4,5,6,7-tetrabromo-1H-benzimidazole, 5,7-Dimethoxy-3-(4-pyridinyl)quinoline dihydrochloride, decitibine, edelfosine, ellagic acid, enzastaurin, ER 27319 maleate, erlotinib, ET18OCH3, fasudil, flavopiridol, gefitinib, GW 5074, H-7, H-8, H-89, HA-100, HA-1004, HA-1077, HA-1100, hydroxyfasudil, indirubin-3'-oxime, 5-Iodotubercidin, kenpaullone, KN-62, KY12420, LFM-A13, lavendustin A, luteolin, LY-294002, LY294002, mallotoxin, ML-9, NSC-154020, NSC-226080, NSC-231634, NSC-664704, NSC-680410, NU6102, olomoucine, oxindole I, PD-153035, PD-98059, PD 169316, phloretin, phloridzin, piceatannol, picropodophyllin, PKI, PP1, PP2, purvalanol A, quercetin, R406, R788, rapamune, rapamycin, Ro 31-8220, roscovitine, rottlerin, SB202190, SB203580, sirolimus, sorafenib, SL327, SP600125, staurosporine, STI-571, SU-11274, SU1498, SU4312, SU6656,4,5,6,7-Tetrabromotriazole, TG101348, Triciribine, Tyrphostin AG 490, Tyrphostin AG 825, Tyrphostin AG 957, Tyrphostin AG 1024, Tyrphostin SU1498, U0126, VX-509, VX-667, VX-680, W-7, wortmannin, XL-019, XL-147, XL-184, XL-228, XL-281, XL-518, XL-647, XL-765, XL-820, XL-844, XL-880, Y-27632, ZD-1839, ZM-252868, ZM-447439, H2O2, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydrophenanthren-2-yl)-2,2-dimethyl-propionamide, α-Bromo-4- hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenyarsine oxide, Pyrrolidine Dithiocarbamate, and Aluminum fluoride.

In some embodiments, the activation level of one or more activatable element is determined by a process comprising the binding of a binding element which is specific to a particular activation state of the particular activatable element. In some embodiments, the binding element comprises an antibody. In some embodiments, the step of determining the activation level comprises the use of flow cytometry, immunofluorescence, confocal microscopy, immunohistochemistry, immunoelectronmicroscopy, nucleic acid amplification, gene array, protein array, mass spectrometry, patch clamp, 2-dimensional gel electrophoresis, differential display gel electrophoresis, microsphere-based multiplex protein assays, ELISA, and label-free cellular assays to determine the activation level of one or more intracellular activatable element in single cells.

In some embodiments, the invention provides methods of drug screening, the method comprising: A] classifying one or more hematopoietic cells associated with acute leukemia, myelodysplastic syndrome or myeloproliferative neoplasms in the individual by a method comprising: a) subjecting a cell population comprising the one or more hematopoietic cells from the individual to a test compound and a plurality of modulators in plurality of cultures, b) characterizing a plurality of pathways in one or more cells from the plurality of cultures by determining an activation level of at least one activatable element within a plurality of pathways, wherein i) at least one of the pathways being characterized in at least one of the plurality of cultures is an apoptosis or a DNA damage pathway, ii) the modulators activate or inhibit one or more of the plurality of pathways being characterized, and c) classifying the one or more hematopoietic cells based on the pathways characterization; and [B] making a decision regarding the test compound and its therapeutic potential for the treatment of acute leukemia, myelodysplastic syndrome or myeloproliferative neoplasms, wherein the decision is based on the classification of the cells.

In some embodiments, the invention provides kits comprising: a) at least two modulators selected from the group consisting of Staurosporine, Etoposide, Mylotarg, Daunorubicin, AraC, G-CSF, IFNg, IFNa, IL-27, IL-3, IL-6, IL-10, FLT3L, SCF, G-CSF, SCF, G-CSF, SDF1a, LPS, PMA, Thapsigargin and H2O2; b) at least three binding elements specific to a particular activation state of the activatable element selected from the group consisting of p-Slp-76, p-Plcg2, p-Stat3, p-Stat5, p-Stat1, p-Stat6, p-Creb, Parp+, Chk2, p-65/Rel-A, p-Akt, p-S6, p-Erk, Cleaved Caspase 3, Cleaved Caspase 8, Cytoplasmic Cytochrome C, and p38; and c) instructions for diagnosis, prognosis, determining acute myeloid leukemia progression, predicting response to a treatment and/or choosing a treatment for acute myeloid leukemia, myelodysplastic syndrome or myeloproliferative neoplasms in an individual. In some embodiments, the kit further comprising a binding element specific for a cytokine receptor, growth factor receptor or drug transporter are selected from the group consisting of MDR1, ABCG2, MRP, P-Glycoprotein, CXCR4, FLT3, and c-kit. In some embodiments, the binding element is an antibody.

One embodiment of the present invention is a method for classifying cells of a myeloid disorder based on the biology of a cell or group of cells derived from a patient with a myeloid malignancy such as AML, MDS, or MPN. In one method of the invention cells are taken and stimulated with a modulator, fixed, permeabilized, contacted with a detection element, and analyzed. Fresh or frozen cells may be used depending on the time between sample acquisition and sample analysis. The method of classification can comprise correlating the cell with a clinical outcome, such as the prognosis and/or diagnosis of a condition, or can correlate with the response to a therapy, such as complete response, partial response, remission, no response, progressive disease, stable disease, hematologic improvement, cytogenetic response and adverse reaction. The method can also involve staging wherein the staging is selected from the group consisting of WHO classification, FAB classification, IPSS score, WPSS score, aggressive, indolent, benign, refractory, limited stage, extensive stage, including information that may inform on time to progression, progression free survival, overall survival, and event-free survival. Treatments or therapies may include chemotherapy, biological therapy, radiation therapy, small molecules, antibodies, bone marrow transplantation, peripheral stem cell transplantation, umbilical cord blood transplantation, autologous stem cell transplantation, allogeneic stem cell transplantation, syngeneic stem cell transplantation, surgery, induction therapy, maintenance therapy, watchful waiting, and other therapy. The classification may comprise correlating the cell with minimal residual disease or emerging resistance.

In some embodiments, univariate analysis is performed on relatively homogeneous clinical groups, such as patents over 60 years old, patients under 60 years old, de novo AML patients, and secondary AML patients. In other embodiments the groups may be molecularly homogeneous groups, such as groups with mutations in the juxtamembrane region of the Flt3 receptor, where these mutations can be internal tandem duplications (ITD) or point mutations. For example, in patients over 60 years, NRs may have a higher $H_2O_2$ response than CRs and/or a higher FLT3L responses than CRs. In patients under 60 years, NRs may have a higher IL-27 response than CRs and/or CRs may undergo apoptosis to Etoposide or Ara-C/Daunorubicin more than NRs. In de novo AML, CRs may induce apoptosis (cleaved PARP) in response to Etoposide or Ara-C/Daunorubicin, they may have higher total p-S6 levels than NRs, or NRs may have higher $H_2O_2$ responses than CRs. In secondary AML, NRs may have higher $H_2O_2$ responses than CRs, NRs may have higher FLT3L, SCF responses than CRs, NRs may have higher G-CSF, IL-27 responses than CRs, and there may be overlapping nodes with the over 60 year old patient set.

In some embodiments, the present invention may stratify patients with a myeloid disease, monitor the patients for disease recurrence, predict their response to a therapeutic agent, predict whether they are resistant or refractory to drugs, and predict whether they will relapse or have minimal residual disease.

Another embodiment of the invention is a method to stratify patients who have AML, MDS, or MPN by gating the AML, MDS, or MPN cell samples after contacting the cells with the modulator. The method may also comprise the steps of: a) providing a population of cells; b) contacting the cells with a plurality of activation state-specific binding elements, wherein the plurality of activation state-specific binding elements comprise: i) a first activation state-specific binding element that binds to a first activatable protein; and ii) a second activation state-specific binding element that binds to a second activatable protein; c) using flow cytometry to detect the presence or absence of binding of the first and second binding elements to determine the activation state of the first and second activatable proteins; and d) gating to separate the cells into discrete subsets. Also, the method may comprise classifying the cell as a cell that is correlated with staging of the disease, response to a therapeutic agent, minimal residual disease or emerging resistance and determining method of treatment.

One embodiment of the present invention is the use of a modulator that is an activator or an inhibitor, and it may be selected from the group consisting of biological entities, and physical or environmental stimuli which act extracellularly or intracellularly, the chemical and biological modulators comprise growth factors, cytokines, mitogens, neurotransmitters, adhesion molecules, hormones, small molecules, inorganic compounds, polynucleotides, antibodies, natural compounds, lectins, lactones, chemotherapeutic agents, biological response modifiers, immune modulators, carbohydrate, proteases, free radicals, cellular or botanical extracts, cellular or glandular secretions, physiologic fluids such as serum, amniotic fluid, or venom; the physical and environmental stimuli include electromagnetic, ultraviolet, infrared or particulate radiation, redox potential and pH, the presence or absences of nutrients, changes in temperature, changes in oxygen partial pressure, changes in ion concentrations and the application of oxidative stress. In another embodiment, the modulators may be selected from the groups consisting of ions, reactive oxygen species, peptides, and protein fragments, either alone or in the context of cells, cells themselves, viruses, and biological and non-biological complexes.

In another embodiment, the modulator is a inhibitor selected from the group consisting of $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy) phenacyl Br, and bis(4-Trifluoromethylsulfonamidophenyl)-1,4-diisopropylbenzene, phenylarsine oxide, Pyrrolidine Dithiocarbamate, and Aluminium fluoride.

In another embodiment of the invention, the activatable elements are selected from the group consisting of kinases, phosphatases, lipid signaling molecules, adaptor/scaffold proteins, cytokines, cytokine regulators, ubiquitination enzymes, adhesion molecules, cytoskeletal/contractile proteins, heterotrimeric G proteins, small molecular weight GTPases, guanine nucleotide exchange factors, GTPase activating proteins, caspases, proteins involved in apoptosis, cell cycle regulators, molecular chaperones, metabolic enzymes, vesicular transport proteins, hydroxylases, isomerases, deacetylases, methylases, demethylases, tumor suppressor genes, proteases, ion channels, molecular transporters, transcription factors/DNA binding factors, regulators of transcription, regulators of translation, HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PPS, inositol phosphatases, PTEN, SHIPs, myotubularins, phosphoinositide kinases, phopsholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon γ, interferon α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases such as, Caspase 2, Caspase 3, Caspase 6, Caspase 7, Caspase 8, Caspase 9, Bcl-2, Mcl-1, Bcl-XL, Bcl-w, Bcl-B, A1, Bax, Bak, Bok, Bik, Bad, Bid, Bim, Bmf, Hrk, Noxa, Puma, IAPB, XIAP, Smac, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pin1 prolyl isomerase, topoisomerases, deacetylases, Histone deacetylases, sirtuins, histone acetylases, CBP/P300 family, MYST family, ATF2, DNA methyl transferases, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, nucleoside transporters, Ets, Elk, SMADs, Rd-A (p65-NFKB), CREB, NFAT, ATF-2, AFT, Myc, Fos, Sp1, Egr-1, T-bet, β-catenin, HIFs, FOXOs, E2Fs, SRFs, TCFs, Egr-1, β-☐catenin, FOXO STAT1, STAT 3, STAT 4, STAT 5, STAT 6, p53, WT-1, HMGA, pS6, 4EPB-1, eIF4E-binding protein, RNA polymerase, initiation factors, elongation factors.

One embodiment of the invention is a method for diagnosing AML, MDS, or MPN, or predicting the outcome of patients sufferring from AML, MDS, or MPN, or screening drugs thought to be useful against AML, MDS, or MPN, or identifying new druggable targets for these diseases. The method comprises classifying a hematopoietic cell, comprising subjecting a hematopoietic cell to at least one modulator that affects signaling mediated by receptors subjecting a hematopoietic cell to at least one modulator that affects signaling mediated by receptors selected from the group comprising SDF-1α, IFN-α, IFN-γ, IL-10, IL-6, IL-27, G-CSF, FLT-3L, IGF-1, M-CSF and SCF; also subjecting the hematopoietic cell to at least one modulator selected from the group comprising PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine; determining the expression level at least one protein selected from the group comprising ABCG2, C-KIT receptor, and FLT3 LIGAND receptor, determining the activation states of a plurality of activatable elements in the cell comprising; and classifying the cell based on the activation states and expression levels. Another embodiment of the invention further includes using the modulators IL-3, IL-4, GM-CSF, EPO, LPS, TNF-α, and CD40L. The term "plurality" as used herein refers to two or more.

One embodiment of the invention is a method for diagnosing AML or predicting the outcome of patients sufferering from AML, screening drugs thought to be useful against AML, or identifying new druggable targets for these diseases, or predicting the outcome of patients undergoing ara-c based induction therapy. The method comprises classifying a hematopoietic cell, comprising subjecting a hematopoietic cell to at least one modulator that affects signaling mediated by receptors selected from the group comprising SDF-1α, IFN-α, IFN-γ, IL-10, IL-6, IL-27, G-CSF, FLT-3L, IGF-1, M-CSF and SCF; also subjecting the hematopoietic cell to at least one modulator selected from the group comprising PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine; determining the expression level at least one protein selected from the group comprising ABCG2, C-KIT receptor, and FLT3 LIGAND receptor, determining the activation states of a plurality of activatable elements in the cell comprising; and classifying the cell based on the activation states and expression levels. Another embodiment of the invention further includes using the modulators IL-3, IL-4, GM-CSF, EPO, LPS, TNF-α, and CD40L.

In another embodiment, for the treatment of myeloid disorders, the method further comprises treatment with a drug selected from the group consisting of therapies traditionally used to treat AML: standard induction therapy[cytarabine (100-200 mg/m$^2$) coupled to an anthracycline such as daunorubicin or idarubicin, +/− thioguanine, etoposide, dexamethasone], consolidation therapy including high dose (1-3 gram) cytarabine, stem cell transplant or hypomethylating drugs such as Azacytidine and Decitabine which induce differentiation in the affected cells by preventing DNA methylation, Arsenic trioxide (apoptosis inducer), Sorafenib (tyrosine kinase inhibitor), gemtuzumab ozogamicin (Mylotarg), Vorinostat and valproic acid (histone deacetylase inhibitors), tipifarnib and lonafarnib (farnesyl transferase and RAF/RAS/ERK inhibitor), bevacizumab (anti-EDGF monoclonal antibody that inhibits angiogenesis), ezatiostat (glutathione S1 transferase inhibitor), and clofarabine (nucleoside analog). In M3 AML all-trans retinoic acid and arsenic trioxide are also used. Therapies traditionally used to treat MDS: supportive care, epo, GCSF, Lenalidomide, Decitabine, Azacytidine, cyclosporine A, Anti-thymocyte globulin, and agents under investigation that include Arsenic trioxide (apoptosis inducer), Sorafenib (tyrosine kinase inhibitor), Vorinostat and valproic acid (histone deacetylase inhibitors), tipifarnib and lonafarnib (farnesyl transferase and RAF/RAS/ERK inhibitor), bevacizumab (anti-EDGF monoclonal antibody that inhibits angiogenesis), FG-2216 (hypoxia-inducible factor stabilizer), ezatiostat (glutathione S1 transferase inhibitor), clofarabine (nucleoside analog). Also included are therapies traditionally used to treat MPNs include blood letting, aspirin, and hydroxyurea.

One embodiment of the invention involves the use of multiparametric flow cytometry to examine the biology and signalling pathways in AML to determine likelihood of response to agents used in consolidation therapy for AML.

One embodiment of the invention involves the use of multiparametric flow cytometry to examine the biology and signalling pathways in AML to determine likelihood of response to agents in development for the treatment of AML.

One embodiment of the invention involves the use of multiparameter flow cytometry to examine the biology and signalling pathways in myelodysplastic syndrome to classify MDS and inform on likelihood of response to agents such as growth factors(e.g. EPO), immunosuppressive agents (e.g. ATG+/−CsA), epigenetic modulators (e.g. hypomethylators Azacytidine and Decitabine and HDAC inhibitors), immunemodulators (e.g. Lenalidomide).

One embodiment of the invention involves the use of multiparametric flow cytometry to examine the biology and signalling pathways in myelodysplastic syndrome to determine likelihood of progression to AML.

One embodiment of the invention involves the use of multiparametric flow cytometry to examine the biology and signalling pathways in myelodysplastic syndrome to determine likelihood of response to agents in development for the treatment of MDS One embodiment of the invention will look cell signaling pathways described above in classifying and diagnosing MPN. Modulators can be designed to investigate these pathways and any relevant parallel pathways.

One embodiment of the invention involves the use of multiparametric flow cytometry to examine the biology and signalling pathways in MPN to determine likelihood of progression to AML.

One embodiment of the invention involves the use of multiparametric flow cytometry to examine the biology and signalling pathways in MPN to determine likelihood of response to agents in development for the treatment of MPN Another embodiment of the invention comprises a method for drug screening comprising; contacting a population of AML, MDS, or MPN cells with a test compound and at least one modulator that affects signaling mediated by receptors selected from the group comprising SDF-1α, IFN-α, IFN-γ, IL-10, IL-6, IL-27, G-CSF, FLT-3L, IGF-1, M-CSF and SCF; also subjecting the hematopoietic cell to at least one modulator selected from the group comprising PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine; determining the expression level at least one protein selected from the group comprising ABCG2, C-KIT receptor, and FLT3 LIGAND receptor, determining the activation states of a plurality of activatable elements in the cell comprising; and classifying the cell based on the activation states and expression levels. Another embodiment of the invention further includes using the modulators IL-3, IL-4, GM-CSF, EPO, LPS, TNF-α, and CD40L.

In a further embodiment the invention comprises a kit. The subject invention also provides kits for use in determining the physiological status of cells in a sample, the kit comprising one or more modulators, inhibitors, specific binding elements for signaling molecules, and may additionally comprise one or more therapeutic agents. The kit may further comprise a software package for data analysis of the physiological status, which may include reference profiles for comparison with the test profile. The kit may also include instructions for use for any of the above applications.

In another embodiment, the invention is a method for analyzing multiparametric data comprising using the following measurements: basal, fold change, total phospho, quadrant frequency, bimodal, spread, fold over isotype, percent over isotype, percent positive above unstimulated and unstained, and mediam fluorescent intensity of percent positive above unstimulated and unstained.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2B measures the frequency of cells with a described property such as cells positive for cleaved PARP (% PARP+), or cells positive for p-S6 and p-Akt. Similarly, measurements examining the changes in the frequencies of cells may be applied such as the Change in % PARP+ which would measure the % PARP+$_{Stimulated\ Stained}$%PARP+$_{Unstimulated\ Stained}$. The AUC$_{unstim}$ metric also measures changes in population frequencies measuring the frequency of cells to become positive compared to an unstimulated condition.

FIG. 4A shows that phosphatase inhibitors, such as $H_2O_2$, can help stratify patient response to induction therapy. FIG. 4B shows $H_2O_2$ target pathways in myeloids cells and monocytes.

FIG. 26A shows p-AKT and p-S6 levels in CD33$^+$, CD11b$^-$, CD34$^+$ cells in an AML patient.

FIG. 27 shows the frequency of pAKT/pS6 myeloid cells responsive to SCF in different AML patients.

DETAILED DESCRIPTION OF THE INVENTION

Figure 1:
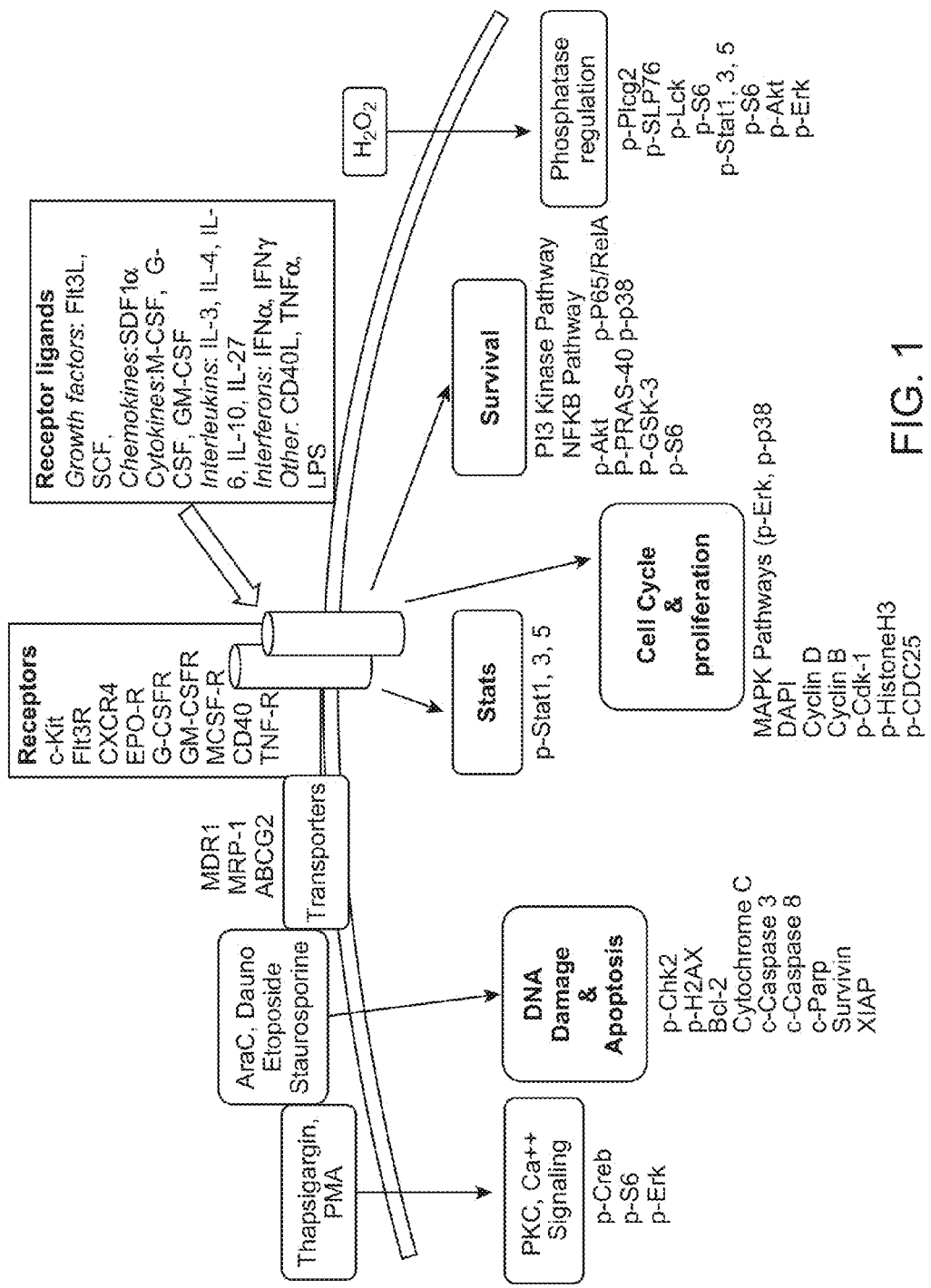
FIG. 1 shows some examples of cellular pathways. For example, cytokines such as G-CSF or growth factors such as FLT-3 Ligand will activate their receptors resulting in activation of intracellular signaling pathways. Also, chemotherapeutics, such as AraC can be transported inside the cell to cause effects, such as DNA damage, caspase activation, PARP cleavage, etc.

The present invention incorporates information disclosed in other applications and texts. The following patent and other publications are hereby incorporated by reference in their entireties: Haskell et al, Cancer Treatment, 5$^{th}$ Ed., W.B. Saunders and Co., 2001; Alberts et al., The Cell, 4$^{th}$ Ed., Garland Science, 2002; Vogelstein and Kinzler, The Genetic Basis of Human Cancer, 2d Ed., McGraw Hill, 2002; Michael, Biochemical Pathways, John Wiley and Sons, 1999; Weinberg, The Biology of Cancer, 2007; Immunobiology, Janeway et al. 7$^{th}$ Ed., Garland, and Leroith and Bondy, Growth Factors and Cytokines in Health and Disease, A Multi Volume Treatise, Volumes 1A and 1B, Growth Factors, 1996. Other conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y.; and Sambrook, Fritsche and Maniatis. "Molecular Cloning A laboratory Manual" 3rd Ed. Cold Spring Harbor Press (2001), all of which are herein incorporated in their entirety by reference for all purposes.

Patents and applications that are also incorporated by reference include U.S. Pat. Nos. 7,381,535 and 7,393,656 and U.S. Ser. Nos. 10/193,462; 11/655,785; 11/655,789; 11/655,821; 11/338,957, 61/048,886; 61/048,920; 61/048,657; and 61/079,766. Some commercial reagents, protocols, software and instruments that are useful in some embodiments of the present invention are available at the Becton Dickinson Website http://www.bdbiosciences.com/features/products/, and the Beckman Coulter website, http://www.beckmancoulter.com/Defaultasp?bhfv=7. Relevant articles include High-content single-cell drug screening with phosphospecific flow cytometry, Krutzik et al., Nature Chemical Biology, 23 Dec. 2007; fish et al., FLt3 ligand Y591 duplication and Bcl-2 over expression are detected in acute myeloid leukemia cells with high levels of phosphorylated wild-type p53, Neoplasia, 2007, Irish et al. Mapping normal and cancer cell signaling networks: towards single-cell proteomics, Nature, Vol. 6 146-155, 2006; and Irish et al., Single cell profiling of potentiated phospho-protein networks in cancer cells, Cell, Vol. 118, 1-20 Jul. 23, 2004; Schulz, K. R., et al., Single-cell phospho-protein analysis by flow cytometry, Curr Protoc Immunol, 2007, 78:8 8.17.1-20; Krutzik, P. O., et al., Coordinate analysis of murine immune cell surface markers and intracellular phosphoproteins by flow cytometry, J Immunol. 2005 Aug. 15; 175(4):2357-65; Krutzik, P. O., et al., Characterization of the murine immunological signaling network with phospho-specific flow cytometry, J Immunol. 2005 Aug. 15; 175(4): 2366-73; Shulz et al., Current Protocols in Immunology 2007, 78:8.17.1-20; Stelzer et al. Use of Multiparameter Flow Cytometry and Immunophenotyping for the Diagnosis and Classification of Acute Myeloid Leukemia, Immunophenotyping, Wiley, 2000; and Krutzik, P. O. and Nolan, G. P., Intracellular phospho-protein staining techniques for flow cytometry: monitoring single cell signaling events, Cytometry A. 2003 October; 55(2):61-70; Hanahan D., Weinberg, The Hallmarks of Cancer, CELL, 2000 Jan. 7; 100(1) 57-70; Krutzik et al, High content single cell drug screening with phophosphospecific flow cytometry, Nat Chem Biol. 2008 February; 4(2):132-42. Experimental and process protocols and other helpful information can be found at http:/proteomices.stanford.edu. The articles and other references cited below are also incorporated by reference in their entireties for all purposes.

One embodiment of the present invention involves the classification, diagnosis, prognosis of disease and outcome after administering a therapeutic to treat the disease; exemplary diseases include AML, MDS and MPN. Another embodiment of the invention involves monitoring and predicting outcome of disease. Another embodiment is drug screening using some of the methods of the invention, to determine which drugs may be useful in particular diseases. In other embodiments, the invention involves the identification of new druggable targets, that can be used alone or in combination with other treatments. The invention allows the selection of patients for specific target therapies. The invention allows for delineation of subpopulations of cells associated with a disease that are differentially susceptible to drugs or drug combinations. In another embodiment, the invention allows to demarkate subpopulations of cells associated with a disease that have different genetic subclone origins. In another embodiment, the invention provides for the identification of a cell type, that in combination other cell type(s), provide ratiometric or metrics that singly or coordinately allow for surrogate identification of subpopulations of cells associated with a disease, diagnosis, prognosis, disease stage of the individual from which the cells were derived, response to treatment, monitoring and predicting outcome of disease. Another embodiment involves the analysis of apoptosis, drug transport and/or drug metabolism. In performing these processes, one preferred analysis method involves looking at cell signals and/or expression markers. One embodiment of cell signal analysis involves the analysis of phosphorylated proteins and the use of flow cytometers in that analysis. In one embodiment, a signal transduction-based classification of AML, MDS, or MPN can be performed using clustering of phospho-protein patterns or biosignatures. See generally FIG. 1.

In some embodiments, the present invention provides methods for classification, diagnosis, prognosis of disease and outcome after administering a therapeutic to treat the disease by characterizing a plurality of pathways in a population of cells. In some embodiments, a treatment is chosen based on the characterization of plurality of pathways in single cells. In some embodiments, characterizing a plurality of pathways in single cells comprises determining whether apoptosis pathways, cell cycle pathways, signaling pathways, or DNA damage pathways are functional in an individual based on the activation levels of activatable elements within the pathways, where a pathway is functional if it is permissive for a response to a treatment. For example, when the apoptosis, cell cycle, signaling, and DNA damage pathways are functional the individual can respond to treatment, and when at least one of the pathways is not functional the individual can not respond to treatment. In some embodiments, if the apoptosis and DNA damage pathways are functional the individual can respond to treatment.

In some embodiments, the characterization of pathways in conditions such as AML, MDS and MPN shows disruptions in cellular pathways that are reflective of increased proliferation, increased survival, evasion of apoptosis, insensitivity to anti-growth signals and other mechanisms. In some embodiments, the disruption in these pathways can be revealed by exposing a cell to one or more modulators that mimic one or more environmental cue. FIG. 1 shows an example of how biology determines response to therapy. For example, without intending to be limited to any theory, a responsive cells treated with Ara-C will undergo cell death through activation of DNA damage and apoptosis pathways. However, a non-responsive cell might escape apoptosis through disruption in one or more pathways that allows the cell to survive. For instance, a non-responsive cell might have increased concentration of a drug transporter (e.g., MPR-1), which causes Ara-C to be removed from the cells. A non-responsive cell might also have disruptions in one or more pathways involve in proliferation, cell cycle progression and cell survival that allows the cell to survive. A non-responsive cell may have a DNA damage response pathway that fails to communicate with apoptosis pathways. A non-responsive cell might also have disruptions in one or more pathways involve in proliferation, cell cycle progression and cell survival that allows the cell to survive. The disruptions in these pathways can be revealed, for example, by exposing the cell to a growth factor such as FLT3L or G-CSF. In addition, the revealed disruptions in these pathways can allow for identification of target therapies that will be more effective in a particular patient and can allow the identification of new druggable targets, which therapies can be used alone or in combination with other treatments. Expression levels of proteins, such as drug transporters and receptors, may not be as informative by themselves for disease management as analysis of activatable elements, such as phosphorylated proteins. However, expression information may be useful in combination with the analysis of activatable elements, such as phosphorylated proteins.

The discussion below describes some of the preferred embodiments with respect to particular diseases. However, it should be appreciated that the principles may be useful for the analysis of many other diseases as well.

Introduction

Hematopoietic cells are blood-forming cells in the body. Hematopoiesis (development of blood cells) begins in the bone marrow and depending on the cell type, further maturation occurs either in the periphery or in secondary lymphoid organs such as the spleen or lymph nodes. Hematopoietic disorders are recognized as clonal diseases, which are initiated by somatic and/or inherited mutations that cause dysregulated signaling in a progenitor cell. The wide range of possible mutations and accompanying signaling defects accounts for the diversity of disease phenotypes observed within this group of disorders. Hematopoietic disorders fall into three major categories: Myelodysplastic syndromes, myeloproliferative disorders, and acute leukemias. Examples of hematopoietic disorders include non-B lineage derived, such as acute myeloid leukemia (AML), Chronic Myeloid Leukemia (CML), non-B cell acute lymphocytic leukemia (ALL), myelodysplastic disorders, myeloproliferative disorders, polycythemias, thrombocythemias, or non-B atypical immune lymphoproliferations. Examples of B-Cell or B cell lineage derived disorder include Chronic Lymphocytic Leukemia (CLL), B lymphocyte lineage leukemia, Multiple Myeloma, acute lymphoblastic leukemia (ALL), B-cell prolymphocytic leukemia, precursor B lymphoblastic leukemia, hairy cell leukemia or plasma cell disorders, e.g., amyloidosis or Waldenstrom's macroglobulinemia.

Acute myeloid leukemia (AML), myelodysplastic syndrome (MDS), and myeloproliferative neoplasms (MPN) are examples of distinct myeloid hematopoietic disorders. However, it is recognized that these disorders share clinical overlap in that 30% of patients with MDS and 5-10% of patients with MPN will go on to develop AML. Below are current descriptions of these myeloid disorders.

Acute Myeloid Leukemia (AML)

AML is characterized by an uncontrolled proliferation of immature progenitor cells of myeloid origin including, but not limited to, myeloid progenitor cells, myelomonocytic progenitor cells, and immature megakaryoblasts. It is becoming clear that AML is really a heterogeneous collection of neoplasms with elements of differing pathophysiology, genetics and prognosis. Under WHO guidelines, diagnosis of AML can be made when blasts (immature cells) are present at 20% or more in peripheral blood or bone marrow sampling.

Though rare, AML is one of the most deadly cancers and can be very aggressive if untreated. Although AML is a relatively rare disease, accounting for approximately 1.2 percent of cancer deaths in the US, it is the most common form of leukemia accounting for about 50 percent of all leukemia cases. Its incidence is expected to increase as the population ages; up to 85 percent of all acute leukemia cases involve adults. SEER data predicts that 13,410 people will be diagnosed with AML in 2008. AML is one of the more deadly cancers with an overall survival of 50% in children, 20% in patients <60 years old and 5% in patients >60 years and is uniformly fatal if left untreated.

AML is a quickly progressive malignant disease involving too many immature blood-forming cells in the blood and bone marrow, the cells being specifically those that are destined to give rise to granulocytes or monocytes—the two types of white blood cells that fight infections. In AML, these blasts do not mature and do not die, thus overwhelming the circulatory system (blasts often represent >90% of peripheral blood leukocytes), suppressing normal hematopoiesis and invading other organs and tissues. It is also known as acute myelogenous leukemia or acute nonlymphocytic leukemia (ANLL).

AML patients are presently classified into groups or subsets based on age, cytogenetics and molecular analysis, with markedly contrasting prognosis. The greatest prognostic factor is age with children diagnosed with AML fareing much better than adults. Cytogenetics also plays a major prognostic role in AML. Genetic translocations, such as inv(16), t(8;21) and t(15;17) characterize AML with a relatively favourable prognosis, whereas the cytogenetically high-risk leukemias include patients with FLt3 ligand mutations, loss of 5(q) or 7(q), t(6;9) and t(9;22) (Lowenberg et al., 1999). More recently, molecular markers have been recognized as having prognostic value. Nucleophosmin1 (NPM1) predicts good risk AML while the presence internal tandem duplications of Flt 3 predicts poor outcome.

Causes

The development of acute myeloid leukemia is currently believed to be a multi-step process. Under the two-hit model proposed by Gilliland et al., a hematopoietic progenitor cell first acquires a mutation that confers a growth advantage, such as a constitutively activated tyrosine kinase (e.g. Flt-3-ITD). This preleukemic cell thus divides more rapidly. Due to the increased proliferation, the odds of acquiring additional stochastic mutations are increased. When one of these secondary mutations disrupts normal differentiation of the progenitor cell (e.g. AML1-ETO), the result is a fully cancerous clone with the regenerative capacity of a progenitor cell, but lacking the developmental checkpoints of differentiation. The unchecked division of this clone produces the immature blast population characteristic of AML. (Kelly, L. M. & Gilliland, D. G. Genetics of myeloid leukemias. *Annu Rev Genomics Hum Genet*, Epub 2002 Apr. 15).

Any endogenous or environmental source of DNA damage has the potential to induce leukemia. As the incidence of AML increases dramatically with age, the most likely causative agent is probably DNA damage from superoxide radicals produced during normal cellular respiration, coupled with imperfect DNA repair. Environmental exposure to high levels of ionizing radiation, such as nuclear industry accidents, increases the risk of developing leukemia. Smoking also increases the risk because of concentrated levels of benzene in cigarette smoke. In rare cases, AML may occur after long-term exposure to benzene (and possibly other solvents) used in industry. Some anti-cancer treatments such as chemotherapy or radiotherapy can result in leukemia being developed years later. The risk is increased when certain types of chemotherapy drugs are combined with radiotherapy. When leukemia develops because of previous anti-cancer treatment, it is known as secondary leukemia or treatment-related leukemia.

AML can also arise from genetic causes. For example, patients with Down's syndrome, Fanconi anemia, Li Fraumeni syndrome, Kostmanns, Kleinfelters, Neurofibromatosis, Diamond Blackfan anemia and Swachman Diamond have an increased risk of developing AML. Non-inherited examples include aplastic anemia, paroxysmal nocturnal hemoglobinuria and MDS, as well as other blood disorders, such as the Myeloproliferative neoplasms polycythemia vera and essential thrombocythemia. Acute myeloid leukemia is not infectious and cannot be passed on to other people.

Symptoms

The main symptoms of AML are pallor, fatigue and breathlessness, which are due to anemia caused by the lack of red blood cells. Decreased white blood cells lead to an increase in infection and fever. Absence of platelets can lead to petichiae (rashes of tiny, flat red spots on the legs, chest, or in the mouth), bleeding of the gums, frequent nosebleeds, or heavy periods in women.

Other symptoms may be caused by an abnormal accumulation of leukemia cells in a particular area of the body, such as bone pain caused by pressure from the accumulation of immature cells in the bone marrow, raised bluish-purple areas under the skin (leukemia cutis), caused by leukemia cells in the skin, and hypertrophied (swollen) gums caused by an infiltration of leukemia cells into the gums. Blasts commonly are found in organs such as the liver, spleen and lymph nodes resulting in organomegaly (large organs), soreness or sensitivity in these areas. In addition, headaches or seizures may arise when the central nervous system is infiltrated with contaminating leukemia cells.

Very rarely, a person does not have any symptoms and the leukemia is discovered during a routine blood test. The symptoms of acute myeloid leukemia usually appear over a few weeks, and people often fall ill quickly necessitating prompt administration of therapy.

Diagnosis

The duration of signs and symptoms before diagnosis of AML is usually 4 to 6 weeks, and may include fever, pallor, weakness, fatigue, and weight loss. An abnormal result on a complete blood count is the most common and oldest method for diagnosing AML. Diagnosis is confirmed by obtaining a small sample of bone marrow and counting the number and percentage of immature blood cells (blasts) in the sample under a microscope, using standard histological techniques. Based on the size of the cells, their shape, cell surface markers and other traits, one can classify the cells into specific cell types.

The percentage of cells in the bone marrow or blood is essential for diagnosing an acute leukemia. At least 20 or more percent of blasts in the blood or marrow is generally required for the diagnosis of AML. Less than 20 percent blasts usually indicates a myeloproliferative disease or myeloproliferative neoplasia. AML can also be diagnosed if the blasts have a chromosome change, which only occurs in a specific type of AML, even though the blast percentage does not reach 20 percent. Sometimes leukemic blasts look similar to normal immature cells in the bone marrow. However, under normal circumstances, blasts are generally not more than 5 percent of the bone marrow cells.

In 90% of cases, morphological and cytochemical studies are sufficient to determine the lineage of the leukemia, but immunophenotyping techniques can be useful to make a diagnosis. Flow cytometry is now routinely used diagnose and classify leukemias, particularly in difficult cases of discriminating between AML and ALL, and is also used to determine the tumor burden (e.g. percent blasts). Cytogenetic techniques help in determining any changes in chromosome or any translocation, deletions, etc. Another similar cytogenetic method for diagnosis is fluorescent in situ hybridization (FISH), which can be used to ascertain specific changes in chromosomal makeup.

One embodiment of the present invention is a method for classifying cells of a myeloid disorder based on the biology of a cell or group of cells derived from a patient with a myeloid malignancy such as AML, MDS, or MPN. One embodiment of the invention combines one or more of these existing tests with the analysis of signalling mediated by receptors to diagnose disease, especially AML, MDS, or MPNs. All tests may be performed in one location and provided as a single service to physicians or other caregivers.

Cell-Signaling Pathways and Differentiating Factors Involved

Alterations of kinases and phosphatases lead to inappropriate signal transduction, whereas alterations of transcription factors give rise to inappropriate gene expression. Both of these mechanisms contribute to the pathogenesis of AML by the induction of increased proliferation, reduced apoptosis and block of differentiation. The dysregulation of one or more of the key signaling pathways (e.g., RAS/MAPK, PI3K/AKT, and JAK/STAT) is believed to result in growth factor-independent proliferation and clonal expansion of hematopoietic progenitors (HOX deregulation in acute myeloid leukemia. *Journal of Clinical Investigation.* 2007, vol. 117, no. 4, p. 865-868.) See generally Table 1 below which depicts pathways relevant for AML Biology. In some embodiments, the pathways depicted in Table 1 are characterized using the methods described herein by exposing cells to the modulators listed in the table and measuring the readout listed in the table, for each corresponding pathways. Disruption in one or more pathways can be revealed by exposing the cells to the modulators. This can then be used for classification, diagnosis, prognosis of AML, selection of treatment and/or predict outcome after administering a therapeutic.

cytokine receptors, which are differentially expressed depending on the cell type and the stage of differentiation. Intrinsic or receptor-associated tyrosine kinases phosphorylate STAT proteins, causing them to form a homodimer. The activated STAT dimer is able to enter the cell nucleus and activate the transcription of target genes, many of which are involved in the regulation of apoptosis and cell cycle progression. Apart from promoting proliferation and survival, some growth factor receptors and signaling intermediates have been shown to play specific and important roles in myeloid differentiation. For example, G-CSF- or TPO-induced activation of the Ras-Raf-MAP Kinase pathway promotes myeloid or megakaryocytic differentiation in the respective

TABLE 1

| Pathway | Readout | Modulator |
| --- | --- | --- |
| DNA Damage | p-Chk1, p-Chk2, p-ATM, p-ATR, p-H2AX | Etoposide, Ara-C/Daunorubicin, Drug Pump Inhibitors, Mylotarg |
| Drug transporters | MDR-1, ABCG2, MPR | Drug Pump Inhibitors |
| Apoptosis | Bcl-2, Mcl-1, cytochrome c, survivin, XIAP PARP, Caspses 3, 7 and 8 | Staurosporine, Etoposide, Ara-C/Daunorubicin, Drug Pump Inhibitors, Mylotarg, Zvad, Caspase Inhibitors, |
| Phosphatases | Shp-1, Shp-2,, CD45 | $H_2O_2$ |
| JAK/STAT | p-Stat 1, 3, 4, 5, 6 | Cytokine and Growth Factors |
| Cell Cycle | Myc, Ki-67, Cyclins, DNA stains, p-RB, p16, p21, p27, p15, cyclin D1, cyclin B1, p-Cdk1, p-histoneH3, p-CDC25 | Cytokine and Growth Factors, Mitogens, Apoptosis inducing agents, |
| MAPK | Ras, p-Mek, p-Erk, p-S6, p-38 | Cytokine and Growth Factors, Mitogens, |
| PI3K-AKT | p-Akt, p-S6, p-PRAS40, p-GSK3, p-TSC2, p-p70S6K, 4-EBP1, p-FOXO proteins | Cytokines, Growth Factors, Mitogens, chemokines, Receptor Tyrosine Kinase (RTK) ligands |
| FLT3 and other RTKs | p-PLCg 1/2, p-CREB, total CREB, p-Akt, p-Erk, p-S6 | Flt3L, Receptor Tyrosine Kinase (RTK) ligands |
| Angiogenesis | PLCγ1, p-Akt, p-Erk | VEGF stim |
| Wnt/b-catenin | Active B-Catenin, Myc, Cyclin D | RTK ligands, growth factors |
| Survival | PI3K, PLCg, Stats | RKT Growth Factors |

There are two main classes of receptors which play an important role in hematopoiesis: Receptors with intrinsic tyrosine kinase activity (RTKs) and those that do not contain their own enzymatic activity and often consist of heterodimers of a ligand-binding alpha subunit and a signal transducing beta subunit, which is frequently shared between a subset of cytokine receptors. Cytoplasmic tyrosine kinases phosphorylate cytokine receptors thereby creating docking sites for signaling molecules resulting in activation of a specific intracellular signaling pathway. Of the first class, Kit and FLt3 receptor have been shown to play an important role in the pathogenesis of AML. Extracellular ligand binding regulates the intracellular substrate specificity, affinity and kinase activity of these proteins. Therefore, the receptor transmits its signal through binding and/or phosphorylation of intracellular signaling intermediates. Despite these differences, the signals transmitted by both classes of receptors ultimately converge on one or more of the key signaling pathways, such as the Ras/Raf/MAPK, PI3K/AKT, and JAK/STAT pathways.

The STAT (signal transducer and activator of transcription) family of proteins, especially STAT3 and STAT5, are emerging as important players in several cancers. (Yu 2004— STATs in cancer. (2008) pp. 9). Of particular relevance to AML, the STATs have been shown to be critical for myeloid differentiation and survival, as well as for long-term maintenance of normal and leukemic stem cells. (Schepers et al. STAT5 is required for long-term maintenance of normal and leukemic human stem/progenitor cells. Blood (2007) vol. 110 (8) pp. 2880-2888) STAT signaling is activated by several progenitor cells by the activation of c/EBPα (frequently inactivated in myeloid leukemias) and GATA-1, respectively. (B. STEFFEN et al. Critical Reviews in *Oncology/Hematology.* 2005, vol. 56, p. 195-221.)

Phosphatases:

One of the earliest events that occurs after engagement of myeloid receptors is the phosphorylation of cellular proteins on serine, threonine, and tyrosine residues 8, 9, 10. The overall level of phosphorylated tyrosine residues is regulated by the competing activities of protein tyrosine kinases (PTKs) and protein tyrosine phosphatases (PTPs). Decreases in the activity of tyrosine phosphatases may also contribute to an increase in cellular tyrosine phosphorylation following stimulation.

SHP-1 (PTPN6) is a non-receptor protein tyrosine phosphatase that is expressed primarily in hematopoietic cells. The enzyme is composed of two SH2 domains, a tyrosine phosphatase catalytic domain and a carboxy-terminal regulatory domain (Yi, T. L. et al. (1992) Mol Cell Biol 12, 836-46). SHP-1 removes phosphates from target proteins to down regulate several tyrosine kinase regulated pathways. In hematopoietic cells, the N-terminal SH2 domain of SHP-1 binds to tyrosine phosphorylated erythropoietin receptors (EpoR) to negatively regulate hematopoietic growth (Yi, T. et al. (1995) Blood 85, 87-95). Following ligand binding in myeloid cells, SHP-1 associates with IL-3R β chain and down regulates IL-3-induced tyrosine phosphorylation and cell proliferation (Yi, T. et al. (1993) Mol Cell Biol 13, 7577-86). Because SHP-1 downregulates signaling pathways emanating from receptor tyrosine kinases, cytokine receptors, multi-chain recognition receptors and integrins, it is considered a potential tumor suppressor (Wu, C. et al. (2003) Gene 306, 1-12, Bhattacharya, R. et al. (2008) J Mol Signal 3, 8).

SHP-2 (PTPN11) is a ubiquitously expressed, nonreceptor protein tyrosine phosphatase (PTP). It participates in signaling events downstream of receptors for growth factors, cytokines, hormones, antigens and extracellular matrices in the control of cell growth, differentiation, migration and death (Qu, C. K. (2000) Cell Res 10, 279-88). Activation of SHP-2 and its association with Gab1 is critical for sustained Erk activation downstream of several growth factor receptors and cytokines (Maroun, C. R. et al. (2000) Mol Cell Biol 20, 8513-25).

FIG. 4 shows the role of phosphaspatases in AML. When active SHP-1 and SHP-2 dephosphorylates protein kinase (See Koretzky G A et al. Nat Rev Immunol. 2006 January; 6(1):67-78. Review). Treatment of cells with a general tyrosine phosphatase inhibitor such as $H_2O_2$ results in an increase in phosphorylation of intracellular signalling molecules. In this experiment, AML patients that were complete responders (CR) to one cycle of standard 7+3 induction therapy showed higher levels of phosphorylated PLCγ2 and SLP-76 upon $H_2O_2$ treatment when compared with non-responders (NR).

FLt3 Ligand Mutations:

During normal hematopoietic development, the FLT3 receptor functions in the differentiation and proliferation of multipotent stem cells and their progeny in the myeloid, B cell, and T cell lineages. (Gilliland, G. D., and Griffin, J. D. The roles of FLT3 in hematopoesis and leukemia. Blood (2002) 100: 1532-42). FLT3 receptor expression is normally restricted to hematopoietic progenitors, and genetic ablation experiments have shown that FLT3 is required for the maturation of these early cells, but is not required in mature cells (Rosnet O., et al, Human FLT3/FLK2 receptor tyrosine kinase is expressed at the surface of normal and malignant hematopoietic cells. Leukemia (1996) 10; 238-48; Mackarehtschian K., et al. Targeted disruption of the flk2/flt3 gene leads to deficiencies in primitive hematopoietic progenitors. Immunity (1995) 3: 147-61).

Mutations in FLT3 are found in 25-45% of all AML patients (Renneville A., et al, Cooperating gene mutations in acute myeloid leukemia: a review of the literature. Leukemia (2008) 22: 915-31). Of the AML-associated FLT3 mutations, the most common is the internal tandem duplication (ITD), which is found in 25-35% of adult AML patients (Id). The ITD is an in-frame duplication of 3-400 nucleotides that encodes a lengthened FLT3 juxtamembrane domain (JMD) (Schnittger S., et al. FLT3 internal tandem duplication in 234 children with acute myeloid leukemia (AML): prognostic significance and relation to cellular drug resistance. Blood (2003) 102: 2387-94). In vitro studies have shown that FLT3/ ITDs promote ligand-independent receptor dimerization, leading to autonomous phosphorylation and constitutive activation of the receptor (Gilliand, G. D, and Griffin, J. D. Blood (2002) 100: 1532-42). Structural studies of FLT3 suggest that in the wild-type receptor, the JMD produces steric hindrance that prevents autodimerization (Griffith, J., et al. The Structural Basis for Autoinhibition of FLT3 by the Juxtamembrane Domain. Molecular Cell (2004) 13: 169-78). The ITD-associated lengthening of the JMD appears to remove this hindrance, resulting in autodimerization and constitutive FLT3 kinase activity. The second class of FLT3 mutation, found in 5-10% of AML patients, comprises missense point mutations in exon 20—commonly in codons D835, I836, N841, or Y842—which produce amino acid substitutions in the activation loop of the FLT3 tyrosine kinase domain (TKD) (Yamamoto Y., et al, Activating mutation of D835 within the activation loop of FLT3 in human hematologic malignancies. Blood (2001) 97: 2434-39). Investigators have also identified several AML-associated point mutations in the FLT3 JMD (Stirewalt D. L., et al. Novel FLT3 point mutations within exon 14 found in patients with acute myeloid leukemia. Br. J. Haematol (2004) 124: 481-84), and one in the N-terminal portion of the Tyrosine Kinase Domain (Schittenheim M. M., et al. FLT3 K663Q is a novel AML-associated oncogenic kinase: determination of biochemical properties and sensitivity to sunitnib. Leukemia (2006) 20: 2008-14).

The AML-associated FLT3 mutations generally cause ligand-independent autophosphorylation of the FLT3 receptor and subsequent activation of downstream signaling pathways, such as PI3K, Ras, and JAK/STAT (Renneville, et al. (2008) 22: 915-31). However, the FLT3-ITD and TKD mutations are associated with significant biological differences (Renneville, et al. (2008) 22: 915-31). FLT3-ITD mutations constitutively induce STATS phosphorylation, while FLT3- TKD mutations only weakly induce STATS phosphorylation (Choudry, C. et al. AML-associated Flt3 kinase domain mutations show signal transduction differences compared with Flt3-ITD mutations. Blood (2005) 106: 265-73). Furthermore, FLT3-ITD, but not TKD mutations suppress expression of the transcription factors, c/EBPα and Pu.1, which function in myeloid differentiation. Additionally, neither class of FLT3 mutation is sufficient to induce AML, suggesting that additional mechanisms may be involved (Renneville, et al. (2008) 22: 915-31). Many investigational new drugs are targeted to FLT3 receptor kinase activity (Gilliland, G. D., and Griffin, J. D. Blood (2002) 100: 1532-42). However, the different cell signaling profiles of AML-associated mutations suggest that different AML patients will exhibit distinct responses to inhibition of FLT3 kinase activity. Pre-screening patient cell samples for a response to a FLT3 kinase inhibitor drug, for example by examining the effects of drug treatment on pSTAT5 levels, may predict whether a patient will respond to that drug.

Clinically, FLT3-TKD mutations correlate with shorter clinical response duration and worse overall survival. than for patients carrying the FLT3-TKD or wild-type alleles (Meshinchi, S and Applebaum, F Clin. Can. Res. (2009) 13: 4263-4269; Frohling et al. Prognostic significance of activating FLT3 mutations in younger adults (16 to 60 years) with acute myeloid leukemia and normal cytogenetics: a study of the AML Study Group Ulm. Blood (2002) 100: 4372-80). The presence of the FLT3-ITD mutation, and the ratio of the FLT3-ITD mutation to other FLT3 alleles are predictive of clinical response duration, cumulative incidence of relapse, and patient overall survival (Renneville, et al. (2008) 22: 915-31).

In healthy myeloid lineages, G-CSF– promotes cell proliferation through activation of JAK/STAT signaling (Touw, I. P., and Marijke, B., Granulocyte colony-stimulating factor: key factor or innocent bystander in the development of secondary myeloid malignancy? (2007). J. Natl. Cancer. Inst. 99: 183-186). A class of AML-associated mutations produces truncated G-CSF receptor, and causes hyperreponsiveness to G-CSF stimulation (Gert-Jan, M. et al. G-CSF receptor truncations found in SCN/AML relieve SOCS3-controlled inhibition of STATS but leave suppression of STATS intact. Blood (2004) 104: 667-74). Stimulation of AML patient blast cells with G-CSF in vitro revealed potentiated Stat3 and Stat5 phosphorylations that correlated with poor response to chemotherapy (fish, J. M., et al. Single Cell Profiling of Potentiated Phospho-Protein Networks in Cancer Cells. Cell (2004) 118: 217-28).

The process of angiogenesis may contribute to leukemic cell survival and a resultant resistance to chemotherapy-triggered cell death. Vascular endothelial growth factor (VEGF) is a major determinant of angiogenesis. A significant proportion of de novo and secondary AML blast populations produce and secrete VEGF protein. Moreover, blasts from some patients with newly diagnosed AML exhibit relative overexpression of VEGF Receptor R2 (Padro T, Bieker R, Ruiz S, et al. Overexpression of vascular endothelial growth factor (VEGF) and its cellular receptor KDR (VEGFR-2) in the bone marrow of patients with acute myeloid leukemia. Leukemia 2002; 16:1302). Furthermore, the incorporation of the anti-VEGF monoclonal antibody bevacizumab (Avastin) into an AML combination therapy reportedly improved tumor clearance rates. (Karp, J. E., et al. Targeting Vascular Endothelial Growth Factor for Relapsed and Refractory Adult Acute Myelogenous Leukemias. Clinical Cancer Res. (2004) 10: 3577-85).

In addition to Flt3, a variety of other genes are mutated in AML and can be divided into two classes based on whether they confer a favorable or non-favorable prognosis. Mutations in the chaperone protein-encoding gene NPM1 have been found in 30% of adults with de novo AML, but not in adults with secondary AML (Renneville, et al. (2008) 22: 915-31). Among patients with cytogenetically normal AML, NPM1 mutations are predictive of higher rates of response to induction therapy and longer overall survival, but only in the absence of FLT3-ITD mutations. Mutations in the basic region leucine zipper-encoding gene CEBPA are found in 15-19% of AML patients, and are predictive of longer overall survival and longer complete response duration (Baldus, C. D., et al. Clinical outcome of de novo acute myeloid leukemia patients with normal cytogenetics is affected by molecular genetic alterations: a concise review. *British J. Haematology* (2007) 137: 387-400).

Mutated genes that confer a non-favorable prognosis include ERG which encodes a transcription factor activated by signal transduction pathways that regulates cell differentiation, proliferation, and tissue invasion (Baldus, C. D., et al. *British J. Haematology* (2007) 137: 387-400). Overexpression of ERG in AML patients is predictive of a higher rate of relapse and shorter overall survival (Marcucci et al, Overexpression of the ETS-related gene, ERG, predicts a worse outcome in acute myeloid leukemia with normal karyotype: a Cancer and Leukemia Goruop B study. *J. Clinical Oncology* (2005) 23: 9234-42). High expression of BAALC in younger AML patients (under 60 years old) is associated with lower rates of disease-free survival and overall survival (Baldus et al, BAALC expression predicts clinical outcome of de novo acute myeloid leukemia patients with normal cytogenetics: a Cancer and Leukemia Group B study. Blood (2003) 102: 1613-18). Overexpression of MN1 in AML patients is associated with a lower rate of response to induction therapy (Baldus, C. D., et al. *British J. Haematology* (2007) 137: 387-400). Gain-of-function mutations in the receptor tyrosine kinase-encoding gene c-KIT are predictive of shorter overall complete response duration and overall survival in AML patients, and may also be predictive of response to treatment with tyrosine kinase inhibitors (Renneville, et al. (2008) 22: 915-31). Mutations in the Wlim's Tumor 1 (WT1) gene are found in 10-15% of AML cases, and in cytogenetically normal AML patients, are predictive of failure to achieve complete response to chemotherapy (Renneville, et al. (2008) 22: 915-31). Point mutations in the RAS oncogenes are found in 10-20% of AML patients, but prognostic uses of these mutations have not yet been identified (Renneville, et al. (2008) 22: 915-31).

RAS Mutations:

Ras proteins normally act as signaling switches, which alternate between the active (GTP-bound) and inactive (GDP-bound) states. Somatic point mutations in codons 12, 13 and 61 of the NRAS and KRAS genes occur in many myeloid malignancies, resulting in persistently active forms of the protein. Analyses of patients with MDS revealed a very high risk of transformation to AML in patients with N-RAS mutations, providing evidence that these mutations might represent an important progression factor in MDS. Under the two-hit model put forth by Gilliland et al., RAS mutations are likely to provide a growth advantage, which when combined with a secondary mutation that blocks differentiation, results in AML. Supporting this model, N-RAS or K-RAS mutations were found in 22% of cases of core binding factor AML (CBF-AML), which is defined by AML1-ETO or CBFβ-MYH11 gene fusions known to disrupt differentiation. (Boissel et al. Incidence and prognostic impact of c-Kit, FLT3 LIGAND, and Ras gene mutations in core binding factor acute myeloid leukemia (CBF-AML). Leukemia (2006) vol. 20 (6) pp. 965-970)

One embodiment of the invention will look at any of the cell signaling pathways described above in classifying diseases, such as AML. Modulators can be designed to investigate these pathways and any relevant parallel pathways.

In some embodiments, the invention provides a method for diagnosis, prognosis, determining progression, predicting response to treatment or choosing a treatment for AML, the method comprising the steps of (a) subjecting a cell population from the individual to a plurality of distinct modulators in separate cultures, (b) characterizing a plurality of pathways in one or more cells from the separate cultures comprising determining an activation level of at least one activatable element in at least three pathways, where the pathways are selected from the group consisting of apoptosis, cell cycle, signaling, or DNA damage pathways, and (c) correlating the characterization with diagnosis, prognosis, determining progression, predicting response to treatment or choosing a treatment for AML, in an individual, where the pathways characterization is indicative of the diagnosis, prognosis, determining progression, response to treatment or the appropriate treatment for AML. In some embodiments the activatable elements and modulators are selected from the activatable elements and modulators listed in Tables 1, 2, 3 or 5. In some embodiments, the activatable elements and modulators are selected from the activatable elements and modulators listed in Table 12 and are used to predict response duration in an individual after treatment. In some embodiments the modulator is selected from the group consisting of FLT3L, GM-CSF, SCF, G-CSF, SDF1a, LPS, PMA, Thapsigargin, IFNg, IFNa, IL-27, IL-3, IL-6, IL-10, ZVAD, $H_2O_2$, Staurosporine, Etoposide, Mylotarg, Daunorubicin, and AraC. In some embodiments, the individual has a predefined clinical parameter and the characterization of multiple pathways in combination with the clinical parameter is indicative of the diagnosis, prognosis, determining progression, predicting response to treatment or choosing a treatment for AML, in an individual. Examples of predetermined clinical parameters include, but are not limited to, age, de novo acute myeloid leukemia patient, secondary acute myeloid leukemia patient, or a biochemical/molecular marker. In some embodiments, the individual is over 60 years old. In some embodiments, the individual is under 60 years old. In some embodiments, when the individual is under 60 years old the activatable elements and modulators are selected from the activatable elements and modulators listed in Table 6. In some embodiments, where the individual is over 60 years the activatable elements and modulators are selected from the activatable elements and modulators listed in Table 7. In some embodiments, where the individual is a secondary acute myeloid leukemia patient the activatable elements and modulators are selected from the activatable elements and modulators listed in Table 8 and Table 9. In some embodiments, where the individual is a de novo acute myeloid leukemia patient the activatable elements and modulators are selected from the activatable elements and modulators listed in Table 10 and Table 11. In some embodiments, where the individual has a wild type FLT3 the activatable elements and modulators are selected from the activatable elements and modulators listed in Table 13.

In some embodiments, the activatable elements can demarkate AML cell subpopulations that have different genetic subclone origins. In some embodiments, the activatable elements can demarkate AML subpopulations that, in combination with additional surface molecules, can allow for surrogate identification of AML cell subpopulations. In some embodiments, the activatable elements can demarkate AML subpopulations that can be used to determine other protein, epitope-based, RNA, mRNA, siRNA, or metabolic markers that singly or coordinately allow for surrogate identification of AML cell subpopulations, disease stage of the individual from which the cells were derived, diagnosis, prognosis, response to treatment, or new druggable targets. In some embodiments, the pathways characterization allows for the delineation of AML cell subpopulations that are differentially susceptible to drugs or drug combinations. In other embodiments, the cell types or activatable elements from a given cell type will, in combination with activatable elements in other cell types, provide ratiometric or metrics that singly or coordinately allow for surrogate identification of AML cell subpopulations, disease stage of the individual from which the cells were derived, diagnosis, prognosis, response to treatment, or new druggable targets.

Therapeutic Agents Effective Against the Disease

Treatment of AML is divided into phases called "induction" where the goal is to induce the leukemia into "remission" (defined as no clinically detectable disease, specifically <5% marrow blasts with peripheral count recovery) and "post-induction therapy" or "consolidation" where the goal is to keep the patient in clinical remission. Approximately 75% of patients (excluding M3 AML) (<60 years old) enter into remission after one or two courses of standard AML therapy cytarabine (100-200 mg/m$^2$) coupled to an anthracycline such as daunorubicin or idarubicin, +/− thioguanine, etoposide, dexamethasone). Unfortunately only ~40% of patients (>60 years old) achieve remission despite significant toxicity.

The M3 form of AML or Promyelocytic leukemia is treated differently than the other subtypes. This form arises from the t(15;17) translocation involving the RARα gene located at 17q12. In 99 percent of the cases the translocation is t(15;17), which fuses large parts of RARα to almost the complete PML coding sequence, generating the PML-RARα fusion protein. APL is unique among the AML subtypes in that it can be cured in approximately 90% of cases using a differentiation-inducing therapy of all-trans retinoic acid, which forces the blasts to mature into granulocytes. Arsenic trioxide has also been shown to be particularly effective in the treatment of M3 AML.

If remission induction is successful, further treatment may be given to try to destroy any remaining leukemia cells and help prevent its relapse. The options for AML consolidation therapy are several courses of high-dose cytarabine (ara-C) chemotherapy, supportive care, experimental therapy, allogeneic (donor) stem cell transplant or autologous stem cell transplant.

Supportive care is important in the treatment of patients with AML. One aspect of supportive care is transfusion therapy which involves blood transfusion (red blood cells or platelets). Red blood cell transfusions are generally performed when the patient has symptoms of fatigue in combination with low red cell numbers or low red cell numbers and an inability to make new red blood cells. Platelet transfusions are generally performed when the patient is bleeding, has a low platelet count and is not producing adequate platelets to prevent bleeding, or having a procedure that may cause bleeding. Patients who receive frequent red blood cell transfusions may suffer from tissue and organ damage due to the accumulation of iron. Reactive oxygen species generated by labile plasma iron are a principal cause of cellular injury and organ dysfunction in patients with iron overload which affects survival and increases the risk of leukemia. Iron chelation therapy is recommended to the patient in these cases. This therapy uses drugs such as deferasirox, which can chelate extra iron and remove it from the body through the passage of urine.

Chemotherapy with stem cell transplant is a method for giving high dose chemotherapy followed by replacement of blood-forming cells, which have been destroyed by the cancer treatment. The stem cells of healthy donors are used for infusion in patients who have undergone chemotherapy. These reinfused stem cells grow into (and restore) the blood cells in the body. Transplantation is most beneficial in high risk patients with AML who have achieved a CR (remission) in first induction (CR1). There is controversy as to whether patients with intermediate risk AML should receive a transplant in CR1 if they have a genetically matched sibling. It is also recommended that patients with intermediate risk AML but high risk molecular markers (e.g Flt 3 ITD) undergo allogeneic transplant in CR1.

A large number of experimental treatment approaches are under the process of development. Agents under investigation include hypomethylating drugs such as Azacytidine and Decitabine which induce differentiation in the affected cells by preventing DNA methylation, Arsenic trioxide (apoptosis inducer), Sorafenib (tyrosine kinase inhibitor), gemtuzumab ozogamicin (Mylotarg), Vorinostat and valproic acid (histone deacetylase inhibitors), tipifarnib and lonafarnib (farnesyl transferase), bevacizumab (anti-VEGF monoclonal antibody that inhibits angiogenesis), ezatiostat (glutathione S1 transferase inhibitor), and clofarabine (nucleoside analog).

One embodiment of the invention involves the use of multiparameter flow cytometry to examine the biology and signalling pathways in AML to inform on likelihood of response to ara-C based induction therapy.

One embodiment of the invention involves the use of multiparametric flow cytometry to examine the biology and signalling pathways in AML to inform on the duration of response to ara-C based induction therapy.

One embodiment of the invention is a method for predicting the outcome of patients undergoing ara-c based induction therapy for AML. The method comprises classifying a hematopoietic cell, comprising subjecting a hematopoietic cell to at least one modulator that affects signaling mediated by receptors subjecting a hematopoietic cell to at least one modulator that affects signaling mediated by receptors selected from the group comprising SDF-1α, IFN-α, IFN-γ, IL-10, IL-6, IL-27, G-CSF, FLT-3L, IGF-1, M-CSF and SCF; also subjecting the hematopoietic cell to at least one modulator selected from the group comprising PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine; determining the expression level at least one protein selected from the group comprising ABCG2, C-KIT receptor, and FLT3 LIGAND receptor, determining the activation states of a plurality of activatable elements in the cell comprising; and classifying the cell based on said activation states and expression levels. Another embodiment of the invention further includes using the modulators IL-3, IL-4, GM-CSF, EPO, LPS, TNF-α, and CD40L.

One embodiment of the invention involves the use of multiparametric flow cytometry to examine the biology and signalling pathways in AML to inform on the choice of consolidation therapy in AML (chemotherapy versus hematopoietic cell transplantation)

One embodiment of the invention involves the use of multiparameter flow cytometry to examine the biology and signalling pathways in AML to inform on likelihood of response to new agents in development for the treatment of AML such as Mylotarg, tipifarnib, or other agents such as Decitabine or Azacytidine.

One embodiment of the invention involves the use of multiparametric flow cytometry to examine the biology and signalling pathways of myeloid disorders to aid in classification and therapeutic selection.

In some embodiments, the invention provides a method for predicting a response to a treatment or choosing a treatment for AML, in an individual, the method comprising the steps: (a) subjecting a cell population from the individual to at least two distinct modulators in separate cultures; (b) determining an activation level of at least one activatable element from each of at least three pathways selected from the group consisting of apoptosis, cell cycle, signaling, and DNA damage pathways in one or more cells from each said separate cultures, where the activatable elements measured in each separate culture are the same or the activatable elements measured in each separate culture are different; and (c) predicting a response to a treatment or choosing a therapeutic for AML, in the individual based on the activation level of said activatable elements. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where if the apoptosis, cell cycle, signaling, and DNA damage pathways are functional the individual can respond to treatment, and where if at least one of the pathways is not functional the individual can not respond to treatment. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, wherein if the apoptosis and DNA damage pathways are functional the individual can respond to treatment. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where a therapeutic is chosen depending of the functional pathways in the individual. In some embodiments the activatable elements and modulators are selected from the activatable elements and modulators listed in Tables 1, 2, 3 or 5. In some embodiments, the activatable elements and modulators are selected from the activatable elements and modulators listed in Table 12 and are used to predict response duration in an individual after treatment. In some embodiments the modulator is selected from the group consisting of FLT3L, GM-CSF, SCF, G-CSF, SDF1a, LPS, PMA, Thapsigargin, IFNg, IFNa, IL-27, IL-3, IL-6, IL-10, ZVAD, $H_2O_2$, Staurosporine, Etoposide, Mylotarg, Daunorubicin, and AraC.

In some embodiments, the invention provides a method of predicting a response to a treatment or choosing a treatment for AML, in an individual, the method comprising the steps of: (a) subjecting a cell population from said individual to at least three distinct modulators in separate cultures, wherein: (i) a first modulator is a growth factor or a mitogen, (ii) a second modulator is a cytokine, (iii) a third modulator is a modulator that slows or stops the growth of cells and/or induces apoptosis of cells or, the third modulator is an inhibitor; (b) determining the activation level of at least one activatable element in one or more cells from each of the separate cultures, where: (i) a first activatable element is an activatable element within the PI3K/AKT, or MAPK pathways and the activation level is measured in response to the growth factor or mitogen, (ii) a second activatable element is an activatable element within the JAK/STAT pathways and the activation level is measured in response to the cytokine, (iii) a third activatable element is an activatable element within an apoptosis pathway and the activation level is measured in response to the modulator that slows or stops the growth of cells and/or induces apoptosis of cells, or the third activatable element is activatable element within the phospholipase C pathway and the activation level is measured in response to the inhibitor, or the third activatable element is a phosphatase and the activation level is measured in response to the inhibitor; and (c) correlating the activation levels of said activatable elements with a response to a treatment or with choosing a treatment for AML in the individual. Examples of predefined clinical parameters include age, de novo acute myeloid leukemia patient, secondary acute myeloid leukemia patient, or a biochemical/molecular marker. In some embodiments, the cytokine is selected from the group consisting of G-CSF, IFNg, IFNa, IL-27, IL-3, IL-6, and IL-10. In some embodiments, the growth factor is selected from the group consisting of FLT3L, SCF, G-CSF, and SDF1a. In some embodiments, the mitogen is selected from the group consisting of LPS, PMA, and Thapsigargin. In some embodiments, the modulator that slows or stops the growth of cells and/or induces apoptosis of cells is selected from the group consisting of Staurosporine, Etoposide, Mylotarg, Daunorubicin, and AraC.

Myelodysplastic Syndromes (MDS)

Myelodysplastic syndromes (MDS) constitute a heterogeneous group of hematologic disorders characterized by ineffective hematopoiesis and dysplasia with varying risks of transformation to acute myeloid leukemia (AML). In addition, evidence of a cellular immunologic response has been implicated in the pathogenesis of a subset of MDS patients (Melchert, et al., Current Opinion in Haematology 2007 Vol. 14, p 123-129).

MDS is predominantly a disease of the elderly. Median age of diagnosis MDS is 68 years. MDS has an overall age-adjusted annual incidence of 3.3 per 100,000, and the rate increases with age to 10 per 100,000 among those aged 70 years or older. Approximately 55% of patients die within 3 years of diagnosis. (Rollison et al. Epidemiology of myelodysplastic syndromes and chronic myeloproliferative neoplasms in the United States, 2001-2004, using data from the NAACCR and SEER programs. Blood (2008) vol. 112 (1) pp. 45-52) Patients with high-risk MDS generally survive for approximately one year. Morbidity and mortality are a result of complications of cytopenias or transformation to acute myeloid leukemia. One of the major morbidities of MDS found in the vast majority of (~60-80%) patients is symptomatic anemia, with associated fatigue. Other cytopenias include neutropenia (~50-60%) and thrombocytopenia (~40-60%). Dysfunctional neutrophils cause an increased risk of infection. Decreased platelets, as mentioned in the AML section, are associated with bleeding. (PETER L. GREENBERG, et. al. Myelodysplastic Syndromes. *The American Society of Hematology.* 2002, p. 136-61.)

Causes

The initiating event for MDS is DNA injury in a hematopoietic progenitor cell. The disruption of genes that control the balance of growth and differentiation results in the clonal proliferation of defective progeny, which are eliminated by apoptosis before they fully mature. The excessive apoptosis contributes to the peripheral cytopenias characteristic of the MDS phenotype. Accumulated genetic damage, particularly anti-apoptotic mutations, may result in neoplastic transformation to acute leukemia. (AUI C, et. al. Pathogenesis, etiology and epidemiology of myelodysplastic syndromes. *Haematologica.* 1998, vol. 83, p. 71-86; HELLSTROM-LINDBERG E, et. al. Achievements in understanding and treatment of myelodysplastic syndromes. Hematology (*American Society of Hematology Education Program*), 2000, p. 110-132; BARRCTT J, et al. Myelodysplastic syndrome and aplastic anemia: diagnostic and conceptual uncertainties. *Leukemia Research,* 2000, vol. 24, p. 595-596.)

Similar to AML, MDS may develop in individuals who have been exposed to environmental or occupational toxins that increase the likelihood of somatic mutations, including, but not limited to: Cancer chemotherapy, e.g., alkylating agents and topoisomerase II inhibitors, excess ionizing radiation, e.g., atomic bombs and radiotherapy for malignant diseases, and industrial chemicals, e.g., benzene, pesticides, fertilizers, herbicides, heavy metals, stone and cereal dusts, nitro-organic explosives, petroleum and diesel derivatives, and organic solvents (benzene, toluene, xylene, and chloramphenicol).

Symptoms

MDS is characterized by cytopenias (anemia, neutropenia, thrombocytopenia) of any or all of the three hematopoietic lineages (red blood cells, white blood cells and platelets) with varying degrees of severity. The common symptoms include fatigue, bruising, and/or bleeding, pallor, ecchymosis, epistaxis, gingival bleeding, and bacterial infections. Patients may be asymptomatic at diagnosis. Bleeding (due to lack of platelets) and infection (due to lack of WBCs) are the two most serious complications in MDS patients. MDS is sometimes underdiagnosed, since patients suffering from mild to moderate anemia are attributed to a chronic disease or a mild renal insufficiency.

Diagnosis

A combination of cellular morphology (to detect multilineage dysplasia in the bone) and cytogenetics (to detect characteristic clonal abnormalities) is used for the diagnosis of MDS. Basic diagnostic criteria involve microscopic morphological examination of bone marrow using a variety of histological stains. Dysplasia, particularly of megakaryocytes, evidence of disruption of the normal marrow architecture, such as abnormal localization of immature precursors (ALIP), and an estimate of the blast percentage are important diagnostic findings in bone marrow examinations. Bone marrows are also examined for dysgranulopoiesis, dysmegakaryocytopoiesis, and dyserythropoiesis. Dysgranulopoiesis include abnormalities in primary granules such as decreased or absent secondary granules, large granules or decreased staining, and nuclear abnormalities or increased blasts. Examples of dysmegakaryocytopoiesis include micromegakaryocytes, large mononuclear or binuclear forms, multiple small nuclei, and reduced numbers. Dyserythropoiesis is characterized by more than 15 percent ringed sideroblasts, nuclear fragments, multiple nuclei, nuclear lobation, internuclear bridges, megaloblastic erythropoiesis, macronormoblastic erythropoiesis, irregular cytoplasmic staining, or less than 5 percent erythroid cells. Such morphologic dysplasias are however not specific for MDS. Mild megaloblastic changes without dyspoiesis in other cell lines are not considered sufficient for a diagnosis of MDS.

In addition to a bone marrow aspirate with biopsy, and a CBC with differential, one usually orders a reticulocyte count, serum epo, ferritin, B12, and folate to differentiate other causes and to optimize treatment of the anemia. Other helpful tests in MDS include HLA typing (if platelet support and/or potential marrow transplant), HLA-DR 15 typing (for possible administration of immunosuppressive therapies), FLAER test (to differentiate MDS from a PNH clone), and a JAK2 mutation if the patient has thrombocytosis (to differentiate essential thrombocythemia).

Deletions or amplifications of large chromosomal regions are more commonly observed in MDS, compared with the balanced translocations commonly observed in de novo AML. Cytogenetic data help stratify patients in terms of diagnosis and evaluating prognosis for survival and risk of transformation to AML (HOFMANN W K, et al. Myelodysplastic syndrome. Annual Review of Medicine. 2005, vol. 56, p. 1-16). Characteristic chromosomal deletions involve chromosome 5 [del(5q),-5], chromosome 11 [del(11q)], chromosome 12 [del(12q)], chromosome 20 [del(20q)], chromosome 7 [del(7q),-7], chromosome 17 [del(17p)], and chromosome 13 [del(13q)]. Other frequent structural and/or numerical chromosomal aberrations include trisomy 8, trisomy 21, and inversion 3(q21q26). Rare reciprocal translocations include t(1;7)(q10;p10), t(1; 3)(p36;q21), t(3;3)(q21;q26), t(6;9) (p23;q34), and t(5; 12)-fusion between PDGFR-β and TEL (ETV-6), (q33;p13); t(5;7)(q33;11.2).

Deletion of chromosomal region 5q31 (5q-) is the most frequent genetic lesion in MDS and is present in more than 20 percent of MDS patients, garnering its own WHO classification. The pathogenic event associated with this genetic lesion has been traced to the hemizygous deletion of RPS14, which encodes a ribosomal subunit protein, and is also implicated in Diamond-Blackfan anemia. (Ebert B L, et al. Identification of RPS14 as a 5q-syndrome gene by RNA interference screen. *Nature,* 2008, Vol. 451, No. 17, pp 335-340)

A chromosomal abnormality commonly implicated in the progression of MDS is monosomy 7q. (STEPHENSON J, et al. Possible co-existence of RAS activation and monosomy 7 in the leukemic transformation of myelodysplastic syndromes. *Leukemia Research,* 1995, vol. 19, p. 741-8). While 5q- is associated with favorable prognosis, uniparental disomy in 7q confers substantially lower prognosis (3 months vs. 39 months survival). (Itzykson R, et al. Meeting report: myelodysplastic syndromes at ASH 2007. Leukemia. 2008, Vol. 22, pp 893-897)

A substantial fraction of MDS patients appear cytogenetically normal because they harbor submicroscopic chromosomal lesions. Recently, SNP array-based methods have been used to detect cryptic genetic lesions in this class of patients, although this is not yet standard in clinical practice. (Itzykson R, et al. Meeting report: myelodysplastic syndromes at ASH 2007. Leukemia. 2008, Vol. 22, pp 893-897). Furthermore, molecular genotyping assays are now being used experimentally to screen for known pathogenic mutations to help stratify MDS patients.

In the context of MDS, multiparameter flow cytometry is used to measure abnormal light scatter properties of dysplastic cells, abnormal antigen density, loss of antigens, and asynchronous expression of antigens which are normally co-expressed during myeloid maturation, and these parameters may correlate to the grade of the disease. (STETLER STEVENSON M, et al. Diagnostic utility of flow cytometric immunophenotyping in myelodysplastic syndromes. *Blood.* 2001, vol. 98, p. 979-987.)

One embodiment of the invention combines one or more of these existing tests with the analysis of signalling mediated by receptors to diagnose disease expecially MDS, AML, or MPN. All tests may be performed in one location and provided as a single service to physicians or other caregivers.

Cell-Signaling Pathways and Differentiating Factors Involved

Regulation of hematopoiesis in MDS is complex and multiple factors are involved. Genetic alterations in signaling molecules have been extensively studied in MDS. These molecules include transcription factors, receptors for growth factors, $RAS^-$ signaling molecules, and cell cycle regulators.

In the early stages of MDS, there is an increased frequency of apoptosis resulting in intramedullary apoptotic bodies. Advanced MDS, which may transform to AML, is characterized by increased proliferation and antiapoptotic factors, such as mutations in p53, RAS, C-MPL or FMS. (Aul et al. Evaluating the prognosis of patients with myelodysplastic syndromes. Ann Hematol (2002) vol. 81 (9) pp. 485-97)

Genetic alterations in the RAS signaling pathway are frequently seen in MDS. The RAS signaling pathway normally promotes cellular proliferation and differentiation. By contrast, pathogenic RAS pathway mutations generally cause continuous kinase activity and signal transduction. The cell surface receptor for macrophage colony stimulating factor (M-CSF), encoded by the FMS gene, normally promotes cellular proliferation and differentiation of monocyte and macrophages, and is upstream of RAS signaling. Activating mutations in this gene are found in 10% of MDS cases, and are associated with poor survival and increased risk of transformation to AML. (PADUA R A, et al. RAS, FMS and p53 mutations and poor clinical outcome in myelodysplasias: a 10-year follow-up. *Leukemia,* 1998, vol. 12, p. 887-892; TOBAL K, et al. Mutation of the human FMS gene (M-CSF receptor) in myelodysplastic syndromes and acute myeloid leukemia. *Leukemia,* 1990, vol. 4, p. 486-489.)

Activating mutations in FLT3, a receptor-type tyrosine kinase also upstream of RAS signaling, have been reported in 3-5% of MDS cases. (Georgiou et al. Serial determination of FLT3 mutations in myelodysplastic syndrome patients at diagnosis, follow up or acute myeloid leukaemia transformation: incidence and their prognostic significance. Br J Haematol (2006) vol. 134 (3) pp. 302-6) Inactivation of the neurofibromatosis type 1 (NF1) gene, normally a negative regulator of RAS signaling, has also been implicated in the progression of MDS. (Stephenson J, et al. Possible co-existence of RAS activation and monosomy 7 in the leukemic transformation of myelodysplastic syndromes. *Leukemia Res* 1995; 19:741-8). Gain-of-function mutations have also been reported in PTPN11 in patients with MDS. (NEUBAUER A, et al. Mutations in the ras proto-oncogenes in patients with myelodysplastic syndromes. *Leukemia.* 1994, vol. 8, p. 638-641). Among the RAS genes themselves, mutations of the N-ras gene are the most frequent and are detected in 20 to 30 percent of human leukemias and approximately 16 percent of MDS cases. K-RAS mutations are found at approximately half that frequency. The majority of studies suggest that RAS mutations in MDS are associated with poor survival and increased probability of developing AML. (YUNIS J J, et al. Mechanisms of ras mutation in myelodysplastic syndrome. *Oncogene.* 1989, vol. 4, p. 609-614; Aul et al. Evaluating the prognosis of patients with myelodysplastic syndromes. Ann Hematol (2002) vol. 81 (9) pp. 485-97).

Although less frequently, AML1, C/EBPα, TEL (ETV6) and p53 genes are also a target of mutations in MDS. AML1-binding sites exist upstream of several genes encoding factors and receptors that determine the lineage specificity of hematopoietic cells. (OKUDA T, et al. AML1, the target of multiple chromosomal translocations in human leukemia, is essential for normal fetal liver hematopoiesis. *Cell.* 1996, vol. 84, p. 321-30.) C/EBPα is an important mediator of granulocyte differentiation and regulates the expression of multiple granulocyte-specific genes including the granulocyte colony-stimulating factor (G-CSF) receptor, neutrophil elastase and myeloperoxidase. C/EBPα knockout mice display a profound block in granulocyte differentiation (COLLINS S J, et al. Multipotent hematopoietic cell lines derived from C/EBPα (−/−) knockout mice display granulocyte macrophage-colony-stimulating factor, granulocyte-colony-stimulating factor and retinoic acid-induced granulocytic differentiation. *Blood.* 2001, vol. 98, p. 2382-8). This suggests that any mutation in C/EBPα will result in defective hematopoiesis. TEL function is essential for the establishment of hematopoiesis of all lineages in the bone marrow, suggesting a critical role for TEL in the normal transition of the hematopoietic activity from fetal liver to bone marrow. Experiments conducted on the role of TEL genes indicate an ineffective hematopoiesis in the case of an alteration in these genes. (WANG L C, et al. The TEL/ETV6 gene is required specifically for hematopoiesis in the bone marrow. *Genes and Development.* 1998, vol. 12, p. 2392-402). Mutations or deletions causing inactivation of the p53 gene in both the alleles have been shown to predispose the cells to neoplastic transformation. Inactivation is detected in 5 to 10 percent of cases of clinically advanced MDS, indicating that p53 mutations may play a role in leukemic progression of MDS. (SUGIMOTO K, et al. Mutations of the p53 gene in MDS and MDS-derived leukemia. Blood. 1993, vol. 81, p. 3022-6.)

Apoptotic genes (increased bcl-2 expression) (KUROTAKI H, et al. Apoptosis, bcl-2 expression and p53 accumulation in MDS, MDS derived acute myeloid leukemia and de novo acute myeloid leukemia. *Acta Haematologica,* 2000, vol. 102, p. 115-123.) and mutations in genes including CHK2, p53, MLL have been implicated in the pathogenesis of MDS (HOFMANN W K, et al. Mutation analysis of the DNA-damage checkpoint gene CHK2 in myelodysplastic syndromes and acute myeloid leukemias. *Leukemia Research,* 2001, vol. 25, p. 333-338; KIKUKAWA M, et al. Study of p53 in elderly patients with myelodysplastic syndromes by immunohistochemistry and DNA analysis. *American Journal of Pathology.* 1999, vol. 155, p. 717-721; POPPE B, et al. Expression analyses identify MEL as a prominent target of 11q23 amplification and support an etiologic role for MLL gain of function in myeloid malignancies. *Blood.* 2004, vol. 103, p. 229-235.)

Dysregulation of genes that encode angiogenic factors involved in the growth of hematopoietic cells may play important role in pathogenesis of MDS. (PRUNERI G, et al. Angiogenesis in myelodysplastic syndromes. *British Journal of Cancer,* 1999, vol. 81, p. 1398-1401.) The immunomodulatory cytokine, TNF-α has been shown to express strong inhibitory activity in hematopoiesis. (BROXMEYER H E, et al. The suppressive influences of human tumor necrosis factors on bone marrow hematopoietic progenitor cells from normal donors and patients with leukemia: synergism of tumor necrosis factor and interferon-gamma. *Journal of Immunology.* 1986, vol. 36, p. 4487-4495.) Other cytokines reportedly involved in the processes leading to ineffective hematopoiesis in MDSs include TGF-β, IL-1β, and TNF-related signaling molecules TRADD/FADD, RIP, and TNF-related apoptosis inducing ligand (TRAIL) (SAWANOBORI M, et al. Expression of TNF receptors and related signaling molecules in the bone marrow from patients with myelodysplastic syndromes. *Leukemia Research,* 2003, vol. 27, p. 583-591; PLASILOVA M, et al. TRAIL (Apo2L) suppresses growth of primary human leukemia and myelodysplasia progenitors. *Leukemia,* 2002, vol. 16, p. 67-73.)

One embodiment of the invention will look at any of the cell signaling pathways described above in classifying diseases, such as MDS. Modulators can be designed to investigate these pathways and any relevant parallel pathways.

In some embodiments, the invention provides a method for diagnosing, prognosing, determining progression, predicting response to treatment or choosing a treatment for MDS or rationale combinations of drugs, or identification of new potentially druggable targets the method, the method comprising the steps of (a) subjecting a cell population from the individual to a plurality of distinct modulators in separate cultures, (b) characterizing a plurality of pathways in one or more cells from the separate cultures comprising determining an activation level of at least one activatable element in at least three pathways, where the pathways are selected from the group consisting of apoptosis, cell cycle, signaling, or DNA damage pathways, and (c) correlating the characterization with diagnosing, prognosing, determining progression, predicting response to treatment or choosing a treatment for MDS, in an individual, where the pathways characterization is indicative of the diagnosing, prognosing, determining progression, response to treatment or the appropriate treatment for MDS. In some embodiments, the individual has a predefined clinical parameter and the characterization of multiple pathaways in combination with the clinical parameter is indicative of the diagnosis, prognosis, determining progression, predicting response to treatment or choosing a treatment for MDS, in an individual. Examples of predetermined clinical parameters include, but are not limited to, biochemical/molecular markers.

In some embodiments, the activatable elements can demarkate MDS cell subpopulations that have different genetic subclone origins. In some embodiments, the activatable elements can demarkate MDS subpopulations that, in combination with additional surface molecules, can allow for surrogate identification of MDS cell subpopulations. In some embodiments, the activatable elements can demarkate MDS subpopulations that can be used to determine other protein, epitope-based, RNA, mRNA, siRNA, or metabolic markers that singly or coordinately allow for surrogate identification of MDS cell subpopulations, disease stage of the individual from which the cells were derived, diagnosis, prognosis, response to treatment, or new druggable targets. In some embodiments, the pathways characterization allows for the delineation of MDS cell subpopulations that are differentially susceptible to drugs or drug combinations. In other embodiments, the cell types or activatable elements from a given cell type will, in combination with activatable elements in other cell types, provide ratiometric or metrics that singly or coordinately allow for surrogate identification of MDS cell subpopulations, disease stage of the individual from which the cells were derived, diagnosis, prognosis, response to treatment, or new druggable targets.

Therapeutic Agents Effective Against the Disease

There are many treatments for MDS. The treatment option typically includes choice of therapy on the basis of risk factors such as patient's age, MDS subtype, and prognostic score. The most commonly used prognostic score for MDS, the International Prognostic Scoring System (IPSS), is calculated based on bone marrow blast percentage, cytogenetics, and the number of cytopenias. Depending on the IPSS score and the patient's symptoms, different treatment paths are pursued.

Supportive care is important in the treatment of all patients with MDS. One aspect of supportive care is transfusion therapy which involves blood transfusion (red blood cells or platelets). Red blood cell transfusions are generally performed when the patient has symptoms of fatigue in combination with low red cell numbers or low red cell numbers and an inability to make new red blood cells. Platelet transfusions are generally performed when the patient is bleeding, has a low platelet count and is not producing adequate platelets to prevent bleeding, or having a procedure that may cause bleeding. Patients who receive frequent red blood cell transfusions may suffer from tissue and organ damage due to accumulation of iron. Reactive oxygen species generated by labile plasma iron are a principal cause of cellular injury and organ dysfunction in patients with iron overload which affects survival and increases the risk of leukemia. Iron chelation therapy is recommended to the patient in these cases. This therapy uses drugs such as deferasirox, which can chelate extra iron and remove it from the body through the urinary passage.

Low-risk MDS patients are generally empirically treated with growth factor therapy. Erythropoietin (EPO) therapy is most effective in patients with serum epo <200 IU/L, low-int-1 IPSS, and an absence of transfusion requirement. A recent study of 403 patients with MDS s/p EPO+/−GCSF showed a 50% overall response rate to this therapy. (Park et al Blood 2008 111:574-582)

EPO is thought to overcome reduced sensitivity of erythroid precursors to EPO at the initial level of signal transduction. (Hoefsloot L H, et al. Erythropoietin-induced activation of STAT5 is impaired in the myelodysplastic syndrome. *Blood.* 1997, vol. 89, p. 1690-1700). Reports show a comparable erythroid response rate when using EPO alone or EPO plus filgrastim (G-CSF) (response rate 49 percent versus 51 percent), whereas higher EPO dose schedules were found to have higher response rate than standard EPO dose schedules. (Moyo V M et al. Treating the anemia of MDS with erythropoietin: Impact of higher dose compared to combination with G/GM-CSF. *Proceeding from the American Society of Clinical Oncology Conference. Chicago, Ill.* 2007. Abstract 7082.)

Hematide, a novel synthetic pegylated peptidic compound, acts as an erythropoiesis stimulating agent that binds to and activates the erythropoietin receptor. It could restore hemoglobin to the target range and eliminate the need for red blood cell transfusions, though hematide is immunologically distinct from EPO (http://www.takeda.com/press/article_28646.html). Another growth factor thrombopoeitin (TPO), the ligand for the c-mpl receptor, is a major regulator of platelet production in vivo. It has been indicated in several studies that TPO increases platelet counts, platelet size, and increases isotope incorporation into platelets of recipient animals. Platelet count begins to increase after 3 to 5 days. TPO is thought to affect megakaryocytopoiesis in several ways: (1) it increases the size and number of megakaryocytes; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow. Romiplostim, a recombinant Fc-peptide fusion protein, is a thrombopoietin receptor agonist which can be used for identification of treatments effective in improving thrombocytopenia. It has recently been used in Phase II trials for MDS. However, its use is complicated by side effects such as disturbances of the gastrointestinal system, and arthralgia.

Immunosuppressive therapy (IST) has emerged as an effective therapy for a subset of MDS patients with clonal amplification of T lymphocytes. T cell clones have been identified in 50% of MDS patients and have been implicated in suppression of hematopoiesis through CD8 cytotoxic T lymphocytes. Immunosuppressive agents like anti-thymocyte globulin, alone or in combination with cyclosporine, inhibit the effects of T-cell clones. Patients enriched for response to this therapy include the younger age group ($\leq 60$ years), those requiring little to nored blood cell transfusion, those with marrow hypocellularity, those with the presence of paroxysmal nocturnal hemoglobinuria clone, and those with human leukocyte antigen (HLA)-DR15 phenotype. using this enrichment criteria, recent data show a 30% response rate with improved overall survival and a decrease in transformation to AML (Sloand et al JCO 2008 26:2505-2511)

The immunomodulatory drugs are agents that target both the MDS clone and the bone marrow microenvironment and have notable erythropoietic activity in patients with low-risk MDS. Lenalidomide, an amino-derivative of thalidomide with greater potency and minimal neurotoxicity, has erythropoietic and cytotoxic remitting activity. The efficacy of lenalidomide is greatest in patients with deletions of chromosome 5q. In this subset, lenalidomide produces and maintains red cell transfusion independence in the majority of low-risk patients for about two years. In a study of 148 patients with MDS RBC dependent anemia and 5q-, 67% of patients achieved a major erythroid response defined as RBC transfusion independence and an absence of any RBC transfusion during any consecutive 56 days (8 weeks) and Hgb increase of at least 1 g/dL during the treatment period (List A, et al. Lenalidomide in the myelodysplastic syndrome with chromosome 5q deletion. *New England Journal of Medicine*. 2006, vol. 355, p. 1456-1465.) Among the vast majority of MDS patients (over 80 percent) without the 5q-chromosomal defect, only about 26% respond to lenalidomide. (Blood 2008 111:86-93 (Raza et al)

A recent study of gene expression profiling identified a cohesive set of erythroid-specific genes used as erythroid gene expression signature to predict the response of lenalidomide. The reduced expression of the erythroid gene signature in responders suggested a defect in erythroid differentiation. This suggests that it might be possible to use the response signature to develop a test that can predict the patients with MDS who will benefit from treatment with lenalidomide. (Benjamin L. Ebert et al. An Erythroid Differentiation Signature Predicts Response to Lenalidomide in Myelodysplastic Syndrome. *PLoS Medicine*. February 2008. Vol. 5, no. 2, p. 312-322).

Hypomethylating drugs such as Azacytidine and Decitabine have been approved for all IPSS scores of MDS. This class of drugs is thought to induce differentiation in the affected cells by preventing DNA methylation. Azacytidine is the first FDA-approved drug for the treatment of MDS. It is a pyrimidine analog that inhibits DNA methyl transferase. A CALGB study indicates that treatment with azacytidine produced higher response rate, improved quality of life, reduced risk of transformation to AML and extended life expectancy. (Silverman L R et al. Randomized controlled trial of azacytidine in patients with the myelodysplastic syndrome: a study of the cancer and leukaemia group B. *Journal of Clinical Oncology*. 2002. vol. 20, p. 2429-2440). Median survival was significantly prolonged to 24.4 months as compared to 15 months with conventional care, with greatest improvement observed in patients with chromosome 7 abnormalities, including monosomy 7. (Lim Z Y et al. Outcomes of MDS patients with chromosome abnormalities treated with 5-azacytidine. *Program and abstracts of 49$^{th}$ Annual Meeting of the American Society of haematology*. December 2007. Atlanta, Ga. Abstract 1449). Further azacytidine treatment delays the progress of MDS to AML to 13 months as compared to 7.6 months in patients given only conventional care. A relatively higher number of patients treated with azacytidine achieved complete remission (CR) and hematologic improvements as compared to best supportive care. Decitabine (DNA methyl transferase inhibitor) is the second FDA-approved drug for treatment of patients with MDS. 170 patients were studied with an overall response rate of 17% (9% CR and 8% PR) with a median duration of response of 10.3 months and a tend toward increased time to AML transformation(Cancer 2006 106:1794-80 (Kantarjian et al)

Combination of hypomethylating agents with histone deacetylase (HDAC) inhibitors (MGCD-0103) is under trial and preliminary data suggests major responses including CR, partial remission or marrow CR in 35% of patients with refractory MDS and 50% of previously untreated patients. (Itzykson et al. Meeting report: myelodysplastic syndromes at ASH 2007. Leukemia (2008) vol. 22 (5) pp. 893-7).

Chemotherapy with stem cell transplants is a method for giving high dose chemotherapy and replacing blood-forming cells, which have been destroyed by the cancer treatment. The stem cells of healthy donors are used for infusion in patients who have undergone chemotherapy. These reinfused stem cells grow into (and restore) the blood cells in the body. Although transplant can be curative in MDS, it is often limited by the patient's performance status and the availability of donors. Transplantation appears to be most beneficial for children with refractory cytopenias and adults with chemotherapy-related MDS, which represent only a small fraction of the MDS population. (Itzykson et al. Meeting report: myelodysplastic syndromes at ASH 2007. Leukemia (2008) vol. 22 (5) pp. 893-7).

A large number of treatment approaches are under the process of development. Agents under investigation include Arsenic trioxide (apoptosis inducer), Sorafenib (tyrosine kinase inhibitor), Vorinostat and valproic acid (histone deacetylase inhibitors), tipifarnib and lonafarnib (farnesyl transferase), bevacizumab (anti-VEGF monoclonal antibody that inhibits angiogenesis), FG-2216 (hypoxia-inducible factor stabilizer), ezatiostat (glutathione S1 transferase inhibitor), clofarabine (nucleoside analog). (ALAN F. LIST, et al. Insights into the pathogenesis, Classification, and treatment of Myelodysplastic Syndromes, Semin. Hematol. 2008 January; 45(1) 31-8). Pharmacologic differentiators, such as TLK199, (liposomal glutathione derivative) mediate proliferation and differentiation of myeloid precursors and production of GM-CSF. A TLK-199 trial on MDS patients showed hematologic improvement in all three hematopoietic lineages—erythrocytes, neutrophils, platelets. Toxicities were limited to infusion reactions, nausea, chills and bone pain. The thrombopoiesis-stimulating agent, IL-11, is an indirect thrombopoietic cytokine that helps to combat platelet dysfunction and thrombocytopenia in MDS. The major side effects of this drug include fever, fluid retention, peripheral edema, pleural effusions and atrial arrhythmias. Pegylated, recombinant human megakaryocyte growth and development factor (PEG-rHuMGDF) stimulates megakaryocyte and platelet production by binding to c-Mpl receptors.

One embodiment of the invention involves the use of multiparameter flow cytometry to examine the biology and signalling pathways in myelodysplastic syndrome to classify MDS identification of possible druggable targets, and inform on likelihood of response to agents such as growth factors (e.g. EPO), immunosuppressive agents (e.g. ATG+/−CsA), epigenetic modulators (e.g. hypomethylators Azacytidine and Decitabine and HDAC inhibitors), immune-modulators (e.g. Lenalidomide), or a rationale combination of the above.

One embodiment of the invention involves the use of multiparametric flow cytometry to examine the biology and signalling pathways in myelodysplastic syndrome to determine likelihood of progression to AML.

One embodiment of the invention involves the use of multiparametric flow cytometry to examine the biology and signalling pathways in myelodysplastic syndrome to determine likelihood of response to agents in development for the treatment of MDS One embodiment of the invention involves the use of multiparametric flow cytometry to examine the biology and signalling pathways of myeloid disorders to aid in classification and therapeutic selection and identification of new potentially druggable targets.

In some embodiments, the invention provides a method for predicting a response to a treatment or choosing a treatment for MDS or designing rationale combinations of drugs, in an individual, in an individual, the method comprising the steps: (a) subjecting a cell population from the individual to at least two distinct modulators in separate cultures; (b) determining an activation level of at least one activatable element from each of at least three pathways selected from the group consisting of apoptosis, cell cycle, signaling, and DNA damage pathways in one or more cells from each said separate cultures, where the activatable elements measured in each separate culture are the same or the activatable elements measured in each separate culture are different; and (c) predicting a response to a treatment or choosing a therapeutic for MDS, in the individual based on the activation level of said activatable elements. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where if the apoptosis, cell cycle, signaling, and DNA damage pathways are functional the individual can respond to treatment, and where if at least one of the pathways is not functional the individual can not respond to treatment. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where if the apoptosis and DNA damage pathways are functional the individual can respond to treatment. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where a therapeutic is chosen depending on the functional pathways in the individual.

In some embodiments, the invention provides a method of predicting a response to a treatment or choosing a treatment for MDS, in an individual, the method comprising the steps of: (a) subjecting a cell population from said individual to at least three distinct modulators in separate cultures, wherein: (i) a first modulator is a growth factor or mitogen, (ii) a second modulator is a cytokine, (iii) a third modulator is a modulator that slows or stops the growth of cells and/or induces apoptosis of cells or, the third modulator is an inhibitor; (b) determining the activation level of at least one activatable element in one or more cells from each of the separate cultures, where: (i) a first activatable element is an activatable element within the PI3K/AKT, or MAPK pathways and the activation level is measured in response to the growth factor or mitogen, (ii) a second activatable element is an activatable element within the STAT pathway and the activation level is measured in response to the cytokine, (iii) a third activatable element is an activatable element within an apoptosis pathway and the activation level is measured in response to the modulator that slows or stops the growth of cells and/or induces apoptosis of cells, or the third activatable element is activatable element within the phospholipase C pathway and the activation level is measured in response to the inhibitor, or the third activatable element is a phosphatase and the activation level is measured in response to the inhibitor; and (c) correlating the activation levels of said activatable elements with a response to a treatment or with choosing a treatment for MDS in the individual. Examples of predefined clinical parameters include age, de novo acute myeloid leukemia patient, secondary acute myeloid leukemia patient, or a biochemical/molecular marker. In some embodiments, the cytokine is selected from the group consisting of G-CSF, IFNg, IFNa, IL-27, IL-3, IL-6, and IL-10. In some embodiments, the growth factor is selected from the group consisting of FLT3L, SCF, G-CSF, and SDF1a. In some embodiments, the mitogen is selected from the group consisting of LPS, PMA, and Thapsigargin. In some embodiments, the modulator that slows or stops the growth of cells and/or induces apoptosis of cells is selected from the group consisting of Staurosporine, Etoposide, Mylotarg, Azacitidine, Dacatabine, Daunorubicin, and AraC.

Myeloproliferative Disease/Myeloproliferative Neoplasm

Myeloproliferative Neoplasms (MPN) are a group of disorders that cause an overproduction of blood cells in the bone marrow. MPN include polycythemia vera (PV), primary or essential thrombocythemia (ET), and primary or idiopathic myelofibrosis (PMF). The incidence of MPN in the USA is 1.3 per 100,000 per year, with a maximum peak at the age of 25-60 years. (PCT/WO 2007085958 A2/3 (CONSORZIO PER GLI STUDI UNI IN) Feb. 8, 2007)

MPN predominantly occur in people older than 60 years, though 20 percent of cases occur in individuals of 40 years or less. Men are two times more likely to develop PV than women. Environmental factors, such as exposure to chemicals in hair dyes or to electrical wiring increase an individual's susceptibility to MPN.

Causes

The biology surrounding MPN remained unclear until the discovery of mutations in the JAK2-STATS pathway. JAK2V617F and JAK2 exon 12 mutant kinases can bind cytokine receptors and are phosphorylated in the absence of ligand. This leads to ligand independent signal transduction of the erythropoietin and other receptors. MPLW515L/K mutant thrombopoietin receptors are able to phosphorylate wild-type JAK2 in the absence of TPO again leading to constitutive activation. (Baxter et al in Lancet 4/2005, Skoda etal reported in the NEJM 5/05, Vainchenker et al Nature 5/05, Gilliland et al Ca Cell 5/05, Zhao et al JBC 6/05, PLOS 2006 3(7)e270 Gilliland & Levine labs Blood 2006 108:3472-3476 Tefferi Gilliland Although JAK2V617F mutation accounts for >90% of patients with PV, the mutation is absent in >50% of patients with ET and PMF suggesting that other as yet undiscovered genetic aberrations that lead to EPO or TPO receptor pathway activation exist and participate in the pathogenesis of these disorders.

Symptoms

Many individuals with MPN are asymptomatic at the time of diagnosis. Depending on the disorder, symptoms may vary from person to person. All patients with MPN have increased risk of heart disease, stroke, or other thromboses. Similar to leukemia, a common sign for the presence of PV and PMF is an enlarged spleen. Polycythemia vera (PV) is characterized by an increased production of blood cells, particularly red blood cells, by the bone marrow. This overproduction can lead to an increase in blood viscosity, which can impair the functioning of the heart or the brain. Other symptoms may include fatigue, general malaise, difficulty in breathing, intense itching after bathing in warm water, bruising or bleeding Polycythemia vera has a survival rate of between 10 and 20 years, with the longest survival occurring in young age groups.

Primary or essential thromboycythemia is a result of overproduction of platelet cells. Symptoms include heart attack or stroke, headache, burning or throbbing pain, redness and swelling of hands and feet, bruising, gastrointestinal bleeding or blood in the urine. Similar to PV, it occurs primarily after 60 years of age, but some cases (20%) occur in persons under 40 years of age. Women are 1.5 times more likely to develop ET than men. Individuals with ET have normal life expectancy with only a low risk of developing cancer.

Primary or idiopathic myelofibrosis (also known as myelosclerosis) is caused by overproduction of collagen or fibrous tissue in the bone marrow. Other symptoms include fatigue, general malaise, difficulty breathing, weight loss, fever and night sweats, and abnormal bleeding. Individuals between the 60 and 70 years are most likely to develop the condition. Exposure to petrochemicals (such as benzene and toluene) and intense radiation may increase an individual's risk of developing the condition. Severe cases of primary myelofibrosis may be fatal within three to six years.

Diagnosis

Elevated hematocrit or platelet count suggests PV or ET respectively. Initial evaluation past history and physical examination commonly includes a bone marrow aspiration with FISH for BCR/ABL to rule out CML. Examination of either bone marrow or peripheral blood for JAK2V617F, MPLW515L/K, or Exon 12 mutations can establish diagnosis.

Primary myelofibrosis is diagnosed in a similar manner as above and is characterized by fibrotic bone marrow that cannot be explained by another diagnosis such as CML or MDS.

One embodiment of the invention combines one or more of these existing tests with the analysis of signalling mediated by receptors to diagnose disease expecially MDS, AML, or MPN. All tests may be performed in one location and provided as a single service to physicians or other caregivers.

Cell-Signaling Pathways and Differentiating Factors Involved

Dysregulation of the JAK-STAT signaling pathway has been implicated in the development and progression of MPN. Alterations in gene expression occur due to the activation of the JAK/STAT pathway by exogenous stimuli (sepsis or G-CSF treatment), or endogenously through activating mutations (e.g. JAK2-V617F. (ROBERT KRALOVICS, et. al. Altered gene expression in myeloproliferative neoplasms correlates with the activation of signaling by the V617F mutation of JAK2. *Blood.* November 2005, vol. 106, no. 10, p. 3374-3376.) Several distinct MPN, polycythemia vera, essential thrombocythemia, and myelofibrosis are found to have JAK2-V617F mutation, supporting the concept that hyperactivation of JAK-STAT signaling is involved in the development of MPN. JAK2 mutations are present in virtually all cases of polycythemia vera, 41 to 72 percent in essential thrombocythemia, and 39 to 57 percent in primary myelofibrosis. (BAXTER E J, et al. Acquired mutation of the tyrosine kinase JAK2 in human myeloproliferative neoplasms. *Lancet.* 2005, vol. 365, no. 9464, p. 1054-1061.) Studies have found 15 gene-expression markers which were elevated in patients with PV, including polycythemia rubra vera 1 (PRV1) and nuclear factor erythroid-derived 2 (NF-E2), as well as one marker, ANKRD15, which was downregulated. (ROBERT KRALOVICS, et. al. Altered gene expression in myeloproliferative neoplasms correlates with the activation of signaling by the V617F mutation of Jak2. Blood. November 2005, vol. 106, no. 10, p. 3374-3376.)

JAK3 important lymphoid development/myeloid differentiation. Loss of function of JAK3 leads to an autosomal recessive form of severe combined immunodeficiency. Gain of function mutations in JAK3 have been shown to lead to acute megakaryocytic leukemia. Leukemia and Lymphoma March 2008 49 (3):388-397

Phosphatases have been implicated in MPN biology. These include SHP-1 (Src homology 2 domain containing tyrosine Phosphatase 1), SHP-2 (Src homology 2 domain containing tyrosine phosphatase 2), TC-PTP (T-cell PTP), RPTPa (Receptor protein tyrosine phosphatase a), DEP (Density enhanced phosphatase), PTP-MEG1(Protein tyrosine phosphatase MEG1), PTP-MEG2 (Protein tyrosine phosphatase MEG2). PTP-MEG2 is thought to be deregulated in Normally PTP-MEG2 decreases as cells differentiate, however PTP-MEG2 displays increased activity in PV.

One embodiment of the invention will look cell signaling pathways described above in classifying and diagnosing MPN and identification of new potentially druggable targets. Modulators can be designed to investigate these pathways and any relevant parallel pathways.

In some embodiments, the invention provides a method for diagnosing, prognosing, determining progression, predicting response to treatment or choosing a treatment for MPN or rationale combination of different drugs, the method comprising the steps of (a) subjecting a cell population from the individual to a plurality of distinct modulators in separate cultures, (b) characterizing a plurality of pathways in one or more cells from the separate cultures comprising determining an activation level of at least one activatable element in at least three pathways, where the pathways are selected from the group consisting of apoptosis, cell cycle, signaling, or DNA damage pathways, and (c) correlating the characterization with diagnosing, prognosing, determining progression, predicting response to treatment or choosing a treatment for MPN, in an individual, where the pathways characterization is indicative of the diagnosing, prognosing, determining progression, response to treatment or the appropriate treatment for MPN. In some embodiments, the individual has a predefined clinical parameter and the characterization of multiple pathways in combination with the clinical parameter is indicative of the diagnoses, prognoses, determining progression, predicting response to treatment or choosing a treatment for MPN, in an individual. Examples of predetermined clinical parameters include, but are not limited to, biochemical/molecular marker.

Therapeutic Agents Effective Against the Disease

For the treatment of polycythemia vera, routine phlebotomy (removal of one unit of blood) is performed. This decreases the viscosity of blood and reduces the risk of stroke. Other therapies include hydroxyurea and aspirin. In severe cases, chemotherapy such as low dose methotrexate is preferred to control excess production of red blood cells. Interferon has also been used to treat this disease.

Essential thrombocythemia can be treated with drugs similar to PV such as hydroxyurea and aspirin.

Treatment of myelofibrosis generally involves blood cell transfusion to increase the number of red blood cells and platelets. Interferon can slow the progression of this disease and some patients benefit from splenectomy. In some cases, bone marrow transplantation is also performed.

There is strong evidence for the efficacy of targeted kinase inhibitors in CML, and the thought to extend this to other myeloproliferative neoplasms has triggered rampant development of additional therapies in this class. In particular inhibitors of JAK 2 that target the activation of the JAK2-STAT5 pathway are underway. However, until new targeted drugs become available, most of the MPN must still be managed with traditional therapies.

Using multiparametric phospho-protein analysis that examine the biology of MPN this invention could: enable patient stratification which would provide an improved classification of these diseases; be used for drug screening to produce biologically informed therapeutics choices; and address the potential for responsiveness to new therapies. The benefits of using the present invention for diagnostic tests includes defining the therapeutic possibilities; identification of aggressive disease giving potentially improved outcomes; and matching signaling profiles to experimental therapeutic outcomes. Additionally, elucidation of disease mechanisms would identify de novo targets applicable to future drug therapy and cohort selection for drug development.

One embodiment of the invention involves the use of multiparametric flow cytometry to examine the biology and signalling pathways in MPN to determine likelihood of progression to AML.

One embodiment of the invention involves the use of multiparametric flow cytometry to examine the biology and signalling pathways in MPN to determine likelihood of response to agents in development for the treatment of MPN One embodiment of the invention involves the use of multiparametric flow cytometry to examine the biology and signalling pathways of myeloid disorders to aid in classification, therapeutic selection and identification of new potentially druggable targets and design of ratione drug combinations.

In some embodiments, the invention provides a method for predicting a response to a treatment or choosing a treatment for MPN, in an individual, the method comprising the steps: (a) subjecting a cell population from the individual to at least two distinct modulators in separate cultures; (b) determining an activation level of at least one activatable element from each of at least three pathways selected from the group consisting of apoptosis, cell cycle, signaling, and DNA damage pathways in one or more cells from each said separate cultures, where the activatable elements measured in each separate culture are the same or the activatable elements measured in each separate culture are different; and (c) predicting a response to a treatment or choosing a therapeutic for MPN, in the individual based on the activation level of said activatable elements. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where if the apoptosis, cell cycle, signaling, and DNA damage pathways are functional the individual can respond to treatment, and where if at least one of the pathways is not functional the individual can not respond to treatment. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where if the apoptosis and DNA damage pathways are functional the individual can respond to treatment. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where a therapeutic is chosen depending of the functional pathways in the individual.

In some embodiments, the invention provides a method of predicting a response to a treatment or choosing a treatment for MPN, in an individual, the method comprising the steps of: (a) subjecting a cell population from said individual to at least three distinct modulators in separate cultures, wherein: (i) a first modulator is a growth factor or mitogen, (ii) a second modulator is a cytokine, (iii) a third modulator is a modulator that slows or stops the growth of cells and/or induces apoptosis of cells or, the third modulator is an inhibitor; (b) determining the activation level of at least one activatable element in one or more cells from each of the separate cultures, where: (i) a first activatable element is an activatable element within the PI3K/AKT, or MAPK pathways and the activation level is measured in response to the growth factor or mitogen, (ii) a second activatable element is an activatable element within the STAT pathway and the activation level is measured in response to the cytokine, (iii) a third activatable element is an activatable element within an apoptosis pathway and the activation level is measured in response to the modulator that slows or stops the growth of cells and/or induces apoptosis of cells, or the third activatable element is activatable element within the phospholipase C pathway and the activation level is measured in response to the inhibitor, or the third activatable element is a phosphatase and the activation level is measured in response to the inhibitor; and (c) correlating the activation levels of said activatable elements with a response to a treatment or with choosing a treatment for MPN in the individual. Examples of predefined clinical parameters include age, de novo acute myeloid leukemia patient, secondary acute myeloid leukemia patient, or a biochemical/molecular marker. In some embodiments, the cytokine is selected from the group consisting of G-CSF, IFNg, IFNa, IL-27, IL-3, IL-6, and IL-10. In some embodiments, the growth factor is selected from the group consisting of FLT3L, SCF, G-CSF, and SDF1a. In some embodiments, the mitogen is selected from the group consisting of LPS, PMA, and Thapsigargin. In some embodiments, the modulator that slows or stops the growth of cells and/or induces apoptosis of cells is selected from the group consisting of Staurosporine, Etoposide, Mylotarg, Daunorubicin, AraC and Jak2 inhibitors.

In some embodiments, the activatable elements can demarkate MPN cell subpopulations that have different genetic subclone origins. In some embodiments, the activatable elements can demarkate MPN subpopulations that, in combination with additional surface molecules, can allow for surrogate identification of MPN cell subpopulations. In some embodiments, the activatable elements can demarkate MPN subpopulations that can be used to determine other protein, epitope-based, RNA, mRNA, siRNA, or metabolomic markers that singly or coordinately allow for surrogate identification of MPN cell subpopulations, disease stage of the individual from which the cells were derived, diagnosis, prognosis, response to treatment, or new druggable targets. In some embodiments, the pathways characterization allows for the delineation of MPN cell subpopulations that are differentially susceptible to drugs or drug combinations. In other embodiments, the cell types or activatable elements from a given cell type will, in combination with activatable elements in other cell types, provide ratiometric or metrics that singly or coordinately allow for surrogate identification of MPN cell subpopulations, disease stage of the individual from which the cells were derived, diagnosis, prognosis, response to treatment, or new druggable targets.

General Methods

Embodiments of the invention may be used to diagnose, predict or to provide therapeutic decisions for disease treatment, such as MDS, AML, or MPN. In some embodiments, the invention may be used to identify new druggrable targets and to design drug combinations. The following will discuss instruments, reagents, kits, and the biology involved with these and other diseases. One aspect of the invention involves contacting a hematopoietic cell with a modulator; determining the activation states of a plurality of activatable elements in the cell; and classifying the cell based on said activation state.

In some embodiments, this invention is directed to methods and compositions, and kits for analysis, drug screening, diagnosis, prognosis, for methods of disease treatment and prediction. In some embodiments, the present invention involves methods of analyzing experimental data. In some embodiments, the physiological status of cells present in a sample (e.g. clinical sample) is used, e.g., in diagnosis or prognosis of a condition, patient selection for therapy using some of the agents identified above, to monitor treatment, modify therapeutic regimens, and to further optimize the selection of therapeutic agents which may be administered as one or a combination of agents. Hence, therapeutic regimens can be individualized and tailored according to the data obtained prior to, and at different times over the course of treatment, thereby providing a regimen that is individually appropriate. In some embodiments, a compound is contacted with cells to analyze the response to the compound.

In some embodiments, the present invention is directed to methods for classifying a sample derived from an individual having or suspected of having a condition, e.g., a neoplastic or a hematopoietic condition. The invention allows for identification of prognostically and therapeutically relevant subgroups of conditions and prediction of the clinical course of an individual. The methods of the invention provide tools useful in the treatment of an individual afflicted with a condition, including but not limited to methods for assigning a risk group, methods of predicting an increased risk of relapse, methods of predicting an increased risk of developing secondary complications, methods of choosing a therapy for an individual, methods of predicting duration of response, response to a therapy for an individual, methods of determining the efficacy of a therapy in an individual, and methods of determining the prognosis for an individual. The present invention provides methods that can serve as a prognostic indicator to predict the course of a condition, e.g. whether the course of a neoplastic or a hematopoietic condition in an individual will be aggressive or indolent, thereby aiding the clinician in managing the patient and evaluating the modality of treatment to be used. In another embodiment, the present invention provides information to a physician to aid in the clinical management of a patient so that the information may be translated into action, including treatment, prognosis or prediction.

In some embodiments, the invention is directed to methods of characterizing a plurality of pathways in single cells. Exemplary pathways include apoptosis, cell cycle, signaling, or DNA damage pathways. In some embodiments, the characterization of the pathways is correlated with diagnosing, prognosing or determining condition progression in an individual. In some embodiments, the characterization of the pathways is correlated with predicting response to treatment or choosing a treatment in an individual. In some embodiments, the characterization of the pathways is correlated with finding a new druggable target. In some embodiments, the pathways' characterization in combination with a predetermined clinical parameter is indicative of the diagnosis, prognosis or progression of the condition. In some embodiments, the pathways' characterization in combination with a predetermined clinical parameter is indicative of a response to treatment or of the appropriate treatment for an individual. In some embodiments, the characterization of the pathways in combination with a predetermined clinical parameter is indicative a new druggable target.

In some embodiments, the invention is directed to methods for determining the activation level of one or more activatable elements in a cell upon treatment with one or more modulators. The activation of an activatable element in the cell upon treatment with one or more modulators can reveal operative pathways in a condition that can then be used, e.g., as an indicator to predict course of the condition, to identify risk group, to predict an increased risk of developing secondary complications, to choose a therapy for an individual, to predict response to a therapy for an individual, to determine the efficacy of a therapy in an individual, and to determine the prognosis for an individual. In some embodiments, the operative pathways can reveal whether apoptosis, cell cycle, signaling, or DNA damage pathways are functional in an individual, where a pathway is functional if it is permissive for a response to a treatment. In some embodiments, when apoptosis, cell cycle, signaling, and DNA damage pathways are functional the individual can respond to treatment, and if at least one of the pathways is not functional the individual can not respond to treatment. In some embodiments, when the apoptosis and DNA damage pathways are functional the individual can respond to treatment. In some embodiments, the operative pathways can reveal new druggable targets.

In some embodiments, the invention is directed to methods for classifying a cell by contacting the cell with an inhibitor, determining the presence or absence of an increase in activation level of an activatable element in the cell, and classifying the cell based on the presence or absence of the increase in the activation of the activatable element. In some embodiments, the invention is directed to methods of determining the presence or absence of a condition in an individual by subjecting a cell from the individual to a modulator and an inhibitor, determining the activation level of an activatable element in the cell, and determining the presence or absence of the condition based on the activation level upon treatment with a modulator and an inhibitor.

In some embodiments, the invention is directed to methods of determining a phenotypic profile of a population of cells by exposing the population of cells to a plurality of modulators in separate cultures, determining the presence or absence of an increase in activation level of an activatable element in the cell population from each of the separate culture and classifying the cell population based on the presence or absence of the increase in the activation of the activatable element from each of the separate culture. In some embodiments at least one of the modulators is an inhibitor. In some embodiments, the presence or absence of an increase in activation level of a plurality of activatable elements is determined. In some embodiments, each of the activatable elements belongs to a particular pathway and the activation level of the activatable elements is used to characterize each of the particular pathways. In some embodiments, a plurality of pathways are characterized by exposing a population of cells to a plurality of modulators in separate cultures, determining the presence or absence of an increase in activation levels of a plurality of activatable elements in the cell population from each of the separate culture, wherein the activatable elements are within the pathways being characterized and classifying the cell population based on the characterizations of said multiple pathways. In some embodiments, the activatable elements and modulators are selected from the activatable elements and modulators listed in Tables 1, 2, 3 or 5. In some embodiments, the activatable elements and modulators are selected from the activatable elements and modulators listed in Table 12 and are used to predict response duration in an individual after treatment.

In some embodiments, the invention is directed to methods for classifying a cell by determining the presence or absence of an increase in activation level of an activatable element in the, in combination with additional expression markers. In some embodiments, expression markers or drug transporters, such as CD34, CD33, CD45, HLADR, CD11B FLT3 Ligand, c-KIT, ABCG2, MDR1, BCRP, MRP1, LRP, and others noted below, can also be used for stratifying responders and non-responders. The expression markers may be detected using many different techniques, for example using nodes from flow cytometry data (see the articles and patent applications referred to above). Other common techniques employ expression arrays (commercially available from Affymetrix, Santa Clara Calif.), taqman (commercially available from ABI, Foster City Calif.), SAGE (commercially available from Genzyme, Cambridge Mass.), sequencing techniques (see the commercial products from Helicos, 454, US Genomics, and ABI) and other commonly know assays. See Golub et al., Science 286: 531-537 (1999). Expression markers are measured in unstimulated cells to know whether they have an impact on functional apoptosis. This provides implications for treatment and prognosis for the disease. Under this hypothesis, the amount of drug transporters correlates with the response of the patient and non-responders may have more levels of drug transporters (to move a drug out of a cell) as compared to responders. In some embodiments, the invention is directed to methods of classifying a cell population by contacting the cell population with at least one modulator that affects signaling mediated by receptors selected from the group comprising of growth factors, mitogens and cytokines. In some embodiments, the invention is directed to methods of classifying a cell population by contacting the cell population with at least one modulator that affects signaling mediated by receptors selected from the group comprising SDF-1α, IFN-α, IFN-γ, IL-10, IL-6, IL-27, G-CSF, FLT-3L, IGF-1, M-CSF, SCF, PMA, and Thapsigargin; determining the activation states of a plurality of activatable elements in the cell comprising; and classifying the cell based on said activation states and expression levels. In some embodiments, the cell population is also exposed in a separate culture to at least one modulator that slows or stops the growth of cells and/or induces apoptosis of cells. In some embodiments, the modulator that slows or stops the growth of cells and/or induces apoptosis of cells is selected from the group consisting of, Etoposide, Mylotarg, AraC, daunorubicin, staurosporine, benzyloxycarbonyl-Val-Ala-Asp (OMe) fluoromethylketone (ZVAD), lenalidomide, EPO, and azacitadine, decitabine. In some embodiments, the cell population is also exposed in a separate culture to at least one modulator that is an inhibitor. In some embodiments the inhibitor is $H_2O_2$. In some embodiments, the expression of a growth factor receptor, cytokine receptor and/or a drug transporter is also measured. In some embodiments, the methods comprise determining the expression level at least one protein selected from the group comprising ABCG2, C-KIT receptor, and FLT3 LIGAND receptor. Another embodiment of the invention further includes using the modulators IL-3, IL-4, GM-CSF, EPO, LPS, TNF-α, and CD40L. In some embodiments, the cell population in a hematopoetic cell population. In some embodiments, the invention is directed to methods of correlating and/or classifying an activation state of an AML, MDS or MPN cell with a clinical outcome in an individual by subjecting the AML, MDS or MPN cell from the individual to a modulator, determining the activation levels of a plurality of activatable elements, and identifying a pattern of the activation levels of the plurality of activatable elements to determine the presence or absence of an alteration in signaling, where the presence of the alteration is indicative of a clinical outcome. In some embodiments, the activatable elements can demarkate AML, MDS or MPN cell subpopulations that have different genetic subclone origins. In some embodiments, the activatable elements can demarkate AML, MDS or MPN subpopulations that can be used to determine other protein, epitope-based, RNA, mRNA, siRNA, or metabolomic markers that singly or coordinately allow for surrogate identification of AML, MDS or MPN cell subpopulations, disease stage of the individual from which the cells were derived, diagnosis, prognosis, response to treatment, or new druggable targets. In some embodiments, the pathways characterization allows for the delineation of AML, MDS or MPN cell subpopulations that are differentially susceptible to drugs or drug combinations. In other embodiments, the cell types or activatable elements from a given cell type will, in combination with activatable elements in other cell types, provide ratiometric or metrics that singly or coordinately allow for surrogate identification of AML, MDS or MPN cell subpopulations, disease stage of the individual from which the cells were derived, diagnosis, prognosis, response to treatment, or new druggable targets.

The subject invention also provides kits for use in determining the physiological status of cells in a sample, the kit comprising one or more modulators, inhibitors, specific binding elements for signaling molecules, and may additionally comprise one or more therapeutic agents. The above reagents for the kit are all recited and listed in the present application below. The kit may further comprise a software package for data analysis of the cellular state and its physiological status, which may include reference profiles for comparison with the test profile and comparisons to other analyses as referred to above. The kit may also include instructions for use for any of the above applications.

In some embodiments, the invention provides methods, including methods to determine the physiological status of a cell, e.g., by determining the activation level of an activatable element upon contact with one or more modulators. In some embodiments, the invention provides methods, including methods to classify a cell according to the status of an activatable element in a cellular pathway. In some embodiments, the cells are classified by analyzing the response to particular modulators and by comparison of different cell states, with or without modulators. The information can be used in prognosis and diagnosis, including susceptibility to disease(s), status of a diseased state and response to changes, in the environment, such as the passage of time, treatment with drugs or other modalities. The physiological status of the cells provided in a sample (e.g. clinical sample) may be classified according to the activation of cellular pathways of interest. The cells can also be classified as to their ability to respond to therapeutic agents and treatments. The physiological status of the cells can provide new druggable targets for the development of treatments. These treatments can be used alone or in combination with other treatments. The physiological status of the cells can be used to design combination treatments.

One or more cells or cell types, or samples containing one or more cells or cell types, can be isolated from body samples. The cells can be separated from body samples by centrifugation, elutriation, density gradient separation, apheresis, affinity selection, panning, FACS, centrifugation with Hypaque, solid supports (magnetic beads, beads in columns, or other surfaces) with attached antibodies, etc. By using antibodies specific for markers identified with particular cell types, a relatively homogeneous population of cells may be obtained. Alternatively, a heterogeneous cell population can be used. Cells can also be separated by using filters. For example, whole blood can also be applied to filters that are engineered to contain pore sizes that select for the desired cell type or class. Rare pathogenic cells can be filtered out of diluted, whole blood following the lysis of red blood cells by using filters with pore sizes between 5 to 10 μm, as disclosed in U.S. patent application Ser. No. 09/790,673. Once a sample is obtained, it can be used directly, frozen, or maintained in appropriate culture medium for short periods of time. Methods to isolate one or more cells for use according to the methods of this invention are performed according to standard techniques and protocols well-established in the art. See also U.S. Ser. Nos. 61/048,886; 61/048,920; and 61/048,657. See also, the commercial products from companies such as BD and BCI as identified above.

See also U.S. Pat. Nos. 7,381,535 and 7,393,656. All of the above patents and applications are incorporated by reference as stated above.

In some embodiments, the cells are cultured post collection in a media suitable for revealing the activation level of an activatable element (e.g. RPMI, DMEM) in the presence, or absence, of serum such as fetal bovine serum, bovine serum, human serum, porcine serum, horse serum, or goat serum. When serum is present in the media it could be present at a level ranging from 0.0001% to 30%.

In some embodiments, the cells are hematopoietic cells. Examples of hematopoietic cells include but are not limited to pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells.

The term "patient" or "individual" as used herein includes humans as well as other mammals. The methods generally involve determining the status of an activatable element. The methods also involve determining the status of a plurality of activatable elements.

In some embodiments, the invention provides a method of classifying a cell by determining the presence or absence of an increase in activation level of an activatable element in the cell upon treatment with one or more modulators, and classifying the cell based on the presence or absence of the increase in the activation of the activatable element. In some embodiments of the invention, the activation level of the activatable element is determined by contacting the cell with a binding element that is specific for an activation state of the activatable element. In some embodiments, a cell is classified according to the activation level of a plurality of activatable elements after the cell have been subjected to a modulator. In some embodiments of the invention, the activation levels of a plurality of activatable elements are determined by contacting a cell with a plurality of binding elements, where each binding element is specific for an activation state of an activatable element.

The classification of a cell according to the status of an activatable element can comprise classifying the cell as a cell that is correlated with a clinical outcome. In some embodiments, the clinical outcome is the prognosis and/or diagnosis of a condition. In some embodiments, the clinical outcome is the presence or absence of a neoplastic or a hematopoietic condition such as acute myeloid leukemia (AML), myelodysplastic syndrome (MDS) or myeloproliferative neoplasms (MPN). In some embodiments, the clinical outcome is the staging or grading of a neoplastic or hematopoietic condition. Examples of staging include, but are not limited to, aggressive, indolent, benign, refractory, Roman Numeral staging, TNM Staging, Rai staging, Binet staging, WHO classification, FAB classification, IPSS score, WPSS score, limited stage, extensive stage, staging according to cellular markers, occult, including information that may inform on time to progression, progression free survival, overall survival, or event-free survival.

The classification of a cell according to the status of an activatable element can comprise classifying a cell as a cell that is correlated to a patient response to a treatment. In some embodiments, the patient response is selected from the group consisting of complete response, partial response, nodular partial response, no response, progressive disease, stable disease and adverse reaction.

The classification of a rare cell according to the status of an activatable element can comprise classifying the cell as a cell that can be correlated with minimal residual disease or emerging resistance. See U.S. No. 61/048,886 which is incorporated by reference.

The classification of a cell according to the status of an activatable element can comprise selecting a method of treatment. Example of methods of treatments include, but are not limited to chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, watchful waiting, and other therapy.

A modulator can be an activator, an inhibitor or a compound capable of impacting cellular signaling networks. Modulators can take the form of a wide variety of environmental cues and inputs. Examples of modulators include but are not limited to growth factors, mitogens, cytokines, adhesion molecules, drugs, hormones, small molecules, polynucleotides, antibodies, natural compounds, lactones, chemotherapeutic agents, immune modulators, carbohydrates, proteases, ions, reactive oxygen species, radiation, physical parameters such as heat, cold, UV radiation, peptides, and protein fragments, either alone or in the context of cells, cells themselves, viruses, and biological and non-biological complexes (e.g. beads, plates, viral envelopes, antigen presentation molecules such as major histocompatibility complex). One exemplary set of modulators, include but are not limited to SDF-1α, IFN-α, IFN-γ, IL-10, IL-6, IL-27, G-CSF, FLT-3L, IGF-1, M-CSF, SCF, PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine, IL-3, IL-4, GM-CSF, EPO, LPS, TNF-α, and CD40L.

In some embodiments, the modulator is an activator. In some embodiments the modulator is an inhibitor. In some embodiments, the invention provides methods for classifying a cell by contacting the cell with an inhibitor, determining the presence or absence of an increase in activation level of an activatable element in the cell, and classifying the cell based on the presence or absence of the increase in the activation of the activatable element. In some embodiments, a cell is classified according to the activation level of a plurality of activatable elements after the cells have been subjected to an inhibitor. In some embodiments, the inhibitor is an inhibitor of a cellular factor or a plurality of factors that participates in a signaling cascade in the cell. In some embodiments, the inhibitor is a phosphatase inhibitor. Examples of phosphatase inhibitors include, but are not limited to $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, 13-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxy-acetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenylarsine oxide, Pyrrolidine Dithiocarbamate, and Aluminium fluoride. In some embodiments, the phosphatase inhibitor is $H_2O_2$.

In some embodiments, the methods of the invention provide methods for classifying a cell population or determining the presence or absence of a condition in an individual by subjecting a cell from the individual to a modulator and an inhibitor, determining the activation level of an activatable element in the cell, and determining the presence or absence of a condition based on the activation level. In some embodiments, the activation level of a plurality of activatable elements in the cell is determined. The inhibitor can be an inhibitor as described herein. In some embodiments, the inhibitor is a phosphatase inhibitor. In some embodiments, the inhibitor is $H_2O_2$. The modulator can be any modulator described herein. In some embodiments, the methods of the invention provides for methods for classifying a cell population by exposing the cell population to a plurality of modulators in separate cultures and determining the status of an activatable element in the cell population. In some embodiments, the status of a plurality of activatable elements in the cell population is determined. In some embodiments, at least one of the modulators of the plurality of modulators is an inhibitor. The modulator can be at least one of the modulators described herein. In some embodiments, at least one modulator is selected from the group consisting of SDF-1α, IFN-α, IFN-γ, IL-10, IL-6, IL-27, G-CSF, FLT-3L, IGF-1, M-CSF, SCF, PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine, IL-3, IL-4, GM-CSF, EPO, LPS, TNF-α, and CD40L or a combination thereof. In some embodiments of the invention, the status of an activatable element is determined by contacting the cell population with a binding element that is specific for an activation state of the activatable element. In some embodiments, the status of a plurality of activatable elements is determined by contacting the cell population with a plurality of binding elements, where each binding element is specific for an activation state of an activatable element.

In some embodiments, the methods of the invention provide methods for determining a phenotypic profile of a population of cells by exposing the population of cells to a plurality of modulators (recited herein) in separate cultures, wherein at least one of the modulators is an inhibitor, determining the presence or absence of an increase in activation level of an activatable element in the cell population from each of the separate cultures and classifying the cell population based on the presence or absence of the increase in the activation of the activatable element from each of the separate culture. In some embodiments, the phenotypic profile is used to characterize multiple pathways in the population of cells.

Patterns and profiles of one or more activatable elements are detected using the methods known in the art including those described herein. In some embodiments, patterns and profiles of activatable elements that are cellular components of a cellular pathway or a signaling pathway are detected using the methods described herein. For example, patterns and profiles of one or more phosphorylated polypeptides are detected using methods known in art including those described herein.

In some embodiments, cells (e.g. normal cells) other than the cells associated with a condition (e.g. cancer cells) or a combination of cells are used, e.g., in assigning a risk group, predicting an increased risk of relapse, predicting an increased risk of developing secondary complications, choosing a therapy for an individual, predicting response to a therapy for an individual, determining the efficacy of a therapy in an individual, and/or determining the prognosis for an individual. That is that cells other than cells associated with a condition (e.g. cancer cells) are in fact reflective of the condition process. For instance, in the case of cancer, infiltrating immune cells might determine the outcome of the disease. Alternatively, a combination of information from the cancer cell plus the immune cells in the blood that are responding to the disease, or reacting to the disease can be used for diagnosis or prognosis of the cancer.

In some embodiments, the invention provides methods to carry out multiparameter flow cytometry for monitoring phospho-protein responses to various factors in acute myeloid leukemia, MDS, or MPN at the single cell level. Phospho-protein members of signaling cascades and the kinases and phosphatases that interact with them are required to initiate and regulate proliferative signals in cells. Apart from the basal level of protein phosphorylation alone, the effect of potential drug molecules on these network pathways was studied to discern unique cancer network profiles, which correlate with the genetics and disease outcome. Single cell measurements of phospho-protein responses reveal shifts in the signaling potential of a phospho-protein network, enabling categorization of cell network phenotypes by multidimensional molecular profiles of signaling. See U.S. Pat. No. 7,393,656. See also fish et. al., Single cell profiling of potentiated phospho-protein networks in cancer cells. *Cell.* 2004, vol. 118, p. 1-20.

Flow cytometry is useful in a clinical setting, since relatively small sample sizes, as few as 10,000 cells, can produce a considerable amount of statistically tractable multidimensional signaling data and reveal key cell subsets that are responsible for a phenotype. See U.S. Pat. Nos. 7,381,535 and 7,393,656. See also Krutzik et al, 2004).

Cytokine response panels have been studied to survey altered signal transduction of cancer cells by using a multidimensional flow cytometry file which contained at least 30,000 cell events. In one embodiment, this panel is expanded and the effect of growth factors and cytokines on primary AML samples studied. See U.S. Pat. Nos. 7,381,535 and 7,393,656. See also fish et. al., CELL July 23;118(2):217-28 In some embodiments, the analysis involves working at multiple characteristics of the cell in parallel after contact with the compound. For example, the analysis can examine drug transporter function; drug transporter expression; drug metabolism; drug activation; cellular redox potential; signaling pathways; DNA damage repair; and apoptosis.

In some embodiments, the modulators include growth factors, cytokines, chemokines, phosphatase inhibitors, and pharmacological reagents. The response panel is composed of at least one of: SDF-1α, IFN-α, IFN-γ, IL-10, IL-6, IL-27, G-CSF, FLT-3L, IGF-1, M-CSF, SCF, PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine, IL-3, IL-4, GM-CSF, EPO, LPS, TNF-α, and CD40L.

Figure 17:
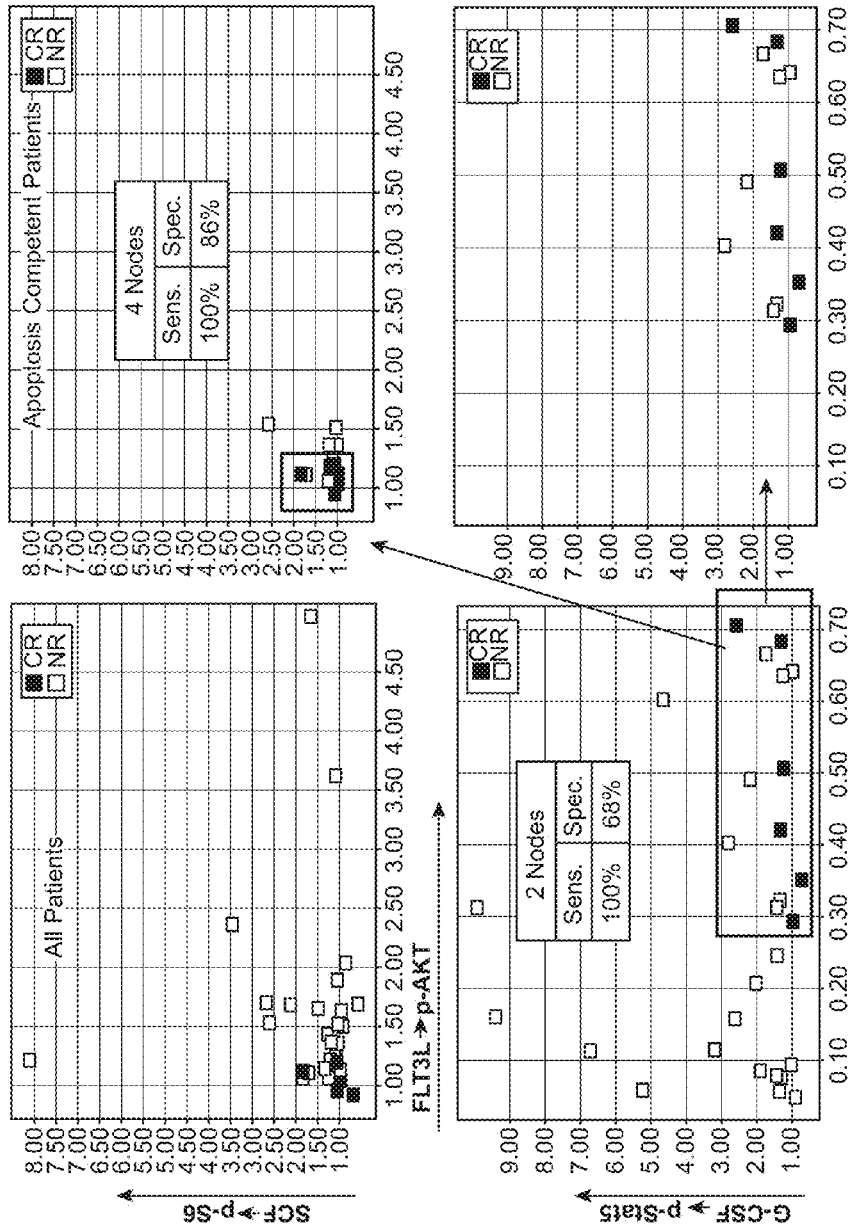
FIG. 17 shows that grouping of data points increases predictive value.

The response of each phospho-protein node is compared to the basal state and can be represented by calculating the $\log_2$ fold difference in the Median Fluorescence Intensity (MFI) of the stimulated sample divided by the unstimulated sample. The data can be analyzed using any of the metrics described in FIGS. 2, 7-9. However, other statistical methods may be used. The growth factor and the cytokine response panel included detection of phosphorylated Stat1, Stat3, Stat5, Stat6, PLCγ2, S6, Akt, Erk1/2, CREB, p38, and NF-KBp-65. In some embodiments, a diagnosis, prognosis, a prediction of outcome such as response to treatment or relapse is performed by analyzing the two or more phosphorylation levels of two or more proteins each in response to one or more modulators. The phosphorylation levels of the independent proteins can be measured in response to the same or different modulators. See FIG. 17 which shows that grouping of data points increases predictive value.

In some embodiments, the AML or other panel of modulators is further expanded to examine the process of DNA damage, apoptosis, drug transport, drug metabolism, and the use of peroxide to evaluate phosphatase activity. Analysis can assess the ability of the cell to undergo the process of apoptosis after exposure to the experimental drug in an in vitro assay as well as how quickly the drug is exported out of the cell or metabolized. The drug response panel can include but is not limited to detection of phosphorylated Chk2, Cleaved Caspase 3, Caspase 8, PARP and mitochondria-released Cytoplasmic Cytochrome C. Modulators may include Stauro, Etoposide, Mylotarg, AraC, daunorubicin. Analysis can assess phosphatase activity after exposure of cells to phosphatase inhibitors including but not limited to hydrogen peroxide ($H_2O_2$), $H_2O_2$+SCF and $H_2O_2$+IFNα. The response panel to evaluate phosphatase activity can include but is not limited to the detection of phosphorylated Slp76, PLCg2, Lck, S6, Akt, Erk, Stat1, Sta3, Stat5. Later, the samples may be analyzed for the expression of drug transporters such as MDR1/PGP, MRP1 and BCRP/ABCG2. Samples may also be examined for XIAP, Survivin, Bcl-2, MCL-1, Bim, Ki-67, Cyclin D1, ID1 and Myc.

Another method of the present invention is a method for determining the prognosis and therapeutic selection for an individual with acute myelogenous leukemia (AML). Using the signaling nodes and methodology described herein, multiparametric flow could separate a patient into "cytarabine responsive", meaning that a cytarabine based induction regimen would yield a complete response or "cytarabine non-responsive", meaning that the patient is unlikely to yield a complete response to a cytarabine based induction regimen. Furthermore, for those patients unlikely to benefit from cytarabine based therapy, the individual's blood or marrow sample could reveal signaling biology that corresponds to either in-vivo or in-vitro sensitivity to a class of drugs including but not limited to direct drug resistance modulators, anti-Bcl-2 or pro-apoptotic drugs, proteosome inhibitors, DNA methyl transferase inhibitors, histone deacetylase inhibitors, anti-angiogenic drugs, farnesyl transferase inhibitors, FLt3 ligand inhibitors, or ribonucleotide reductase inhibitors. An individual with AML with a complete response to induction therapy could further benefit from the present invention. The individual's blood or marrow sample could reveal signaling biology that corresponds to likelihood of benefit from further cytarabine based chemotherapy versus myeloablative therapy followed by and stem cell transplant versus reduced intensity therapy followed by stem cell transplantation.

In some embodiments, the invention provides a method for diagnosing, prognosing, determining progression, predicting response to treatment or choosing a treatment for AML, MDS or MPN in an individual where the individual has a predefined clinical parameter, the method comprising the steps of (a) subjecting a cell population from the individual to a plurality of distinct modulators in separate cultures, (b) characterizing a plurality of pathways in one or more cells from the separate cultures comprising determining an activation level of at least one activatable element in at least three pathways, where (i) the pathways are selected from the group consisting of apoptosis, cell cycle, signaling, or DNA damage pathways (ii) at least one of the pathways being characterized in at least one of the separate cultures is an apoptosis or DNA damage pathway, (iii) the distinct modulators independently activate or inhibit said one or more pathways being characterized, and (c) correlating the characterization with diagnosing, prognosing, determining progression, predicting response to treatment or choosing a treatment for AML, MDS or MPN in an individual, where the pathways characterization in combination with the clinical parameter is indicative of the diagnosing, prognosing, determining progression, response to treatment or the appropriate treatment for AML, MDS or MPN. Examples of predetermined clinical parameters include, but are not limited to, age, de novo acute myeloid leukemia patient, secondary acute myeloid leukemia patient, or a biochemical/molecular marker. In some embodiments, the individual is over 60 years old. In some embodiments, the individual is under 60 years old. In some embodiments the activatable elements and modulators are selected from the activatable elements and modulators listed in Tables 1, 2, 3 or 5. In some embodiments, the activatable elements and modulators are selected from the activatable elements and modulators listed in Table 12 and are used to predict response duration in an individual after treatment. In some embodiments the modulator is selected from the group consisting of FLT3L, GM-CSF, SCF, G-CSF, SDF1a, LPS, PMA, Thapsigargin, IFNg, IFNa, IL-27, IL-3, IL-6, IL-10, ZVAD, $H_2O_2$, Staurosporine, Etoposide, Mylotarg, Daunorubicin, and AraC. In some embodiments, when the individual is under 60 years old the activatable elements and modulators are selected from the activatable elements and modulators listed in Table 6. In some embodiments, where the individual is over 60 years the activatable elements and modulators are selected from the activatable elements and modulators listed in Table 7. In some embodiments, where the individual is a secondary acute myeloid leukemia patient the activatable elements and modulators are selected from the activatable elements and modulators listed in Table 8 and Table 9. In some embodiments, where the individual is a de novo acute myeloid leukemia patient the activatable elements and modulators are selected from the activatable elements and modulators listed in Table 10 and Table 11. In some embodiments, where the individual has a wild type FLT3 the activatable elements and modulators are selected from the activatable elements and modulators listed in Table 13.

In some embodiments, the invention provides a method for predicting a response to a treatment or choosing a treatment for AML, MDS or MPN in an individual, the method comprising the steps: (a) subjecting a cell population from the individual to at least two distinct modulators in separate cultures; (b) determining an activation level of at least one activatable element from each of at least three pathways selected from the group consisting of apoptosis, cell cycle, signaling, and DNA damage pathways in one or more cells from each said separate cultures, where at least one of the activatable elements is from an apoptosis or DNA damage pathway, and where the activatable elements measured in each separate culture are the same or the activatable elements measured in each separate culture are different; and (c) predicting a response to a treatment or choosing a therapeutic for AML, MDS or MPN in the individual based on the activation level of said activatable elements. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where if the apoptosis, cell cycle, signaling, and DNA damage pathways are functional the individual can respond to treatment, and where if at least one of the pathways is not functional the individual can not respond to treatment. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where if the apoptosis and DNA damage pathways are functional the individual can respond to treatment. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where a therapeutic is chosen depending of the functional pathways in the individual. In some embodiments the activatable elements and modulators are selected from the activatable elements and modulators listed in Tables 1, 2, 3 or 5. In some embodiments, the activatable elements and modulators are selected from the activatable elements and modulators listed in Table 12 and are used to predict response duration in an individual after treatment. In some embodiments the modulator is selected from the group consisting of FLT3L, GM-CSF, SCF, G-CSF, SDF1a, LPS, PMA, Thapsigargin, IFNg, IFNa, IL-27, IL-3, IL-6, IL-10, ZVAD, $H_2O_2$, Staurosporine, Etoposide, Mylotarg, Daunorubicin, and AraC.

In some embodiments, the invention provides a method of predicting a response to a treatment or choosing a treatment for AML, MDS or MPN in an individual, the method comprising the steps of: (a) subjecting a cell population from said individual to at least three distinct modulators in separate cultures, wherein: (i) a first modulator is a growth factor or mitogen, (ii) a second modulator is a cytokine, (iii) a third modulator is a modulator that slows or stops the growth of cells and/or induces apoptosis of cells or, the third modulator is an inhibitor; (b) determining the activation level of at least one activatable element in one or more cells from each of the separate cultures, where: (i) a first activatable element is an activatable element within the PI3K/AKT, or MAPK pathways and the activation level is measured in response to the growth factor or mitogen, (ii) a second activatable element is an activatable element within the STAT pathway and the activation level is measured in response to the cytokine, (iii) a third activatable element is an activatable element within an apoptosis pathway and the activation level is measured in response to the modulator that slows or stops the growth of cells and/or induces apoptosis of cells, or the third activatable element is activatable element within the phospholipase C pathway and the activation level is measured in response to the inhibitor, or the third activatable element is a phosphatase and the activation level is measured in response to the inhibitor; and (c) correlating the activation levels of said activatable elements with a response to a treatment or with choosing a treatment for AML, MDS or MPN in the individual. Examples of predefined clinical parameters include age, de novo acute myeloid leukemia patient, secondary acute myeloid leukemia patient, or a biochemical/molecular marker. In some embodiments, the cytokine is selected from the group consisting of G-CSF, IFNg, IFNa, IL-27, IL-3, IL-6, and IL-10. In some embodiments, the growth factor is selected from the group consisting of FLT3L, SCF, G-CSF, and SDF1a. In some embodiments, the mitogen is selected from the group consisting of LPS, PMA, and Thapsigargin. In some embodiments, the modulator that slows or stops the growth of cells and/or induces apoptosis of cells is selected from the group consisting of Staurosporine, Etoposide, Mylotarg, Daunorubicin, and AraC.

In some embodiments, activation levels of an activatable element within the STAT pathway higher than a threshold level in response to a cytokine are indicative that an individual can not respond to treatment. In some embodiment, a treatment is chosen based on the ability of the cells to respond to treatment. In some embodiments, the activatable element within the STAT pathway is selected from the group consisting of p-Stat3, p-Stat5, p-Stat1, and p-Stat6 and the cytokine is selected from the group consisting of IFNg, IFNa, IL-27, IL-3, IL-6, IL-10, and G-CSF. In some embodiments, the activatable element within the STAT pathway is Stat1 and the cytokine is IL-27 or G-CSF.

In some embodiments, activation levels of an activatable element within the PI3K/AKT, or MAPK pathway higher than a threshold level in response to a growth factor or mitogen is indicative that an individual can not respond to treatment. In some embodiment, a treatment is chosen based on the ability of the cells to respond to treatment with a modulator. In some embodiments, the activatable element within the PI3K/AKT, or MAPK pathway is selected from the group consisting of p-ERK, p38 and pS6 and the growth factor or mitogen is selected from the group consisting of FLT3L, SCF, G-CSF, SDF1a, LPS, PMA, and Thapsigargin.

In some embodiments, activation levels of an activatable element within the phospholipase C pathway higher than a threshold level in response to an inhibitor is indicative that an individual can respond to treatment. In some embodiment, a treatment is chosen based on the ability of the cells to respond to treatment. In some embodiments, the activatable element within the phospholipase C pathway is selected from the group consisting of p-Slp-76, and Plcg2 and the inhibitor is $H_2O_2$.

In some embodiments, activation levels of an activatable element within the apoptosis pathway higher than a threshold in response to a modulator that slows or stops the growth of cells and/or induces apoptosis of cells is indicative that an individual can respond to treatment. In some embodiment, a treatment is chosen based on the ability of the cells to respond to treatment. In some embodiments, the activatable element within the apoptosis pathway is selected from the group consisting of Parp+, Cleaved Caspase 8, and Cytoplasmic Cytochrome C, and the modulator that slows or stops the growth of cells and/or induces apoptosis of cells is selected from the group consisting of Staurosporine, Etoposide, Mylotarg, Daunorubicin, and AraC.

In some embodiments, activation levels of an activatable element within the apoptosis pathway higher than a threshold in response to a modulator that slows or stops the growth of cells and/or induces apoptosis of cells and activation levels of an activatable element within the STAT pathway higher than a threshold level in response to a cytokine is indicative that an individual can not respond to treatment. In some embodiments, the activatable element within the apoptosis pathway is selected from the group consisting of Parp+, Cleaved Caspase 8, and Cytoplasmic Cytochrome C, and the modulator that slows or stops the growth of cells and/or induces apoptosis of cells is selected from the group consisting of Staurosporine, Etoposide, Mylotarg, Daunorubicin, and AraC. In some embodiments, the activatable element within the STAT pathway is selected from the group consisting of p-Stat3, p-Stat5, p-Stat 1, and p-Stat6 and the cytokine is selected from the group consisting of IFNg, IFNa, IL-27, IL-3, IL-6, IL-10, and G-CSF. In some embodiments, the activatable element within the STAT pathway is Stat 1 and the cytokine is IL-27 or G-CSF.

In some embodiments, the methods of the invention further comprise determining an activation level of an activatable element within a DNA damage pathway in response to a modulator that slows or stops the growth of cells and/or induces apoptosis of cells. In some embodiments, the activatable element within a DNA damage pathway is selected from the group consisting of Chk2, ATM, ATR and 14-3-3 and the modulator that slows or stops the growth of cells and/or induces apoptosis of cells is selected from the group consisting of Staurosporine, Etoposide, Mylotarg, Daunorubicin, and AraC.

In some embodiments, activation levels higher than a threshold of an activatable element within a DNA damage pathway and activation levels lower than a threshold of an activatable element within the apoptosis pathway in response to a modulator that slows or stops the growth of cells and/or induces apoptosis of cells are indicative of a communication breakdown between the DNA damage response pathway and the apoptotic machinery and that an individual can not respond to treatment. In some embodiment, a treatment is chosen based on the ability of the cells to respond to treatment.

In some embodiments, the methods of the invention further comprise determining an activation level of an activatable element within a cell cycle pathway in response to a modulator that slows or stops the growth of cells and/or induces apoptosis of cells. In some embodiments, the activatable element within a DNA damage pathway is selected from the group consisting of Cdc25, p53, CyclinA-Cdk2, CyclinE-Cdk2, CyclinB-Cdk1, p21, and Gadd45 and the modulator that slows or stops the growth of cells and/or induces apoptosis of cells is selected from the group consisting of Staurosporine, Etoposide, Mylotarg, Daunorubicin, and AraC.

In some embodiments, the methods of the invention further comprise determining the levels of a drug transporter and/or a cytokine receptor. In some embodiments, the cytokine receptor or drug transporter are selected from the group consisting of MDR1, ABCG2, MRP, P-Glycoprotein, CXCR4, FLT3, and c-kit. In some embodiments, levels higher than a threshold of the drug transporter and/or said cytokine receptor are indicative that an individual can not respond to treatment. In some embodiment, a treatment is chosen based on the ability of the cells to respond to treatment.

In some embodiments, the methods of the invention further comprise determining the activation levels of an activatable element within the Akt pathway in response to an inhibitor, where activation levels higher that a threshold of the activatable element within the Akt pathway in response to the inhibitor are indicative that the individual can not respond to treatment. In some embodiment, a treatment is chosen based on the ability of the cells to respond to treatment.

In some embodiments, activation levels higher than a threshold of an activatable element in the PI3K/AKT pathway in response to a growth factor is indicative that the individual can not respond to treatment. In some embodiments, the activatable element in the PI3K/Akt pathway is Akt and the growth factor is FLT3L.

In some embodiments, activation levels higher than a threshold of an activatable element in the apoptosis pathway in response to a modulator that slows or stops the growth of cells and/or induces apoptosis of cells is indicative that the individual can respond to treatment. In some embodiments, the activatable element within the apoptosis pathway is Parp+ and the modulator that slows or stops the growth of cells and/or induces apoptosis of cells is selected from the group consisting of Staurosporine, Etoposide, Mylotarg, Daunorubicin, and AraC.

In some embodiments, the invention provides a method of predicting a response to a treatment or choosing a treatment for AML in an individual where the individual is a secondary acute myeloid leukemia patient, the method comprising the steps of; (a) subjecting a cell population from the individual to IL-27 and G-CSF in separate cultures, (b) determining an activation level of pStat1 in one or more cells from each separate culture, (c) predicting a response to a treatment or choosing a treatment for AML, in the individual, where if the activation levels of pStat1 are higher than a threshold level in response to both IL-27 and G-CSF the individual can not respond to treatment and if the levels of pStat1 are lower than a threshold in response to both IL-27 and G-CSF the individual can respond to treatment. In some embodiments, the treatment is chemotherapy agent. Examples of chemotherapy agents include, but are not limited to, cytarabine (ara-C), daunorubicin (Daunomycin), idarubicin (Idamycin), mitoxantrone and 6-thioguanine. In some embodiments, the treatment is allogeneic stem cell transplant or autologous stem cell transplant.

In some embodiments, the invention provides a method of predicting a response to a treatment or choosing a treatment for AML, MDS or MPN in an individual, the method comprising the steps of: (a) subjecting a cell population from the individual to FLT3L, (b) determining an activation level of pAkt in one or more cells from the population (c) predicting a response to a treatment or choosing a treatment for AML, MDS or MPN in the individual, where if the activation levels of pAkt are higher than a predetermined threshold in response to FLT3L the individual can not respond to treatment. In some embodiments, the method further comprises the steps of: (d) subjecting a cell population from said individual to IL-27 in a separate culture, (e) determining an activation level of Stat1 in one or more cells from the separate culture, (f) predicting a response to a treatment or choosing a treatment for AML, MDS or MPN in the individual, where if the activation levels of pStat1 are higher than a predetermined threshold in response to IL-27 the individual can not respond to treatment. In some embodiments where the individual is over 60 years old the method further comprises the step of: (g) subjecting a cell population from the individual to H2O2 in a separate culture, (h) determining an activation level of Plcg2 in one or more cells from the separate culture (i) predicting a response to a treatment or choosing a treatment for AML, MDS or MPN in the individual, wherein if the activation levels of Plcg2 are higher than a predetermined threshold in response to H2O2 the individual can not respond to treatment. In some embodiments where the individual is under 60 years old the method further comprises the steps of (g) subjecting a cell population from said individual to Etoposide in a separate culture, (h) determining an activation level of Parp in one or more cells from the separate culture, and (i) predicting a response to a treatment for AML, MDS or MPN in said individual, where if the activation levels of Parp are higher than a predetermined threshold in response to Etoposide the individual can respond to treatment. In some embodiments, the treatment is chemotherapy agent. Examples of chemotherapy agents include, but are not limited to, cytarabine (ara-C), daunorubicin (Daunomycin), idarubicin (Idamycin), mitoxantrone and 6-thioguanine. In some embodiments, the treatment is allogeneic stem cell transplant or autologous stem cell transplant.

In some embodiments, the invention provides methods of prediction response to a treatment and/or risk of relapse for AML, MDS or MPN in an individual, the method comprising the steps of: (a) subjecting a cell population from the individual to SCF, (b) determining an activation level of pAkt and S6 in one or more cells from the population (c) predicting a response to a treatment, choosing a treatment or predicting risk of relapse for AML, MDS or MPN in the individual, where if the activation levels of pAkt and S6 are higher than a predetermined threshold in response to SCF the individual can not respond to treatment or will have a higher probability of relapse.

In some embodiments, a diagnosis, prognosis, a prediction of outcome such as response to treatment or relapse is performed by analyzing the two or more phosphorylation levels of two or more proteins each in response to one or more modulators. The phosphorylation levels of the independent proteins can be measured in response to the same or different modulators. See FIG. 17 which shows that grouping of data points increases predictive value.

In some embodiments, the invention provides a method of diagnosing, prognosing or predicting a response to a treatment or choosing a treatment for AML, MDS or MPN in an individual, the method comprising the steps of: (a) subjecting a cell population from the individual in separate cultures to at least two modulators selected from the group consisting of Staurosporine, Etoposide, Mylotarg, Daunorubicin, AraC, G-CSF, IFNg, IFNa, IL-27, IL-3, IL-6, IL-10, FLT3L, SCF, G-CSF, SDF1a, LPS, PMA, Thapsigargin and H2O2; b) determining the activation level of at least three activatable elements selected from the group consisting of p-Slp-76, p-Plcg2, p-Stat3, p-Stat5, p-Stat1, p-Stat6, p-Creb, Parp+, Chk2, p-65/RelA, p-Akt, p-S6, p-ERK, Cleaved Caspase 8, Cytoplasmic Cytochrome C, and p38; and (c) diagnosing, prognosing, or predicting a response to a treatment or choosing a treatment for AML, MDS or MPN based on the activation levels of the activatable elements. In some embodiments, the method further comprises determining the expression of a cytokine receptor or drug transporter selected from the group consisting of MDR1, ABCG2, MRP, P-Glycoprotein, CXCR4, FLT3, and c-Kit.

In some embodiments, the invention provides methods for predicting response to a treatment for AML, MDS or MPN, wherein the positive predictive value (PPV) is higher than 60, 70, 80, 90, 95, or 99.9%. In some embodiments, the invention provides methods for predicting response to a treatment for AML, MDS or MPN, wherein the PPV is equal or higher than 95%. In some embodiments, the invention provides methods for predicting response to a treatment for AML, MDS or MPN, wherein the negative predictive value (NPV) is higher than 60, 70, 80, 90, 95, or 99.9%. In some embodiments, the invention provides methods for predicting response to a treatment for AML, MDS or MPN, wherein the NPV is higher than 85%.

In some embodiments, the invention provides methods for predicting risk of relapse at 2 years, wherein the PPV is higher than 60, 70, 80, 90, 95, or 99.9%. In some embodiments, the invention provides methods for predicting risk of relapse at 2 years, wherein the PPV is equal or higher than 95%. In some embodiments, the invention provides methods for predicting risk of relapse at 2 years, wherein the NPV is higher than 60, 70, 80, 90, 95, or 99.9%. In some embodiments, the invention provides methods for predicting risk of relapse at 2 years, wherein the NPV is higher than 80%. In some embodiments, the invention provides methods for predicting risk of relapse at 5 years, wherein the PPV is higher than 60, 70, 80, 90, 95, or 99.9%. In some embodiments, the invention provides methods for predicting risk of relapse at 5 years, wherein the PPV is equal or higher than 95%. In some embodiments, the invention provides methods for predicting risk of relapse at 5 years, wherein the NPV is higher than 60, 70, 80, 90, 95, or 99.9%. In some embodiments, the invention provides methods for predicting risk of relapse at 5 years, wherein the NPV is higher than 80%. In some embodiments, the invention provides methods for predicting risk of relapse at 10 years, wherein the PPV is higher than 60, 70, 80, 90, 95, or 99.9%. In some embodiments, the invention provides methods for predicting risk of relapse at 10 years, wherein the PPV is equal or higher than 95%. In some embodiments, the invention provides methods for predicting risk of relapse at 10 years, wherein the NPV is higher than 60, 70, 80, 90, 95, or 99.9%. In some embodiments, the invention provides methods for predicting risk of relapse at 10 years, wherein the NPV is higher than 80%.

In some embodiments, the p value in the analysis of the methods described herein is below 0.05, 04, 0.03, 0.02, 0.01, 0.009, 0.005, or 0.001. In some embodiments, the p value is below 0.001. Thus in some embodiments, the invention provides methods for diagnosing, prognosing, determining progression or predicting response for treatment of AML, MDS or MPN wherein the p value is below 0.05, 04, 0.03, 0.02, 0.01, 0.009, 0.005, or 0.001. In some embodiments, the p value is below 0.001. In some embodiments, the invention provides methods for diagnosing, prognosing, determining progression or predicting response for treatment of AML, MDS or MPN wherein the AUC value is higher than 0.5, 0.6, 07, 0.8 or 0.9. In some embodiments, the invention provides methods for diagnosing, prognosing, determining progression or predicting response for treatment of AML, MDS or MPN wherein the AUC value is higher than 0.7. In some embodiments, the invention provides methods for diagnosing, prognosing, determining progression or predicting response for treatment of AML, MDS or MPN wherein the AUC value is higher than 0.8. In some embodiments, the invention provides methods for diagnosing, prognosing, determining progression or predicting response for treatment of AML, MDS or MPN wherein the AUC value is higher than 0.9.

Another method of the present invention is a method for determining the prognosis and therapeutic selection for an individual with myelodysplasia or MDS. Using the signaling nodes and methodology described herein, multiparametric flow cytometry could separate a patient into one of five groups consisting of: "AML-like", where a patient displays signaling biology that is similar to that seen in acute myelogenous leukemia (AML) requiring intensive therapy, "Epo-Responsive", where a patient's bone marrow or potentially peripheral blood, shows signaling biology that corresponds to either in-vivo or in-vitro sensitivity to erythropoietin, "Lenalidomide responsive", where a patient's bone marrow or potentially peripheral blood, shows signaling biology that corresponds to either in-vivo or in-vitro sensitivity to Lenalidomide, "Auto-immune", where a patient's bone marrow or potentially peripheral blood, shows signaling biology that corresponds to sensitivity to cyclosporine A(CSA) and anti-thymocyte globulin(ATG).

In those cases where an individual is classified as "AML-like", the individual's blood or marrow sample could reveal signaling biology that corresponds to either in-vivo or in-vitro sensitivity to cytarabine or to a class of drugs including but not limited to direct drug resistance modulators, anti-Bcl-2 or pro-apoptotic drugs, proteosome inhibitors, DNA methyl transferase inhibitors, histone deacetylase inhibitors, anti-angiogenic drugs, farnesyl transferase inhibitors, FLt3 ligand inhibitors, or ribonucleotide reductase inhibitors.

Figure 6:
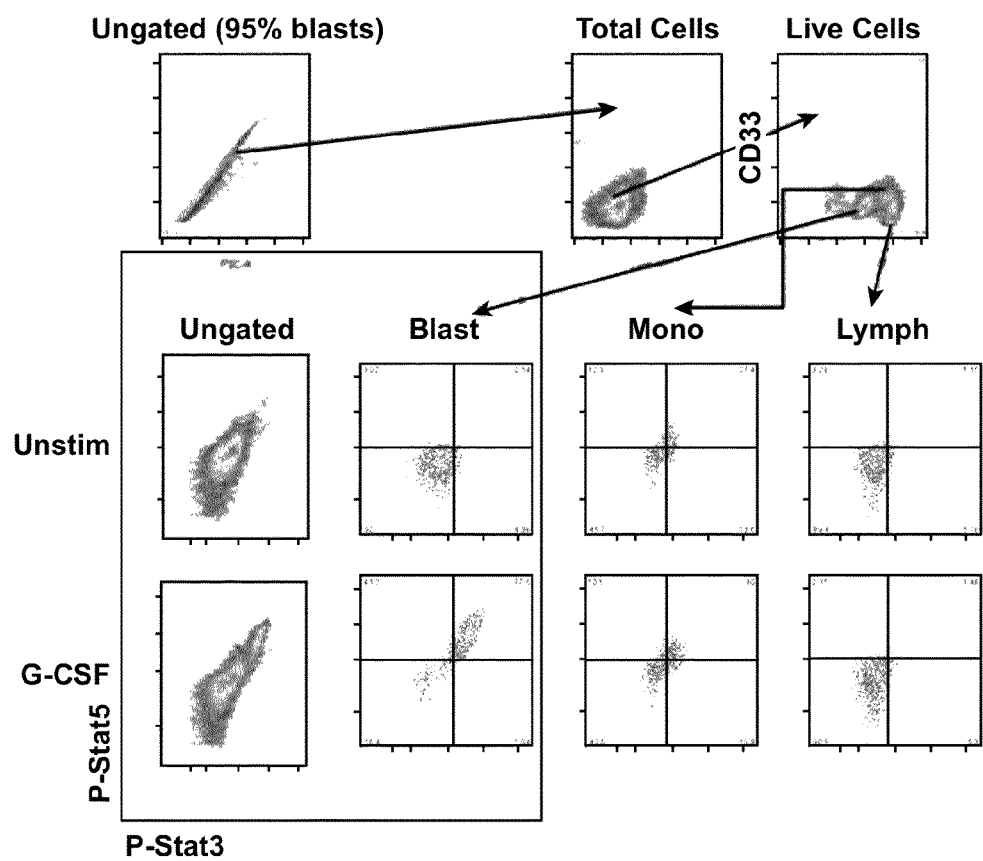
FIG. 6 shows how cell populations can be gated to select subpopulations.

In some embodiments of the invention, different gating strategies can be used in order to analyze only blasts in the sample of mixed population after treatment with the modulator. These gating strategies can be based on the presence of one or more specific surface marker expressed on each cell type. In some embodiments, the first gate eliminates cell doublets so that the user can focus on singlets. The following gate can differentiate between dead cells and live cells and subsequent gating of live cells classifies them into blasts, monocytes and lymphocytes. A clear comparison can be carried out to study the effect of potential modulators, such as G-SCF on activable elements in: ungated samples, blasts, monocytes, granulocytes and lymphocytes by using two-dimensional contour plot representations of Stat5 and Stat3 phosphorylation (x and Y axis) of patient samples. The level of basal phosphorylation and the change in phosphylation in both Stat3 and Stat5 phosphorylation in response to G-CSF can be compared. G-CSF increases both STATS and STATS phosphorylation and this dual signaling can occur concurrently (subpopulations with increases in both pSTAT 3 and pSTAT5) or individually (subpopulations with either an increase in phospho pSTAT 3 or pSTAT5 alone). The advantage of gating is to get a clearer picture and more precise results of the effect of various activable elements on blasts. See FIG. 6.

In some embodiments, a gate is established after learning from a responsive subpopulation. That is, a gate is developed from one data set. This gate can then be applied restrospectively or prospectively to other data sets (See FIGS. 26 and 27). The cells in this gate can be used for the diagnosis or prognosis of a condition. The cells in this gate can also be used to predict response to a treatment or for treatment selection. The mere presence of cells in this gate may be indicative of a diagnosis, prognosis, or a response to treatment. In some embodiments, the presence of cells in this gate at a number higher than a threshold number may be indicative of a diagnosis, prognosis, or a response to treatment.

Figure 2A:
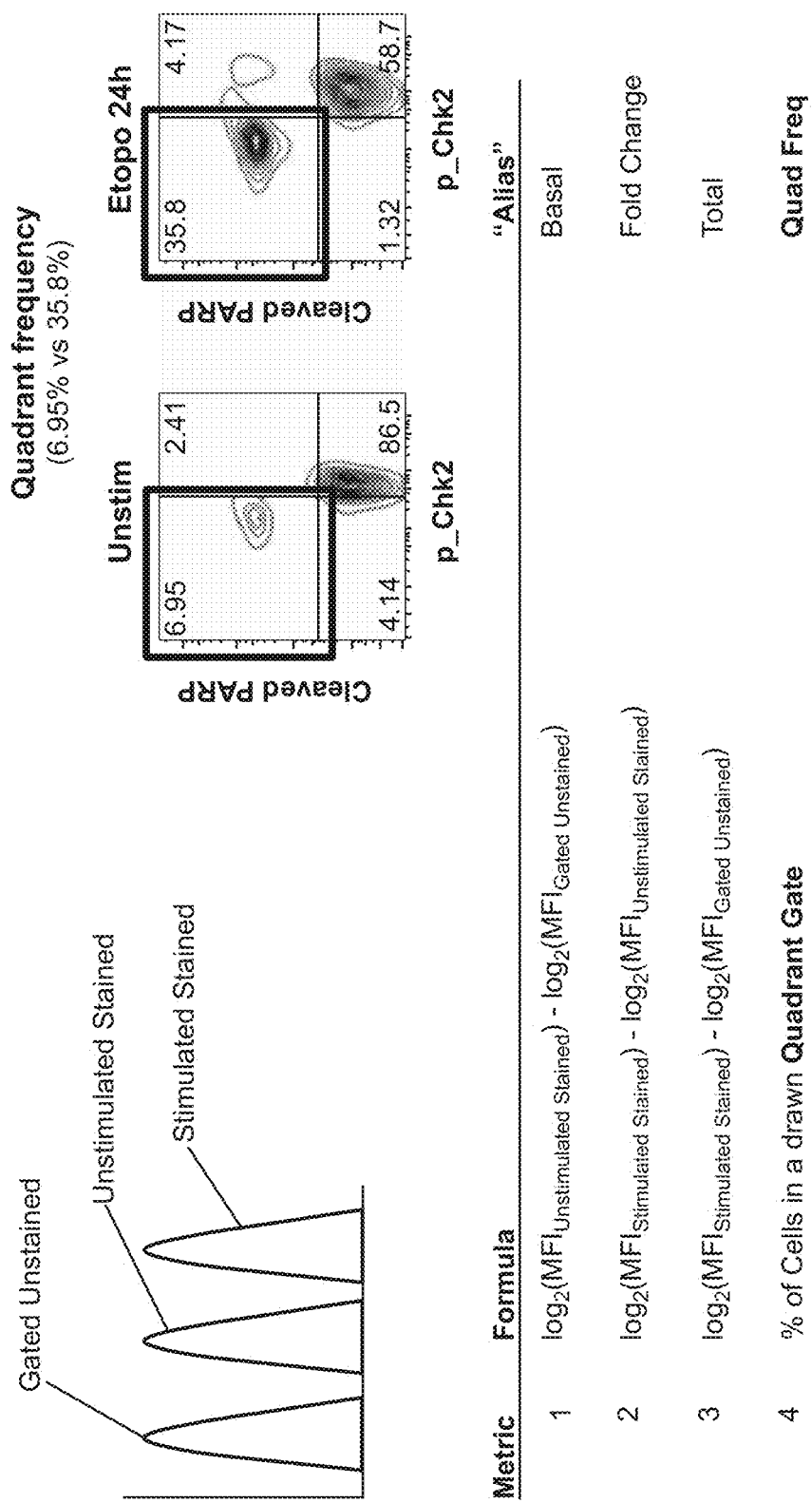
FIG. 2A shows the use of four metrics used to analyze data from cells that may be subject to a disease, such as AML. For these metrics the median (mean can be used as well) fluorescence intensity (MFI) was computed for the cells in one of the gated populations measured under various conditions of staining and stimulation. For example, the "basal" metric is calculated by subtracting the MFI of cells in the absence of a stimulant and stain (autofluorescence) from the MFI for cell measured in the absence of a stimulant (autofluorescence) ($\log_2(MFI_{Unstimulated\ Stained})-\log_2(MFI_{Gated\ Unstained})$). The "total phospho" metric is calculated by measuring the fluorescence of a cell that has been stimulated with a modulator and stained with a labeled antibody and then subtracting the value for autofluorescence ($\log_2(MFI_{Stimulated\ Stained})-\log_2(MFI_{Gated\ Unstained})$). The "fold change" metric is the measurement of the fluorescence of a cell that has been stimulated with a modulator and stained with a labeled antibody and then subtracting the value for unstimulated stained cells ($\log_2(MFI_{Stimulated\ Stained})-\log_2(MFI_{Unstimulated\ Stained})$). The "quadrant frequency" metric is the percentage of cells in each quadrant of the contour plot.
Figure 2B:
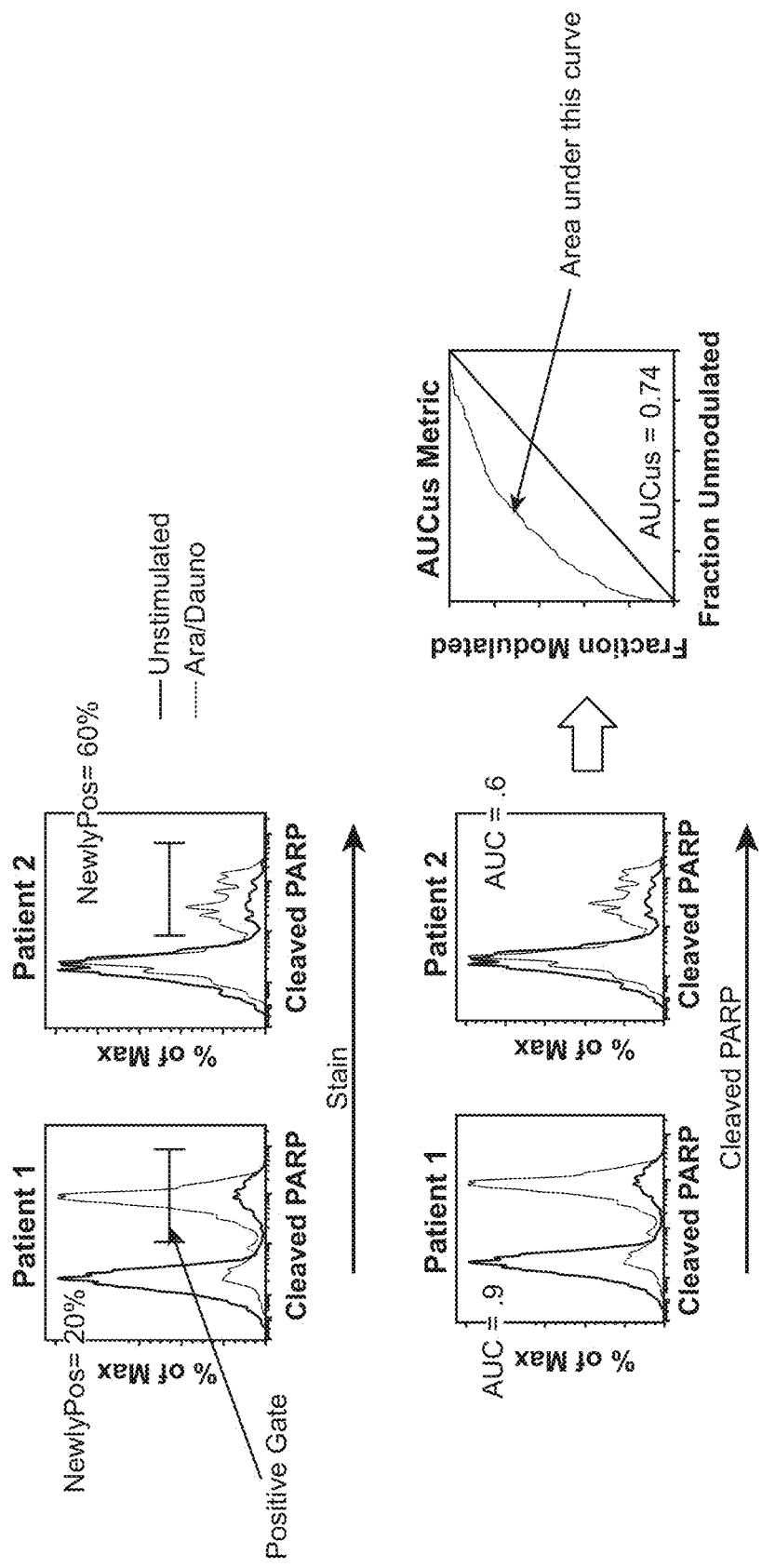
FIG. 2B shows that additional metrics can also be derived directly from the distribution of cell for a protein in a gated population for various condictions. NewlyPos=% of newly positive cells by modulator, based on a positive gate for a stain. AUC unstim=Area under the curve of frequency of un-modulated cells and modulated cells for a stain. NewlyPos: % Positive Cells modulated–% Positive Cells unmodulated.

Some methods of analysis, also called metrics are: 1) measuring the difference in the log of the median fluorescence value between an unstimulated fluorochrome-antibody stained sample and a sample that has not been treated with a stimulant or stained ($\log(\text{MFI}_{Unstimulated\ Stained}) - \log(\text{MFI}_{Gated\ Unstained})$), 2) measuring the difference in the log of the median fluorescence value between a stimulated fluorochrome-antibody stained sample and a sample that has not been treated with a stimulant or stained ($\log(\text{MFI}_{Stimulated\ Stained}) - \log(\text{MFI}_{Gated\ Unstained})$), 3) Measuring the change between the stimulated fluorochrome-antibody stained sample and the unstimulated fluorochrome-antibody stained sample $\log(\text{MFI}_{Stimulated\ Stained}) - \log(\text{MFI}_{Unstimulated\ Stained})$, also called "fold change in median fluorescence intensity", 4) Measuring the percentage of cells in a Quadrant Gate of a contour plot which measures multiple populations in one or more dimension 5) measuring MFI of phosphor positive population to obtain percentage positivity above the background; and 6) use of multimodality and spread metrics for large sample population and for subpopulation analysis. Other metrics used to analyze data are population frequency metrics measuring the frequency of cells with a described property such as cells positive for cleaved PARP (% PARP+), or cells positive for p-S6 and p-Akt (See FIG. 2B). Similarly, measurements examining the changes in the frequencies of cells may be applied such as the Change in % PARP+ which would measure the % PARP+$_{Stimulated\ Stained}$-% PARP+$_{Unstimulated\ Stained}$. The AUC$_{unstim}$ metric also measures changes in population frequencies measuring the frequency of cells to become positive compared to an unstimulated condition (FIG. 2B). The metrics described in FIG. 2B can be use to measure apoptosis. For example, these metrics can be applied to cleaved Caspase-3 and Caspase-8, e.g., Change in % Cleaved Caspase-3 or Cleaved Caspase-8.

Other possible metrics include third-color analysis (3D plots); percentage positive and relative expression of various markers; clinical analysis on an individual patient basis for various parameters, including, but not limited to age, race, cytogenetics, mutational status, blast percentage, CD34+ percentage, time of relapse, survival, etc. See FIG. 2. In alternative embodiments, there are other ways of analyzing data, such as third color analysis (3D plots), which can be similar to Cytobank 2D, plus third D in color.

Disease Conditions

The methods of the invention are applicable to any condition in an individual involving, indicated by, and/or arising from, in whole or in part, altered physiological status in a cell. The term "physiological status" includes mechanical, physical, and biochemical functions in a cell. In some embodiments, the physiological status of a cell is determined by measuring characteristics of cellular components of a cellular pathway. Cellular pathways are well known in the art. In some embodiments the cellular pathway is a signaling pathway. Signaling pathways are also well known in the art (see, e.g., Hunter T., Cell 100(1): 113-27 (2000); Cell Signaling Technology, Inc., 2002 Catalogue, Pathway Diagrams pgs. 232-253). A condition involving or characterized by altered physiological status may be readily identified, for example, by determining the state in a cell of one or more activatable elements, as taught herein.

In some embodiments, the present invention is directed to methods for classifying one or more cells in a sample derived from an individual having or suspected of having a condition. Example conditions include AML, MDS, or MPN. In some embodiments, the invention allows for identification of prognostically and therapeutically relevant subgroups of the conditions and prediction of the clinical course of an individual. In some embodiments, the invention provides methods of classifying a cell according to the activation levels of one or more activatable elements in a cell from an individual having or suspected of having a condition. In some embodiments, the classification includes classifying the cell as a cell that is correlated with a clinical outcome. The clinical outcome can be the prognosis and/or diagnosis of a condition, and/or staging or grading of a condition. In some embodiments, the classifying of the cell includes classifying the cell as a cell that is correlated with a patient response to a treatment. In some embodiments, the classifying of the cell includes classifying the cell as a cell that is correlated with minimal residual disease or emerging resistance.

Activatable Elements

The methods and compositions of the invention may be employed to examine and profile the status of any activatable element in a cellular pathway, or collections of such activatable elements. Single or multiple distinct pathways may be profiled (sequentially or simultaneously), or subsets of activatable elements within a single pathway or across multiple pathways may be examined (again, sequentially or simultaneously). In some embodiments, apoptosis, signaling, cell cycle and/or DNA damage pathways are characterized in order to classify one or more cells in an individual. The characterization of multiple pathways can reveal operative pathways in a condition that can then be used to classify one or more cells in an individual. In some embodiments, the classification includes classifying the cell as a cell that is correlated with a clinical outcome. The clinical outcome can be the prognosis and/or diagnosis of a condition, and/or staging or grading of a condition. In some embodiments, the classifying of the cell includes classifying the cell as a cell that is correlated with a patient response to a treatment. In some embodiments, the classifying of the cell includes classifying the cell as a cell that is correlated with minimal residual disease or emerging resistance.

As will be appreciated by those in the art, a wide variety of activation events can find use in the present invention. In general, the basic requirement is that the activation results in a change in the activatable protein that is detectable by some indication (termed an "activation state indicator"), preferably by altered binding of a labeled binding element or by changes in detectable biological activities (e.g., the activated state has an enzymatic activity which can be measured and compared to a lack of activity in the non-activated state). What is important is to differentiate, using detectable events or moieties, between two or more activation states (e.g. "off" and "on").

The activation state of an individual activatable element is either in the on or off state. As an illustrative example, and without intending to be limited to any theory, an individual phosphorylatable site on a protein can activate or deactivate the protein. Additionally, phosphorylation of an adapter protein may promote its interaction with other components/proteins of distinct cellular signaling pathways. The terms "on" and "off," when applied to an activatable element that is a part of a cellular constituent, are used here to describe the state of the activatable element, and not the overall state of the cellular constituent of which it is a part. Typically, a cell possesses a plurality of a particular protein or other constituent with a particular activatable element and this plurality of proteins or constituents usually has some proteins or constituents whose individual activatable element is in the on state and other proteins or constituents whose individual activatable element is in the off state. Since the activation state of each activatable element is measured through the use of a binding element that recognizes a specific activation state, only those activatable elements in the specific activation state recognized by the binding element, representing some fraction of the total number of activatable elements, will be bound by the binding element to generate a measurable signal. The measurable signal corresponding to the summation of individual activatable elements of a particular type that are activated in a single cell is the "activation level" for that activatable element in that cell.

Activation levels for a particular activatable element may vary among individual cells so that when a plurality of cells is analyzed, the activation levels follow a distribution. The distribution may be a normal distribution, also known as a Gaussian distribution, or it may be of another type. Different populations of cells may have different distributions of activation levels that can then serve to distinguish between the populations.

In some embodiments, the basis for classifying cells is that the distribution of activation levels for one or more specific activatable elements will differ among different phenotypes. A certain activation level, or more typically a range of activation levels for one or more activatable elements seen in a cell or a population of cells, is indicative that that cell or population of cells belongs to a distinctive phenotype. Other measurements, such as cellular levels (e.g., expression levels) of biomolecules that may not contain activatable elements, may also be used to classify cells in addition to activation levels of activatable elements; it will be appreciated that these levels also will follow a distribution, similar to activatable elements. Thus, the activation level or levels of one or more activatable elements, optionally in conjunction with levels of one or more levels of biomolecules that may or may not contain activatable elements, of cell or a population of cells may be used to classify a cell or a population of cells into a class. Once the activation level of intracellular activatable elements of individual single cells is known they can be placed into one or more classes, e.g., a class that corresponds to a phenotype. A class encompasses a class of cells wherein every cell has the same or substantially the same known activation level, or range of activation levels, of one or more intracellular activatable elements. For example, if the activation levels of five intracellular activatable elements are analyzed, predefined classes of cells that encompass one or more of the intracellular activatable elements can be constructed based on the activation level, or ranges of the activation levels, of each of these five elements. It is understood that activation levels can exist as a distribution and that an activation level of a particular element used to classify a cell may be a particular point on the distribution but more typically may be a portion of the distribution.

In some embodiments, the basis for classifying cells may use the position of a cell in a contour or density plot. The contour or density plot represents the number of cells that share a characteristic such as the activation level of activatable proteins in response to a modulator. For example, when referring to activation levels of activatable elements in response to one or more modulators, normal individuals and patients with a condition might show populations with increased activation levels in response to the one or more modulators. However, the number of cells that have a specific activation level (e.g. specific amount of an activatable element) might be different between normal individuals and patients with a condition. Thus, a cell can be classified according to its location within a given region in the contour or density plot. In other embodiments, the basis for classifying cells may use a series of population clusters whose centers, centroids, boundaries, relative positions describe the state of a cell, the diagnosis or prognosis of a patient, selection of treatment, or predicting reponse to treatment or to a combination of treatments, or long term outcome.

In some embodiments, the basis for classifying cells may use an N-dimensional Eigen map that describe the state of a cell, the diagnosis or prognosis of a patient, selection of treatment, or predicting reponse to treatment or to a combination of treatments, or long term outcome.

In other embodiments, the basis for classifying cells may use a Bayesian inference network of activatable elements interaction capabilities that together, or in part, describe the state of a cell, the diagnosis or prognosis of a patient, selection of treatment, or predicting reponse to treatment or to a combination of treatments, or long term outcome. See U.S. publication no. 2007/0009923 entitled Use of Bayesian Networks for Modeling Signaling Systems, incorporated herein by reference on its entirety.

In addition to activation levels of intracellular activatable elements, levels of intracellular or extracellular biomolecules, e.g., proteins, may be used alone or in combination with activation states of activatable elements to classify cells. Further, additional cellular elements, e.g., biomolecules or molecular complexes such as RNA, DNA, carbohydrates, metabolites, and the like, may be used in conjunction with activatable states or expression levels in the classification of cells encompassed here.

In some embodiments, cellular redox signaling nodes are analyzed for a change in activation level. Reactive oxygen species (ROS) are involved in a variety of different cellular processes ranging from apoptosis and necrosis to cell proliferation and carcinogenesis. ROS can modify many intracellular signaling pathways including protein phosphatases, protein kinases, and transcription factors. This activity may indicate that the majority of the effects of ROS are through their actions on signaling pathways rather than via non-specific damage of macromolecules. The exact mechanisms by which redox status induces cells to proliferate or to die, and how oxidative stress can lead to processes evoking tumor formation are still under investigation. See Mates, J M et al., Arch Toxicol. 2008 May: 82(5):271-2; Galaris D., et al., Cancer Lett. 2008 Jul. 18; 266(1)21-9.

Reactive oxygen species can be measured. One example technique is by flow cytometry. See Chang et al., Lymphocyte proliferation modulated by glutamine: involved in the endogenous redox reaction; Clin Exp Immunol. 1999 September; 117(3): 482-488. Redox potential can be evaluated by means of an ROS indicator, one example being 2',7'-dichlorofluorescein-diacetate (DCFH-DA) which is added to the cells at an exemplary time and temperature, such as 37° C. for 15 minutes. DCF peroxidation can be measured using flow cytometry. See Yang K D, Shaio M F. Hydroxyl radicals as an early signal involved in phorbol ester-induced monocyte differentiation of HL60 cells. Biochem Biophys Res Commun. 1994; 200:1650-7 and Wang J F, Jerrells T R, Spitzer J J. Decreased production of reactive oxygen intermediates is an early event during in vitro apoptosis of rat thymocytes. Free Radic Biol Med. 1996; 20:533-42.

In some embodiments, other characteristics that affect the status of a cellular constituent may also be used to classify a cell. Examples include the translocation of biomolecules or changes in their turnover rates and the formation and disassociation of complexes of biomolecule. Such complexes can include multi-protein complexes, multi-lipid complexes, homo- or hetero-dimers or oligomers, and combinations thereof. Other characteristics include proteolytic cleavage, e.g. from exposure of a cell to an extracellular protease or from the intracellular proteolytic cleavage of a biomolecule.

In some embodiments, cellular pH is analyzed. See June, C H and Moore, and J S, Curr Protoc Immulon, 2004 December; Chapter 5: Unit 5.5; Leyval, D et al., Flow cytometry for the intracellular pH measurement of glutamate producing *Corynebacterium glutamicum*, Journal of Microbiological Methods, Volume 29, Issue 2, 1 May 1997, Pages 121-127; Weider, E D, et al., Measurement of intracellular pH using flow cytometry with carboxy-SNARF-1. Cytometry, 1993 November; 14(8):916-21; and Valli, M, et al., Intracellular pH Distribution in *Saccharomyces cerevisiae* Cell Populations, Analyzed by Flow Cytometry, Applied and Environmental Microbiology, March 2005, p. 1515-1521, Vol. 71, No. 3.

In some embodiments, the activatable element is the phosphorylation of immunoreceptor tyrosine-based inhibitory motif (ITIM). An immunoreceptor tyrosine-based inhibition motif (ITIM), is a conserved sequence of amino acids (S/I/V/LxYxxI/V/L) that is found in the cytoplasmic tails of many inhibitory receptors of the immune system. After ITIM-possessing inhibitory receptors interact with their ligand, their ITIM motif becomes phosphorylated by enzymes of the Src family of kinases, allowing them to recruit other enzymes such as the phosphotyrosine phosphatases SHP-1 and SHP-2, or the inositol-phosphatase called SHIP. These phosphatases decrease the activation of molecules involved in cell signaling. See Barrow A, Trowsdale J (2006). "You say ITAM and I say ITIM, let's call the whole thing off: the ambiguity of immunoreceptor signalling". Eur J Immunol 36 (7): 1646-53. When phosphorylated, these phospho-tyrosine residues provide docking sites for the Shps which may result in transmission of inhibitory signals and effect the signaling of neighboring membrane receptor complexes (Paul et al., Blood (2000 96:483).

ITIMs can be analyzed by flow cytometry.

Additional elements may also be used to classify a cell, such as the expression level of extracellular or intracellular markers, nuclear antigens, enzymatic activity, protein expression and localization, cell cycle analysis, chromosomal analysis, cell volume, and morphological characteristics like granularity and size of nucleus or other distinguishing characteristics. For example, B cells can be further subdivided based on the expression of cell surface markers such as CD19, CD20, CD22 or CD23.

Alternatively, predefined classes of cells can be aggregated or grouped based upon shared characteristics that may include inclusion in one or more additional predefined class or the presence of extracellular or intracellular markers, similar gene expression profile, nuclear antigens, enzymatic activity, protein expression and localization, cell cycle analysis, chromosomal analysis, cell volume, and morphological characteristics like granularity and size of nucleus or other distinguishing cellular characteristics.

In some embodiments, the physiological status of one or more cells is determined by examining and profiling the activation level of one or more activatable elements in a cellular pathway. In some embodiments, a cell is classified according to the activation level of a plurality of activatable elements. In some embodiments, a hematopoietic cell is classified according to the activation levels of a plurality of activatable elements. In some embodiments, 1, 2, 3, 4, 5, 6, 7, 8, 9, 10 or more activatable elements may be analysed in a cell signaling pathway. In some embodiments, the activation levels of one or more activatable elements of a hematopoietic cell are correlated with a condition. In some embodiments, the activation levels of one or more activatable elements of a hematopoietic cell are correlated with a neoplastic or hematopoietic condition as described herein. Examples of hematopoietic cells include, but are not limited to, AML, MDS or MPN cells.

In some embodiments, the activation level of one or more activatable elements in single cells in the sample is determined. Cellular constituents that may include activatable elements include without limitation proteins, carbohydrates, lipids, nucleic acids and metabolites. The activatable element may be a portion of the cellular constituent, for example, an amino acid residue in a protein that may undergo phosphorylation, or it may be the cellular constituent itself, for example, a protein that is activated by translocation, change in conformation (due to, e.g., change in pH or ion concentration), by proteolytic cleavage, degradation through ubiquitination and the like. Upon activation, a change occurs to the activatable element, such as covalent modification of the activatable element (e.g., binding of a molecule or group to the activatable element, such as phosphorylation) or a conformational change. Such changes generally contribute to changes in particular biological, biochemical, or physical properties of the cellular constituent that contains the activatable element. The state of the cellular constituent that contains the activatable element is determined to some degree, though not necessarily completely, by the state of a particular activatable element of the cellular constituent. For example, a protein may have multiple activatable elements, and the particular activation states of these elements may overall determine the activation state of the protein; the state of a single activatable element is not necessarily determinative. Additional factors, such as the binding of other proteins, pH, ion concentration, interaction with other cellular constituents, and the like, can also affect the state of the cellular constituent.

In some embodiments, the activation levels of a plurality of intracellular activatable elements in single cells are determined. In some embodiments, at least about 2, 3, 4, 5, 6, 7, 8, 9, 10 or more than 10 intracellular activatable elements are determined.

Activation states of activatable elements may result from chemical additions or modifications of biomolecules and include biochemical processes such as glycosylation, phosphorylation, acetylation, methylation, biotinylation, glutamylation, glycylation, hydroxylation, isomerization, prenylation, myristoylation, lipoylation, phosphopantetheinylation, sulfation, ISGylation, nitrosylation, palmitoylation, SUMOylation, ubiquitination, neddylation, citrullination, amidation, and disulfide bond formation, disulfide bond reduction. Other possible chemical additions or modifications of biomolecules include the formation of protein carbonyls, direct modifications of protein side chains, such as o-tyrosine, chloro-, nitrotyrosine, and dityrosine, and protein adducts derived from reactions with carbohydrate and lipid derivatives. Other modifications may be non-covalent, such as binding of a ligand or binding of an allosteric modulator.

One example of a covalent modification is the substitution of a phosphate group for a hydroxyl group in the side chain of an amino acid (phosphorylation). A wide variety of proteins are known that recognize specific protein substrates and catalyze the phosphorylation of serine, threonine, or tyrosine residues on their protein substrates. Such proteins are generally termed "kinases." Substrate proteins that are capable of being phosphorylated are often referred to as phosphoproteins (after phosphorylation). Once phosphorylated, a substrate phosphoprotein may have its phosphorylated residue converted back to a hydroxyl one by the action of a protein phosphatase that specifically recognizes the substrate protein. Protein phosphatases catalyze the replacement of phosphate groups by hydroxyl groups on serine, threonine, or tyrosine residues. Through the action of kinases and phosphatases a protein may be reversibly phosphorylated on a multiplicity of residues and its activity may be regulated thereby. Thus, the presence or absence of one or more phosphate groups in an activatable protein is a preferred readout in the present invention.

Another example of a covalent modification of an activatable protein is the acetylation of histones. Through the activity of various acetylases and deacetylylases the DNA binding function of histone proteins is tightly regulated. Furthermore, histone acetylation and histone deactelyation have been linked with malignant progression. See Nature, 2004 May 27; 429(6990): 457-63.

Another form of activation involves cleavage of the activatable element. For example, one form of protein regulation involves proteolytic cleavage of a peptide bond. While random or misdirected proteolytic cleavage may be detrimental to the activity of a protein, many proteins are activated by the action of proteases that recognize and cleave specific peptide bonds. Many proteins derive from precursor proteins, or proproteins, which give rise to a mature isoform of the protein following proteolytic cleavage of specific peptide bonds. Many growth factors are synthesized and processed in this manner, with a mature isoform of the protein typically possessing a biological activity not exhibited by the precursor form. Many enzymes are also synthesized and processed in this manner, with a mature isoform of the protein typically being enzymatically active, and the precursor form of the protein being enzymatically inactive. This type of regulation is generally not reversible. Accordingly, to inhibit the activity of a proteolytically activated protein, mechanisms other than "reattachment" must be used. For example, many proteolytically activated proteins are relatively short-lived proteins, and their turnover effectively results in deactivation of the signal. Inhibitors may also be used. Among the enzymes that are proteolytically activated are serine and cysteine proteases, including cathepsins and caspases respectively.

In one embodiment, the activatable enzyme is a caspase. The caspases are an important class of proteases that mediate programmed cell death (referred to in the art as "apoptosis"). Caspases are constitutively present in most cells, residing in the cytosol as a single chain proenzyme. These are activated to fully functional proteases by a first proteolytic cleavage to divide the chain into large and small caspase subunits and a second cleavage to remove the N-terminal domain. The subunits assemble into a tetramer with two active sites (Green, Cell 94:695-698, 1998). Many other proteolytically activated enzymes, known in the art as "zymogens," also find use in the instant invention as activatable elements.

In an alternative embodiment the activation of the activatable element involves prenylation of the element. By "prenylation", and grammatical equivalents used herein, is meant the addition of any lipid group to the element. Common examples of prenylation include the addition of farnesyl groups, geranylgeranyl groups, myristoylation and palmitoylation. In general these groups are attached via thioether linkages to the activatable element, although other attachments may be used.

In alternative embodiment, activation of the activatable element is detected as intermolecular clustering of the activatable element. By "clustering" or "multimerization", and grammatical equivalents used herein, is meant any reversible or irreversible association of one or more signal transduction elements. Clusters can be made up of 2, 3, 4, etc., elements. Clusters of two elements are termed dimers. Clusters of 3 or more elements are generally termed oligomers, with individual numbers of clusters having their own designation; for example, a cluster of 3 elements is a trimer, a cluster of 4 elements is a tetramer, etc.

Clusters can be made up of identical elements or different elements. Clusters of identical elements are termed "homo" dimers, while clusters of different elements are termed "hetero" clusters. Accordingly, a cluster can be a homodimer, as is the case for the $\beta_2$-adrenergic receptor.

Alternatively, a cluster can be a heterodimer, as is the case for GABA In other embodiments, the cluster is a homotrimer, as in the case of TNFα, or a heterotrimer such the one formed by membrane-bound and soluble CD95 to modulate apoptosis. In further embodiments the cluster is a homo-oligomer, as in the case of Thyrotropin releasing hormone receptor, or a hetero-oligomer, as in the case of TGFβ1.

In a preferred embodiment, the activation or signaling potential of elements is mediated by clustering, irrespective of the actual mechanism by which the element's clustering is induced. For example, elements can be activated to cluster a) as membrane bound receptors by binding to ligands (ligands including both naturally occurring or synthetic ligands), b) as membrane bound receptors by binding to other surface molecules, or c) as intracellular (non-membrane bound) receptors binding to ligands.

In a preferred embodiment the activatable elements are membrane bound receptor elements that cluster upon ligand binding such as cell surface receptors. As used herein, "cell surface receptor" refers to molecules that occur on the surface of cells, interact with the extracellular environment, and transmit or transduce (through signals) the information regarding the environment intracellularly in a manner that may modulate cellular activity directly or indirectly, e.g., via intracellular second messenger activities or transcription of specific promoters, resulting in transcription of specific genes. One class of receptor elements includes membrane bound proteins, or complexes of proteins, which are activated to cluster upon ligand binding. As is known in the art, these receptor elements can have a variety of forms, but in general they comprise at least three domains. First, these receptors have a ligand-binding domain, which can be oriented either extracellularly or intracellularly, usually the former. Second, these receptors have a membrane-binding domain (usually a transmembrane domain), which can take the form of a seven pass transmembrane domain (discussed below in connection with G-protein-coupled receptors) or a lipid modification, such as myristylation, to one of the receptor's amino acids which allows for membrane association when the lipid inserts itself into the lipid bilayer. Finally, the receptor has an signaling domain, which is responsible for propagating the downstream effects of the receptor.

Examples of such receptor elements include hormone receptors, steroid receptors, cytokine receptors, such as IL1-α, IL-β, IL-2, IL-3, IL-4, IL-5, IL-6, IL-7, IL-8, IL-9, IL-10. IL-12, IL-15, IL-18, IL-21, CCR5, CCR7, CCR-1-10, CCL20, chemokine receptors, such as CXCR4, adhesion receptors and growth factor receptors, including, but not limited to, PDGF-R (platelet derived growth factor receptor), EGF-R (epidermal growth factor receptor), VEGF-R (vascular endothelial growth factor), uPAR (urokinase plasminogen activator receptor), ACHR (acetylcholine receptor), IgE-R (immunoglobulin E receptor), estrogen receptor, thyroid hormone receptor, integrin receptors (β1, β2, β3, β4, β5, β6, α1, α2, α3, α4, α5, α6), MAC-1 (β2 and cd11b), αVβ33, opioid receptors (mu and kappa), FC receptors, serotonin receptors (5-HT, 5-HT6,5-HT7), β-adrenergic receptors, insulin receptor, leptin receptor, TNF receptor (tissue-necrosis factor), statin receptors, FAS receptor, BAFF receptor, FLT3 LIGAND receptor, GMCSF receptor, and fibronectin receptor.

In a preferred embodiment the activatable element is a cytokine receptor. Cytokines are a family of soluble mediators of cell-to-cell communication that includes interleukins, interferons, and colony-stimulating factors. The characteristic features of cytokines lie in their pleiotropy and functional redundancy. Most of the cytokine receptors that constitute distinct superfamilies do not possess intrinsic protein tyrosine kinase domains, yet receptor stimulation usually invokes rapid tyrosine phosphorylation of intracellular proteins, including the receptors themselves. Many members of the cytokine receptor superfamily activate the Jak protein tyrosine kinase family, with resultant phosphorylation of the STAT family of transcription factors. IL-2, IL-4, IL-7 and Interferon γ have all been shown to activate Jak kinases (Frank et al. (1995) Proc. Natl. Acad. Sci. USA 92:7779-7783); Scharfe et al. (1995) Blood 86:2077-2085); (Bacon et al. (1995) Proc. Natl. Acad. Sci. USA 92:7307-7311); and (Sakatsume et al. (1995) J. Biol. Chem. 270:17528-17534). Events downstream of Jak phosphorylation have also been elucidated. For example, exposure of T lymphocytes to IL-2 has been shown to lead to the phosphorylation of signal transducers and activators of transcription (STAT) proteins STAT 1α, STAT1β, and STATS, as well as of two STAT-related proteins, p94 and p95. The STAT proteins translocate to the nucleus and bind to a specific DNA sequence, thus suggesting a mechanism by which IL-2 may activate specific genes involved in immune cell function (Frank et al. supra). Jak3 is associated with the gamma chain of the IL-2, IL-4, and IL-7 cytokine receptors (Fujii et al. (1995) Proc. Natl. Acad. Sci. 92:5482-5486) and (Musso et al. (1995) J. Exp. Med. 181:1425-1431). The Jak kinases have been shown to be activated by numerous ligands that signal via cytokine receptors such as, growth hormone, erythropoietin and IL-6 (Kishimoto (1994) Stem cells Suppl. 12:37-44). Preferred activatable elements are selected from the group p-STAT1, p-STAT3, p-STATS, p-STAT6, p-PLCγ2, p-S6, pAkt, p-Erk, p-CREB, p-38, and NF-KBp-65.

In a preferred embodiment the activatable element is a member of the nerve growth factor receptor superfamily, such as the Tumor necrosis factor alpha receptor. Tumor necrosis factor α (TNF-α or TNF-alpha) is a pleiotropic cytokine that is primarily produced by activated macrophages and lymphocytes but is also expressed in endothelial cells and other cell types. TNF-alpha is a major mediator of inflammatory, immunological, and pathophysiological reactions. (Grell, M., et al., (1995) Cell, 83:793-802). Two distinct forms of TNF exist, a 26 kDa membrane expressed form and the soluble 17 kDa cytokine which is derived from proteolytic cleavage of the 26 kDa form. The soluble TNF polypeptide is 157 amino acids long and is the primary biologically active molecule.

TNF-alpha exerts its biological effects through interaction with high-affinity cell surface receptors. Two distinct membrane TNF-alpha receptors have been cloned and characterized. These are a 55 kDa species, designated p55 TNF-R and a 75 kDa species designated p75 TNF-R (Corcoran. A. E., et al., (1994) Eur. J. Biochem., 223:831-840). The two TNF receptors exhibit 28% similarity at the amino acid level. This is confined to the extracellular domain and consists of four repeating cysteine-rich motifs, each of approximately 40 amino acids. Each motif contains four to six cysteines in conserved positions. Dayhoff analysis shows the greatest intersubunit similarity among the first three repeats in each receptor. This characteristic structure is shared with a number of other receptors and cell surface molecules, which comprise the TNF-R/nerve growth factor receptor superfamily (Corcoran. A. E., et al., (1994) Eur. J. Biochem., 223:831-840).

TNF signaling is initiated by receptor clustering, either by the trivalent ligand TNF or by cross-linking monoclonal antibodies (Vandevoorde, V., et al., (1997) J. Cell Biol., 137: 1627-1638). Crystallographic studies of TNF and the structurally related cytokine, lymphotoxin (LT), have shown that both cytokines exist as homotrimers, with subunits packed edge to edge in threefold symmetry. Structurally, neither TNF nor LT reflect the repeating pattern of the their receptors. Each monomer is cone shaped and contains two hydrophilic loops on opposite sides of the base of the cone. Recent crystal structure determination of a p55 soluble TNF-R/LT complex has confirmed the hypothesis that loops from adjacent monomers join together to form a groove between monomers and that TNF-R binds in these grooves (Corcoran. A. E., et al., (1994) Eur. J. Biochem., 223:831-840).

In one embodiment, the activatable element is a receptor tyrosine kinase. The receptor tyrosine kinases can be divided into subgroups on the basis of structural similarities in their extracellular domains and the organization of the tyrosine kinase catalytic region in their cytoplasmic domains. Subgroups I (epidermal growth factor (EGF) receptor-like), II (insulin receptor-like) and the EPH/ECK family contain cysteine-rich sequences (Hirai et al., (1987) Science 238:1717-1720 and Lindberg and Hunter, (1990) Mol. Cell. Biol. 10:6316-6324). The functional domains of the kinase region of these three classes of receptor tyrosine kinases are encoded as a contiguous sequence (Hanks et al. (1988) Science 241: 42-52). Subgroups III (platelet-derived growth factor (PDGF) receptor-like) and IV (the fibro-blast growth factor (FGF) receptors) are characterized as having immunoglobulin (Ig)-like folds in their extracellular domains, as well as having their kinase domains divided in two parts by a variable stretch of unrelated amino acids (Yanden and Ullrich (1988) supra and Hanks et al. (1988) supra).

The family with the largest number of known members is the Eph family (with the first member of the family originally isolated from an erythropoietin producing hepatocellular carcinoma cell line). Since the description of the prototype, the Eph receptor (Hirai et al. (1987) Science 238:1717-1720), sequences have been reported for at least ten members of this family, not counting apparently orthologous receptors found in more than one species. Additional partial sequences, and the rate at which new members are still being reported, suggest the family is even larger (Maisonpierre et al. (1993) Oncogene 8:3277-3288; Andres et al. (1994) Oncogene 9:1461-1467; Henkemeyer et al. (1994) Oncogene 9:1001-1014; Ruiz et al. (1994) Mech. Dev. 46:87-100; Xu et al. (1994) Development 120:287-299; Zhou et al. (1994) J. Neurosci. Res. 37:129-143; and references in Tuzi and Gullick (1994) Br. J. Cancer 69:417-421). Remarkably, despite the large number of members in the Eph family, all of these molecules were identified as orphan receptors without known ligands.

As used herein, the terms "Eph receptor" or "Eph-type receptor" refer to a class of receptor tyrosine kinases, comprising at least eleven paralogous genes, though many more orthologs exist within this class, e.g. homologs from different species. Eph receptors, in general, are a discrete group of receptors related by homology and easily recognizable, e.g., they are typically characterized by an extracellular domain containing a characteristic spacing of cysteine residues near the N-terminus and two fibronectin type III repeats (Hirai et al. (1987) Science 238:1717-1720; Lindberg et al. (1990) Mol. Cell. Biol. 10:6316-6324; Chan et al. (1991) Oncogene 6:1057-1061; Maisonpierre et al. (1993) Oncogene 8:3277-3288; Andres et al. (1994) Oncogene 9:1461-1467; Henkemeyer et al. (1994) Oncogene 9:1001-1014; Ruiz et al. (1994) Mech. Dev. 46:87-100; Xu et al. (1994) Development 120: 287-299; Zhou et al. (1994) J. Neurosci. Res. 37:129-143; and references in Tuzi and Gullick (1994) Br. J. Cancer 69:417-421). Exemplary Eph receptors include the eph, elk, eck, sek, mek4, hek, hek2, eek, erk, tyro1, tyro4, tyro5, tyro6, tyro111, cek4, cek5, cek6, cek7, cek8, cek9, cek10, bsk, rtk1, rtk2, rtk3, myk1, myk2, ehk1, ehk2, pagliaccio, htk, erk and nuk receptors.

In another embodiment the receptor element is a member of the hematopoietin receptor superfamily. Hematopoietin receptor superfamily is used herein to define single-pass transmembrane receptors, with a three-domain architecture: an extracellular domain that binds the activating ligand, a short transmembrane segment, and a domain residing in the cytoplasm. The extracellular domains of these receptors have low but significant homology within their extracellular ligand-binding domain comprising about 200-210 amino acids. The homologous region is characterized by four cysteine residues located in the N-terminal half of the region, and a Trp-Ser-X-Trp-Ser (WSXWS) motif located just outside the membrane-spanning domain. Further structural and functional details of these receptors are provided by Cosman, D. et al., (1990). The receptors of IL-1, IL-2, IL-3, IL-4, IL-5, IL-6, IL-7, prolactin, placental lactogen, growth hormone GM-CSF, G-CSF, M-CSF and erythropoietin have, for example, been identified as members of this receptor family.

In a further embodiment, the receptor element is an integrin other than Leukocyte Function Antigen-1 (LFA-1). Members of the integrin family of receptors function as heterodimers, composed of various α and β subunits, and mediate interactions between a cell's cytoskeleton and the extracellular matrix. (Reviewed in, Giancotti and Ruoslahti, Science 285, 13 Aug. 1999). Different combinations of the α and β subunits give rise to a wide range of ligand specificities, which may be increased further by the presence of cell-type-specific factors. Integrin clustering is know to activate a number of intracellular signals, such as RAS, MAP kinase, and phosphotidylinosital-3-kinase. In a preferred embodiment the receptor element is a heterodimer (other than LFA-1) composed of a β integrin and an α integrin chosen from the following integrins; β1, β2, β3, β4, β5, β6, α1, α2, α3, α4, α5, and α6, or is MAC-1 (β2 and cd11b), or αVβ3.

In a preferred embodiment the element is an intracellular adhesion molecule (ICAM). ICAMs-1, -2, and -3 are cellular adhesion molecules belonging to the immunoglobulin superfamily. Each of these receptors has a single membrane-spanning domain and all bind to 132 integrins via extracellular binding domains similar in structure to Ig-loops. (Signal Transduction, Gomperts, et al., eds, Academic Press Publishers, 2002, Chapter 14, pp 318-319).

In another embodiment the activatable elements cluster for signaling by contact with other surface molecules. In contrast to the receptors discussed above, these elements cluster for signaling by contact with other surface molecules, and generally use molecules presented on the surface of a second cell as ligands. Receptors of this class are important in cell-cell interactions, such mediating cell-to-cell adhesion and immunorecognition.

Examples of such receptor elements are CD3 (T cell receptor complex), BCR (B cell receptor complex), CD4, CD28, CD80, CD86, CD54, CD102, CD50 and ICAMs 1, 2 and 3.

In a preferred embodiment the receptor element is a T cell receptor complex (TCR). TCRs occur as either of two distinct heterodimers, αβ, or γξ both of which are expressed with the non-polymorphic CD3 polypeptides γ, Σ, ε, ξ. The CD3 polypeptides, especially 4 and its variants, are critical for intracellular signaling. The αβ TCR heterodimer expressing cells predominate in most lymphoid compartments and are responsible for the classical helper or cytotoxic T cell responses. In most cases, the αβ TCR ligand is a peptide antigen bound to a class I or a class II MHC molecule (Fundamental Immunology, fourth edition, W. E. Paul, ed., Lippincott-Raven Publishers, 1999, Chapter 10, pp 341-367).

In another embodiment, the activatable element is a member of the large family of G-protein-coupled receptors. It has recently been reported that a G-protein-coupled receptors are capable of clustering. (Kroeger, et al., J Biol Chem 276:16, 12736-12743, Apr. 20, 2001; Bai, et al., J Biol Chem 273:36, 23605-23610, Sep. 4, 1998; Rocheville, et al., J Biol Chem 275 (11), 7862-7869, Mar. 17, 2000). As used herein G-protein-coupled receptor, and grammatical equivalents thereof, refers to the family of receptors that bind to heterotrimeric "G proteins." Many different G proteins are known to interact with receptors. G protein signaling systems include three components: the receptor itself, a GTP-binding protein (G protein), and an intracellular target protein. The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha ($\alpha$), beta ($\beta$) and gamma ($\gamma$) subunits, are complexed with the nucleotide guanosine diphosphate (GDP) and are in contact with receptors. When a hormone or other first messenger binds to a receptor, the receptor changes conformation and this alters its interaction with the G protein. This spurs a subunit to release GDP, and the more abundant nucleotide guanosine triphosphate (GTP), replaces it, activating the G protein. The G protein then dissociates to separate the $\alpha$ subunit from the still complexed beta and gamma subunits. Either the G$\alpha$ subunit, or the G$\beta\gamma$ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the G$\alpha$ converts the GTP to GDP, thereby inactivating itself. The inactivated G$\alpha$ may then reassociate with the G$\beta\gamma$ complex.

Hundreds, if not thousands, of receptors convey messages through heterotrimeric G proteins, of which at least 17 distinct forms have been isolated. Although the greatest variability has been seen in a subunit, several different $\beta$ and $\gamma$ structures have been reported. There are, additionally, many different G protein-dependent effectors.

Most G protein-coupled receptors are comprised of a single protein chain that passes through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (1993) Cell 72, 415; Kouba et al. FEBS Lett. (1993)321, 173; and Birkenbach et al. (1993) J. Virol. 67, 2209.

Known ligands for G protein coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, histamine, noradrenaline, tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheromones, galanin, gastric inhibitory polypeptide receptor (gip), glucagon-like peptides (gips), glucagon, gonadotropin releasing hormone (gnrh), growth hormone releasing hormone(ghrh), insect diuretic hormone, interleukin-8, leutropin (1 h/hcg), met-enkephalin, opioid peptides, oxytocin, parathyroid hormone (pth) and pthrp, pituitary adenylyl cyclase activating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Preferred G protein coupled receptors include, but are not limited to: $\alpha$1-adrenergic receptor, $\alpha$1B-adrenergic receptor, $\alpha$2-adrenergic receptor, $\alpha$2B-adrenergic receptor, $\beta$1-adrenergic receptor, $\beta$2-adrenergic receptor, $\beta$3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2a adenosine receptor, A2b adenosine receptor, A3 adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor (FPR), fMLP-like receptor (FPRL-1), angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, CXCR1 (IL-8 receptor A), CXCR2 (IL-8 receptor B), Delta Opioid receptor, Kappa Opioid receptor, mip-1 alpha/RANTES receptor (CRR1), Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor, antidiuretic hormone receptor, glucagon receptor, and adrenocorticotropic hormone II receptor. In addition, there are at least five receptors (CC and CXC receptors) involved in HIV viral attachment to cells. The two major co-receptors for HIV are CXCR4, (fusin receptor, LESTR, SDF-1$\alpha$ receptor) and CCR5 (m-trophic). More preferred receptors include the following human receptors: melatonin receptor 1a, galanin receptor 1, neurotensin receptor, adenosine receptor 2a, somatostatin receptor 2 and corticotropin releasing factor receptor 1. Melatonin receptor 1a is particularly preferred. Other G protein coupled receptors (GPCRs) are known in the art.

In one embodiment, Lnk is a protein to be measured. Hematopoietic stem cells (HSCs) give rise to variety of hematopoietic cells via pluripotential progenitors. Lineage-committed progenitors are responsible for blood production throughout adult life. Amplification of HSCs or progenitors represents a potentially powerful approach to the treatment of various blood disorders. Animal model studies demonstrated that Lnk acts as a broad inhibitor of signaling pathways in hematopoietic lineages. Lnk is an adaptor protein which belongs to a family of proteins sharing several structural motifs, including a Src homology 2 (SH2) domain which binds phospho-tyrosines in various signal-transducing proteins. The SH2 domain is essential for Lnk-mediated negative regulation of several cytokine receptors (i.e. Mpl, EpoR, c-Kit, Il-3R and IL7R). Therefore, inhibition of the binding of Lnk to cytokine receptors might lead to enhanced downstream signaling of the receptor and thereby to improved hematopoiesis in response to exposure to cytokines (i.e. erythropoietin in anemic patients). (Gueller et al, Adaptor protein Lnk associates with Y568 in c-Kit. 1: Biochem J. 2008 Jun. 30.) It has been shown that overexpression of Lnk in Ba/F3-MPLW515L cells inhibits cytokine-independent growth, while suppression of Lnk in UT7-MPLW515L cells enhances proliferation. Lnk blocks the activation of Jak2, Stat3, Erk, and Akt in these cells. (Gery et al., Adaptor protein Lnk negatively regulates the mutant MPL, MPLW515L associated with myeloproliferative neoplasms, Blood, 1 Nov. 2007, Vol. 110, No. 9, pp. 3360-3364.) Thus, Lnk is an important protein to measure for the evaluation of AML/MDS/MPS.

In one embodiment, the activatable elements are intracellular receptors capable of clustering. Elements of this class are not membrane-bound. Instead, they are free to diffuse through the intracellular matrix where they bind soluble ligands prior to clustering and signal transduction. In contrast to the previously described elements, many members of this class are capable of binding DNA after clustering to directly effect changes in RNA transcription.

In another embodiment the intracellular receptors capable of clustering are perioxisome proliferator-activated receptors (PPAR). PPARs are soluble receptors responsive to lipophillic compounds, and induce various genes involved in fatty acid metabolism. The three PPAR subtypes, PPAR α, β, and γ have been shown to bind to DNA after ligand binding and heterodimerization with retinoid X receptor. (Summanasekera, et al., J Biol Chem, M211261200, Dec. 13, 2002.)

In another embodiment the activatable element is a nucleic acid. Activation and deactivation of nucleic acids can occur in numerous ways including, but not limited to, cleavage of an inactivating leader sequence as well as covalent or non-covalent modifications that induce structural or functional changes. For example, many catalytic RNAs, e.g. hammerhead ribozymes, can be designed to have an inactivating leader sequence that deactivates the catalitic activity of the ribozyme until cleavage occurs. An example of a covalent modification is methylation of DNA. Deactivation by methylation has been shown to be a factor in the silencing of certain genes, e.g. STAT regulating SOCS genes in lymphomas. See Leukemia. See February 2004; 18(2): 356-8. SOCS1 and SHPT hypermethylation in mantle cell lymphoma and follicular lymphoma: implications for epigenetic activation of the Jak/STAT pathway. Chim C S, Wong K Y, Loong F, Srivastava G.

In another embodiment the activatable element is a small molecule, carbohydrate, lipid or other naturally occurring or synthetic compound capable of having an activated isoform. In addition, as pointed out above, activation of these elements need not include switching from one form to another, but can be detected as the presence or absence of the compound. For example, activation of cAMP (cyclic adenosine mono-phosphate) can be detected as the presence of cAMP rather than the conversion from non-cyclic AMP to cyclic AMP.

In some embodiments, the activatable element is a protein. Examples of proteins that may include activatable elements include, but are not limited to kinases, phosphatases, lipid signaling molecules, adaptor/scaffold proteins, cytokines, cytokine regulators, ubiquitination enzymes, adhesion molecules, cytoskeletal/contractile proteins, heterotrimeric G proteins, small molecular weight GTPases, guanine nucleotide exchange factors, GTPase activating proteins, caspases, proteins involved in apoptosis, cell cycle regulators, molecular chaperones, metabolic enzymes, vesicular transport proteins, hydroxylases, isomerases, deacetylases, methylases, demethylases, tumor suppressor genes, proteases, ion channels, molecular transporters, transcription factors/DNA binding factors, regulators of transcription, and regulators of translation. Examples of activatable elements, activation states and methods of determining the activation level of activatable elements are described in US Publication Number 20060073474 entitled "Methods and compositions for detecting the activation state of multiple proteins in single cells" and US Publication Number 20050112700 entitled "Methods and compositions for risk stratification" the content of which are incorporate here by reference. See also U.S. Ser. Nos. 61/048,886; 61/048,920; and Shulz et al., Current Protocols in Immunology 2007, 78:8.17.1-20.

In some embodiments, the protein is selected from the group consisting of HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6 Kinase, Prks, PKCs, PKAs, ROCK 1, ROCK 2, Auroras, CaMKs, MNKs, AMPKs, MELK, MARKs, Chk1, Chk2, LKB-1, MAP-KAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PPS, inositol phosphatases, PTEN, SHIPs, myotubularins, phosphoinositide kinases, phopsholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon γ, interferon α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, Bcl-2, Mcl-1, Bcl-XL, Bch w, Bcl-B, A1, Bax, Bak, Bok, Bik, Bad, Bid, Bim, Bmf, Hrk, Noxa, Puma, IAPB, XIAP, Smac, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pin1 prolyl isomerase, topoisomerases, deacetylases, Histone deacetylases, sirtuins, histone acetylases, CBP/P300 family, MYST family, ATF2, DNA methyl transferases, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, nucleoside transporters, Ets, Elk, SMADs, Rel-A (p65-NFKB), CREB, NFAT, ATF-2, AFT, Myc, Fos, Sp1, Egr-1, T-bet, β-catenin, HIFs, FOXOs, E2Fs, SRFs, TCFs, Egr-1, β-☐catenin, FOXO STAT1, STAT 3, STAT 4, STAT 5, STAT 6, p53, WT-1, HMGA, pS6, 4EPB-1, eIF4E-binding protein, RNA polymerase, initiation factors, elongation factors.

In some embodiments of the invention, the methods described herein are employed to determine the activation level of an activatable element, e.g., in a cellular pathway. Methods and compositions are provided for the classification of a cell according to the activation level of an activatable element in a cellular pathway. The cell can be a hematopoietic cell. Examples of hematopoietic cells include but are not limited to pluripotent hematopoietic stem cells, granulocyte lineage progenitor or derived cells, monocyte lineage progenitor or derived cells, macrophage lineage progenitor or derived cells, megakaryocyte lineage progenitor or derived cells and erythroid lineage progenitor or derived cells.

In some embodiments, the cell is classified according to the activation level of an activatable element, e.g., in a cellular pathway comprises classifying the cell as a cell that is correlated with a clinical outcome. In some embodiments, the clinical outcome is the prognosis and/or diagnosis of a condition. In some embodiments, the clinical outcome is the presence or absence of a neoplastic or a hematopoietic condition. In some embodiments, the clinical outcome is the staging or grading of a neoplastic or hematopoietic condition. Examples of staging include, but are not limited to, aggressive, indolent, benign, refractory, Roman Numeral staging, TNM Staging, Rai staging, Binet staging, WHO classification, FAB classification, IPSS score, WPSS score, limited stage, extensive stage, staging according to cellular markers such as ZAP70 and CD38, occult, including information that may inform on time to progression, progression free survival, overall survival, or event-free survival.

In some embodiments, methods and compositions are provided for the classification of a cell according to the activation level of an activatable element, e.g., in a cellular pathway wherein the classification comprises classifying a cell as a cell that is correlated to a patient response to a treatment. In some embodiments, the patient response is selected from the group consisting of complete response, partial response, nodular partial response, no response, progressive disease, stable disease and adverse reaction.

In some embodiments, methods and compositions are provided for the classification of a cell according to the activation level of an activatable element, e.g., in a cellular pathway wherein the classification comprises classifying the cell as a cell that is correlated with minimal residual disease or emerging resistance.

In some embodiments, methods and compositions are provided for the classification of a cell according to the activation level of an activatable element, e.g., in a cellular pathway wherein the classification comprises selecting a method of treatment. Example of methods of treatments include, but are not limited to, chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, and watchful waiting.

Generally, the methods of the invention involve determining the activation levels of an activatable element in a plurality of single cells in a sample.

Signaling Pathways

In some embodiments, the methods of the invention are employed to determine the status of an activatable element in a signaling pathway. In some embodiments, a cell is classified, as described herein, according to the activation level of one or more activatable elements in one or more signaling pathways. Signaling pathways and their members have been described. See (Hunter T. Cell Jan. 7, 2000; 100(1): 13-27). Exemplary signaling pathways include the following pathways and their members: The MAP kinase pathway including Ras, Raf, MEK, ERK and elk; the PI3K/Akt pathway including PI-3-kinase, PDK1, Akt and Bad; the NF-κB pathway including IKKs, IkB and the Wnt pathway including frizzled receptors, beta-catenin, APC and other co-factors and TCF (see Cell Signaling Technology, Inc. 2002 Catalog pages 231-279 and Hunter T., supra.). In some embodiments of the invention, the correlated activatable elements being assayed (or the signaling proteins being examined) are members of the MAP kinase, Akt, NFkB, WNT, RAS/RAF/MEK/ERK, JNK/SAPK, p38 MAPK, Src Family Kinases, JAK/STAT and/or PKC signaling pathways. See FIG. 1 generally.

In some embodiments, the status of an activatable element within the PI3K/AKT, or MAPK pathways in response to a growth factor or mitogen is determined. In some embodiments, the activatable element within the PI3K/AKT or MAPK pathway is selected from the group consisting of Akt, p-Erk, p38 and pS6 and the growth factor or mitogen is selected from the group consisting of FLT3L, SCF, G-CSF, SCF, G-CSF, SDF1a, LPS, PMA and Thapsigargin.

In some embodiments, the status of an activatable element within JAk/STAT pathways in response to a cytokine is determined. In some embodiments, the activatable element within the JAK/STAT pathway is selected from the group consisting of p-Stat3, p-Stat5, p-Stat1, and p-Stat6 and the cytokine is selected from the group consisting of IFNg, IFNa, IL-27, IL-3, IL-6, IL-10, and G-CSF. In some embodiments, the activatable element within the STAT pathway is Stat 1 and the cytokine is IL-27 or G-CSF.

In some embodiments, the status of an activatable element within the phospholipase C pathway in response to an inhibitor is determined. In some embodiments, the activatable element within the phospholipase C pathway is selected from the group consisting of p-Slp-76, and Plcg2 and the inhibitor is H2O2.

In some embodiments, the status of a phosphatase in response to an inhibitor is determined. In some embodiments, the inhibitor is H2O2.

In some embodiments, the methods of the invention are employed to determine the status of a signaling protein in a signaling pathway known in the art including those described herein. Exemplary types of signaling proteins within the scope of the present invention include, but are not limited to kinases, kinase substrates (i.e. phosphorylated substrates), phosphatases, phosphatase substrates, binding proteins (such as 14-3-3), receptor ligands and receptors (cell surface receptor tyrosine kinases and nuclear receptors)). Kinases and protein binding domains, for example, have been well described (see, e.g., Cell Signaling Technology, Inc., 2002 Catalogue "The Human Protein Kinases" and "Protein Interaction Domains" pgs. 254-279).

Nuclear Factor-kappaB (NF-κB) Pathway:

Nuclear factor-kappaB (NF-kappaB) transcription factors and the signaling pathways that activate them are central coordinators of innate and adaptive immune responses. More recently, it has become clear that NF-kappaB signaling also has a critical role in cancer development and progression. NF-kappaB provides a mechanistic link between inflammation and cancer, and is a major factor controlling the ability of both pre-neoplastic and malignant cells to resist apoptosis-based tumor-surveillance mechanisms. In mammalian cells, there are five NF-κB family members, RelA (p65), RelB, c-Rel, p50/p105 (NF-κB1) and p52/p100 (NF-κB2) and different NF-κB complexes are formed from their homo and heterodimers. In most cell types, NF-κB complexes are retained in the cytoplasm by a family of inhibitory proteins known as inhibitors of NF-κB (IκBs). Activation of NF-κB typically involves the phosphorylation of IκB by the IκB kinase (IKK) complex, which results in IκB ubiquitination with subsequent degradation. This releases NF-κB and allows it to translocate freely to the nucleus. The genes regulated by NF-κB include those controlling programmed cell death, cell adhesion, proliferation, the innate- and adaptive-immune responses, inflammation, the cellular-stress response and tissue remodeling. However, the expression of these genes is tightly coordinated with the activity of many other signaling and transcription-factor pathways. Therefore, the outcome of NF-κB activation depends on the nature and the cellular context of its induction. For example, it has become apparent that NF-κB activity can be regulated by both oncogenes and tumor suppressors, resulting in either stimulation or inhibition of apoptosis and proliferation. See Perkins, N. *Integrating cell-signaling pathways with NF-κB and IKK function*. Reviews: Molecular Cell Biology. January, 2007; 8(1): 49-62, hereby fully incorporated by reference in its entirety for all purposes. Hayden, M. *Signaling to NF-κB*. Genes & Development. 2004; 18: 2195-2224, hereby fully incorporated by reference in its entirety for all purposes. Perkins, N. *Good Cop, Bad Cop: The Different Faces of NF-κB*. Cell Death and Differentiation. 2006; 13: 759-772, hereby fully incorporated by reference in its entirety for all purposes.

Phosphatidylinositol 3-Kinase (PI3-K)/AKT Pathway:

PI3-Ks are activated by a wide range of cell surface receptors to generate the lipid second messengers phosphatidylinositol 3,4-biphosphate ($PIP_2$) and phosphatidylinositol 3,4,5-trisphosphate ($PIP_3$). Examples of receptor tyrosine kinases include but are not limited to FLT3 LIGAND, EGFR, IGF-1R, HER2/neu, VEGFR, and PDGFR. The lipid second messengers generated by PI3Ks regulate a diverse array of cellular functions. The specific binding of $PI3,4P_2$ and $PI3,4,5P_3$ to target proteins is mediated through the pleckstrin homology (PH) domain present in these target proteins. One key downstream effector of PI3-K is Akt, a serine/threonine kinase, which is activated when its PH domain interacts with $PI3, 4P_2$ and $PI3,4,5P_3$ resulting in recruitment of Akt to the plasma membrane. Once there, in order to be fully activated, Akt is phosphorylated at threonine 308 by 3-phosphoinositide-dependent protein kinase-1 (PDK-1) and at serine 473 by several PDK2 kinases. Akt then acts downstream of PI3K to regulate the phosphorylation of a number of substrates, including but not limited to forkhead box 0 transcription factors, Bad, GSK-3β, I-KB, mTOR, MDM-2, and S6 ribosomal subunit. These phosphorylation events in turn mediate cell survival, cell proliferation, membrane trafficking, glucose homeostasis, metabolism and cell motility. Deregulation of the PI3K pathway occurs by activating mutations in growth factor receptors, activating mutations in a PI3-K gene (e.g. PIK3CA), loss of function mutations in a lipid phosphatase (e.g. PTEN), up-regulation of Akt, or the impairment of the tuberous sclerosis complex (TSC1/2). All these events are linked to increased survival and proliferation. See Vivanco, I. *The Phosphatidylinositol 3-Kinase-AKT Pathway in Human Cancer*. Nature Reviews: Cancer. July, 2002; 2: 489-501 and Shaw, R. *Ras, PI(3)K and mTOR signaling controls tumor cell growth*. Nature. May, 2006; 441: 424-430, Marone et al., Biochimica et Biophysica Acta, 2008; 1784, p159-185 hereby fully incorporated by reference in their entirety for all purposes.

Wnt Pathway:

The Wnt signaling pathway describes a complex network of proteins well known for their roles in embryogenesis, normal physiological processes in adult animals, such as tissue homeostasis, and cancer. Further, a role for the Wnt pathway has been shown in self-renewal of hematopoietic stem cells (Reya T et al., Nature. 2003 May 22; 423(6938):409-14). Cytoplasmic levels of β-catenin are normally kept low through the continuous proteosomal degradation of β-catenin controlled by a complex of glycogen synthase kinase 3β (GSK-3 β) axin, and adenomatous polyposis coli (APC). When Wnt proteins bind to a receptor complex composed of the Frizzled receptors (Fz) and low density lipoprotein receptor-related protein (LRP) at the cell surface, the GSK-3/axin/APC complex is inhibited. Key intermediates in this process include disheveled (Dsh) and axin binding the cytoplasmic tail of LRP. Upon Wnt signaling and inhibition of the β-catenin degradation pathway, β-catenin accumulates in the cytoplasm and nucleus. Nuclear β-catenin interacts with transcription factors such as lymphoid enhanced-binding factor 1 (LEF) and T cell-specific transcription factor (TCF) to affect transcription of target genes. See Gordon, M. *Wnt Signaling: Multiple Pathways, Multiple Receptors, and Multiple Transcription Factors*. J of Biological Chemistry. June, 2006; 281(32): 22429-22433, Logan C Y, Nusse R: The Wnt signaling pathway in development and disease. Annu Rev Cell Dev Biol 2004, 20:781-810, Clevers H: Wnt/beta-catenin signaling in development and disease. Cell 2006, 127:469-480. hereby fully incorporated by reference in its entirety for all purposes.

Protein Kinase C (PKC) Signaling:

The PKC family of serine/threonine kinases mediate signaling pathways following activation of receptor tyrosine kinases, G-protein coupled receptors and cytoplasmic tyrosine kinases. Activation of PKC family members is associated with cell proliferation, differentiation, survival, immune function, invasion, migration and angiogenesis. Disruption of PKC signaling has been implicated in tumorigenesis and drug resistance. PKC isoforms have distinct and overlapping roles in cellular functions. PKC was originally identified as a phospholipid and calcium-dependent protein kinase. The mammalian PKC superfamily consists of 13 different isoforms that are divided into four subgroups on the basis of their structural differences and related cofactor requirements cPKC (classical PKC) isoforms (α, βI, βII and γ), which respond both to $Ca2+$ and DAG (diacylglycerol), nPKC (novel PKC) isoforms (δ, ε, θ and η), which are insensitive to Ca2+, but dependent on DAG, atypical PKCs (aP-KCs, ι/λ, ζ), which are responsive to neither co-factor, but may be activated by other lipids and through protein-protein interactions, and the related PKN (protein kinase N) family (e.g. PKN1, PKN2 and PKN3), members of which are subject to regulation by small GTPases. Consistent with their different biological functions, PKC isoforms differ in their structure, tissue distribution, subcellular localization, mode of activation and substrate specificity. Before maximal activation of its kinase, PKC requires a priming phosphorylation which is provided constitutively by phosphoinositide-dependent kinase 1 (PDK-1). The phospholipid DAG has a central role in the activation of PKC by causing an increase in the affinity of classical PKCs for cell membranes accompanied by PKC activation and the release of an inhibitory substrate (a pseudo-substrate) to which the inactive enzyme binds. Activated PKC then phosphorylates and activates a range of kinases. The downstream events following PKC activation are poorly understood, although the MEK-ERK (mitogen activated protein kinase kinase-extracellular signal-regulated kinase) pathway is thought to have an important role. There is also evidence to support the involvement of PKC in the PI3K-Akt pathway. PKC isoforms probably form part of the multiprotein complexes that facilitate cellular signal transduction. Many reports describe dysregulation of several family members. For example alterations in PKCε have been detected in thyroid cancer, and have been correlated with aggressive, metastatic breast cancer and PKCι was shown to be associated with poor outcome in ovarian cancer. (Knauf J A, et al. *Isozyme-Specific Abnormalities of PKC in Thyroid Cancer: Evidence for Post-Transcriptional Changes in PKC Epsilon. The Journal of Clinical Endocrinology & Metabolism*. Vol. 87, No. 5, pp 2150-2159; Zhang L et al. *Integrative Genomic Analysis of Protein Kinase C (PKC) Family Identifies PKC{iota} as a Biomarker and Potential Oncogene in Ovarian Carcinoma*. Cancer Res. 2006, Vol 66, No. 9, pp 4627-4635)

Mitogen Activated Protein (MAP) Kinase Pathways:

MAP kinases transduce signals that are involved in a multitude of cellular pathways and functions in response to a variety of ligands and cell stimuli. (Lawrence et al., Cell Research (2008) 18: 436-442). Signaling by MAPKs affects specific events such as the activity or localization of individual proteins, transcription of genes, and increased cell cycle entry, and promotes changes that orchestrate complex processes such as embryogenesis and differentiation. Aberrant or inappropriate functions of MAPKs have now been identified in diseases ranging from cancer to inflammatory disease to obesity and diabetes. MAPKs are activated by protein kinase cascades consisting of three or more protein kinases in series: MAPK kinase kinases (MAP3Ks) activate MAPK kinases (MAP2Ks) by dual phosphorylation on S/T residues; MAP2Ks then activate MAPKs by dual phosphorylation on Y and T residues MAPKs then phosphorylate target substrates on select S/T residues typically followed by a proline residue. In the ERK1/2 cascade the MAP3K is usually a member of the Raf family. Many diverse MAP3Ks reside upstream of the p38 and the c-Jun N-terminal kinase/stress-activated protein kinase (JNK/SAPK) MAPK groups, which have generally been associated with responses to cellular stress. Downstream of the activating stimuli, the kinase cascades may themselves be stimulated by combinations of small G proteins, MAP4Ks, scaffolds, or oligomerization of the MAP3K in a pathway. In the ERK1/2 pathway, Ras family members usually bind to Raf proteins leading to their activation as well as to the subsequent activation of other downstream members of the pathway.

a. Ras/RAF/MEK/ERK Pathway:

Classic activation of the RAS/Raf/MAPK cascade occurs following ligand binding to a receptor tyrosine kinase at the cell surface, but a vast array of other receptors have the ability to activate the cascade as well, such as integrins, serpentine receptors, heterotrimeric G-proteins, and cytokine receptors. Although conceptually linear, considerable cross talk occurs between the Ras/Raf/MAPK/Erk kinase (MEK)/Erk MAPK pathway and other MAPK pathways as well as many other signaling cascades. The pivotal role of the Ras/Raf/MEK/Erk MAPK pathway in multiple cellular functions underlies the importance of the cascade in oncogenesis and growth of transformed cells. As such, the MAPK pathway has been a focus of intense investigation for therapeutic targeting. Many receptor tyrosine kinases are capable of initiating MAPK signaling. They do so after activating phosphorylation events within their cytoplasmic domains provide docking sites for src-homology 2 (SH2) domain-containing signaling molecules. Of these, adaptor proteins such as Grb2 recruit guanine nucleotide exchange factors such as SOS-1 or CDC25 to the cell membrane. The guanine nucleotide exchange factor is now capable of interacting with Ras proteins at the cell membrane to promote a conformational change and the exchange of GDP for GTP bound to Ras. Multiple Ras isoforms have been described, including K-Ras, N-Ras, and H-Ras. Termination of Ras activation occurs upon hydrolysis of RasGTP to RasGDP. Ras proteins have intrinsically low GTPase activity. Thus, the GTPase activity is stimulated by GTPase-activating proteins such as NF-1 GTPase-activating protein/neurofibromin and p120 GTPase activating protein thereby preventing prolonged Ras stimulated signaling. Ras activation is the first step in activation of the MAPK cascade. Following Ras activation, Raf (A-Raf, B-Raf, or Raf-1) is recruited to the cell membrane through binding to Ras and activated in a complex process involving phosphorylation and multiple cofactors that is not completely understood. Raf proteins directly activate MEK1 and MEK2 via phosphorylation of multiple serine residues. MEK1 and MEK2 are themselves tyrosine and threonine/serine dual-specificity kinases that subsequently phosphorylate threonine and tyrosine residues in Erk1 and Erk2 resulting in activation. Although MEK1/2 have no known targets besides Erk proteins, Erk has multiple targets including Elk-1, c-Ets1, c-Ets2, p90RSK1, MNK1, MNK2, and TOB. The cellular functions of Erk are diverse and include regulation of cell proliferation, survival, mitosis, and migration. McCubrey, J. *Roles of the Raf/MEK/ERK pathway in cell growth, malignant transformation and drug resistance*. Biochimica et Biophysica Acta. 2007; 1773: 1263-1284, hereby fully incorporated by reference in its entirety for all purposes, Friday and Adjei, Clinical Cancer Research (2008) 14, p342-346.

b c-Jun N-Terminal Kinase (JNK)/Stress-Activated Protein Kinase (SAPK) Pathway:

The c-Jun N-terminal kinases (JNKs) were initially described as a family of serine/threonine protein kinases, activated by a range of stress stimuli and able to phosphorylate the N-terminal transactivation domain of the c-Jun transcription factor. This phosphorylation enhances c-Jun dependent transcriptional events in mammalian cells. Further research has revealed three JNK genes (JNK1, JNK2 and JNK3) and their splice-forms as well as the range of external stimuli that lead to JNK activation. JNK1 and JNK2 are ubiquitous, whereas JNK3 is relatively restricted to brain. The predominant MAP2Ks upstream of JNK are MEK4 (MKK4) and MEK7 (MKK7). MAP3Ks with the capacity to activate JNK/SAPKs include MEKKs (MEKK1, -2, -3 and -4), mixed lineage kinases (MLKs, including MLK1-3 and DLK), Tpl2, ASKs, TAOs and TAK1. Knockout studies in several organisms indicate that different MAP3Ks predominate in JNK/SAPK activation in response to different upstream stimuli. The wiring may be comparable to, but perhaps even more complex than, MAP3K selection and control of the ERK1/2 pathway. JNK/SAPKs are activated in response to inflammatory cytokines; environmental stresses, such as heat shock, ionizing radiation, oxidant stress and DNA damage; DNA and protein synthesis inhibition; and growth factors. JNKs phosphorylate transcription factors c-Jun, ATF-2, p53, Elk-1, and nuclear factor of activated T cells (NFAT), which in turn regulate the expression of specific sets of genes to mediate cell proliferation, differentiation or apoptosis. JNK proteins are involved in cytokine production, the inflammatory response, stress-induced and developmentally programmed apoptosis, actin reorganization, cell transformation and metabolism. Raman, M. *Differential regulation and properties of MAPKs*. Oncogene. 2007; 26: 3100-3112, hereby fully incorporated by reference in its entirety for all purposes.

c. p38 MAPK Pathway:

Several independent groups identified the p38 Map kinases, and four p38 family members have been described (α, β, γ, δ). Although the p38 isoforms share about 40% sequence identity with other MAPKs, they share only about 60% identity among themselves, suggesting highly diverse functions. p38 MAPKs respond to a wide range of extracellular cues particularly cellular stressors such as UV radiation, osmotic shock, hypoxia, pro-inflammatory cytokines and less often growth factors. Responding to osmotic shock might be viewed as one of the oldest functions of this pathway, because yeast p38 activates both short and long-term homeostatic mechanisms to osmotic stress. p38 is activated via dual phosphorylation on the TGY motif within its activation loop by its upstream protein kinases MEK3 and MEK6. MEK3/6 are activated by numerous MAP3Ks including MEKK1-4, TAOs, TAK and ASK. p38 MAPK is generally considered to be the most promising MAPK therapeutic target for rheumatoid arthritis as p38 MAPK isoforms have been implicated in the regulation of many of the processes, such as migration and accumulation of leucocytes, production of cytokines and pro-inflammatory mediators and angiogenesis, that promote disease pathogenesis. Further, the p38 MAPK pathway plays a role in cancer, heart and neurodegenerative diseases and may serve as promising therapeutic target. Cuenda, A. *p38 MAP-Kinases pathway regulation, function, and role in human diseases*. Biochimica et Biophysica Acta. 2007; 1773: 1358-1375; Thalhamer et al., Rheumatology 2008; 47:409-414; Roux, P. *ERK and p38 MAPK-Activated Protein Kinases: a Family of Protein Kinases with Diverse Biological Functions*. Microbiology and Molecular Biology Reviews. June, 2004; 320-344 hereby fully incorporated by reference in its entirety for all purposes.

Src Family Kinases:

Src is the most widely studied member of the largest family of nonreceptor protein tyrosine kinases, known as the Src family kinases (SFKs). Other SFK members include Lyn, Fyn, Lck, Hck, Fgr, Blk, Yrk, and Yes. The Src kinases can be grouped into two sub-categories, those that are ubiquitously expressed (Src, Fyn, and Yes), and those which are found primarily in hematopoietic cells (Lyn, Lck, Hck, Blk, Fgr). (Benati, D. *Src Family Kinases as Potential Therapeutic Targets for Malignancies and Immunological Disorders*. Current Medicinal Chemistry. 2008; 15: 1154-1165) SFKs are key messengers in many cellular pathways, including those involved in regulating proliferation, differentiation, survival, motility, and angiogenesis. The activity of SFKs is highly regulated intramolecularly by interactions between the SH2 and SH3 domains and intermolecularly by association with cytoplasmic molecules. This latter activation may be mediated by focal adhesion kinase (FAK) or its molecular partner Crk-associated substrate (CAS), which play a prominent role in integrin signaling, and by ligand activation of cell surface receptors, e.g. epidermal growth factor receptor (EGFR). These interactions disrupt intramolecular interactions within Src, leading to an open conformation that enables the protein to interact with potential substrates and downstream signaling molecules. Src can also be activated by dephosphorylation of tyrosine residue Y530. Maximal Src activation requires the autophosphorylation of tyrosine residue Y419 (in the human protein) present within the catalytic domain. Elevated Src activity may be caused by increased transcription or by deregulation due to overexpression of upstream growth factor receptors such as EGFR, HER2, platelet-derived growth factor receptor (PDGFR), fibroblast growth factor receptor (FGFR), vascular endothelial growth factor receptor, ephrins, integrin, or FAK. Alternatively, some human tumors show reduced expression of the negative Src regulator, Csk. Increased levels, increased activity, and genetic abnormalities of Src kinases have been implicated in both solid tumor development and leukemias. Ingley, E. *Src family kinases: Regulation of their activities, levels and identification of new pathways*. Biochimica et Biophysica Acta. 2008; 1784 56-65, hereby fully incorporated by reference in its entirety for all purposes. Benati and Baldari., Curr Med Chem. 2008; 15(12):1154-65, Finn (2008) Ann Oncol. May 16, hereby fully incorporated by reference in its entirety for all purposes.

Janus Kinase (JAK)/Signal Transducers and Activators of Transcription (STAT) Pathway:

The JAK/STAT pathway plays a crucial role in mediating the signals from a diverse spectrum of cytokine receptors, growth factor receptors, and G-protein-coupled receptors. Signal transducers and activators of transcription (STAT) proteins play a crucial role in mediating the signals from a diverse spectrum of cytokine receptors growth factor receptors, and G-protein-coupled receptors. STAT directly links cytokine receptor stimulation to gene transcription by acting as both a cytosolic messenger and nuclear transcription factor. In the Janus Kinase (JAK)-STAT pathway, receptor dimerization by ligand binding results in JAK family kinase (JFK) activation and subsequent tyrosine phosphorylation of the receptor, which leads to the recruitment of STAT through the SH2 domain, and the phosphorylation of conserved tyrosine residue. Tyrosine phosphorylated STAT forms a dimer, translocates to the nucleus, and binds to specific DNA elements to activate target gene transcription, which leads to the regulation of cellular proliferation, differentiation, and apoptosis. The entire process is tightly regulated at multiple levels by protein tyrosine phosphatases, suppressors of cytokine signaling and protein inhibitors of activated STAT. In mammals seven members of the STAT family (STAT1, STAT2, STAT3, STAT4, STAT5a, STAT5b and STAT6) have been identified. JAKs contain two symmetrical kinase-like domains; the C-terminal JAK homology 1 (JH1) domain possesses tyrosine kinase function while the immediately adjacent JH2 domain is enzymatically inert but is believed to regulate the activity of JH1. There are four JAK family members: JAK1, JAK2, JAK3 and tyrosine kinase 2 (Tyk2). Expression is ubiquitous for JAK1, JAK2 and TYK2 but restricted to hematopoietic cells for JAK3. Mutations in JAK proteins have been described for several myeloid malignancies. Specific examples include but are not limited to: Somatic JAK3 (e.g. JAK3A572V, JAK3V722I, JAK3P132T) and fusion JAK2 (e.g. ETV6-JAK2, PCM1-JAK2, BCR-JAK2) mutations have respectively been described in acute megakaryocytic leukemia and acute leukemia/chronic myeloid malignancies, JAK2 (V617F, JAK2 exon 12 mutations) and MPL MPLW515L/K/S, MPLS505N) mutations associated with myeloproliferative disorders and myeloproliferative neoplasms. JAK2 mutations, primarily JAK2V617F, are invariably associated with polycythemia vera (PV). This mutation also occurs in the majority of patients with essential thrombocythemia (ET) or primary myelofibrosis (PMF) (Tefferi n., Leukemia & Lymphoma, March 2008; 49(3): 388-397). STATs can be activated in a JAK-independent manner by src family kinase members and by oncogenic FLt3 ligand-ITD (Hayakawa and Naoe, Ann N Y Acad Sci. 2006 November; 1086:213-22; Choudhary et al. Activation mechanisms of STAT5 by oncogenic FLt3 ligand-ITD. Blood (2007) vol. 110 (1) pp. 370-4). Although mutations of STATs have not been described in human tumors, the activity of several members of the family, such as STAT1, STAT3 and STAT5, is dysregulated in a variety of human tumors and leukemias. STAT3 and STAT5 acquire oncogenic potential through constitutive phosphorylation on tyrosine, and their activity has been shown to be required to sustain a transformed phenotype. This was shown in lung cancer where tyrosine phosphorylation of STAT3 was JAK-independent and mediated by EGF receptor activated through mutation and Src. (Alvarez et al., Cancer Research, Cancer Res 2006; 66) STAT5 phosphorylation was also shown to be required for the long-term maintenance of leukemic stem cells. (Schepers et al. STAT5 is required for long-term maintenance of normal and leukemic human stem/progenitor cells. Blood (2007) vol. 110 (8) pp. 2880-2888) In contrast to STAT3 and STAT5, STAT1 negatively regulates cell proliferation and angiogenesis and thereby inhibits tumor formation. Consistent with its tumor suppressive properties, STAT1 and its downstream targets have been shown to be reduced in a variety of human tumors (Rawlings, J. *The JAK/STAT signaling pathway*. J of Cell Science. 2004; 117 (8):1281-1283, hereby fully incorporated by reference in its entirety for all purposes).

Drug Transporters

A key issue in the treatment of many cancers is the development of resistance to chemotherapeutic drugs. Of the many resistance mechanisms, two classes of transporters play a major role. The human ATP-binding cassette (ABC) superfamily of proteins consists of 49 membrane proteins that transport a diverse array of substrates, including sugars, amino acids, bile salts lipids, sterols, nucleotides, endogenous metabolites, ions, antibiotics drugs and toxins out of cells using the energy of hydrolysis of ATP. ATP-binding-cassette (ABC) transporters are evolutionary extremely well-conserved transmembrane proteins that are highly expressed in hematopoietic stem cells (HSCs). The physiological function in human stem cells is believed to be protection against genetic damage caused by both environmental and naturally occurring xenobiotics. Additionally, ABC transporters have been implicated in the maintenance of quiescence and cell fate decisions of stem cells. These physiological roles suggest a potential role in the pathogenesis and biology of stem cell-derived hematological malignancies such as acute and chronic myeloid leukemia (Raaijmakers, Leukemia (2007) 21, 2094-2102, Zhou et al., Nature Medicine, 2001, 7, p1028-1034

Several ABC proteins are multidrug efflux pumps that not only protect the body from exogenous toxins, but also play a role in uptake and distribution of therapeutic drugs. Expression of these proteins in target tissues causes resistance to treatment with multiple drugs. (Gillet et al., Biochimica et Biophysica Acta (2007) 1775, p23'7, Sharom (2008) Pharmacogenomics 9 p105). A more detailed discussion of the ABC family members with critical roles in resistance and poor outcome to treatment is discussed below The second class of plasma membrane transporter proteins that play a role in the uptake of nucleoside-derived drugs are the Concentrative and Equilibrative Nucleoside Transporters (CNT and ENT, respectively), encoded by gene families SLC28 and SLC29 (Pastor-Anglada (2007) J. Physiol. Biochem 63, p97). They mediate the uptake of natural nucleosides and a variety of nucleoside-derived drugs, mostly used in anti-cancer therapy. In vitro studies, have shown that one mechanism of nucleoside resistance can be mediated through mutations in the gene for ENT1/SLC29A1 resulting in lack of detectable protein (Cai et al., Cancer Research (2008) 68, p2349). Studies have also described in vivo mechanisms of resistance to nucleoside analogues involving low or non-detectable levels of ENT1 in Acute Myeloid Leukemia (AML), Mantle Cell lymphoma and other leukemias (Marce et al., Malignant Lymphomas (2006), 91, p895).

Of the ABC transporter family, three family members account for most of the multiple drug resistance (MDR) in humans; P-gycoprotein (Pgp/MDR1/ABCB1), MDR-associated protein (MRP1, ABCC1) and breast cancer resistance protein (BCRP, ABCG2 or MXR). Pgp/MDR1 and ABCG2 can export both unmodified drugs and drug conjugates, whereas MRP1 exports glutathione and other drug conjugates as well as unconjugated drugs together with free glutathione. All three ABC transporters demonstrate export activity for a broad range of structurally unrelated drugs and display both distinct and overlapping specificities. For example, MRP1 promotes efflux of drug-glutathione conjugates, vinca alkaloids, camptothecin, but not taxol. Examples of drugs exported by ABCG2 include mitoxantrone, etoposide, daunorubicin as well as the tyrosine kinase inhibitors Gleevec and Iressa. In treatment regimens for leukemias, one of the main obstacles to achieving remission is intrinsic and acquired resistance to chemotherapy mediated by the ABC drug transporters. Several reports have described correlations between transporter expression levels as well as their function, evaluated through the use of fluorescent dyes, with resistance of patients to chemotherapy regimens. Notably, in AML, studies have shown that expression of Pgp/MDR1 is associated with a lower rate of complete response to induction chemotherapy and a higher rate of resistant disease in both elderly and younger AML patients (Leith et al., Blood (1997) 89 p3323, Leith et al., Blood (1999) 94, p1086). Legrand et al., (Blood (1998) 91, p4480) showed that Pgp/MDR1 and MRP1 function in CD34+ blast cells are negative prognostic factors in AML and further, the same group showed that a high level of simultaneous activity of Pgp/MDR1 and MRP1 was predictive of poor treatment outcome (Legrand et al., (Blood (1999) 94, p1046). In two more recent studies, elevated expression of Pgp/MDR1 and BCRP in CD34+/CD38-AML subpopulations were found in 8 out of 10 non-responders as compared to 0 out of 10 in responders to induction chemotherapy (Ho et al., Experimental Hematology (2008) 36, p433). In a second study, evaluation of Pgp/MDR1, MRP1, BCRP/ABCG2 and lung resistance protein showed that the more immature subsets of leukemic stem cells expressed higher levels of these proteins compared more mature leukemic subsets (Figueiredo-Pontes et al., Clinical Cytometry (2008) 74B p163).

Experimentally, it is possible to correlate expression of transporter proteins with their function by the use of inhibitors including but not limited to cyclosporine (measures Pgp function), probenecid (measures MRP1 function), fumitremorgin C, and a derivative Ko143, reserpine (measures ABCG2 function). Although these molecules inhibit a variety of transporters, they do permit some correlations to be made between protein expression and function (Legrand et al., (Blood (1998) 91, p4480), Legrand et al., (Blood (1999) 94, p1046, Zhou et al., Nature Medicine, 2001, 7, p1028-1034, Sarkardi et al., Physiol Rev 2006 86: 1179-1236).

Extending the use of these inhibitors, they can be used to make correlations within subpopulations of cells gated both for phenotypic markers denoting stages of development along hematopoietic and lymphoid lineages, as well as reagents that recognize the transporter proteins themselves. Thus it will be possible to simultaneously measure protein expression and function.

Expression levels of drug transporters and receptors may not be as informative by themselves for disease management as analysis of activatable elements, such as phosphorylated proteins. However, expression information may be useful in combination with the analysis of activatable elements, such as phosphorylated proteins. In some embodiments, the methods described herein analyze the expression of drug transporters and receptors in combination with the analysis of one or more activatable elements for the diagnosis, prognosis, selection of treatment, or predicting reponse to treatment for a condition.

DNA Damage and Apoptosis

The response to DNA damage is a protective measure taken by cells to prevent or delay genetic instability and tumorigenesis. It allows cells to undergo cell cycle arrest and gives them an opportunity to either: repair the broken DNA and resume passage through the cell cycle or, if the breakage is irreparable, trigger senescence or an apoptotic program leading to cell death (Wade Harper et al., Molecular Cell, (2007) 28 p739-745, Bartek J et al., Oncogene (2007)26 p7773-9).

Several protein complexes are positioned at strategic points within the DNA damage response pathway and act as sensors, transducers or effectors of DNA damage. Depending on the nature of DNA damage for example; double stranded breaks, single strand breaks, single base alterations due to alkylation, oxidation etc, there is an assembly of specific DNA damage sensor protein complexes in which activated ataxia telangiectasia mutated (ATM) and ATM- and Rad3 related (ATR) kinases phosphorylate and subsequently activate the checkpoint kinases Chk1 and Chk2. Both of these DNA-signal transducer kinases amplify the damage response by phosphorylating a multitude of substrates. Both checkpoint kinases have overlapping and distinct roles in orchestrating the cell's response to DNA damage.

Maximal kinase activation of Chk2 involves phosphorylation and homo-dimerization with ATM-mediated phosphorylation of T68 on Chk2 as a preliminary event. This in turn activates the DNA repair. As mentioned above, in order for DNA repair to proceed, there must be a delay in the cell cycle. Chk2 seems to have a role at the G1/S and G2/M junctures and may have overlapping functions with Chk1. There are multiple ways in which Chk1 and Chk2 mediate cell cycle suspension. In one mechanism Chk2 phosphorylates the CDC25A and CDC25C phosphatases resulting in their removal from the nucleus either by proteosomal degradation or by sequestration in the cytoplasm by 14-3-3. These phosphatases are no longer able to act on their nuclear CDK substrates. If DNA repair is successful cell cycle progression is resumed (Antoni et al., Nature reviews cancer (2007)7, p925-936).

When DNA repair is no longer possible the cell undergoes apoptosis with participation from Chk2 in p53 independent and dependent pathways. Chk2 substrates that operate in a p53-independent manner include the E2F1 transcription factor, the tumor suppressor promyelocytic leukemia (PML) and the polo-like kinases 1 and 3 (PLK1 and PLK3). E2F1 drives the expression of a number of apoptotic genes including caspases 3, 7, 8 and 9 as well as the pro-apoptotic Bcl-2 related proteins (Bim, Noxa, PUMA).

In its response to DNA damage, the p53 activates the transcription of a program of genes that regulate DNA repair, cell cycle arrest, senescence and apoptosis. The overall functions of p53 are to preserve fidelity in DNA replication such that when cell division occurs tumorigenic potential can be avoided. In such a role, p53 is described as "The Guardian of the Genome (Riley et al., Nature Reviews Molecular Cell Biology (2008) 9 p402-412). The diverse alarm signals that impinge on p53 result in a rapid increase in its levels through a variety of post translational modifications. Worthy of mention is the phosphorylation of amino acid residues within the amino terminal portion of p53 such that p53 is no longer under the regulation of Mdm2. The responsible kinases are ATM, Chk1 and Chk2. The subsequent stabilization of p53 permits it to transcriptionally regulate multiple pro-apoptotic members of the Bcl-2 family, including Bax, Bid, Puma, and Noxa (Discussion below).

The series of events that are mediated by p53 to promote apoptosis including DNA damage, anoxia and imbalances in growth-promoting signals are sometimes termed the "intrinsic apoptotic" program since the signals triggering it originate within the cell. An alternate route of activating the apoptotic pathway can occur from the outside of the cell mediated by the binding of ligands to transmembrane death receptors. This extrinsic or receptor mediated apoptotic program acting through their receptor death domains eventually converges on the intrinsic, mitochondrial apoptotic pathway as discussed below (Sprick et al., Biochim Biophys Acta. (2004) 1644 p125-32).

Key regulators of apoptosis are proteins of the Bcl-2 family. The founding member, the Bcl-2 proto-oncogene was first identified at the chromosomal breakpoint of t(14:18) bearing human follicular B cell lymphoma. Unexpectedly, expression of Bcl-2 was proved to block rather than promote cell death following multiple pathological and physiological stimuli (Danial and Korsemeyer, Cell (2204) 116, p205-219). The Bcl-2 family has at least 20 members which are key regulators of apoptosis, functioning to control mitochondrial permeability as well as the release of proteins important in the apoptotic program. The ratio of anti- to pro-apoptotic molecules such as Bcl-2/Bax constitutes a rheostat that sets the threshold of susceptibility to apoptosis for the intrinsic pathway, which utilizes organelles such as the mitochondrion to amplify death signals. The family can be divided into 3 subclasses based on structure and impact on apoptosis. Family members of subclass 1 including Bcl-2, Bcl-$X_L$ and Mcl-1 are characterized by the presence of 4 Bcl-2 homology domains (BH1, BH2, BH3 and BH4) and are anti-apoptotic. The structure of the second subclass members is marked for containing 3 BH domains and family members such as Bax and Bak possess pro-apoptotic activities. The third subclass, termed the BH3-only proteins include Noxa, Puma, Bid, Bad and Bim. They function to promote apoptosis either by activating the pro-apoptotic members of group 2 or by inhibiting the anti-apoptotic members of subclass 1 (Er et al., Biochimica et Biophysica Act (2006) 1757, p1301-1311, Fernandez-Luna Cellular Signaling (2008) Advance Publication Online)

The role of mitochondria in the apoptotic process was clarified as involving an apoptotic stimulus resulting in depolarization of the outer mitochondrial membrane leading to a leak of cytochrome C into the cytoplasm. Association of Cytoplasmic cytochrome C molecules with adaptor apoptotic protease activating factor (APAF) forms a structure called the apoptosome which can activate enzymatically latent procaspase 9 into a cleaved activated form. Caspase 9 is one member of a family of cysteine aspartyl-specific proteases; genes encoding 11 of these proteases have been mapped in the human genome. Activated caspase 9, classified as an intiator caspase, then cleaves procaspase 3 which cleaves more downstream procaspases, classified as executioner caspases, resulting in an amplification cascade that promotes cleavage of death substrates including poly(ADP-ribose) polymerase 1 (PARP). The cleavage of PARP produces 2 fragments both of which have a role in apoptosis (Soldani and Scovassi Apoptosis (2002)7, p321). A further level of apoptotic regulation is provided by smac/Diablo, a mitochondrial protein that inactivates a group of anti-apoptotic proteins termed inhibitors of apoptosis (IAPB) (Huang et al., Cancer Cell (2004) 5 p1-2). IAPB operate to block caspase activity in 2 ways; they bind directly to and inhibit caspase activity and in certain cases they can mark caspases for ubiquitination and degradation.

Members of the caspase gene family (cysteine proteases with aspartate specificity) play significant roles in both inflammation and apoptosis. Caspases exhibit catalytic and substrate recognition motifs that have been highly conserved. These characteristic amino acid sequences allow caspases to interact with both positive and negative regulators of their activity. The substrate preferences or specificities of individual caspases have been exploited for the development of peptides that successfully compete for caspase binding. In addition to their distinctive aspartate cleavage sites at the P1 position, the catalytic domains of the caspases require at least four amino acids to the left of the cleavage site with P4 as the prominent specificity-determining residue. WEHD, VDVAD, and DEVD are examples of peptides that preferentially bind caspase-1, caspase-2 and caspase-3, respectively. It is possible to generate reversible or irreversible inhibitors of caspase activation by coupling caspase-specific peptides to certain aldehyde, nitrile or ketone compounds. These caspase inhibitors can successfully inhibit the induction of apoptosis in various tumor cell lines as well as normal cells. Fluoromethyl ketone (FMK)-derivatized peptides act as effective irreversible inhibitors with no added cytotoxic effects. Inhibitors synthesized with a benzyloxycarbonyl group (also known as BOC or Z) at the N-terminus and O-methyl side chains exhibit enhanced cellular permeability thus facilitating their use in both in vitro cell culture as well as in vivo animal studies. Benzyloxycarbonyl-Val-Ala-Asp (OMe) fluoromethylketone (ZVAD) is a caspase inhibitor. See Misaghi, et al., z-VAD-fmk inhibits peptide:N-glycanase and may result in ER stress Cell Death and Differentiation (2006) 13, 163-165.

Figure 3:
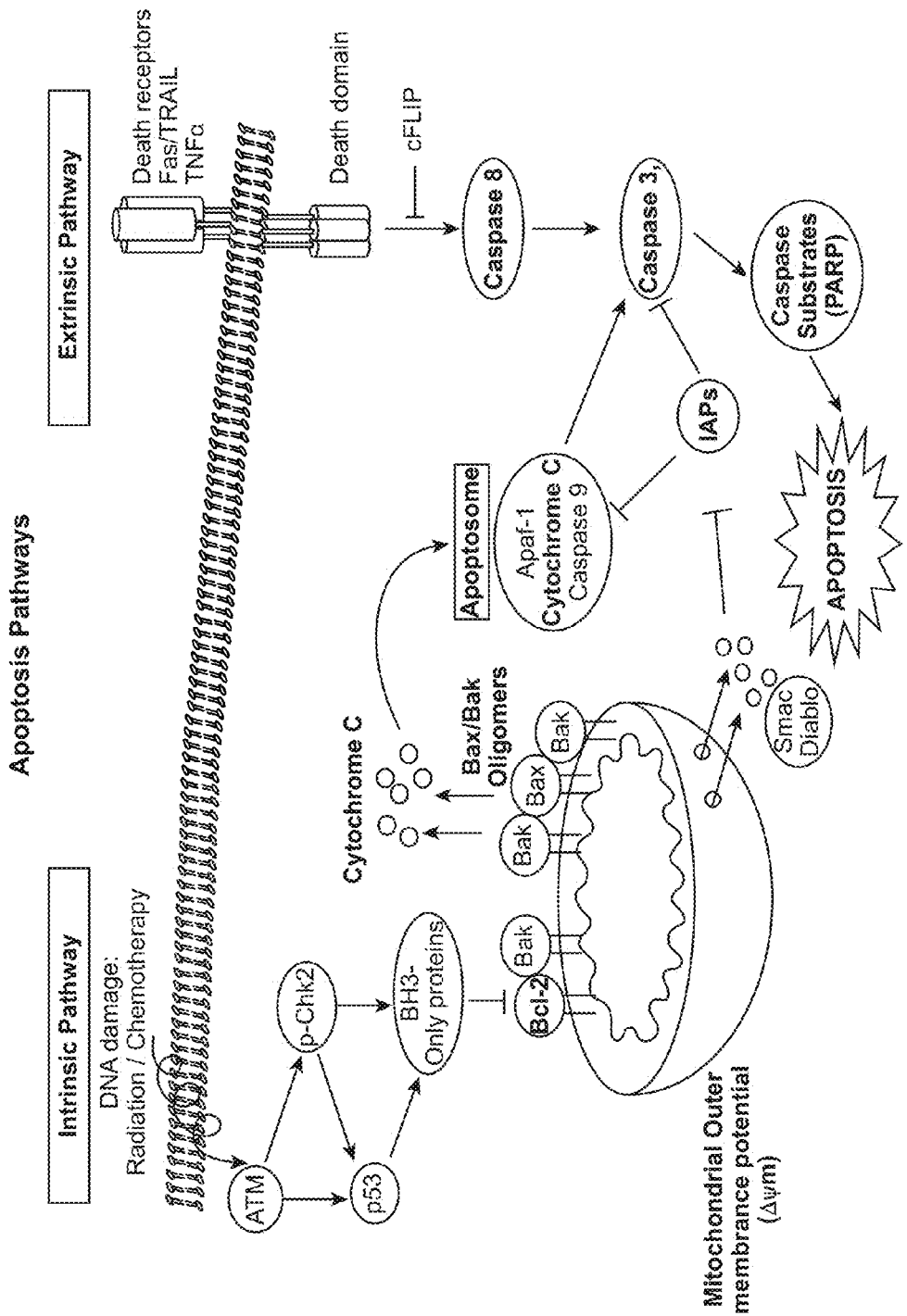
FIG. 3 shows a diagram of apoptosis pathways.
Figure 5:
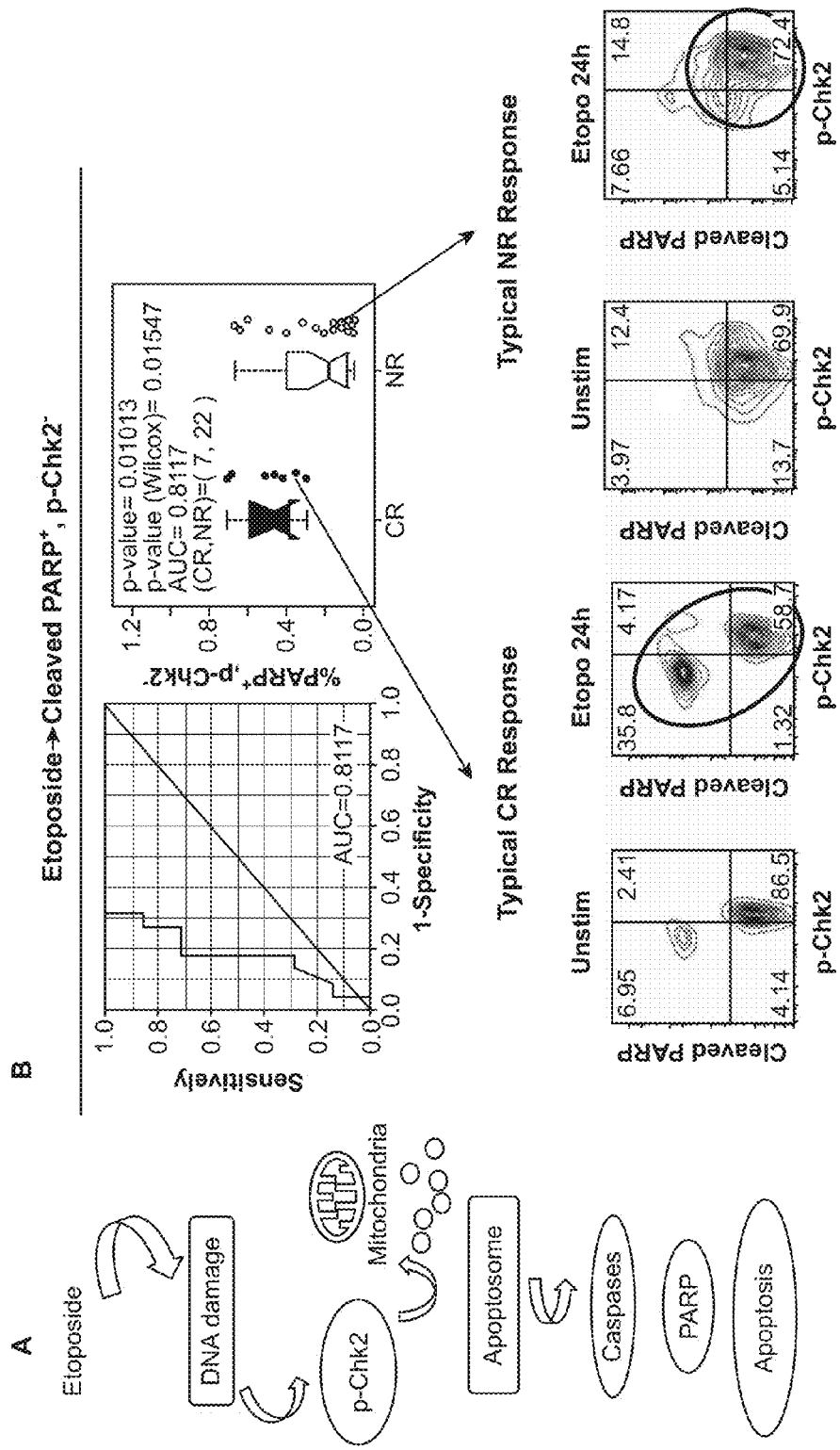
FIG. 5A show a chemotherapeutic agent, for example etoposide, can induce DNA damage and apoptosis. Etoposide induces DNA damage, which results in the phosphorylation and activation of Chk2, a DNA damage checkpoint response protein. If DNA repair is unsuccessful, subsequent activation of the intrinsic mitochondrial apoptotic pathway results in release of cytochrome c into the cytoplasm, formation of the apoptotsome and cleavage of caspases that work in a coordinated cascade to cleave crucial substrates and dismantle the cell and then caspases are activated with PARP cleavage.
FIG. 5B show examples of responses to Etoposide from NR and CR patients.

The balance of pro- and anti-apoptotic proteins is tightly regulated under normal physiological conditions. Tipping of this balance either way results in disease. An oncogenic outcome results from the inability of tumor cells to undergo apoptosis and this can be caused by over-expression of anti-apoptotic proteins or reduced expression or activity of pro-apoptotic protein FIGS. 3 and 5 show the role of apoptosis in AML.

In some embodiments, the status of an activatable element within an apoptosis pathway in response to a modulator that slows or stops the growth of cells and/or induces apoptosis of cells is determined. In some embodiments, the activatable element within the apoptosis pathway is selected from the group consisting of PARP+, Cleaved Caspase 8, and Cytoplasmic Cytochrome C, and the modulator that slows or stops the growth of cells and/or induces apoptosis of cells is selected from the group consisting of Staurosporine, Etoposide, Mylotarg, Daunorubicin, and AraC.

In some embodiments, the status of an activatable element within a DNA damage pathway in response to a modulator that slows or stops the growth of cells and/or induces apoptosis of cells is determined. In some embodiments, the activatable element within a DNA damage pathway is selected from the group consisting of Chk1, Chk2, ATM, and ATR and the modulator that slows or stops the growth of cells and/or induces apoptosis of cells is selected from the group consisting of Staurosporine, Etoposide, Mylotarg, Daunorubicin, and AraC.

In some embodiments, interrogation of the apoptotic machinery will also be performed by etoposide with or without ZVAD, an inhibitor of caspases, or a combination of Cytarabine and Daunorubicin at clinically relevant concentrations based on peak plasma drug levels. The standard dose of Cytarabine, 100 mg/m2, yields a peak plasma concentration of approximately 40 nM, whereas high dose Cytarabine, 3 g/m2, yields a peak plasma concentration of 2 uM. Daunorubicin at 25 mg/m2 yields a peak plasma concentration of 50 ng/ml and at 50 mg/m2 yields a peak plasma concentration of 200 ng/ml. Our in vitro apoptosis assay will use concentrations of Cytarabine up to 2 uM, and concentrations of Daunorubicin up to 200 ng/ml.

Etoposide phosphate (brand names: Eposin, Etopophos, Vepesid, VP-16) is an inhibitor of the enzyme topoisomerase II and a semisynthetic derivative of podophyllotoxin, a substance extracted from the mandrake root *Podophyllum peltatum*. Possessing potent antineoplastic properties, etoposide binds to and inhibits topoisomerase II and its function in ligating cleaved DNA molecules, resulting in the accumulation of single- or double-strand DNA breaks, the inhibition of DNA replication and transcription, and apoptotic cell death. Etoposide acts primarily in the G2 and S phases of the cell cycle. See the NCI Drug Dictionary at http://www.cancer.gov/Templates/drugdictionary.aspx?CdrID=39207.

Cell Cycle

The cell cycle, or cell-division cycle, is the series of events that take place in a cell leading to its division and duplication (replication). The cell cycle consists of five distinct phases: G1 phase, S phase (synthesis), G2 phase (collectively known as interphase) and M phase (mitosis). M phase is itself composed of two tightly coupled processes: mitosis, in which the cell's chromosomes are divided between the two daughter cells, and cytokinesis, in which the cell's cytoplasm divides forming distinct cells. Activation of each phase is dependent on the proper progression and completion of the previous one. Cells that have temporarily or reversibly stopped dividing are said to have entered a state of quiescence called G0 phase.

Regulation of the cell cycle involves processes crucial to the survival of a cell, including the detection and repair of genetic damage as well as the prevention of uncontrolled cell division. The molecular events that control the cell cycle are ordered and directional; that is, each process occurs in a sequential fashion and it is impossible to "reverse" the cycle.

Two key classes of regulatory molecules, cyclins and cyclin-dependent kinases (CDKs), determine a cell's progress through the cell cycle. Many of the genes encoding cyclins and CDKs are conserved among all eukaryotes, but in general more complex organisms have more elaborate cell cycle control systems that incorporate more individual components. Many of the relevant genes were first identified by studying yeast, especially *Saccharomyces cerevisiae* genetic nomenclature in yeast dubs many these genes cdc (for "cell division cycle") followed by an identifying number, e.g., cdc25.

Cyclins form the regulatory subunits and CDKs the catalytic subunits of an activated heterodimer; cyclins have no catalytic activity and CDKs are inactive in the absence of a partner cyclin. When activated by a bound cyclin, CDKs perform a common biochemical reaction called phosphorylation that activates or inactivates target proteins to orchestrate coordinated entry into the next phase of the cell cycle. Different cyclin-CDK combinations determine the downstream proteins targeted. CDKs are constitutively expressed in cells whereas cyclins are synthesised at specific stages of the cell cycle, in response to various molecular signals.

Upon receiving a pro-mitotic extracellular signal, G1 cyclin-CDK complexes become active to prepare the cell for S phase, promoting the expression of transcription factors that in turn promote the expression of S cyclins and of enzymes required for DNA replication. The G1 cyclin-CDK complexes also promote the degradation of molecules that function as S phase inhibitors by targeting them for ubiquitination. Once a protein has been ubiquitinated, it is targeted for proteolytic degradation by the proteasome. Active S cyclin-CDK complexes phosphorylate proteins that make up the pre-replication complexes assembled during G1 phase on DNA replication origins. The phosphorylation serves two purposes: to activate each already-assembled pre-replication complex, and to prevent new complexes from forming. This ensures that every portion of the cell's genome will be replicated once and only once. The reason for prevention of gaps in replication is fairly clear, because daughter cells that are missing all or part of crucial genes will die. However, for reasons related to gene copy number effects, possession of extra copies of certain genes would also prove deleterious to the daughter cells.

Mitotic cyclin-CDK complexes, which are synthesized but inactivated during S and G2 phases, promote the initiation of mitosis by stimulating downstream proteins involved in chromosome condensation and mitotic spindle assembly. A critical complex activated during this process is a ubiquitin ligase known as the anaphase-promoting complex (APC), which promotes degradation of structural proteins associated with the chromosomal kinetochore. APC also targets the mitotic cyclins for degradation, ensuring that telophase and cytokinesis can proceed. Interphase: Interphase generally lasts at least 12 to 24 hours in mammalian tissue. During this period, the cell is constantly synthesizing RNA, producing protein and growing in size. By studying molecular events in cells, scientists have determined that interphase can be divided into 4 steps: Gap 0 (G0), Gap 1 (G1), S (synthesis) phase, Gap 2 (G2).

Cyclin D is the first cyclin produced in the cell cycle, in response to extracellular signals (e.g. growth factors). Cyclin D binds to existing CDK4, forming the active cyclin D-CDK4 complex. Cyclin D-CDK4 complex in turn phosphorylates the retinoblastoma susceptibility protein (Rb). The hyperphosphorylated Rb dissociates from the E2F/DP1/Rb complex (which was bound to the E2F responsive genes, effectively "blocking" them from transcription), activating E2F. Activation of E2F results in transcription of various genes like cyclin E, cyclin A, DNA polymerase, thymidine kinase, etc. Cyclin E thus produced binds to CDK2, forming the cyclin E-CDK2 complex, which pushes the cell from G1 to S phase (G1/S transition). Cyclin B along with cdc2 (cdc2-fission yeasts (CDK1-mammalia)) forms the cyclin B-cdc2 complex, which initiates the G2/M transition. Cyclin B-cdc2 complex activation causes breakdown of nuclear envelope and initiation of prophase, and subsequently, its deactivation causes the cell to exit mitosis.

Two families of genes, the Cip/Kip family and the INK4a/ARF (Inhibitor of Kinase 4/Alternative Reading Frame) prevent the progression of the cell cycle. Because these genes are instrumental in prevention of tumor formation, they are known as tumor suppressors.

The Cip/Kip family includes the genes p21, p27 and p57. They halt cell cycle in G1 phase, by binding to, and inactivating, cyclin-CDK complexes. p21 is a p53 response gene (which, in turn, is triggered by DNA damage eg. due to radiation). p27 is activated by Transforming Growth Factor β (TGF β), a growth inhibitor.

The INK4a/ARF family includes p16INK4a, which binds to CDK4 and arrests the cell cycle in G1 phase, and p14arf which prevents p53 degradation.

Cell cycle checkpoints are used by the cell to monitor and regulate the progress of the cell cycle. Checkpoints prevent cell cycle progression at specific points, allowing verification of necessary phase processes and repair of DNA damage. The cell cannot proceed to the next phase until checkpoint requirements have been met.

Several checkpoints are designed to ensure that damaged or incomplete DNA is not passed on to daughter cells. Two main checkpoints exist: the G1/S checkpoint and the G2/M checkpoint. G1/S transition is a rate-limiting step in the cell cycle and is also known as restriction point. An alternative model of the cell cycle response to DNA damage has also been proposed, known as the postreplication checkpoint. p53 plays an important role in triggering the control mechanisms at both G1/S and G2/M checkpoints.

A disregulation of the cell cycle components may lead to tumor formation. As mentioned above, some genes like the cell cycle inhibitors, RB, p53 etc., when they mutate, may cause the cell to multiply uncontrollably, forming a tumor. Although the duration of cell cycle in tumor cells is equal to or longer than that of normal cell cycle, the proportion of cells that are in active cell division (versus quiescent cells in G0 phase) in tumors is much higher than that in normal tissue. Thus there is a net increase in cell number as the number of cells that die by apoptosis or senescence remains the same.

In some embodiments, the status of an activatable element within a cell cycle pathway in response to a modulator that slows or stops the growth of cells and/or induces apoptosis of cells is determined. In some embodiments, the activatable element within a DNA damage pathway is selected from the group consisting of, Cdc25, p53, CyclinA-Cdk2, CyclinE-Cdk2, CyclinB-Cdk1, p21, and Gadd45. In some embodiments, the modulator that slows or stops the growth of cells and/or induces apoptosis of cells is selected from the group consisting of Staurosporine, Etoposide, Mylotarg, Daunorubicin, and AraC.

Modulators

In some embodiments, the methods and composition utilize a modulator. A modulator can be an activator, a therapeutic compound, an inhibitor or a compound capable of impacting a cellular pathway. Modulators can also take the form of environmental cues and inputs.

Modulation can be performed in a variety of environments. In some embodiments, cells are exposed to a modulator immediately after collection. In some embodiments where there is a mixed population of cells, purification of cells is performed after modulation. In some embodiments, whole blood is collected to which a modulator is added. In some embodiments, cells are modulated after processing for single cells or purified fractions of single cells. As an illustrative example, whole blood can be collected and processed for an enriched fraction of lymphocytes that is then exposed to a modulator. Modulation can include exposing cells to more than one modulator. For instance, in some embodiments, cells are exposed to at least 2, 3, 4, 5, 6, 7, 8, 9, or 10 modulators. See U.S. Patent Application 61/048,657 which is incorporated by reference.

In some embodiments, cells are cultured post collection in a suitable media before exposure to a modulator. In some embodiments, the media is a growth media. In some embodiments, the growth media is a complex media that may include serum. In some embodiments, the growth media comprises serum. In some embodiments, the serum is selected from the group consisting of fetal bovine serum, bovine serum, human serum, porcine serum, horse serum, and goat serum. In some embodiments, the serum level ranges from 0.0001% to 30%. In some embodiments, the growth media is a chemically defined minimal media and is without serum. In some embodiments, cells are cultured in a differentiating media.

Modulators include chemical and biological entities, and physical or environmental stimuli. Modulators can act extracellularly or intracellularly. Chemical and biological modulators include growth factors, mitogens, cytokines, drugs, immune modulators, ions, neurotransmitters, adhesion molecules, hormones, small molecules, inorganic compounds, polynucleotides, antibodies, natural compounds, lectins, lactones, chemotherapeutic agents, biological response modifiers, carbohydrate, proteases and free radicals. Modulators include complex and undefined biologic compositions that may comprise cellular or botanical extracts, cellular or glandular secretions, physiologic fluids such as serum, amniotic fluid, or venom. Physical and environmental stimuli include electromagnetic, ultraviolet, infrared or particulate radiation, redox potential and pH, the presence or absences of nutrients, changes in temperature, changes in oxygen partial pressure, changes in ion concentrations and the application of oxidative stress. Modulators can be endogenous or exogenous and may produce different effects depending on the concentration and duration of exposure to the single cells or whether they are used in combination or sequentially with other modulators. Modulators can act directly on the activatable elements or indirectly through the interaction with one or more intermediary biomolecule. Indirect modulation includes alterations of gene expression wherein the expressed gene product is the activatable element or is a modulator of the activatable element.

In some embodiments the modulator is selected from the group consisting of growth factors, mitogens, cytokines, adhesion molecules, drugs, hormones, small molecules, polynucleotides, antibodies, natural compounds, lactones, chemotherapeutic agents, immune modulators, carbohydrates, proteases, ions, reactive oxygen species, peptides, and protein fragments, either alone or in the context of cells, cells themselves, viruses, and biological and non-biological complexes (e.g. beads, plates, viral envelopes, antigen presentation molecules such as major histocompatibility complex). In some embodiments, the modulator is a physical stimuli such as heat, cold, UV radiation, and radiation. Examples of modulators, include but are not limited to SDF-1α, IFN-α, IFN-γ, IL-10, IL-6, IL-27, G-CSF, FLT-3L, IGF-1, M-CSF, SCF, PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine, IL-3, IL-4, GM-CSF, EPO, LPS, TNF-α, and CD40L.

In some embodiments, the modulator is an activator. In some embodiments the modulator is an inhibitor. In some embodiments, cells are exposed to one or more modulator. In some embodiments, cells are exposed to at least 2, 3, 4, 5, 6, 7, 8, 9, or 10 modulators. In some embodiments, cells are exposed to at least two modulators, wherein one modulator is an activator and one modulator is an inhibitor. In some embodiments, cells are exposed to at least 2, 3, 4, 5, 6, 7, 8, 9, or 10 modulators, where at least one of the modulators is an inhibitor.

In some embodiments, the cross-linker is a molecular binding entity. In some embodiments, the molecular binding entity is a monovalent, bivalent, or multivalent is made more multivalent by attachment to a solid surface or tethered on a nanoparticle surface to increase the local valency of the epitope binding domain.

In some embodiments, the inhibitor is an inhibitor of a cellular factor or a plurality of factors that participates in a cellular pathway (e.g. signaling cascade) in the cell. In some embodiments, the inhibitor is a phosphatase inhibitor. Examples of phosphatase inhibitors include, but are not limited to $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, 13-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenylarsine oxide, Pyrrolidine Dithiocarbamate, and Aluminium fluoride. In some embodiments, the phosphatase inhibitor is $H_2O_2$.

In some embodiments, the activation level of an activatable element in a cell is determined by contacting the cell with at least 2, 3, 4, 5, 6, 7, 8, 9, or 10 modulators. In some embodiments, the activation level of an activatable element in a cell is determined by contacting the cell with at least 2, 3, 4, 5, 6, 7, 8, 9, or 10 modulators where at least one of the modulators is an inhibitor. In some embodiments, the activation level of an activatable element in a cell is determined by contacting the cell with an inhibitor and a modulator, where the modulator can be an inhibitor or an activator. In some embodiments, the activation level of an activatable element in a cell is determined by contacting the cell with an inhibitor and an activator. In some embodiments, the activation level of an activatable element in a cell is determined by contacting the cell with two or more modulators.

In some embodiments, a phenotypic profile of a population of cells is determined by measuring the activation level of an activatable element when the population of cells is exposed to a plurality of modulators in separate cultures. In some embodiments, the modulators include $H_2O_2$, PMA, SDF1α, CD40L, IGF-1, IL-7, IL-6, IL-10, IL-27, IL-4, IL-2, IL-3, thapsigardin and/or a combination thereof. For instance a population of cells can be exposed to one or more, all or a combination of the following combination of modulators: $H_2O_2$, PMA; SDF1α; CD40L; IGF-1; IL-7; IL-6; IL-10; IL-27; IL-4; IL-2; IL-3; thapsigardin; In some embodiments, the phenotypic profile of the population of cells is used to classify the population as described herein.

Gating

In another embodiment, a user may analyze the signaling in subpopulations based on surface markers. For example, the user could look at: "stem cell populations" by CD34+ CD38− or CD34+ CD33− expressing cells; drug transporter positive cells; i.e. FLT3 LIGAND+ cells; or multiple leukemic subclones based on CD33, CD45, HLA-DR, CD11b and analyzing signaling in each subpopulation. In another alternative embodiment, a user may analyze the data based on intracellular markers, such as transcription factors or other intracellular proteins; based on a functional assay (i.e. dye negative "side population" aka drug transporter+cells, or fluorescent glucose uptake, or based on other fluorescent markers. In some embodiments, a gate is established after learning from a responsive subpopulation. That is, a gate is developed from one data set after finding a population that correlates with a clinical outcome. This gate can then be applied restrospectively or prospectively to other data sets (See FIGS. 26 and 27).

In some embodiments where flow cytometry is used, prior to analyzing of data the populations of interest and the method for characterizing these populations are determined. For instance, there are at least two general ways of identifying populations for data analysis: (i) "Outside-in" comparison of Parameter sets for individual samples or subset (e.g., patients in a trial). In this more common case, cell populations are homogenous or lineage gated in such a way as to create distinct sets considered to be homogenous for targets of interest. An example of sample-level comparison would be the identification of signaling profiles in tumor cells of a patient and correlation of these profiles with non-random distribution of clinical responses. This is considered an outside-in approach because the population of interest is pre-defined prior to the mapping and comparison of its profile to other populations. (ii) "Inside-out" comparison of Parameters at the level of individual cells in a heterogeneous population. An example of this would be the signal transduction state mapping of mixed hematopoietic cells under certain conditions and subsequent comparison of computationally identified cell clusters with lineage specific markers. This could be considered an inside-out approach to single cell studies as it does not presume the existence of specific populations prior to classification. A major drawback of this approach is that it creates populations which, at least initially, require multiple transient markers to enumerate and may never be accessible with a single cell surface epitope. As a result, the biological significance of such populations can be difficult to determine. The main advantage of this unconventional approach is the unbiased tracking of cell populations without drawing potentially arbitrary distinctions between lineages or cell types.

Each of these techniques capitalizes on the ability of flow cytometry to deliver large amounts of multiparameter data at the single cell level. For cells associated with a condition (e.g. neoplastic or hematopoetic condition), a third "meta-level" of data exists because cells associated with a condition (e.g. cancer cells) are generally treated as a single entity and classified according to historical techniques. These techniques have included organ or tissue of origin, degree of differentiation, proliferation index, metastatic spread, and genetic or metabolic data regarding the patient.

In some embodiments, the present invention uses variance mapping techniques for mapping condition signalling space. These methods represent a significant advance in the study of condition biology because it enables comparison of conditions independent of a putative normal control. Traditional differential state analysis methods (e.g., DNA microarrays, subtractive Northern blotting) generally rely on the comparison of cells associated with a condition from each patient sample with a normal control, generally adjacent and theoretically untransformed tissue. Alternatively, they rely on multiple clusterings and reclusterings to group and then further stratify patient samples according to phenotype. In contrast, variance mapping of condition states compares condition samples first with themselves and then against the parent condition population. As a result, activation states with the most diversity among conditions provide the core parameters in the differential state analysis. Given a pool of diverse conditions, this technique allows a researcher to identify the molecular events that underlie differential condition pathology (e.g., cancer responses to chemotherapy), as opposed to differences between conditions and a proposed normal control.

In some embodiments, when variance mapping is used to profile the signaling space of patient samples, conditions whose signaling response to modulators is similar are grouped together, regardless of tissue or cell type of origin. Similarly, two conditions (e.g. two tumors) that are thought to be relatively alike based on lineage markers or tissue of origin could have vastly different abilities to interpret environmental stimuli and would be profiled in two different groups.

When groups of signaling profiles have been identified it is frequently useful to determine whether other factors, such as clinical responses, presence of gene mutations, and protein expression levels, are non-randomly distributed within the groups. If experiments or literature suggest such a hypothesis in an arrayed flow cytometry experiment, it can be judged with simple statistical tests, such as the Student's t-test and the $X^2$ test. Similarly, if two variable factors within the experiment are thought to be related, the Pearson, and/or Spearman is used to measure the degree of this relationship.

Examples of analysis for activatable elements are described in US publication number 20060073474 entitled "Methods and compositions for detecting the activation state of multiple proteins in single cells" and US publication number 20050112700 entitled "Methods and compositions for risk stratification" the content of which are incorporate here by reference.

Detection

In practicing the methods of this invention, the detection of the status of the one or more activatable elements can be carried out by a person, such as a technician in the laboratory. Alternatively, the detection of the status of the one or more activatable elements can be carried out using automated systems. In either case, the detection of the status of the one or more activatable elements for use according to the methods of this invention is performed according to standard techniques and protocols well-established in the art.

One or more activatable elements can be detected and/or quantified by any method that detect and/or quantitates the presence of the activatable element of interest. Such methods may include radioimmunoassay (RIA) or enzyme linked immunoabsorbance assay (ELISA), immunohistochemistry, immunofluorescent histochemistry with or without confocal microscopy, reversed phase assays, homogeneous enzyme immunoassays, and related non-enzymatic techniques, Western blots, whole cell staining, immunoelectronmicroscopy, nucleic acid amplification, gene array, protein array, mass spectrometry, patch clamp, 2-dimensional gel electrophoresis, differential display gel electrophoresis, microsphere-based multiplex protein assays, label-free cellular assays and flow cytometry, etc. U.S. Pat. No. 4,568,649 describes ligand detection systems, which employ scintillation counting. These techniques are particularly useful for modified protein parameters. Cell readouts for proteins and other cell determinants can be obtained using fluorescent or otherwise tagged reporter molecules. Flow cytometry methods are useful for measuring intracellular parameters.

In some embodiments, the present invention provides methods for determining an activatable element's activation profile for a single cell. The methods may comprise analyzing cells by flow cytometry on the basis of the activation level of at least two activatable elements. Binding elements (e.g. activation state-specific antibodies) are used to analyze cells on the basis of activatable element activation level, and can be detected as described below. Alternatively, non-binding elements systems as described above can be used in any system described herein.

Detection of cell signaling states may be accomplished using binding elements and labels. Cell signaling states may be detected by a variety of methods known in the art. They generally involve a binding element, such as an antibody, and a label, such as a fluorchrome to form a detection element. Detection elements do not need to have both of the above agents, but can be one unit that possesses both qualities. These and other methods are well described in U.S. Pat. Nos. 7,381,535 and 7,393,656 and U.S. Ser. Nos. 10/193,462; 11/655,785; 11/655,789; 11/655,821; 11/338,957, 61/048,886; 61/048,920; and 61/048,657 which are all incorporated by reference in their entireties.

In one embodiment of the invention, it is advantageous to increase the signal to noise ratio by contacting the cells with the antibody and label for a time greater than 5, 6, 7, 8, 9, 10, 11, 12, 13, 14, 15, 16, 17, 18, 19, 20, 24 or up to 48 or more hours.

When using fluorescent labeled components in the methods and compositions of the present invention, it will recognized that different types of fluorescent monitoring systems, e.g., Cytometric measurement device systems, can be used to practice the invention. In some embodiments, flow cytometric systems are used or systems dedicated to high throughput screening, e.g. 96 well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation that has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. In general, known robotic systems and components can be used.

Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci. USA (2000) 18:553-8, each expressly incorporated herein by reference) as well as confocal microscopy. In general, flow cytometry involves the passage of individual cells through the path of a laser beam. The scattering the beam and excitation of any fluorescent molecules attached to, or found within, the cell is detected by photomultiplier tubes to create a readable output, e.g. size, granularity, or fluorescent intensity.

In some embodiments, the activation level of an activatable element is measured using Inductively Coupled Plasma Mass Spectrometer (ICP-MS). A binding element that has been labeled with a specific element binds to the activativatable. When the cell is introduced into the ICP, it is atomized and ionized. The elemental composition of the cell, including the labeled binding element that is bound to the activatable element, is measured. The presence and intensity of the signals corresponding to the labels on the binding element indicates the level of the activatable element on that cell (Tanner et al. Spectrochimica Acta Part B: Atomic Spectroscopy, 2007 March; 62(3):188-195).

The detecting, sorting, or isolating step of the methods of the present invention can entail fluorescence-activated cell sorting (FACS) techniques, where FACS is used to select cells from the population containing a particular surface marker, or the selection step can entail the use of magnetically responsive particles as retrievable supports for target cell capture and/or background removal. A variety of FACS systems are known in the art and can be used in the methods of the invention (see e.g., WO99/54494, filed Apr. 16, 1999; U.S. Ser. No. 20010006787, filed Jul. 5, 2001, each expressly incorporated herein by reference).

In some embodiments, a FACS cell sorter (e.g. a FACSVantage™ Cell Sorter, Becton Dickinson Immunocytometry Systems, San Jose, Calif.) is used to sort and collect cells based on their activation profile (positive cells) in the presence or absence of an increase in activation level in an activatable element in response to a modulator. Other flow cytometers that are commercially available include the LSR II and the Canto II both available from Becton Dickinson. See Shapiro, Howard M., Practical Flow Cytometry, 4th Ed., John Wiley & Sons, Inc., 2003 for additional information on flow cytometers.

In some embodiments, the cells are first contacted with fluorescent-labeled activation state-specific binding elements (e.g. antibodies) directed against specific activation state of specific activatable elements. In such an embodiment, the amount of bound binding element on each cell can be measured by passing droplets containing the cells through the cell sorter. By imparting an electromagnetic charge to droplets containing the positive cells, the cells can be separated from other cells. The positively selected cells can then be harvested in sterile collection vessels. These cell-sorting procedures are described in detail, for example, in the FACSVantage™. Training Manual, with particular reference to sections 3-11 to 3-28 and 10-1 to 10-17, which is hereby incorporated by reference in its entirety. See the patents, applications and articles referred to, and incorporated above for detection systems.

Fluorescent compounds such as Daunorubicin and Enzastaurin are problematic for flow cytometry based biological assays due to their broad fluorescence emission spectra. These compounds get trapped inside cells after fixation with agents like paraformaldehyde, and are excited by one or more of the lasers found on flow cytometers. The fluorescence emission of these compounds is often detected in multiple PMT detectors which complicates their use in multiparametric flow cytometry. A way to get around this problem is to compensate out the fluorescence emission of the compound from the PMT detectors used to measure the relevant biological markers. This is achieved using a PMT detector with a bandpass filter near the emission maximum of the fluorescent compound, and cells incubated with the compound as the compensation control when calculating a compensation matrix. The cells incubated with the fluorescent compound are fixed with paraformaldehyde, then washed and permeabilized with 100% methanol. The methanol is washed out and the cells are mixed with unlabeled fixed/permed cells to yield a compensation control consisting of a mixture of fluorescent and negative cell populations.

In another embodiment, positive cells can be sorted using magnetic separation of cells based on the presence of an isoform of an activatable element. In such separation techniques, cells to be positively selected are first contacted with specific binding element (e.g., an antibody or reagent that binds an isoform of an activatable element). The cells are then contacted with retrievable particles (e.g., magnetically responsive particles) that are coupled with a reagent that binds the specific element. The cell-binding element-particle complex can then be physically separated from non-positive or non-labeled cells, for example, using a magnetic field. When using magnetically responsive particles, the positive or labeled cells can be retained in a container using a magnetic filed while the negative cells are removed. These and similar separation procedures are described, for example, in the Baxter Immunotherapy Isolex training manual which is hereby incorporated in its entirety.

In some embodiments, methods for the determination of a receptor element activation state profile for a single cell are provided. The methods comprise providing a population of cells and analyze the population of cells by flow cytometry. Preferably, cells are analyzed on the basis of the activation level of at least two activatable elements. In some embodiments, a multiplicity of activatable element activation-state antibodies is used to simultaneously determine the activation level of a multiplicity of elements.

In some embodiment, cell analysis by flow cytometry on the basis of the activation level of at least two elements is combined with a determination of other flow cytometry readable outputs, such as the presence of surface markers, granularity and cell size to provide a correlation between the activation level of a multiplicity of elements and other cell qualities measurable by flow cytometry for single cells.

As will be appreciated, the present invention also provides for the ordering of element clustering events in signal transduction. Particularly, the present invention allows the artisan to construct an element clustering and activation hierarchy based on the correlation of levels of clustering and activation of a multiplicity of elements within single cells. Ordering can be accomplished by comparing the activation level of a cell or cell population with a control at a single time point, or by comparing cells at multiple time points to observe subpopulations arising out of the others.

The present invention provides a valuable method of determining the presence of cellular subsets within cellular populations. Ideally, signal transduction pathways are evaluated in homogeneous cell populations to ensure that variances in signaling between cells do not qualitatively nor quantitatively mask signal transduction events and alterations therein. As the ultimate homogeneous system is the single cell, the present invention allows the individual evaluation of cells to allow true differences to be identified in a significant way.

Thus, the invention provides methods of distinguishing cellular subsets within a larger cellular population. As outlined herein, these cellular subsets often exhibit altered biological characteristics (e.g. activation levels, altered response to modulators) as compared to other subsets within the population. For example, as outlined herein, the methods of the invention allow the identification of subsets of cells from a population such as primary cell populations, e.g. peripheral blood mononuclear cells that exhibit altered responses (e.g. response associated with presence of a condition) as compared to other subsets. In addition, this type of evaluation distinguishes between different activation states, altered responses to modulators, cell lineages, cell differentiation states, etc.

As will be appreciated, these methods provide for the identification of distinct signaling cascades for both artificial and stimulatory conditions in complex cell populations, such a peripheral blood mononuclear cells, or naive and memory lymphocytes.

When necessary cells are dispersed into a single cell suspension, e.g. by enzymatic digestion with a suitable protease, e.g. collagenase, dispase, etc; and the like. An appropriate solution is used for dispersion or suspension. Such solution will generally be a balanced salt solution, e.g. normal saline, PBS, Hanks balanced salt solution, etc., conveniently supplemented with fetal calf serum or other naturally occurring factors, in conjunction with an acceptable buffer at low concentration, generally from 5-25 mM. Convenient buffers include HEPES1 phosphate buffers, lactate buffers, etc. The cells may be fixed, e.g. with 3% paraformaldehyde, and are usually permeabilized, e.g. with ice cold methanol; HEPES-buffered PBS containing 0.1% saponin, 3% BSA; covering for 2 min in acetone at −200 C; and the like as known in the art and according to the methods described herein.

In some embodiments, one or more cells are contained in a well of a 96 well plate or other commercially available multiwell plate. In an alternate embodiment, the reaction mixture or cells are in a cytometric measurement device. Other multiwell plates useful in the present invention include, but are not limited to 384 well plates and 1536 well plates. Still other vessels for containing the reaction mixture or cells and useful in the present invention will be apparent to the skilled artisan.

The addition of the components of the assay for detecting the activation level or activity of an activatable element, or modulation of such activation level or activity, may be sequential or in a predetermined order or grouping under conditions appropriate for the activity that is assayed for. Such conditions are described here and known in the art. Moreover, further guidance is provided below (see, e.g., in the Examples).

In some embodiments, the activation level of an activatable element is measured using Inductively Coupled Plasma Mass Spectrometer (ICP-MS). A binding element that has been labeled with a specific element binds to the activativatable. When the cell is introduced into the ICP, it is atomized and ionized. The elemental composition of the cell, including the labeled binding element that is bound to the activatable element, is measured. The presence and intensity of the signals corresponding to the labels on the binding element indicates the level of the activatable element on that cell (Tanner et al. Spectrochimica Acta Part B: Atomic Spectroscopy, 2007 March; 62(3):188-195).

As will be appreciated by one of skill in the art, the instant methods and compositions find use in a variety of other assay formats in addition to flow cytometry analysis. For example, DNA microarrays are commercially available through a variety of sources (Affymetrix, Santa Clara Calif.) or they can be custom made in the lab using arrayers which are also know (Perkin Elmer). In addition, protein chips and methods for synthesis are known. These methods and materials may be adapted for the purpose of affixing activation state binding elements to a chip in a prefigured array. In some embodiments, such a chip comprises a multiplicity of element activation state binding elements, and is used to determine an element activation state profile for elements present on the surface of a cell.

In some embodiments, a chip comprises a multiplicity of the "second set binding elements," in this case generally unlabeled. Such a chip is contacted with sample, preferably cell extract, and a second multiplicity of binding elements comprising element activation state specific binding elements is used in the sandwich assay to simultaneously determine the presence of a multiplicity of activated elements in sample. Preferably, each of the multiplicity of activation state-specific binding elements is uniquely labeled to facilitate detection.

In some embodiments confocal microscopy can be used to detect activation profiles for individual cells. Confocal microscopy relies on the serial collection of light from spatially filtered individual specimen points, which is then electronically processed to render a magnified image of the specimen. The signal processing involved confocal microscopy has the additional capability of detecting labeled binding elements within single cells, accordingly in this embodiment the cells can be labeled with one or more binding elements. In some embodiments the binding elements used in connection with confocal microscopy are antibodies conjugated to fluorescent labels, however other binding elements, such as other proteins or nucleic acids are also possible.

In some embodiments, the methods and compositions of the instant invention can be used in conjunction with an "In-Cell Western Assay." In such an assay, cells are initially grown in standard tissue culture flasks using standard tissue culture techniques. Once grown to optimum confluency, the growth media is removed and cells are washed and trypsinized. The cells can then be counted and volumes sufficient to transfer the appropriate number of cells are aliquoted into microwell plates (e.g., Nunc™ 96 Microwell™ plates). The individual wells are then grown to optimum confluency in complete media whereupon the media is replaced with serum-free media. At this point controls are untouched, but experimental wells are incubated with a modulator, e.g. EGF. After incubation with the modulator cells are fixed and stained with labeled antibodies to the activation elements being investigated. Once the cells are labeled, the plates can be scanned using an imager such as the Odyssey Imager (LiCor, Lincoln Nebr.) using techniques described in the Odyssey Operator's Manual v1.2., which is hereby incorporated in its entirety. Data obtained by scanning of the multiwell plate can be analyzed and activation profiles determined as described below.

In some embodiments, the detecting is by high pressure liquid chromatography (HPLC), for example, reverse phase HPLC, and in a further aspect, the detecting is by mass spectrometry.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells.

Flow cytometry or capillary electrophoresis formats can be used for individual capture of magnetic and other beads, particles, cells, and organisms.

Flexible hardware and software allow instrument adaptability for multiple applications. The software program modules allow creation, modification, and running of methods. The system diagnostic modules allow instrument alignment, correct connections, and motor operations. Customized tools, labware, and liquid, particle, cell and organism transfer patterns allow different applications to be performed. Databases allow method and parameter storage. Robotic and computer interfaces allow communication between instruments.

In some embodiment, the methods of the invention include the use of liquid handling components. The liquid handling systems can include robotic systems comprising any number of components. In addition, any or all of the steps outlined herein may be automated; thus, for example, the systems may be completely or partially automated. See U.S. Ser. No. 61/048,657.

As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In some embodiments, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In some embodiments, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station. In some embodiments, the methods of the invention include the use of a plate reader.

In some embodiments, thermocycler and thermoregulating systems are used for stabilizing the temperature of heat exchangers such as controlled blocks or platforms to provide accurate temperature control of incubating samples from 0° C. to 100° C.

In some embodiments, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In some embodiments, useful detectors include a microscope(s) with multiple channels of fluorescence; plate readers to provide fluorescent, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; and a computer workstation.

In some embodiments, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

Any of the steps above can be performed by a computer program product that comprises a computer executable logic that is recorded on a computer readable medium. For example, the computer program can execute some or all of the following functions: (i) exposing reference population of cells to one or more modulators, (ii) exposing reference population of cells to one or more binding elements, (iii) detecting the activation levels of one or more activatable elements, (iv) characterizing one or more cellular pathways and/or (v) classifying one or more cells into one or more classes based on the activation level.

The computer executable logic can work in any computer that may be any of a variety of types of general-purpose computers such as a personal computer, network server, workstation, or other computer platform now or later developed. In some embodiments, a computer program product is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

The program can provide a method of determining the status of an individual by accessing data that reflects the activation level of one or more activatable elements in the reference population of cells.

Analysis

Advances in flow cytometry have enabled the individual cell enumeration of up to thirteen simultaneous parameters (De Rosa et al., 2001) and are moving towards the study of genomic and proteomic data subsets (Krutzik and Nolan, 2003; Perez and Nolan, 2002). Likewise, advances in other techniques (e.g. microarrays) allow for the identification of multiple activatable elements. As the number of parameters, epitopes, and samples have increased, the complexity of experiments and the challenges of data analysis have grown rapidly. An additional layer of data complexity has been added by the development of stimulation panels which enable the study of activatable elements under a growing set of experimental conditions. See Krutzik et al, Nature Chemical Biology February 2008. Methods for the analysis of multiple parameters are well known in the art. See U.S. Ser. No. 61/079,579 for gating analysis.

In some embodiments where flow cytometry is used, flow cytometry experiments are performed and the results are expressed as fold changes using graphical tools and analyses, including, but not limited to a heat map or a histogram to facilitate evaluation. One common way of comparing changes in a set of flow cytometry samples is to overlay histograms of one parameter on the same plot. Flow cytometry experiments ideally include a reference sample against which experimental samples are compared. Reference samples can include normal and/or cells associated with a condition (e.g. tumor cells). See also U.S. Ser. No. 61/079,537 for visualization tools The patients are stratified based on nodes that inform the clinical question using a variety of metrics. To stratify the patients between those patients with No Response (NR) versus a Complete Response (CR), a prioritization of the nodes can be made according to statistical significance (such as p-value from a t-test or Wilcoxon test or area under the receiver operator characteristic (ROC) curve) or their biological relevance. See FIGS. 2, and 7-9 for methods for analyzing the cell signaling pathway data. For example, FIG. 2 shows four methods to analyze data, such as from AML patients. Other characteristics such as expression markers may also be used. See FIG. 8.

Figure 7:
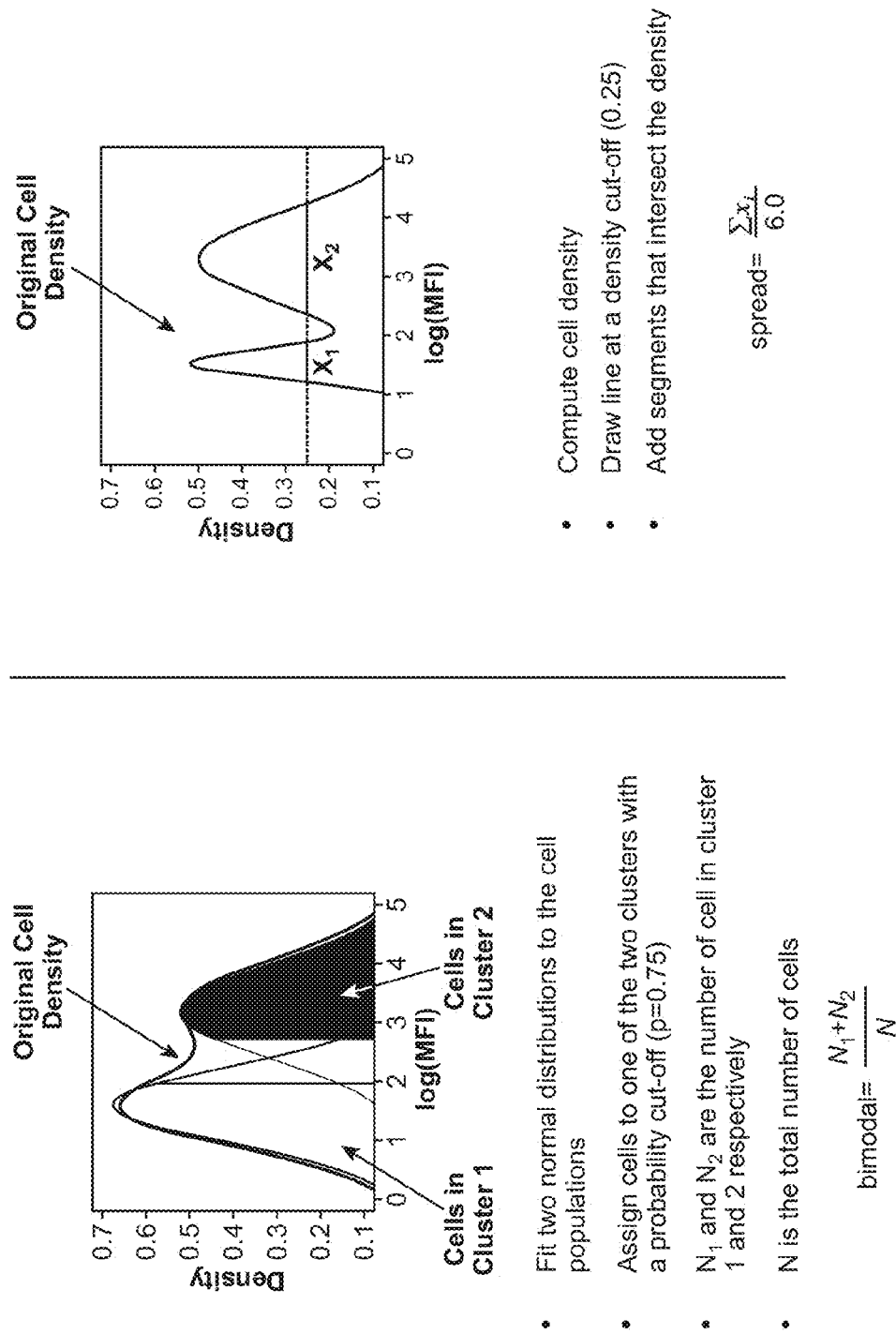
FIG. 7 shows bimodal and spread metrics for analyzing cell populations.

FIG. 2 shows the use of four metrics used to analyze data from cells that may be subject to a disease, such as AML. For example, the "basal" metric is calculated by measuring the autofluorescence of a cell that has not been stimulated with a modulator or stained with a labeled antibody. The "total phospho" metric is calculated by measuring the autofluorescence of a cell that has been stimulated with a modulator and stained with a labeled antibody. The "fold change" metric is the measurement of the total phospho metric divided by the basal metric. The quadrant frequency metric is the frequency of cells in each quadrant of the contour plot A user may also analyze multimodal distributions to separate cell populations. FIG. 7 provides some metrics for analyzing bimodal and spread distribution.

Figure 8:
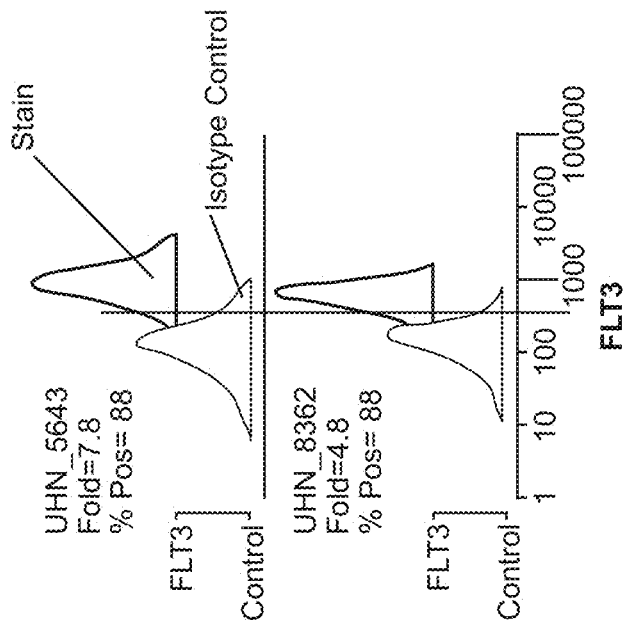
FIG. 8 shows expression marker metric using fold change over isotype and percent positive over isotype.

FIG. 8 provides metrics to calculate expression markers. Metric 5 calculates the fold over isotype control ad metric 6 calculates positive above isotype control.

Figure 9:
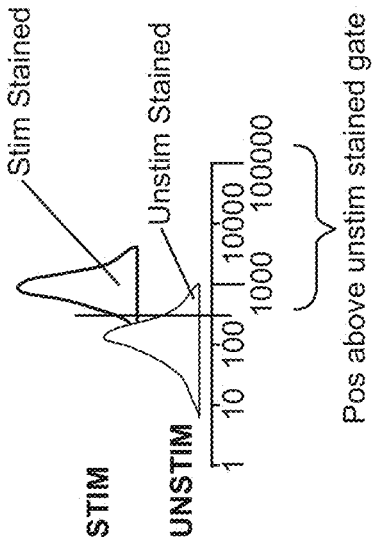
FIG. 9 shows two other methods for analyzing cells including the percent of the population that is positive and has a fluorescence that is greater than the unstimulated/stained; and the median fluorescent intensity (MFI) of percent positive above unstimulated/stained.

FIG. 9 provides two more metrics, metric 7 calculates the percent of positive above unstained and metric 8 calculates MFI of positive over untreated stained.

A user can create other metrics for measuring the negative signal. For example, a user may analyze a "gated unstained" or ungated unstained autofluorescence population as the negative signal for calculations such as "basal" and "total". This is a population that has been stained with surface markers such as CD33 and CD45 to gate the desired population, but is unstained for the fluorescent parameters to be quantitatively evaluated for node determination. However, every antibody has some degree of nonspecific association or "stickyness" which is not taken into account by just comparing fluorescent antibody binding to the autofluorescence. To obtain a more accurate "negative signal", the user may stain cells with isotype-matched control antibodies. In addition to the normal fluorescent antibodies, in one embodiment, (phospho) or non phosphopeptides which the antibodies should recognize will take away the antibody's epitope specific signal by blocking its antigen binding site allowing this "bound" antibody to be used for ebaluation of non-specific binding. In another embodiment, a user may block with unlabeled antibodies. This method uses the same antibody clones of interest, but uses a version that lacks the conjugated fluorophore. The goal is to use an excess of unlabeled antibody with the labeled version.

In another embodiment, a user may block other high protein concentration solutions including, but not limited to fetal bovine serum, and normal serum of the species in which the antibodies were made, i.e. using normal mouse serum in a stain with mouse antibodies. (It is preferred to work with primary conjugated antibodies and not with stains requiring secondary antibodies because the secondary antibody will recognize the blocking serum). In another embodiment, a user may treat fixed cells with phosphatases to enzymatically remove phosphates, then stain.

In alternative embodiments, there are other ways of analyzing data, such as third color analysis (3D plots), which can be similar to Cytobank 2D, plus third D in color.

One embodiment of the present invention is software to examine the correlations among phosphorylation or expression levels of pairs of proteins in response to stimulus or modulation. The software examines all pairs of proteins for which phosphorylation and/or expression was measured in an experiment. The Total phosho metric (sometimes called "FoldAF") is used to represent the phosphorylation or expression data for each protein; this data is used either on linear scale or log 2 scale. See FIG. 2, metric 3 for Total Phospho.

For each protein pair under each experimental condition (unstimulated, stimulated, or treated with drug/modulator), the Pearson correlation coefficient and linear regression line fit are computed. The Pearson correlation coefficients for samples representing responding and non-responding patients are calculated separately for each group and compared to the unperturbed (unstimulated) data. The following additional metrics are derived:
1. Delta CRNR unstim: the difference between Pearson correlation coefficients for each protein pair for the responding patients and for the non-responding patients in the basal or unstimulated state.
2. Delta CRNR stim: the difference between Pearson correlation coefficients for each protein pair for the responding patients and for the non-responding patients in the stimulated or treated state.
3. DeltaDelta CRNR: the difference between Delta CRNRstim and Delta CRNRunstim.

The correlation coefficients, line fit parameters (R, p-value, and slope), and the three derived parameters described above are computed for each protein-protein pair. Protein-protein pairs are identified for closer analysis by the following criteria:
1. Large shifts in correlations within patient classes as denoted by large positive or negative values (top and bottom quartile or $10^{th}$ and $90^{th}$ percentile) of the Delta-Delta CRNR parameter.
2. Large positive or negative (top and bottom quartile or $10^{th}$ and $90^{th}$ percentile) Pearson correlation for at least one patient group in either unstimulated or stimulated/treated condition.
3. Significant line fit (p-value <=0.05 for linear regression) for at least one patient group in either unstimulated or stimulated/treated condition.

All pair data is plotted as a scatter plot with axes representing phosphorylation or expression level of a protein. Data for each sample (or patient) is plotted with color indicating whether the sample represents a responder (generally blue) or non-responder (generally red). Further line fits for responders, non-responders and all data are also represented on this graph, with significant line fits (p-value <=0.05 in linear regression) represented by solid lines and other fits represented by dashed line, enabling rapid visual identification of significant fits. Each graph is annotated with the Pearson correlation coefficient and linear regression parameters for the individual classes and for the data as a whole. The resulting plots are saved in PNG format to a single directory for browsing using Picassa. Other visualization software can also be used.

Each protein pair can be further annotated by whether the proteins comprising the pair are connected in a "canonical" pathway. In the current implementation canonical pathways are defined as the pathways curated by the NCI and Nature Publishing Group. This distinction is important; however, it is likely not an exclusive way to delineate which protein pairs to examine. High correlation among proteins in a canonical pathway in a sample may indicate the pathway in that sample is "intact" or consistent with the known literature. One embodiment of the present invention identifies protein pairs that are not part of a canonical pathway with high correlation in a sample as these may indicate the non-normal or pathological signaling. This method will be used to identify stimulator/modulator-stain-stain combinations that distinguish classes of patients.

Another method of the present invention relates to display of information using scatter plots. Scatter plots are known in the art and are used to visually convey data for visual analysis of correlations. See U.S. Pat. No. 6,520,108. The scatter plots illustrating protein pair correlations can be annotated to convey additional information, such as one, two, or more additional parameters of data visually on a scatter plot.

Previously, scatter plots used equal size plots to denote all events. FIGS. 10-15 show that CR events are represented with a black plot and NR patients are represented with a white plot, however using the method two additional parameters can be visualized as follows. First, the diameter of the circles representing the phosphorylation or expression levels of the pair of proteins may be scaled according to another parameter. For example they may be scaled according to expression level of one or more other proteins such as transporters (if more than one protein, scaling is additive, concentric rings may be used to show individual contributions to diameter).

Second, additional shapes may be used to indicate subclasses of patients. For example they could be used to denote patients who responded to a second drug regimen or where CRp status. Another example is to show how samples or patients are stratified by another parameter (such as a different stim-stain-stain combination). Many other shapes, sizes, colors, outlines, or other distinguishing glyphs may be used to convey visual information in the scatter plot.

In this example the size of the dots is relative to the measured expression and the box around a dot indicates a NRCR patient that is a patient that became CR (Responsive) after more aggressive treatment but was initially NR (Non-Responsive). Patients without the box indicates a NR patient that stayed NR.

Figure 10:
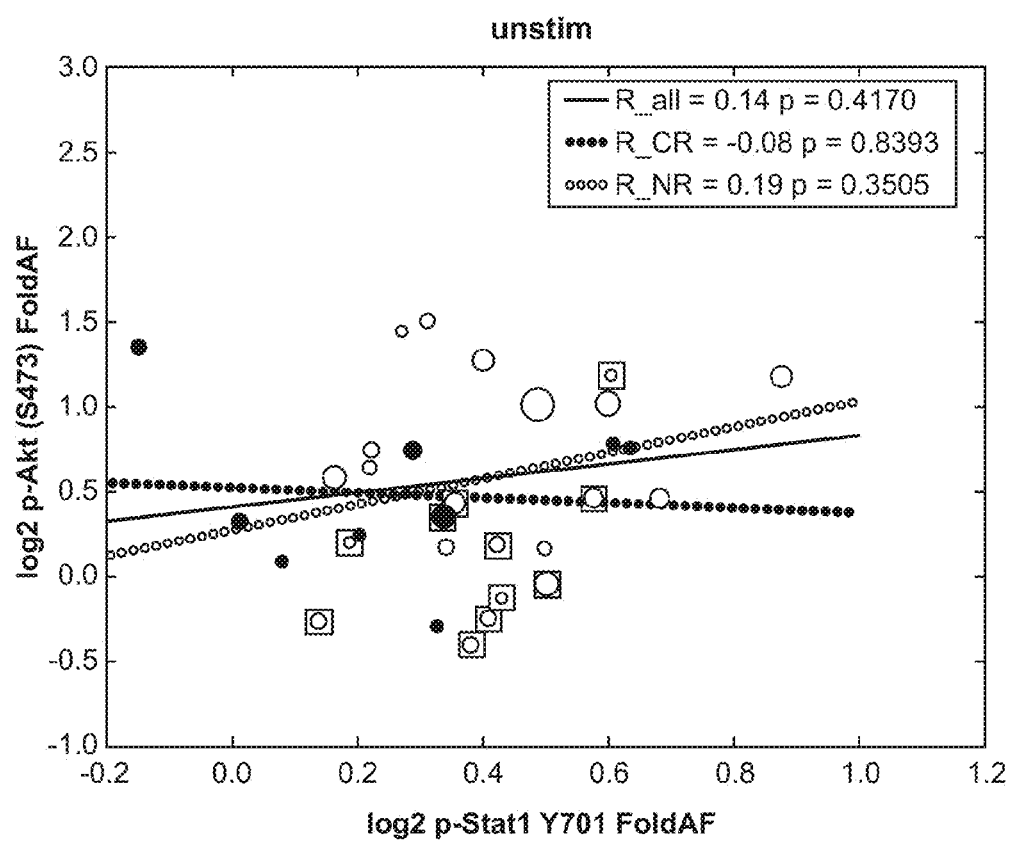
FIG. 10 shows a p-Stat 1/p-Akt scatter plot, all patient samples, basal (unstimulated). White=NR, White with box=NR-CR, black=CR, circles scaled by ABCG2 and MDR-1 expression
Figure 11:
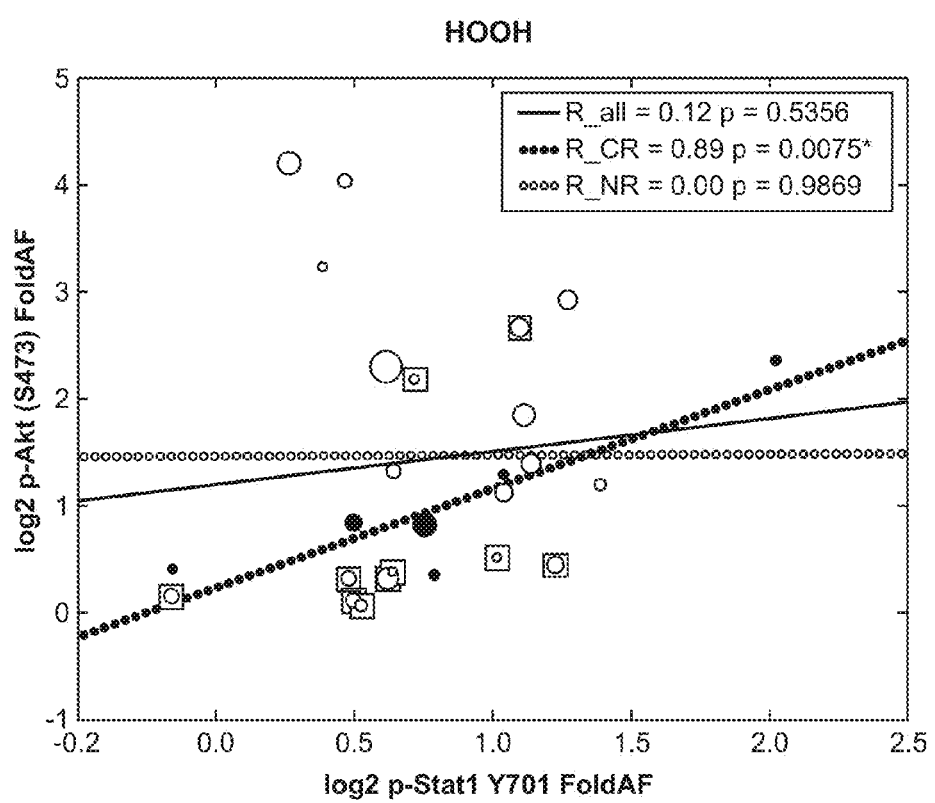
FIG. 11 shows a p-Stat 1/p-Akt scatter plot, all patient samples, $H_2O_2$ treated. White=NR, white with box=NR-CR, black=CR, circles scaled by ABCG2 and MDR-1 expression.
Figure 12:
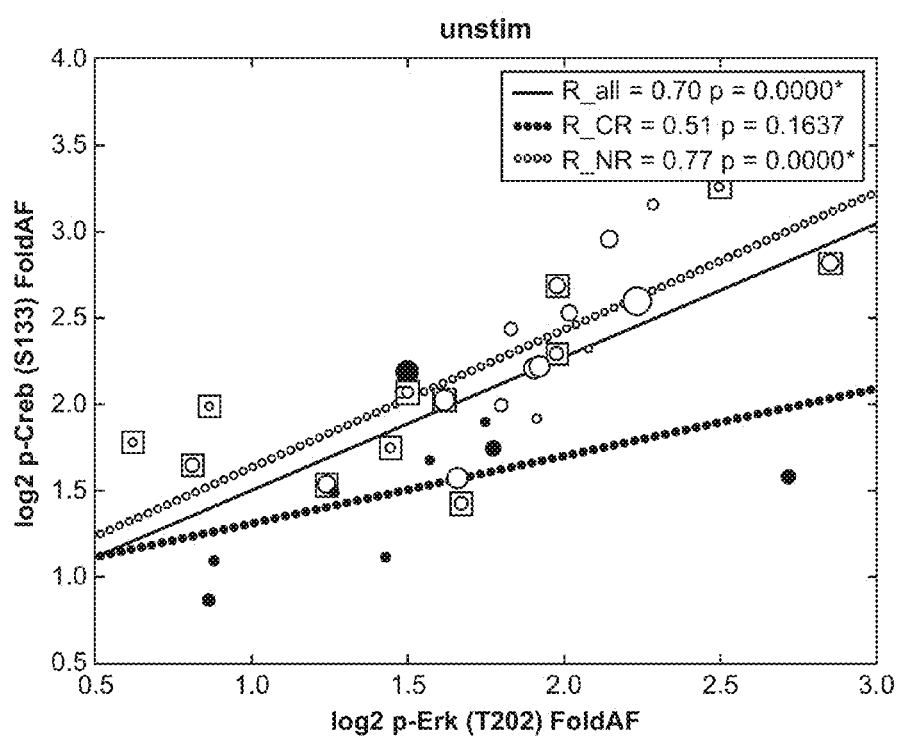
FIG. 12 shows a p-Erk/p-CREB scatter plot, all patient samples, basal (unstimulated). White=NR, white with box=NR-CR, black=CR, circles scaled by ABCG2 and MDR-1 expression.
Figure 13:
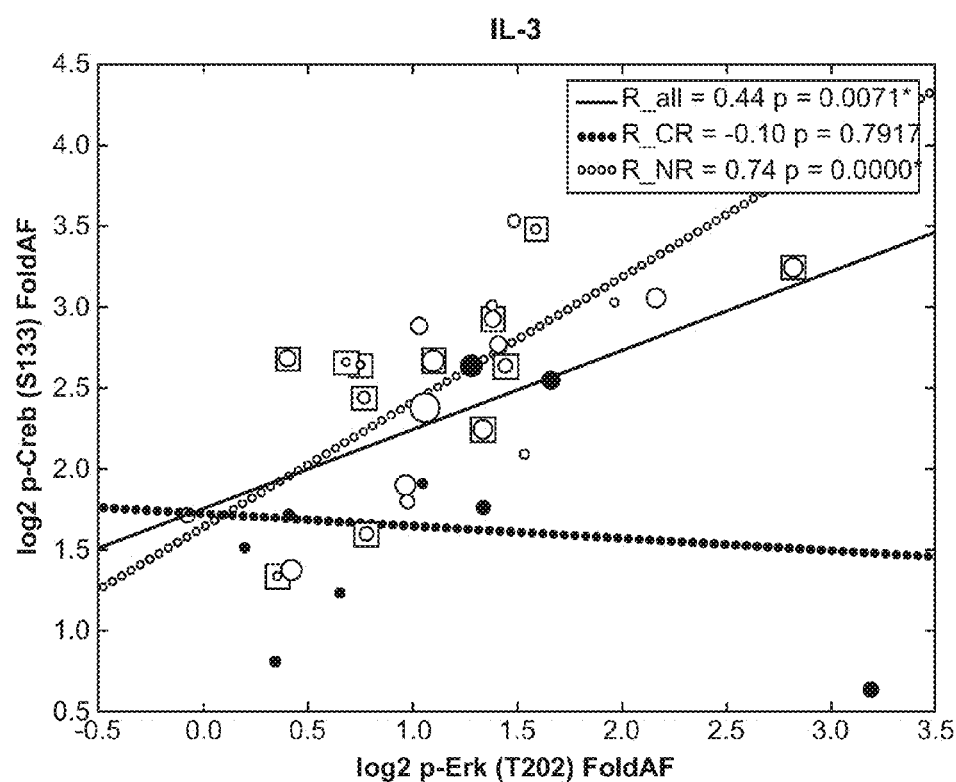
FIG. 13 shows a p-Erk/p-CREB scatter plot, all patient samples, IL-3 treated cells. White=NR, white with box=NR-CR, black=CR, circles scaled by ABCG2 and MDR-1 expression.
Figure 14:
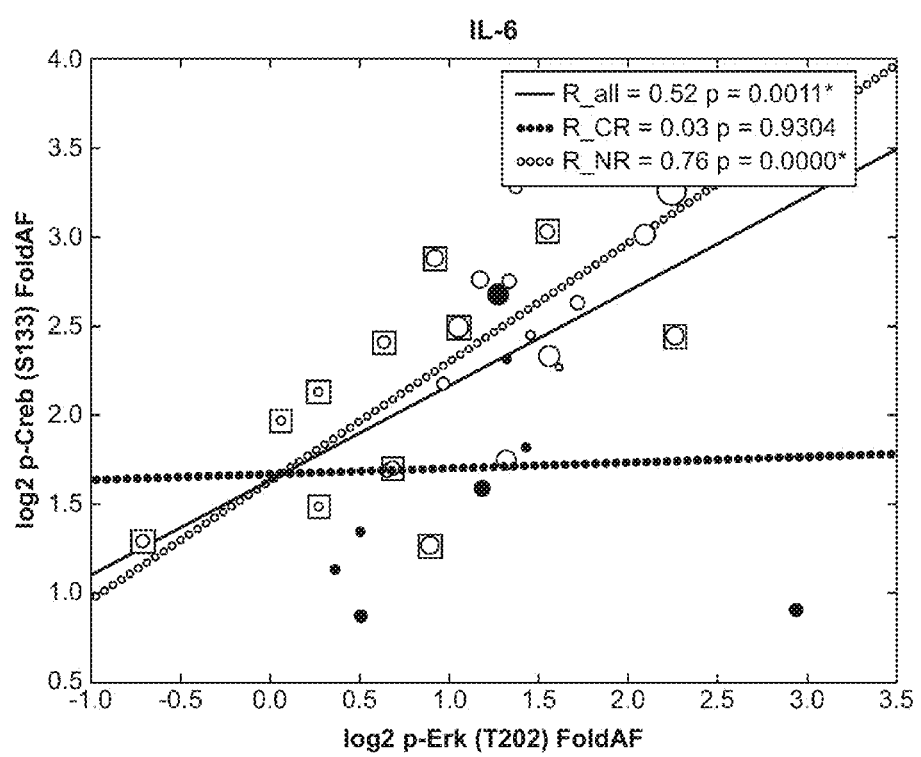
FIG. 14 shows a p-Erk/p-CREB scatter plot, all patient samples, IL-6 treated cells. White=NR, white with box=NR-CR, black=CR, circles scaled by ABCG2 and MDR-1 expression.
Figure 15:
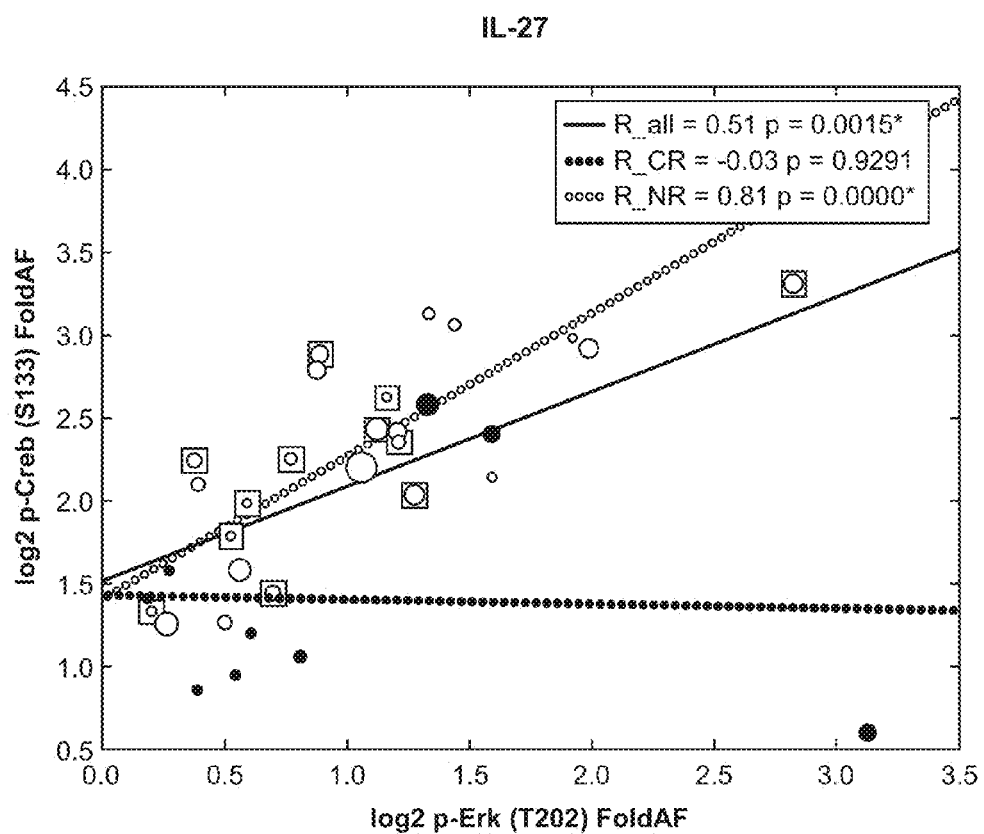
FIG. 15 shows a p-Erk/p-CREB scatter plot, all patient samples, IL-27 treated cells. White=NR, white with box=NR-CR, black=CR, circles scaled by ABCG2 and MDR-1 expression.

Applying the methods of the present invention, the Total Phospho metric for p-Akt and p-Stat 1 are correlated in response to peroxide ("HOOH") treatment. (Total phoshpo is calculated as shown in FIG. 2, metric #3). On log 2 scale the Pearson correlation coefficient for p-Akt and p-Stat1 in response to HOOH for samples from patients who responded to first treatment is 0.89 and the p-value for linear regression line fit is 0.0075. In contrast there appeared to be no correlation observed for p-Akt and p-Stat 1 in HOOH treated samples from patients annotated as "NR" (non-responder) or "NRCR" (initial non-responder, who responded to later more intensive treatment). Further there are no significant correlations observed for these proteins in any patient class for untreated samples. FIG. 10 shows p-Stat 1 v. p-Akt scatter plot for unstimulated cells and FIG. 11 shows similar scatter plot for HOOH treated cells. The figures also incorporate the annotation techniques described herein.

The Total phospho metric for p-Erk and p-CREB also appeared to be correlated in response to IL-3, IL-6, and IL-27 treatment in samples from non-responding patients (NR and NR-CR). When considering all data in log 2 scale the Pearson correlation coefficients for p-Erk and p-CREB in response to IL-3, IL-6, and IL-27 for samples from patients who did not respond to first treatment are 0.74, 0.76, 0.81, respectively, and the respective p-values for linear regression line fits are <0.0001, <0.0001, and <0.0001. In contrast there appeared to be no correlation observed for p-Erk and p-Creb in IL-3, IL-6, and IL-27 experiments for patients annotated as "CR". This data are presented in FIGS. 12 through 15. Table 2 below shows nodes identified by a fold change metric. Table 3 below shows node identified by a variety of methods. In some embodiments, the nodes depicted in Table 2 and 3 are used according to the methods described herein for classification, diagnosis, prognosis of AML, MDS or MPN or for the selection of treatment and/or predict outcome after administering a therapeutic.

TABLE 2

Nodes Identified by Fold Change Metric

| Node | Metric | Relevant Biology/ Known Role in AML | p-Val | AUC |
|---|---|---|---|---|
| SDF-1 → p-Akt | Fold Change | BM Chemokine | .025 | .71 |
| SCF→ p-Akt | Fold Change | Stem Cell Growth Factor Upreg, Mutated In AML | .018 | .809 |
| SCF→ p-S6 | Fold Change | Stem Cell Growth Factor Upreg, Mutated In AML | .055 | .66 |
| FLT3L→ p-Akt | Fold Change | Growth Factor Mutated In AML | .003 | .82 |
| FLT3L→ p-S6 | Fold Change | Growth Factor Mutated In AML | .026 | .66 |
| G-CSF→ p-Stat3 | Fold Change | Myeloid Growth Factor | .090 | .68 |
| G-CSF→ p-Stat5 | Fold Change | Myeloid Growth Factor | .038 | .70 |
| Peroxide → p-Slp-76 | Fold Change | Phosphatase Inhibition Novel AML Biology | .02 | .78 |
| Peroxide→ p-Plcγ2 | Fold Change | Phosphatase Inhibition Novel AML Biology | .09 | .75 |
| IFNα→ p-Stat1 | Fold Change | | .017 | .747 |
| IFNγ→ p-Stat1 | Fold Change | | .038 | .707 |
| Thapsi→ p-S6 | Fold Change | Pharmacological stim | .020 | .707 |
| PMA → p-Erk | Fold Change | Pharmacological stim | .062 | .702 |

TABLE 3

Nodes Identified by Variety of Metrics

| Node | Metric | Relevant Biology/ Known Role in AML | p-Val | AUC |
|---|---|---|---|---|
| Etoposide → cleaved PARP + p-Chk2− | Quadrant Gate Frequency | DNA damage & Apoptosis | .001 | .82 |
| p-Creb | Basal | Over-expressed in AML | .0005 | .87 |
| p-Erk | Basal | Activated in AML | .02 | .77 |
| p-Stat6 | Basal | Novel AML Biology | .008 | .76 |
| p-Plcγ2 | Basal | Novel AML Biology | .007 | .79 |
| p-Stat3 | Basal | Activated in AML | .005 | .81 |

TABLE 3-continued

Nodes Identified by Variety of Metrics

| Node | Metric | Relevant Biology/ Known Role in AML | p-Val | AUC |
|---|---|---|---|---|
| IL-27→ p-Stat3 | Total | p-Stat3 Active in AML | .00004 | .80 |
| IL-10→ p-Stat3 | Total | p-Stat3 Active in AML | .0009 | .84 |
| IL-6 → p-Stat3 | Total | p-pStat3 Active in AML | .001 | .77 |
| Etopo + Zvad → Cleaved Caspse 3 | Total | Apoptosis | | |
| ABCG2 | % Positive Above Isotype | Drug Transporter | .00093 | .75 |
| C-KITR | Fold over Isotype | Growth Factor Receptor | .012 | .78 |
| FLT3R | Fold over Isotype | Growth Factor Receptor | .0004 | .82 |

Drug Screening

Another embodiment of the present invention is a method for screening drugs that are in development and indicated for patients that have been diagnosed with acute myelogenous leukemia (AML), myelodysplasia (MDS) or myelodyspastic syndrome (MPN).

Using the signaling nodes and methodology described herein, multiparametric flow cytometry could be used in-vitro to predict both on and off-target cell signaling effects. Using an embodiment of the present invention, the bone marrow or peripheral blood obtained from a patient diagnosed with AML, MDS or MPN could be divided and part of the sample subjected to a therapeutic. Modulators (e.g. GM-CSF or PMA) could then be added to the untreated and treated specimens. Activatable elements (e.g. JAKs/STATs/AKT), including the proposed target of the therapeutic, or those that may be affected by the therapeutic (off-target) can then be assessed for an activation state. This activation state can be used to predict the therapeutics' potential for on and off target effects prior to first in human studies.

Using the signaling nodes and methodology described herein, one embodiment of the present invention, such as multiparametric flow cytometry, could be used after in-vivo exposure to a therapeutic in development for patients that have been diagnosed with AML, MDS or MPN to determine both on and off-target effects. Using an embodiment of the present invention, the bone marrow or peripheral blood (fresh, frozen, ficoll purified, etc.) obtained from a patient diagnosed with AML or MDS at time points before and after exposure to a given therapeutic may be subjected to a modulator as above. Activatable elements (e.g. JAKs/STATs/ AKT), including the proposed target of the therapeutic, or those that may be affected by the therapeutic (off-target) can then be assessed for an activation state. This activation state can then be used to determine the on and off target signaling effects on the bone marrow or blast cells.

The apoptosis and peroxide panel study may reveal new biological classes of stratifying nodes for drug screening. Some of the important nodes could include changes on levels of p-Lck, pSlp-76, p PLCγ2, in response to peroxide alone or in combination with growth factors or cytokines. These important nodes are induced Cleaved Caspase 3 and Cleaved Caspase 8, and etoposide induced p-Chk2, peroxide ($H_2O_2$) induced p-SLP-76, peroxide ($H_2O_2$) induced p-PLCγ2 and peroxide ($H_2O_2$) induced P-Lck. The apoptosis panel may include but is not limited to, detection of changes in phosphorylation of Chk2, changes in amounts of cleaved caspase 3, cleaved caspase 8, cleaved poly (ACP ribose) polymerase PARP, cytochrome C released from the mitochondria these apoptotic nodes are measured in response to agents that included but are not limited to DNA damaging agents such as Etoposide, Mylotarg, AraC and daunorubicin either alone or in combination as well as to the global kinase inhibitor staurosporine.

Using the signaling nodes and methodology described herein, multiparametric flow cytometry could be used to find new target for treatment (e.g. new druggable targets). Using an embodiment of the present invention, the bone marrow or peripheral blood obtained from a patient diagnosed with AML, MDS or MPN could be divided and part of the sample subjected to one or more modulators (e.g. GM-CSF or PMA). Activatable elements (e.g. JAKs/STATs/AKT) can then be assessed for an activation state. This activation state can be used to predict find new target molecule for new existing therapeutics. These therapeutics can be used alone or in combination with other treatments for the treatment of AML, MDS or MPN.

Kits

In some embodiments the invention provides kits. Kits provided by the invention may comprise one or more of the state-specific binding elements described herein, such as phospho-specific antibodies. A kit may also include other reagents that are useful in the invention, such as modulators, fixatives, containers, plates, buffers, therapeutic agents, instructions, and the like.

In some embodiments, the kit comprises one or more of the phospho-specific antibodies specific for the proteins selected from the group consisting of PI3-Kinase (p85, p110a, p110b, p110d), Jak1, Jak2, SOCs, Rac, Rho, Cdc42, Ras-GAP, Vav, Tiam, Sos, Dbl, Nck, Gab, PRK, SHPT, and SHP2, SHIP1, SHIP2, sSHIP, PTEN, Shc, Grb2, PDK1, SGK, Akt1, Akt2, Akt3, TSC1,2, Rheb, mTor, 4EBP-1, p70S6Kinase, S6, LKB-1, AMPK, PFK, Acetyl-CoAa Carboxylase, DokS, Rafs, Mos, Tpl2, MEK1/2, MLK3, TAK, DLK, MKK3/6, MEKK1, 4, MLK3, ASK1, MKK4/7, SAPK/JNK1,2,3, p38s, Erk1/2, Syk, Btk, BLNK, LAT, ZAP70, Lck, Cbl, SLP-76, PLCγ☐, PLCγ 2, STAT1, STAT 3, STAT 4, STAT 5, STAT 6, FAK, p130CAS, PAKs, LIMK1/2, Hsp90, Hsp70, Hsp27, SMADs, Rel-A (p65-NFKB), CREB, Histone H$_2$B, HATs, HDACs, PKR, Rb, Cyclin D, Cyclin E, Cyclin A, Cyclin B, P16, p14Arf, p27KIP, p21CIP, Cdk4, Cdk6, Cdk7, Cdk1, Cdk2, Cdk9, Cdc25, A/B/C, Abl, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, IAPB, Smac, Fodrin, Actin, Src, Lyn, Fyn, Lck, NIK, IκB, p65(RelA), IKKα, PKA, PKCα☐☐, PKCβ☐☐, PKCθ☐☐☐, PKCδ, CAMK, Elk, AFT, Myc, Egr-1, NFAT, ATF-2, Mdm2, p53, DNA-PK, Chk1, Chk2, ATM, ATR, β☐catenin, CrkL, GSK3α, GSK3β, and FOXO. In some embodiments, the kit comprises one or more of the phospho-specific antibodies specific for the proteins selected from the group consisting of Erk, Syk, Zap70, Lck, Btk, BLNK, Cbl, PLCγ2, Akt, RelA, p38, S6. In some embodiments, the kit comprises one or more of the phospho-specific antibodies specific for the proteins selected from the group consisting of Akt1, Akt2, Akt3, SAPK/JNK1,2,3, p38s, Erk1/2, Syk, ZAP70, Btk, BLNK, Lck, PLCγ, PLCγ 2, STAT1, STAT 3, STAT 4, STAT 5, STAT 6, CREB, Lyn, p-S6, Cbl, NF-κB, GSK3β, CARMA/Bcl10 and Tcl-1.

Kits provided by the invention may comprise one or more of the modulators described herein. In some embodiments, the kit comprises one or more modulators selected from the group consisting of H$_2$O$_2$, PMA, BAFF, April, SDF1α, CD40L, IGF-1, Imiquimod, polyCpG, IL-7, IL-6, IL-10, IL-27, IL-4, IL-2, IL-3, thapsigardin and a combination thereof.

The state-specific binding element of the invention can be conjugated to a solid support and to detectable groups directly or indirectly. The reagents may also include ancillary agents such as buffering agents and stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The kit may be packaged in any suitable manner, typically with an elements in a single container along with a sheet of printed instructions for carrying out the test.

Such kits enable the detection of activatable elements by sensitive cellular assay methods, such as IHC and flow cytometry, which are suitable for the clinical detection, prognosis, and screening of cells and tissue from patients, such as leukemia patients, having a disease involving altered pathway signaling.

Such kits may additionally comprise one or more therapeutic agents. The kit may further comprise a software package for data analysis of the physiological status, which may include reference profiles for comparison with the test profile.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

In some embodiments, the invention provides a kit comprising: (a) at least two modulators selected from the group consisting of Staurosporine, Etoposide, Mylotarg, Daunorubicin, AraC, G-CSF, IFNg, IFNa, IL-27, IL-3, IL-6, IL-10, FLT3L, SCF, G-CSF, SCF, G-CSF, SDF1a, LPS, PMA, Thapsigargin and H2O2; b) at least three binding elements specific to a particular activation state of the activatable element selected from the group consisting of p-Slp-76, p-Plcg2, p-Stat3, p-Stat5, p-Stat1, p-Stat6, P-Creb, Parp+, Chk2, Rel-A (p65-NFKB), p-AKT, p-S6, p-ERK, Cleaved Caspase 8, Cytoplasmic Cytochrome C, and p38; and (c) instructions for diagnosis, prognosis, determining acute myeloid leukemia progression and/or predicting response to a treatment for acute myeloid leukemia in an individual. In some embodiments, the kit further comprises a binding element specific for a cytokine receptor or drug transporter are selected from the group consisting of MDR1, ABCG2, MRP, P-Glycoprotein, CXCR4, FLT3, and c-kit. In some embodiments, the binding element is an antibody.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entireties.

EXAMPLES

Example 1

Materials and Methods

The present illustrative example represents how to analyze cells in one embodiment of the present invention. There are several steps in the process, such as the stimulation step, the staining step and the flow cytometry step. The stimulation step of the phospho-flow procedure can start with vials of frozen cells and end with cells fixed and permeabilized in methanol. Then the cells can be stained with an antibody directed to a particular protein of interest and then analyzed using a flow cytometer.

The materials used in this invention include thawing medium which comprises PBS-CMF+10% FBS+2 mM EDTA; 70 um Cell Strainer (BD); anti-CD45 antibody conjugated to Alexa 700 (Invitrogen) used at 1 ul per sample; propidium iodide (PI) solution (Sigma 10 ml, 1 mg/ml) used at 1 ug/ml; RPMI+1% FBS medium; media A comprising RPMI+1% FBS+1× Penn/Strep; Live/Dead Reagent, Amine Aqua (Invitrogen); 2 ml, 96-Deep Well, U-bottom polypropylene plates (Nunc); 300 ul 96-Channel Extended-Length D.A.R.T. tips for Hydra (Matrix); Phosphate Buffered Saline (PBS) (MediaTech); 16% Paraformaldehyde (Electron Microscopy Sciences); 100% Methanol (EMD) stored at −20 C; Transtar 96 dispensing apparatus (Costar); Transtar 96 Disposable Cartridges (Costar, Polystyrene, Sterile); Transtar reservoir (Costar); and foil plate sealers.

a. Thawing Cell and Live/Dead Staining:

Frozen cells are thawed in a 37° C. water bath and gently resuspended in the vial and transferred to the 15 mL conical tube. The 15 mL tube is centrifuged at 930 RPM (200×g) for 8 minutes at room temperature. The supernatant is aspirated and the pellet is gently resuspended in 1 mL media A. The cell suspension is filtered through a 70 um cell strainer into a new 15 mL tube. The cell strainer is rinsed with 1 mL media A and another 12 ml of media A into the 15 mL tube. The cells are mixed into an even suspension. A 20 µL aliquot is immediately removed into a 96-well plate containing 180 µL PBS+4% FBS+CD45 Alexa 700+PI to determine cell count and viability post spin. After the determination, the 15 mL tubes are centrifuged at 930 RPM (200×g) for 8 minutes at room temperature. The supernatant is aspirated and the cell pellet is gently resuspended in 4 mL PBS+4 µL Amine Aqua and incubated for 15 min in a 37° C. incubator. 10 mL RPMI+1% FBS is added to the cell suspension and the tube is inverted to mix the cells. The 15 mL tubes are centrifuged at 930 RPM (200×g) for 8 minutes at room temperature. The cells are resuspended in Media A at the desired cell concentration ($1.25 \times 10^6$/mL). For samples with low numbers of cells (<$18.5 \times 10^6$), the cells are resuspended in up to 15 mL media. For samples with high numbers of cells (>$18.5 \times 10^6$), the volume is raised to 10 mL with media A and the desired volume is transferred to a new 15 mL tube, and the cell concentration is adjusted to $1.25 \times 10^6$ cells/ml. 1.6 mL of the above cell suspension (concentration at $1.25 \times 10^6$ cells/ml) is transferred into wells of a multi-well plate. From this plate, 80 ul is dispensed into each well of a subsequent plate. The plates are covered with a lid (Nunc) and placed in a 37° C. incubator for 2 hours to rest.

b. Cell Stimulation:

A concentration for each stimulant that is five folds more (5×) than the final concentration is prepared using Media A as diluent. 5× stimuli are arrayed into wells of a standard 96 well v-bottom plate that correspond to the wells on the plate with cells to be stimulated.

Preparation of fixative: Stock vial contains 16% paraformaldehyde which is diluted with PBS to a concentration that is 1.5×. The stock vial is placed in a 37° C. water bath.

Adding the stimulant: The cell plate(s) are taken out of the incubator and placed in a 37° C. water bath next to the pipette apparatus. The cell plate is taken from the water bath and gently swirled to resuspend any settled cells. With pipettor, the stimulant is dispensed into the cell plate and vortexed at "7" for 5 seconds. The deep well plate is put back into the water bath.

Adding Fixative: 200 µl of the fixative solution (final concentration at 1.6%) is dispensed into wells and then mixed on the titer plate shaker on high for 5 seconds. The plate is covered with foil sealer and incubated in a 37° C. water bath for 10 minutes. The plate is spun for 6 minutes at 2000 rpm at room temperature. The cells are aspirated using a 96 well plate aspirator (VP Scientific). The plate is vortexed to resuspend cell pellets in the residual volume. The pellet is ensured to be dispersed before the Methanol step (see cell permeabilization) or clumping will occur.

Cell Permeabilization: Permeability agent, for example methanol, is added slowly and while the plate is vortexing. To do this, the cell plate is placed on titer plate shaker and made sure it is secure. The plate is set to shake using the highest setting. A pipetter is used to add 0.6 mls of 100% methanol to the plate wells. The plate(s) are put on ice until this step has been completed for all plates. Plates are covered with a foil seal using the plate roller to achieve a tight fit. At this stage the plates may be stored at −80° C.

c. Staining Protocol

Reagents for staining include FACS/Stain Buffer-PBS+0.1% Bovine serum albumen (BSA)+0.05% Sodium Azide; Diluted Bead Mix-1 mL FACS buffer+1 drop anti-mouse Ig Beads+1 drop negative control beads. The general protocol for staining cells is as follows, although numerous variations on the protocol may be used for staining cells:

Cells are thawed if frozen. Cells are pelleted at 2000 rpm 5 minutes. Supernatant is aspirated with vacuum aspirator. Plate is vortexed on a "plate vortex" for 5-10 seconds. Cells are washed with 1 mL FACS buffer. Repeat the spin, aspirate and vortex steps as above. 50 µL of FACS/stain buffer with the desired, previously optimized, antibody cocktail is added to two rows of cells at a time and agitate the plate. The plate is covered and incubated in a shaker for 30 minutes at room temperature (RT). During this incubation, the compensation plate is prepared. For the compensation plate, in a standard 96 well V-bottom plate, 20 µL of "diluted bead mix" is added per well. Each well gets 5 µL of 1 fluorophor conjugated control IgG (examples: Alexa488, PE, Pac Blue, Aqua, Alexa647, Alexa700). For the Aqua well, add 200 uL of Aqua−/+ cells. Incubate the plate for 10 minutes at RT. Wash by adding 200 µL FACS/stain buffer, centrifuge at 2000 rpm for 5 minutes, and remove supernatant. Repeat the washing step and resuspend the cells/beads in 200 µL FACS/stain buffer and transfer to a U-bottom 96 well plate. After 30 min, 1 mL FACS/stain buffer is added and the plate is incubated on a plate shaker for 5 minutes at room temperature. Centrifuge, aspirate and vortex cells as described above. 1 mL FACS/stain buffer is added to the plate and the plate is covered and incubated on a plate shaker for 5 minutes at room temperature. Repeat the above two steps and resuspend the cells in 75 µl FACS/stain buffer. The cells are analyzed using a flow cytometer, such as a LSRII (Becton Disckinson). All wells are selected and Loader Settings are described below: Flow Rate: 2 uL/sec; Sample Volume: 40 uL; Mix volume: 40 uL; Mixing Speed: 250 uL/sec; # Mixes: 5; Wash Volume: 800 uL; STANDARD MODE. When a plate has completed, a Batch analysis is performed to ensure no clogging.

d. Gating Protocol

Data acquired from the flow cytometer are analyzed with Flowjo software (Treestar, Inc). The Flow cytometry data is first gated on single cells (to exclude doublets) using Forward Scatter Characteristics Area and Height (FSC-A, FSC-H). Single cells are gated on live cells by excluding dead cells that stain positive with an amine reactive viability dye (Aqua-Invitrogen). Live, single cells are then gated for subpopulations using antibodies that recognize surface markers as follows: CD45++, CD33– for lymphocytes, CD45++, CD33++ for monocytes+granulocytes and CD45+, CD33+ for leukemic blasts. Signaling, determined by the antibodies that interact with intracellular signaling molecules, in these subpopulation gates that select for "lymphs", "monos+grans, and "blasts" is analyzed.

e. Gating of Flow Cytometry Data to Identify Live Cells and the Lymphoid and Myeloid Subpopulations:

Flow cytometry data can be analyzed using several commercially available software programs including FACSDiva™, FilowJo, and Winlist™. The initial gate is set on a two-parameter plot of forward light scatter (FSC) versus side light scatter (SSC) to gate on "all cells" and eliminate debris and some dead cells from the analysis. A second gate is set on the "live cells" using a two-parameter plot of Amine Aqua (a dye that brightly stains dead cells, commercially available from Invitrogen) versus SSC to exclude dead cells from the analysis. Subsequent gates are be set using antibodies that recognize cell surface markers and in so doing define cell sub-sets within the entire population. A third gate is set to separate lymphocytes from all myeloid cells (acute myeloid leukemia cells reside in the myeloid gate). This is done using a two-parameter plot of CD45 (a cell surface antigen found on all white blood cells) versus SSC. The lymphocytes are identified by their characteristic high CD45 expression and low SSC. The myeloid population typically has lower CD45 expression and a higher SSC signal allowing these different populations to be discriminated. The gated region containing the entire myeloid population is also referred to as the P1 gate.

f. Phenotypic Gating to Identify Subpopulations of Acute Myeloid Leukemia Cells:

The antibodies used to identify subpopulations of AML blast cells are CD34, CD33, and CD11b. The CD34$^+$ CD11b$^-$ blast population represents the most immature phenotype of AML blast cells. This population is gated on CD34 high and CD11b negative cells using a two-parameter plot of CD34 versus CD11b. The CD33 and CD11b antigens are used to identify AML blast cells at different stages of monocytic differentiation. All cells that fall outside of the CD34$^+$ CD11b$^-$ gate described above (called "Not CD34+") are used to generate a two-parameter plot of CD33 versus CD11b. The CD33$^+$ CD11b$^{hi}$ myeloid population represents the most differentiated monocytic phenotype. The CD33$^+$ CD11b$^{intermediate}$ and CD33$^+$ CD11b$^{lo}$ populations represent less differentiated monocytic phenotypes.

The data can then be analyzed using various metrics, such as basal level of a protein or the basal level of phosphorylation in the absence of a stimulant, total phosphorylated protein, or fold change (by comparing the change in phosphorylation in the absence of a stimulant to the level of phosphorylation seen after treatment with a stimulant), on each of the cell populations that are defined by the gates in one or more dimensions. These metrics are then organized in a database tagged by: the Donor ID, plate identification (ID), well ID, gated population, stain, and modulator. These metrics tabulated from the database are then combined with the clinical data to identify nodes that are correlated with a pre-specified clinical variable (for example; response or non response to therapy) of interest.

Example 2

Multi-parameter flow cytometric analysis was performed on peripheral blasts taken at diagnosis from 9 AML patients who achieved a complete response (CR) and 24 patients who were non-responders (NR) to one cycle of standard 7+3 induction therapy (100-200 mg/m2 cytarabine and 60 mg/m2 daunorubicin). The signaling nodes were organized into 4 biological categories: 1) Protein expression of receptors and drug transporters 2) Response to cytokines and growth factors, 3) Phosphatase activity, and 4) Apoptotic signaling pathways.

The data showed that expression of the receptors for c-Kit and FLT3 Ligand and the drug transporter ABCG2, were increased in patients who achieved an NR versus CR (data not shown). Readouts from the cytokine-Stat response panels and the growth factor-Map kinase and PI3-Kinase response panels (see Table 4) revealed increased signaling in blasts taken from NR patients versus blasts taken from patients who clinically responded to therapy. To determine the role of phosphatases, peroxide, ($H_2O_2$) a physiologic phosphatase inhibitor revealed increased phosphatase activity in CRs versus NRs for some signaling molecules and increased phosphatase activity in NRs versus CRs for others. In the absence of treatment with $H_2O_2$, CRs had lower levels of phosphorylated PLCγ2 and SLP-76 versus NRs, and attained higher levels of phosphorylated PLCγ2 and SLP-76 upon $H_2O_2$ treatment (See FIG. 4). In contrast, $H_2O_2$ revealed higher levels of p-Akt in NR patients versus CR patients. Lastly, interrogation of the apoptotic machinery using agents such as staurosporine and etoposide showed that NR patient blasts failed to undergo cell death, as determined by cleaved PARP and cleaved Caspase 8 (See FIG. 5). Of note, in NR patient blasts, these agents did promote an increase in phosphorylated Chk2 suggesting a communication breakdown between the DNA damage response pathway and the apoptotic machinery. In contrast, blasts from CR patients showed significant populations of cells with cleaved PARP and caspase 8 consistent with their clinical outcomes.

In this study, 152 signaling nodes per patient sample were measured by multi-parameter flow cytometry and revealed distinct signaling profiles that correlate with patient response to ara-C based induction therapy. This study identified 29 individuals nodes strongly associated (i.e. AUC >0.7, p value 0.05) with clinical response to 1 cycle of ara-C based induction therapy. Most of these nodes were highly correlated. Table 4 below shows 26 of the 29 nodes strongly associated with clinical responses. Expression levels of c-Kit, Flt-3L receptors and ABCG2 drug transporter also associated with clinical responses.

Alterations were seen in expression for the c-Kit and Flt-3L receptors, the ABCG2 drug transporter, cytokine and growth factor pathway response, phosphatase activity and apoptotic response, all of which could stratify the NR from the CR patient subsets.

Figure 16:
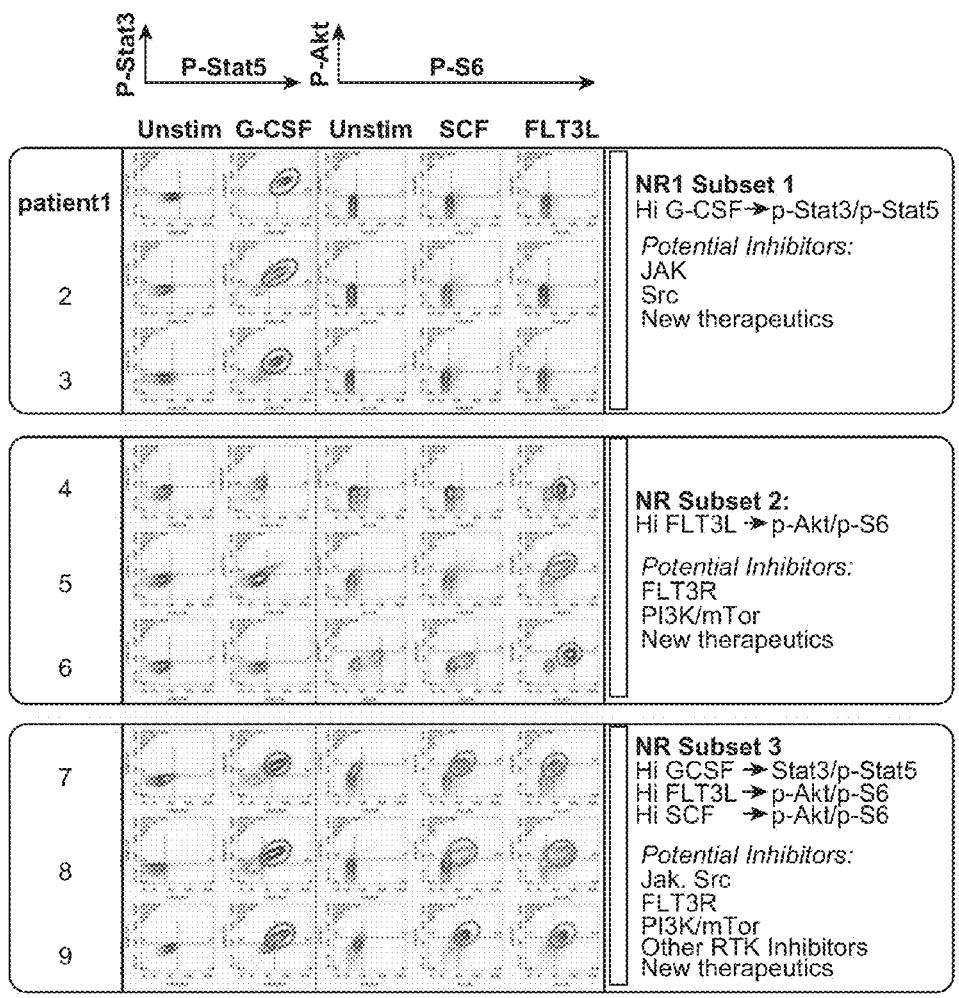
FIG. 16 shows the use of signaling nodes to select patients for specific targeted therapies.

It was also determined that evoked signaling to biologically relevant modulators reveals nodes that stratify non-responding patients from complete responders in this AML sample set. For example, FIG. 16 shows different activation profiles for NR patients. The operative pathways in these patients can be used to predict response to a treatment or to choose a specific treatment for the patients. FIG. 16 shows that NR patients in subset 1 have high levels of p-Stat3 and p-Stat5 in response to G-CSF. This suggests that JAK, Src and other new therapeutics could be good candidates for the treatment of these patients. In addition, FIG. 16 shows that NR patients in subset 2 have high levels of p-Akt and p-S6 in response to FLT3L. This suggests that inhibitors to FLT3R, PI-3K/mTor and other new therapeutics could be good candidates for the treatment of these patients. FIG. 16 also shows that NR patients in subset 2 have high levels of p-Stat3 and p-Stat5 in response to G-CSF, high levels of p-Akt and p-S6 in response to FLT3L, and high levels of p-Akt and p-S6 in response to SCF. This suggests that inhibitors to JAK, Src, FLT3R, PI-3K/mTor, RKT inhibitors and other new therapeutics could be good candidates for the treatment of these patients.

However, some patients with a functional apoptosis response to Etoposide as measured by p-Chk2 and cleaved PARP have a CR phenotype despite having high levels of p-Stat3 and p-Stat5 in response to G-CSF (data not shown). Even though high levels of p-Stat3 and p-Stat5 in response to G-CSF is associated with NR, if the apoptotic machinery is still active the patient might be able to respond to treatment. This suggests that there may be a requirement for more than one signaling pathway to prevent or veto apoptosis. In this case G-CSF signaling is not able alone to prevent apoptosis. These results indicate that multivariate analysis of signaling nodes can improve the specificity of the patient stratification.

Figure 18:
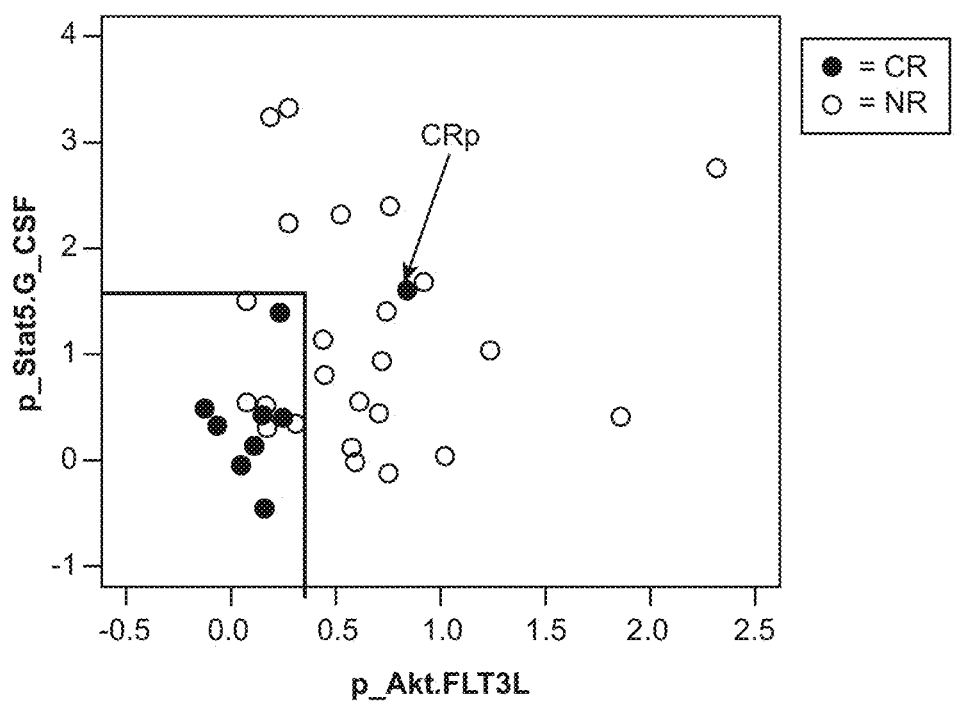
FIG. 18 shows an example of a combination of two independent nodes which correctly classified all but one CR patients and misclassified only 5 NR patients. White=NR, black=CR

Although univariate analysis of signaling nodes can stratify patients based on response to induction therapy as several predictives nodes were independent of each other, multivariate analysis of signaling nodes can improve specificity while providing insight into the pathophysiology of the disease/potential response to therapy. FIG. 18 shows an example of combination of two independent nodes which classify correctly all CR (but one CRp) and misclassify only 5 NR.

Additionally, Phospho-Flow technology allows detection of multiple signaling subpopulations within the AML blast population which could be instrumental in disease monitoring and following rare populations after therapy. See FIGS. 16 and 17. Overall, phospho-flow identifies patient subgroups of AML with different clinical outcomes to induction therapy, reveals mechanisms of potential pathophysiology, and provides a tool for personalized treatment options based on unique patient-specific signaling networks and for disease monitoring under therapeutic pressure.

Example 3

An analysis of a hetergenous population of AML patients may be conducted as outlined above. The results may show the following. In some embodiments, univariate analysis is performed on relatively homogeneous clinical groups, such as patents over 60 years old, patients under 60 years old, de novo AML patients, and secondary AML patients. In other embodiments the groups may be molecularly homogeneous groups, such as Flt-3-ITD WT. For example, in patients over 60 years old, NRs may have a higher $H_2O_2$ response than CRs and/or a higher FLT3L response than CRs. In patients under 60, NRs may have a higher IL-27 response than CRs and/or CRs may induce apoptosis to Etoposide or Ara-C/Daunorubicin more than NRs. In de novo AML, CRs may induce apoptosis (cleaved PARP) in response to Etoposide or Ara-C/Daunorubicin, they may have higher total p-S6 levels than NRs, or NRs may have higher $H_2O_2$ response than CRs. In secondary AML, NRs may have higher $H_2O_2$ responses than CRs, NRs may have higher FLT3L, SCF response than CRs, NRs may have higher G-CSF, IL-27 response than CRs, and there may be overlapping nodes with the over 60 patient set. The following tables may illustrate the above. The tables show the node, metric, and patient subpopulations. For example, the node can be shown as the node (readout) followed by the stimulant/modulator, and in some instances the receptor through which they act (Table 11 also lists some labels that can be employed in the readout). The metric is the way the result may be calculated (see definitions above and in the figures; ppos is percent positive). The leukemic blast cell subpopulations are: P1 all leukemic cells, S1 most immature blast population, S3 most mature blast population and S2 median mature blast population. All nodes: AUC ≥0.7, p values ≤0.05, lowest N=4

TABLE 4

NR = Nodes in which activation is greater in a NR patient than in a CR patient
CR = Nodes in which activation is greater in a CR patient than an NR patient

| | Unstim | IFNa | IFNg | IL-27 | IL-6 | IL-10 | G-CSF | FLT-3L | SCF | SDF-1a | Thapsigargin | PMA | Staurosporine | Etoposide | $H_2O_2$ |
|---|---|---|---|---|---|---|---|---|---|---|---|---|---|---|---|
| p-Stat1(Y701) | | NR | NR | | | | | | | | | | | | |
| p-Stat3(Y703) | NR | | | NR | NR | NR | NR | | | | | | | | |
| p-Stat5(Y694) | | | | | | | NR | | | | | | | | |
| p-Stat6(Y641) | NR | | | | | | | | | | | | | | |
| p-S6(S235/236) | | | | | | | NR | NR | | NR | | | | | |
| p-Akt(S473) | | | | | | | NR | NR | NR | | | | | | |
| p-Erk (T202/Y204) | NR | | | | | | | | | | | NR | | | |
| p-PLCg2(Y759) | NR | | | | | | | | | | | | | | CR |
| p-SLP76 (Y128) | | | | | | | | | | | | | | | CR |
| p-CREB(S133) | NR | | | | | | | | | | | | | | |
| Cleaved PARP | | | | | | | | | | | | | | CR | CR |
| Cleaved Caspase 8 | | | | | | | | | | | | | | CR | |
| Cleaved Caspase 3 | | | | | | | | | | | | | | CR | CR |

TABLE 5

Univariate analysis of All patients can reveal predictive signaling nodes for Response
Failed Pts removed, NR = Resistant only

| Node | Metric | P1 | S1 | S2 | S3 |
|---|---|---|---|---|---|
| Cleaved.PARP.Ara.C.Daunorubicin.HCl | Fold | X |  | X |  |
|  | TotalPhospho | X |  | X |  |
| Cleaved.PARP.Etoposide | Fold |  |  | X |  |
| Flt3.CD135.Mouse.IgG1 | ppos |  | X |  |  |
| p.Akt.Hydrogen.Peroxide | Fold |  |  |  | X |
| p.Chk2..Ara.C.Daunorubicin.HCl | Fold |  |  | X |  |
| p.CREB.SDF.1a.CXCL12 | Fold |  |  |  | X |
|  | TotalPhospho |  |  | X |  |
| p.PLCg2.Hydrogen.Peroxide | Fold |  |  |  | X |
| p.S6.SCF | TotalPhospho |  |  | X |  |
| p.SLP.76.Hydrogen.Peroxide | Fold |  |  |  | X |
| p.Stat1.IL.27 | Fold |  |  | X |  |
|  | TotalPhospho | X | X |  |  |
| p.Stat3.IL.27 | Fold | X |  | X |  |
|  | TotalPhospho |  |  | X |  |
| p.Stat5.IL.27 | Fold |  |  | X |  |
| SCF.R.c.kit.CD117.IgG1. | Fold |  |  |  | X |
| SCF.R.c.kit.CD117.IgG2b | Fold |  | X |  |  |
|  | ppos |  |  | X | X |
| MDR.Family.ABCG2.BRCP1.IgG1. | ppos |  | X |  |  |
| P.glycoprotein.MDR1.IgG1 | Fold |  |  | X |  |

TABLE 6

Univariate analysis of Young Pts (Age < 60) can reveal predictive signaling nodes for Response
Failed Pts removed, NR = Resistant only

| Node | Metric | P1 | S1 | S2 |
|---|---|---|---|---|
| Cleaved.PARP.Etoposide | Fold | X | X | X |
|  | TotalPhospho | X | X |  |
| Cleaved.PARP.No.Modulator | Total Phospho | X |  |  |
| p.Akt.SCF | Fold |  |  | X |
| p.CREB..SDF.1a.CXCL12 | Fold |  | X |  |
| p.ERK.FLT.3.Ligand | Fold | X |  |  |
| p.Stat1.IL.27 | Fold | X | X |  |
|  | TotalPhospho | X | X |  |
| p.Stat3.IL.27 | Fold | X | X |  |
|  | TotalPhospho | X | X |  |

TABLE 7

Univariate analysis of Age > 60 patients can reveas predictive signaling nodes CR vs NR:
Failed Pts removed, NR = Resistant only

| Node | Metric | P1 | S2 | S3 |
|---|---|---|---|---|
| p.Akt.Hydrogen.Peroxide | Fold | X |  |  |
| p.Akt.FLT.3.Ligand | Fold | X | X | X |
| p.ERK.FLT.3.Ligand | Fold | X |  |  |
| p.PLCg2.Hydrogen.Peroxide | TotalPhospho | X |  |  |
| p.S6.FLT.3.Ligand | Fold | X | X | X |
| p.S6.SCF | Fold | X | X |  |
| p.SLP.76.Hydrogen.Peroxide | Fold | X |  |  |

TABLE 8

Univariate analysis of 2ndary AML pts can reveal predictive signaling nodes for Response:
Including Failed Pts

| Node | Metric | P1 | S1 | S2 | S3 |
|---|---|---|---|---|---|
| p.Akt.Hydrogen.Peroxide | Fold |  |  |  | X |
| p.Akt.FLT.3.Ligand | Fold | X |  |  |  |
| p.Akt.SDF.1a.CXCL12 | Fold |  |  | X |  |
| p.ERK.FLT.3.Ligand | Fold | X | X |  |  |
| p.PLCg2.Hydrogen.Peroxide | Fold |  |  |  | X |
|  | TotalPhospho |  |  |  | X |
| p.S6.FLT.3.Ligand | Fold | X |  |  |  |
| p.S6.A.SCF | Fold | X |  |  |  |
| p.SLP.76.Hydrogen.Peroxide | Fold |  |  |  | X |
| p.Stat1.G.CSF | Fold | X |  |  |  |
| p.Stat1.A.IL.27 | Fold | X |  | X |  |
|  | TotalPhospho | X |  |  |  |
| p.Stat3.A.G.CSF | Fold | X |  |  |  |
| p.Stat3.IL.27 | Fold | X |  |  |  |
|  | TotalPhospho | X |  |  |  |
| p.Stat5.G.CSF | Fold | X |  |  |  |
|  | TotalPhospho | X |  |  |  |
| SCF.R.c.kit.CD117.Mouse.IgG1. | Fold |  | X |  |  |
|  | ppos |  | X | X |  |

TABLE 9

Univariate analysis of 2ndary AML pts can reveal predictive signaling nodes for Response:
Failed Pts removed, NR = Resistant only

| Node | Metric | P1 | S1 | S2 | S3 |
|---|---|---|---|---|---|
| p.Akt.Hydrogen.Peroxide | Fold |  |  |  | X |
| p.Akt.FLT.3.Ligand | Fold | X |  |  |  |
| p.Akt.SCF | TotalPhospho | X |  |  |  |
| p.ERK.FLT.3.Ligand | Fold | X | X |  |  |
| p.ERK.SCF | Fold | X |  |  |  |
| p.PLCg2.Hydrogen.Peroxide | Fold |  |  |  | X |
| p.S6.FLT.3.Ligand | Fold | X |  |  |  |
| p.S6.SCF | Fold | X | X |  |  |
| p.Stat1.IL.27 | Fold | X |  | X |  |
|  | TotalPhospho | X |  |  |  |
| p.Stat3.G.CSF | Fold | X |  |  |  |
| p.Stat3.IL.27 | Fold | X |  |  |  |
| p.Stat5.G.CSF | Fold | X |  |  |  |
| SCF.R.c.kit.CD117.Mouse.IgG1. | Fold |  | X |  |  |
|  | ppos |  | X | X |  |

TABLE 10

Univariate analysis of DeNovo AML can reveal predictive signaling nodes for Response: Including Failed Pts

| Node | Metric | P1 | S1 | S2 | S3 |
|---|---|---|---|---|---|
| Cleaved.PARP.Etoposide | Fold |  | X |  |  |
| Cytochrome.C.Staurosporine.Z.VAD.Caspase.Inhibitor | Fold |  | X |  |  |
|  | TotalPhospho | X | X |  |  |
| Cytochrome.C. No.Modulator | TotalPhospho |  |  | X | X |
| p.Akt.Hydrogen.Peroxide | Fold |  | X |  |  |
| p.Akt.FLT.3.Ligand | TotalPhospho |  |  |  | X |
| p.Akt.SCF | Fold |  | X | X |  |
|  | TotalPhospho |  |  |  | X |
| p.Akt.SDF.1a.CXCL12 | Fold |  |  | X |  |
| p.CREB.SDF.1a.CXCL12 | Fold |  |  | X |  |
| p.ERK.Thapsigargin | Fold |  | X |  | X |
| p.ERK.No.Modulator | TotalPhospho |  | X |  |  |
| p.Stat1.GM.CSF | TotalPhospho |  |  |  | X |
| p.Stat1.IL.10 | Fold |  |  | X |  |
|  | TotalPhospho |  |  | X |  |
| p.Stat1.IL.3 | TotalPhospho |  | X |  |  |
| p.Stat1.A.IL.6 | Fold |  | X |  |  |
|  | TotalPhospho |  | X | X | X |
| p.Stat3.GM.CSF | TotalPhospho |  | X | X | X |
| p.Stat3.IFN.g | Fold |  | X | X | X |
|  | TotalPhospho |  | X | X | X |
| p.Stat3..Y705..PE.A.IL.10 | Fold |  | X | X | X |
|  | TotalPhospho |  | X | X | X |
| p.Stat3..Y705..PE.A.IL.3 | TotalPhospho |  | X |  |  |
| p.Stat3..Y705..PE.A.IL.6 | Fold |  |  |  | X |
|  | TotalPhospho |  | X |  | X |
| p.Stat5.G.CSF | Fold |  |  |  | X |
|  | TotalPhospho |  |  |  | X |
| p.Stat5.IL.10 | Fold |  | X | X | X |
| p.Stat5.IL.3 | Fold |  | X |  |  |
| p.Stat5.IL.6 | Fold |  | X | X | X |
| p.Stat6.No.Modulator | TotalPhospho |  | X | X |  |
| pERK.LPS | Fold |  |  | X |  |
| SCF.R.c.kit.CD117.IgG1. | Fold |  |  | X |  |
|  | ppos |  |  | X | X |
| SCF.R.c.kit.CD117.IgG2b | Fold |  | X | X |  |
|  | ppos |  |  | X | X |
| X.MDR.Family.MRP.1.IgG2a | Fold |  | X |  |  |
|  | ppos |  | X |  |  |
| P.glycoprotein.MDR1.IgG2a | Fold |  | X |  |  |

TABLE 11

Univariate analysis of De Novo AML patients can reveals predictive signaling nodes CR vs NR: Removed Failed Pts. NR = Resistant

| Node | Metric | P1 | S1 | S2 | S3 |
|---|---|---|---|---|---|
| Cleaved.PARP.Cytosine.b.arabino.furanoside..Daunorubicin.HCl | Fold |  |  | X |  |
|  | TotalPhospho |  |  | X |  |
| Cleaved.PARP..D214..FITC.A.Etoposide | Fold | X | X | X |  |
| p.Akt..S473..Alexa.Fluor.488.A.Hydrogen.Peroxide | Fold |  | X |  |  |
| p.Akt..S473..Alexa.Fluor.647.A.FLT.3.Ligand | TotalPhospho |  |  |  | X |
| p.Akt..S473..Alexa.Fluor.647.A.SCF | Fold |  | X | X |  |
|  | TotalPhospho |  |  |  | X |
| p.Akt..S473..Alexa.Fluor.647.A.SDF.1a.CXCL12 | Fold |  |  | X |  |
| p.CREB..S133..PE.A.SDF.1a.CXCL12 | Fold |  |  | X |  |
| p.S6..S235.236..Alexa.Fluor.488.A.FLT.3.Ligand | TotalPhospho | X |  | X |  |
| p.S6..S235.236..Alexa.Fluor.488.A.PMA | TotalPhospho | X |  | X |  |
| p.S6..S235.236..Alexa.Fluor.488.A.SCF | TotalPhospho | X |  | X |  |
| p.S6..S235.236..Alexa.Fluor.488.A.Thapsigargin | TotalPhospho |  |  | X | X |
| p.SLP.76..Y128..Alexa.Fluor.647.A.Hydrogen.Peroxide | Fold |  | X |  |  |
| p.Stat5..Y694..Alexa.Fluor.647.A.G.CSF | TotalPhospho |  |  |  | X |
| p.Stat5..Y694..Alexa.Fluor.647.A.IFN.a.2b | Fold |  |  | X |  |
| SCF.R..c.kit.CD117..APC.A.Mouse.IgG2b | Fold |  |  | X |  |

TABLE 12

Univariate analysis of All patients can reveal predictive signaling nodes for Response Duration

| Node | Metric | P1 | S1 | S2 | S3 |
|---|---|---|---|---|---|
| Cleaved.PARP.araC.Daunorubicin.HCl | Fold | X | | | |
| Cleaved.PARP.Etoposide | Fold | X | | | |
| CXCR4.IgG1 | Fold | | X | X | X |
| CXCR4.IgG1 | ppos | | X | | |
|  | Fold | | | X | X |
| p.Akt.Hydrogen.Peroxide | TotalPhospho | | X | | |
| p.Akt.SDF.1a.CXCL12 | TotalPhospho | | X | | |
| p.ERK.FLT.3.Ligand | Fold | | | X | |
| p.PLCg2.Hydrogen.Peroxide | TotalPhospho | | X | | X |
| p.S6..Thapsigargin | TotalPhospho | | X | | |
| p.SLP.76.Hydrogen.Peroxide | TotalPhospho | | X | | X |
| p.Stat3.IL.10 | Fold | | | X | |
| p.Stat5.IL.6 | TotalPhospho | | | X | |
| MDR.Family.ABCG2.BRCP1.IgG1. | Fold | | | | X |
| MDR.Family.ABCG2.IgG2b | ppos | | | X | X |

TABLE 13

Univariate analysis of Flt3 WT Pts can reveal predictive signaling nodes for Response Duration

| Node | Metric | P1 | S1 | S2 | S3 |
|---|---|---|---|---|---|
| Cleaved.PARP.araC.Daunorubicin.HCl | Fold | X | | X | |
| Cleaved.PARP.Etoposide | Fold | X | | | |
|  | TotalPhospho | | X | | |
| CXCR4.IgG1 | Fold | | | X | X |
|  | ppos | | | X | X |
| CXCR4.IgG1 | Fold | | X | | |
| CXCR4.No.Modulator | TotalPhospho | | | X | X |
| p.Akt.Hydrogen.Peroxide | Fold | | X | | |
|  | TotalPhospho | | X | | |
| p.ERK.FLT.3.Ligand | Fold | | | X | X |
| p.PLCg2.Hydrogen.Peroxide | Fold | X | | | |
|  | TotalPhospho | | X | | |
| p.S6..Thapsigargin | TotalPhospho | | X | | |
| p.SLP.76.Hydrogen.Peroxide | TotalPhospho | | X | | |
| MDR.Family.ABCG2.BRCP1.IgG2b | ppos | | | X | X |
| MDR.Family.MRP.IgG2a | Fold | | | | X |

Example 4

Multi-parameter flow cytometric analysis was performed on BMMC samples taken at diagnosis from 61 AML patients. The samples were balanced for complete response (CR) and non-responders (NR) after 1 to 3 cycles of induction therapy and de novo versus secondary AML. Nodes in Tables 2 to 10 were examined.

10 nodes are common in stratifying NR and CR between the studies in Example 2 and these studies. Table 14 shows the common stratifying nodes.

TABLE 14

| Cytokine Pathways: 5 Nodes | |
|---|---|
| IL-27 | p-Stat 3 and p-Stat 1 |
| IL-27 | p-Stat 1 |
| IL-6 | p-Stat 3 |
| IL-10 | p-Stat 3 |
| IFNa | p-Stat 1 |
| Growth Factors: 4 Nodes | |
| Flt3L | p-Akt and p-S6 |
| SCF | p-Akt and p-S6 |
| Apoptosis Pathways | |
| Etoposide or AraC/Dauno | Cleaved PARP+ |

In secondary analysis patient subpopulations were stratified by clinical variables. Patients are stratified by age, de novo acute myeloid leukemia patient, secondary acute myeloid leukemia patient, or a biochemical/molecular marker.

Patients were stratified by age (as split variable <60 years old vs >60 years old and as co-variate). In patients younger than 60 years old, NRs have higher H2O2 and FLT3L responses than CRs. In patients younger than 60 years old, NRs have higher IL-27 response than CRs. In addition, in patients younger than 60 years old, CRs induce apoptosis to Etoposide or Ara-C/Daunorubicin more than NRs.

Patients were stratified by de novo versus secondary AML. Stratifying nodes for de novo group show overlapping nodes with patients younger than 60 year old. Stratifying nodes for secondary group show overlapping nodes with patients older than 60 year old group.

Figure 23:
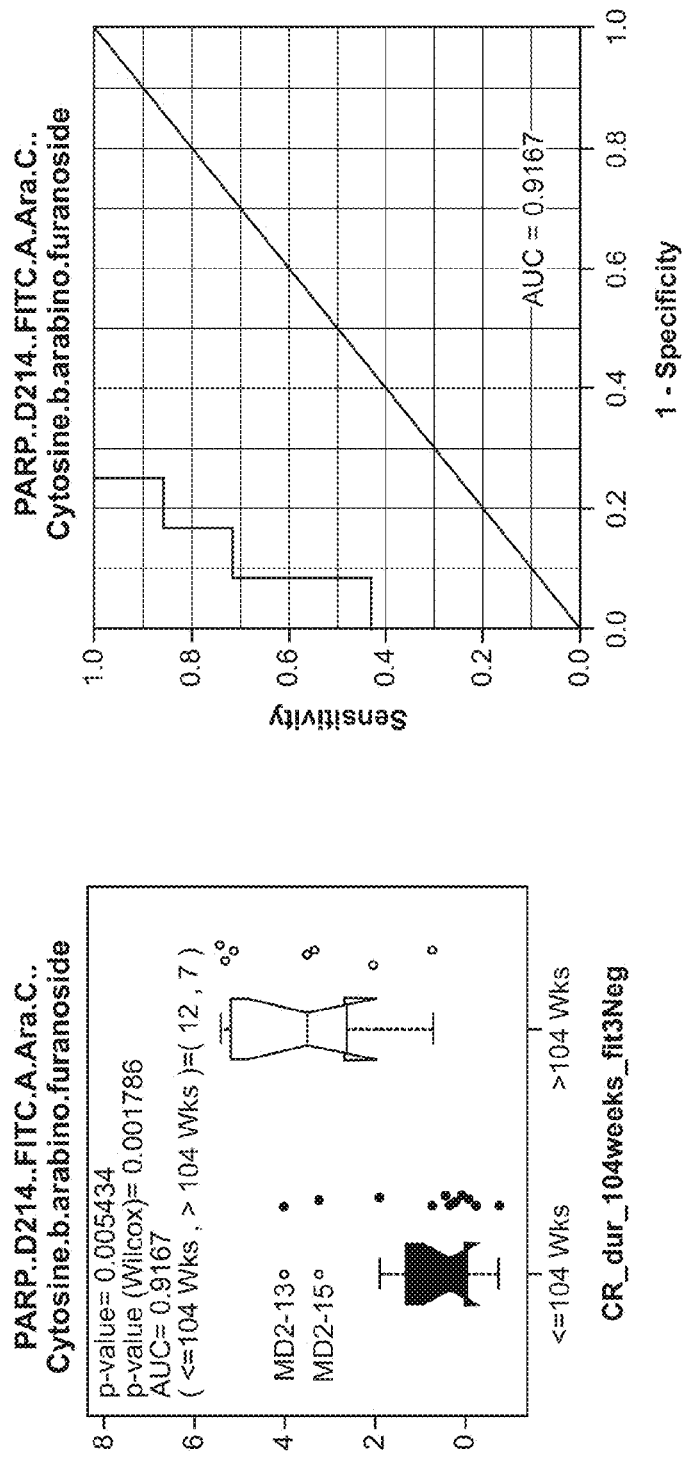
FIG. 23 shows an example of an identified node informative for relapse risk in patients who achieved CR and have FLT3 WT and normal karyotype disease.

Patients were stratified by FLT3 ITD mutation vs FLT3 wild type phenotypes. The signaling was significantly different between the patients with FLT3 ITD mutation vs FLT3 wild type. FIG. 23 shows an example of an identified node informative on relapse risk in patients who achieved CR and have FLT3 WT and normal karyotype disease.

Individuals nodes can be combined for analysis. Several methods can be used for the analysis.

The nodes can be analyzed using additive linear models to discover combinations that provide better accuracy of prediction for response to induction therapy than the individual nodes. These models can also include clinical covariates like age, gender, secondary AML that may already be predictive of the outcome. Only nodes that add to the accuracy of the model after accounting for these clinical covariates are considered to be useful. The formula below is an example of how additive linear models can be used $$Reponse(CR\ or\ NR) = a + b*C_1 + c*C_2 + d*Node_1 + e*Node_2$$

C1 and C2 are the clinical covariates that are considered to be predictive of response, Node1 and Node2 are the two nodes from the biological data. The coefficient a, b, c, d, e are determined by the regression process. The significance of the coefficients if tested against them being equal to zero; i.e. if the p-value for d=0 if very small (say <0.05), then the contribution from the Node1 is considered to the important. Several such models can be explored to find combinations of nodes that are complimentary. Examples of methods for exploring multiple such models include bootstrapping, and stepwise regression.

Figure 19:
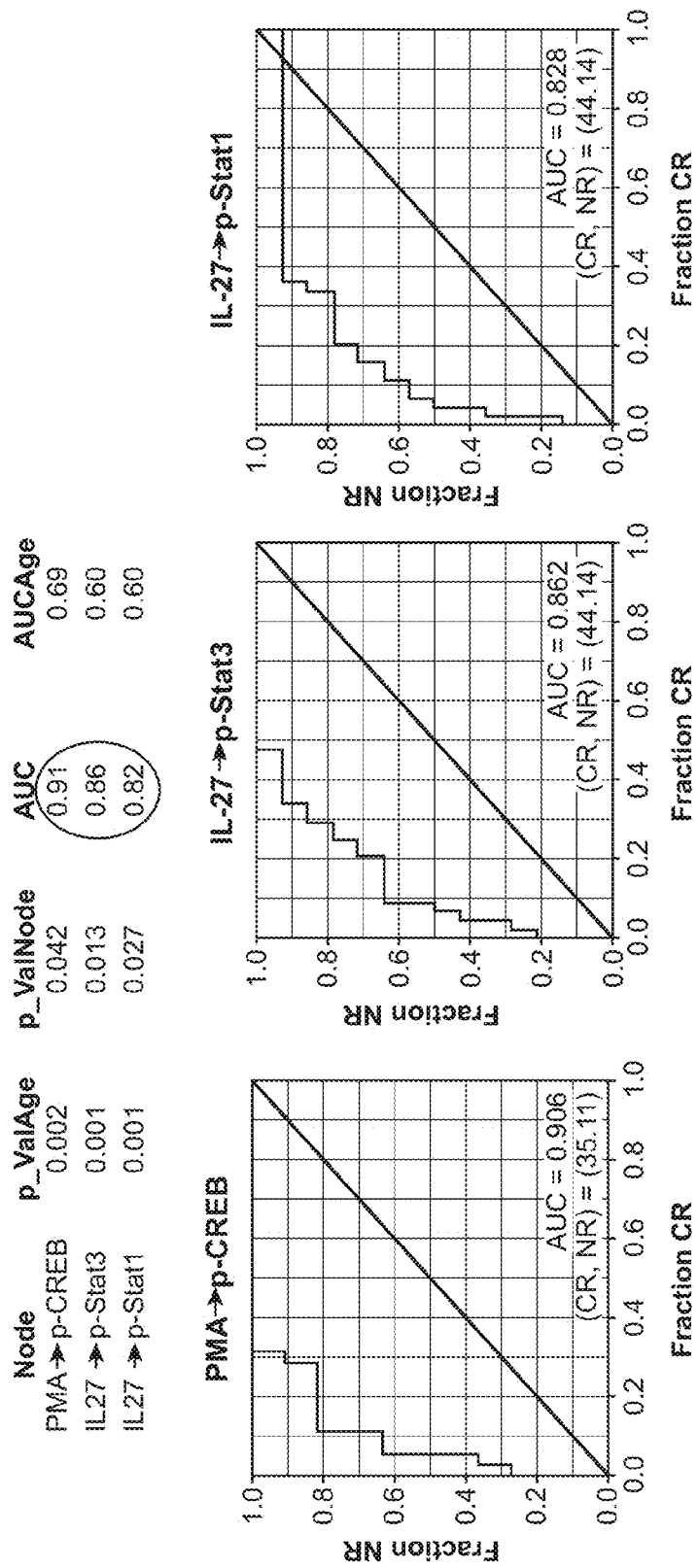
FIG. 19 shows an example of node analysis using an additive linear model.

FIG. 19 shows an example of an additive lineal model. FIG. 19 shows a model represented in the following equations $$CR\ or\ NR = a + b*Age(categorical) + c*Node\ for\ \text{"all blast"\ population}$$

FIG. 19 shows that incorporating age as a clinical variable increases the significance of the resulting combination model.

Figure 20:
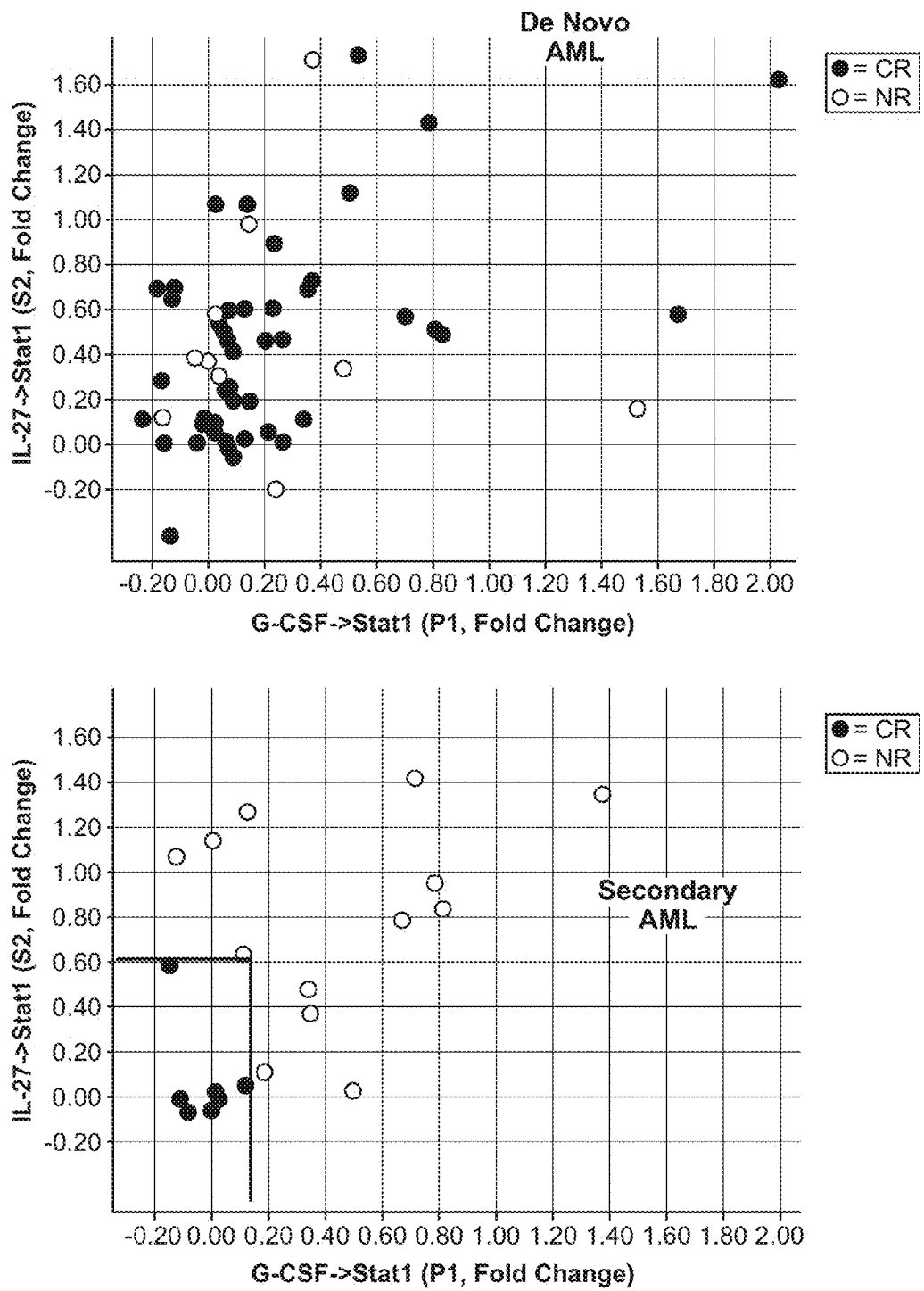
FIG. 20 shows an example of node analysis using an independent combination of nodes model. White =NR, black=CR

The nodes can be analyzed using independent combinations of nodes. This method seeks threshold along different node axes independently. FIG. 20 shows an example of an independent combination of nodes model. FIG. 20 shows that this model among clinical sub-groups improves predictive value.

Figure 21:
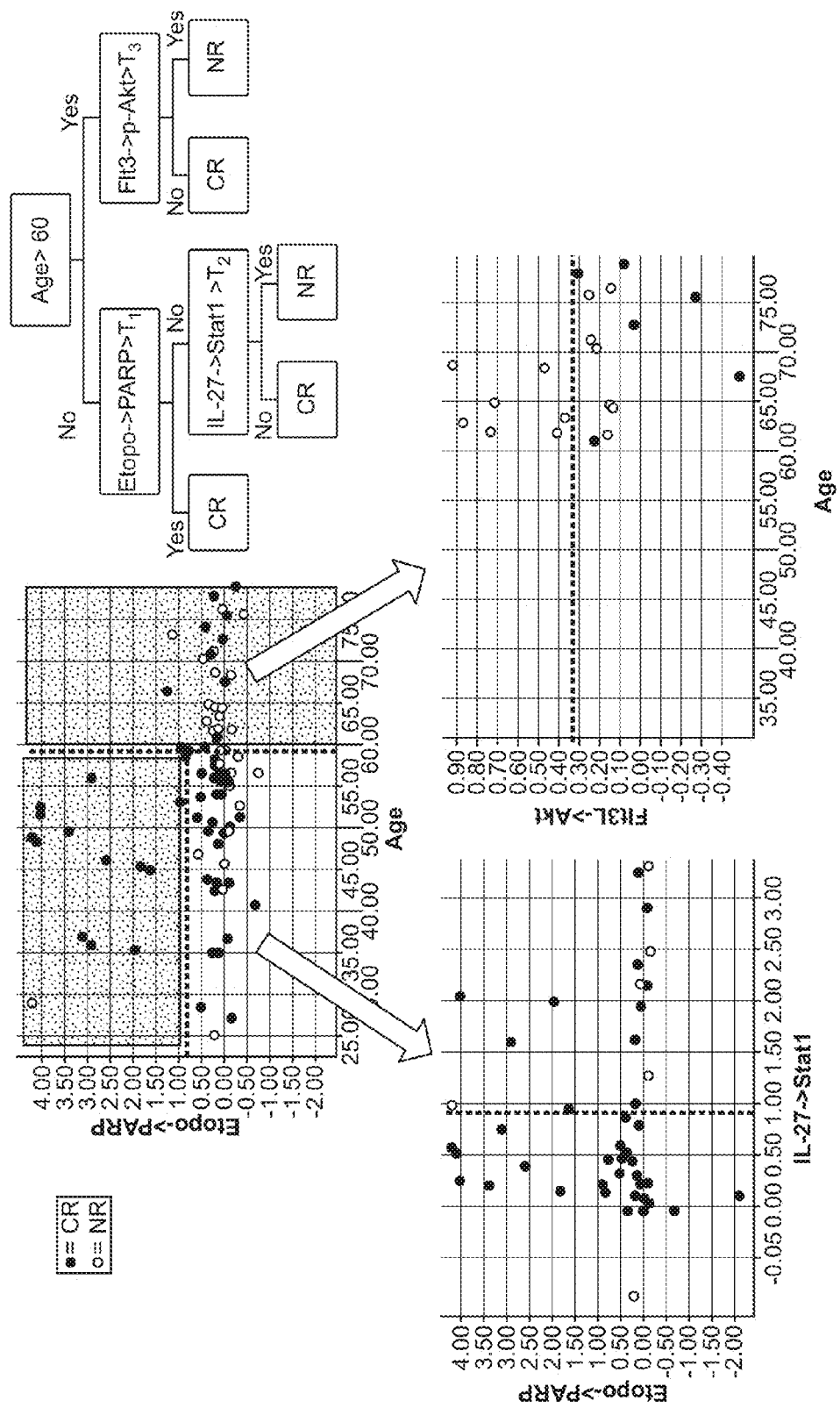
FIG. 21 shows an example of analysis using a decision tree model. White=NR, black=CR

The nodes can be analyzed using decision trees model. This model involves the hierarchical splitting of data. This model might mimic a more natural decision process. FIG. 21 shows an example of the decision tree model. FIG. 21 shows the analysis of some nodes of interest in the two age groups. Each node is evaluated on sub-set of data at each level of the tree.

Figure 22:
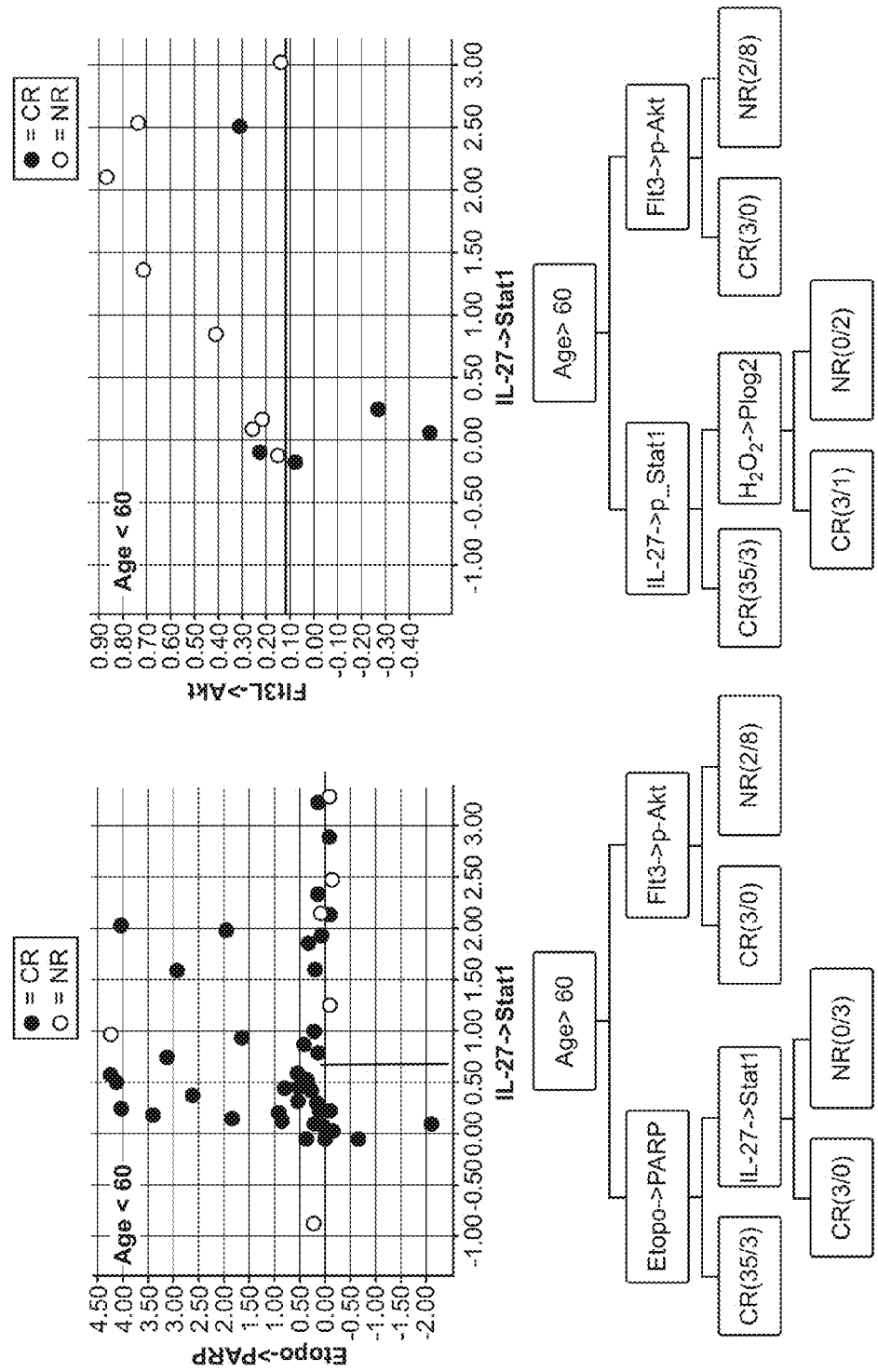
FIG. 22 shows that analyses using both independent node combinations and a decision tree model provide node combinations of interest. White=NR, black=CR

FIG. 22 shows that both independent node combinations and decision tree provide node combinations of interest.

Results from the BMMC samples were compared with PBMC samples from the same patients in 10 of the patients. The samples were compared for sub-populations and signaling. The same phenotypic sub-populations are present in PBMC and BMMC, but in different percentage. It was observed that 2/3 of nodes correlate (i.e. Pearson >0.8 or Spearman>0.8) in "all blast" population of PBMC vs BMMC. The correlations are node and subpopulation specific.

Example 5

The objective if this study is to identify cells in a diagnosis sample and compare the results with a sample taken at a later time point after induction therapy from the same patient that will: (i) identify functional signatures associated with resistance to therapy (post treatment sample) and (ii) identify cell subsets with pre-existing functional signature that predicts refractoriness to a therapy at diagnosis.

To achieve this objective, myeloid populations were gated in the samples. Gates are drawn on cells with increased signaling to then back-gated to identify the phenotype of cells as defined by cell surface markers. This method allows for the identification of differences in signaling between diagnosis and later time-point samples. The gates delineating cells with increased signaling are applied to myeloid populations from independent studies with AML samples.

a. Gating of Flow Cytometry Data to Identify Live Cells and the Lymphoid and Myeloid Subpopulations:

Flow cytometry data can be analyzed using several commercially available software programs including FACS-Diva™, FlowJo, and Winlist™. The initial gate is set on a two-parameter plot of forward light scatter (FSC) versus side light scatter (SSC) to gate on "all cells" and eliminate debris and some dead cells from the analysis. A second gate is set on the "live cells" using a two-parameter plot of Amine Aqua (a dye that brightly stains dead cells, commercially available from Invitrogen) versus SSC to exclude dead cells from the analysis. Subsequent gates be set using antibodies that recognize cell surface markers and in so doing define cell subsets within the entire population. A third gate is set to separate lymphocytes from all myeloid cells (acute myeloid leukemia cells reside in the myeloid gate). This is done using a two-parameter plot of CD45 (a cell surface antigen found on all white blood cells) versus SSC. The lymphocytes are identified by their characteristic high CD45 expression and low SSC. The myeloid population typically has lower CD45 expression and a higher SSC signal allowing these different populations to be discriminated. The gated region containing the entire myeloid population is also referred to as the P1 gate.

b. Phenotypic Gating to Identify Subpopulations of Acute Myeloid Leukemia Cells:

The antibodies used to identify subpopulations of AML blast cells are CD34, CD33, and CD11b. The $CD34^+ CD11b^-$ blast population represents the most immature phenotype of AML blast cells. This population is gated on CD34 high and CD11b negative cells using a two-parameter plot of CD34 versus CD11b. The CD33 and CD11b antigens are used to identify AML blast cells at different stages of monocytic differentiation. All cells that fall outside of the $CD34^+ CD11b^-$ gate described above (called "Not CD34+") are used to generate a two-parameter plot of CD33 versus CD11b. The $CD33^+ CD11b^{hi}$ myeloid population represents the most differentiated monocytic phenotype. The $CD33^+ CD11b^{intermediate}$ and $CD33^+ CD11b^{lo}$ populations represent less differentiated monocytic phenotypes.

c. Back Gating to Identify the Phenotype of G-CSF and SCF Responsive Cells:

A two-parameter or 3-parameter (3-D) plot was generated from the P1 gate (all myeloid cells). For G-CSF stimulation, the signaling responses measured were p-Stat 1, p-Stat3, and p-Stat5. The 3-D plot of p-Stat1 vs. p-Stat3 vs. pStat5 was generated in Spotfire. The two-parameter plots were generated in FlowJo.

The data files for the unstimulated control sample and the G-CSF treated sample were overlaid for comparison. In the results discussed below, the paired patient samples at diagnosis (MDL-7) and at relapse (MDL-8) are shown. On the 3-D plot, the G-CSF responsive population was readily visible as a p-Stat5 positive population (See FIG. 24). A gate was set on the p-Stat5 positive population and was used to back gate onto a 3-D plot of CD34 vs. CD33 vs. CD11b generated from the P1 gate. The data shows that the G-CSF responsive cells were found mainly in the $CD33^+ CD11b^-$ population and that in the relapse sample there was an increase in G-CSF responsive cells within the $CD33^+ CD11b^-$ population (4% at diagnosis compared to 27% at relapse). Analysis of G-CSF responsive populations in healthy bone marrow showed that the responding cells are mainly CD34+.

d. Results

Figure 24:
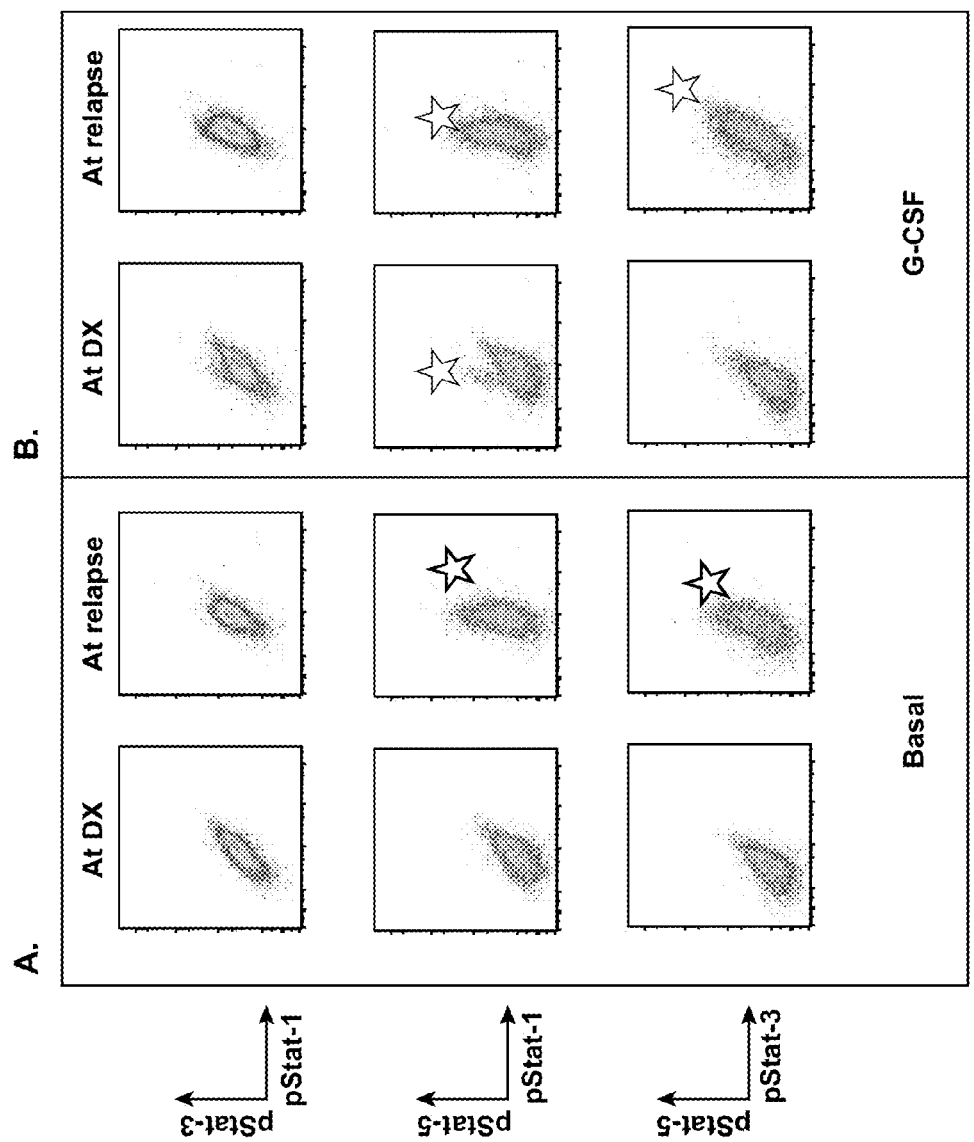
FIGS. 24 A and B show G-CSF-mediated Stat signaling in two patient samples, one taken at diagnosis and the second at a later timepoint post induction.
Figure 25:
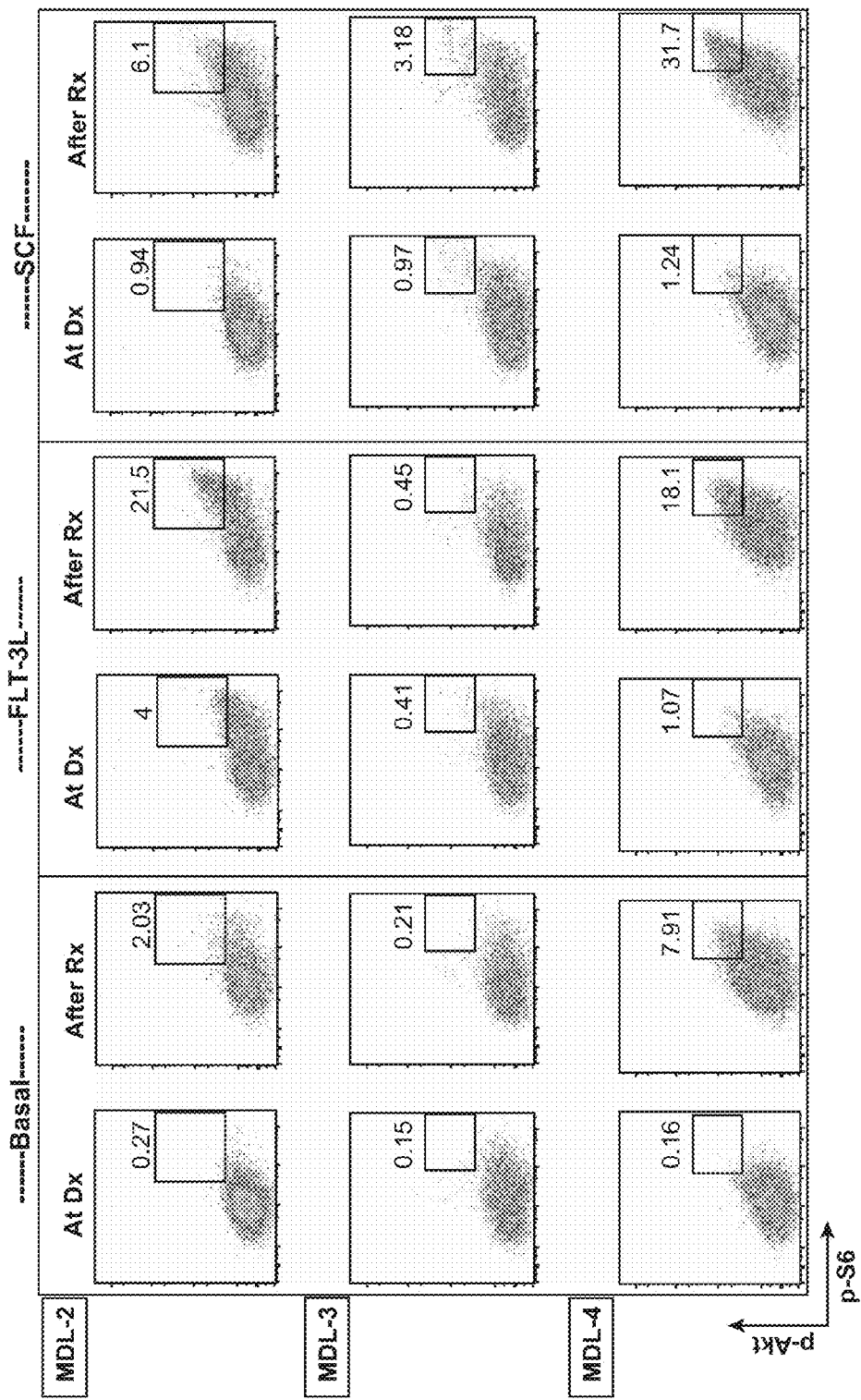
FIG. 25 shows SCF-mediated-p-AKT and p-S6 signaling in two patient samples, one taken at diagnosis and the second at a later timepoint post induction.

In these patients two samples are available for analysis. One sample was taken at the time of diagnosis and the second was taken at a timepoint after induction therapy. Two samples from one patient were evaluated for basal and G-CSF-induced levels of p-Stat proteins (FIG. 24). Levels of basally phosphorylated Stat proteins were increased in the sample taken at the later (relapse) timepoint. (See star annotations in the left hand panel of FIG. 24). A small G-CSF-inducible population of cells was seen in the sample at diagnosis. However, in the sample taken at the later timepoint, even though the basal levels of phosphorylated Stat proteins had increased significantly G-CSF still provided a modest increase in phosphorylation. Three AML sample pairs were evaluated for their basal levels of phosphorylated Akt (p-Akt) and ribosomal S6 protein (p-S6) and Stat proteins (p-Stat1, 3, 5) (FIG. 25). Comparison of the two samples from each patient revealed more basal levels of p-Akt and p-S6 in the samples taken at relapse. The two samples from each patient were also treated with stem cell factor (SCF) and the signaling response was evaluated by determining the levels of p-Akt and p-S6 after the stimulus. In the samples taken at diagnosis, a small population of cells showed a response to SCF and the gates show cells with an increase in p-Akt and p-S6. However, there was a far greater increase in the SCF-mediated increase in p-Akt and p-S6 in the sample taken at relapse and this was true for all sample pairs taken from three patients (FIGS. 25 and 26A). Back-gating revealed the phenotype of the responding cell population which was identified as a myeloid cell sub-set defined by CD33+, CD11b-, CD34-. This contrasts with healthy bone marrow in which the SCF responsive cells are restricted to the CD34+ subset. These responding cells did not respond as robustly to FLT3 ligand stimulation (FIG. 25). Table 15 describes the phenotypes of the SCF-responsive cells

TABLE 15

| Subject | Phenotype of SCF Responsive Cell Subsets |
|---|---|
| AML Patient 1 | CD34+, CD33-, CD11b- |
| AML Patient 2 | CD34+, CD33+, CD11b- |
| AML Patient 3 | CD34-, CD33+, CD11b- |
| Healthy | CD34+, CD33-, CD11b- |

In this small patient subset all except one patient had the double positive SCF responding cells. However, not all patients that had a poor outcome exhibited this response.

Figure 26B:
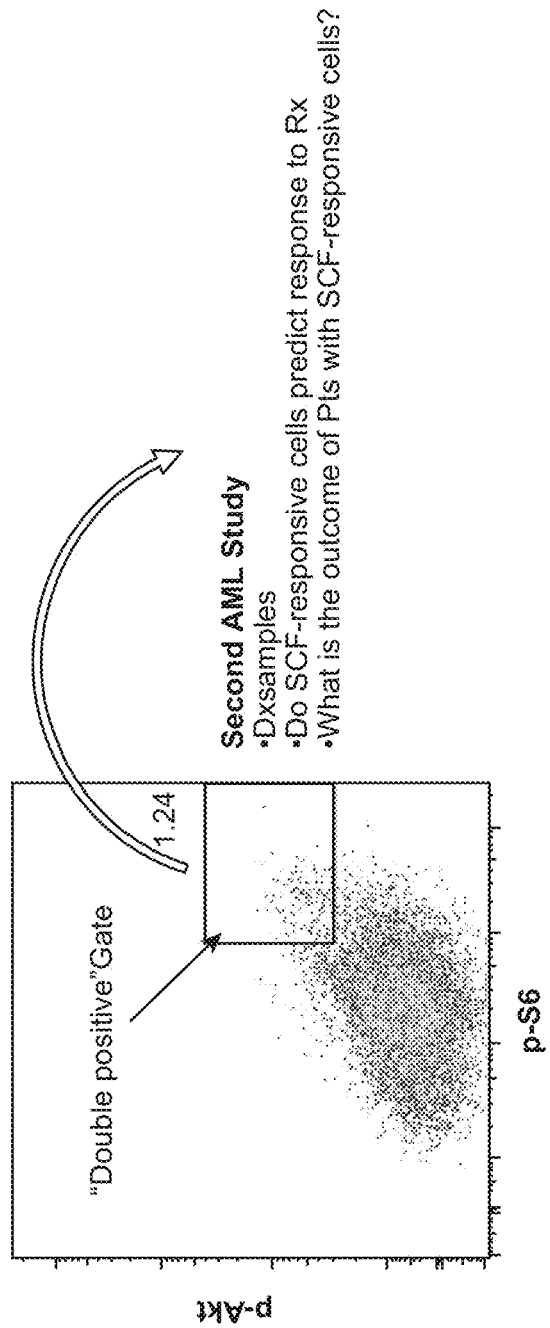
FIG. 26B shows a double positive gate used to stratify AML patients at diagnosis.

In order to predict whether the presence of a small population of SCF responsive (p-Akt/p-S6) double positive population at diagnosis could predict outcome, a gate that delineated the double positive population (FIG. 26B) was applied to a set of historical phosphoflow data from a set of AML samples taken at diagnosis and evaluated for SCF signaling in an independent study. FIG. 26 shows results from the bone marrow of a CR relapse 34 year old patient with M2 AML and Flt3 ITD+. The results show that 9/10 patients with an SCF responding double positive cell frequency of >3% relapsed within two years (FIG. 27). Only one patient in which there was an SCF-responding double population had a complete clinical response (CCR). Furthermore, only a small number of cells were necessary to stratify these patients. As shown in FIG. 27, in one particular patient, 183 double positive cells were captured.

When the analysis using the same gate was performed in peripheral blood mononuclear cells (PBMCs) from AML patients, a trend similar to the bone marrow data was seen (data not shown). Since SCF-responsive cells are not present in the blood circulation of healthy subjects, PBMCs or whole peripheral blood may be a preferred source of cells for an assay that measures the SCF responsive double positives since background "assay noise" could be avoided. It would be predicted that any SCF signaling would emanate from the diseased cells.

Example 6 a. Exposure of AML Blasts In Vitro to Staurosporine and Etoposide Reveals Three Distinct Apoptosis Profiles Jak/Stat and PI3 kinase pathways are tied to cancer cell survival. For this reason, apoptotic proficiency in AML samples was determined in response to etoposide and staurosporine exposure in vitro. In addition, the ability of etoposide and staurosporine to induce a DNA damage response was also evaluated for these samples.

Single cell network profiling using flow cytometry was used to determine DNA damage response and apoptosis in AML blasts after in vitro exposure to staurosporine and etoposide. After treatment of samples with staurosporine for 6 h or etoposide for 24 hours, cells were stained with Amine Aqua viability dye then fixed, permeabilized and incubated with a cocktail of fluorochrome-conjugated antibodies that delineated AML blasts by their surface markers and measured levels of intracellular signaling molecules within the canonical intrinsic apoptosis pathway: cleavage products of Caspase 3, Caspase-8, and PARP.

Figure 28A:
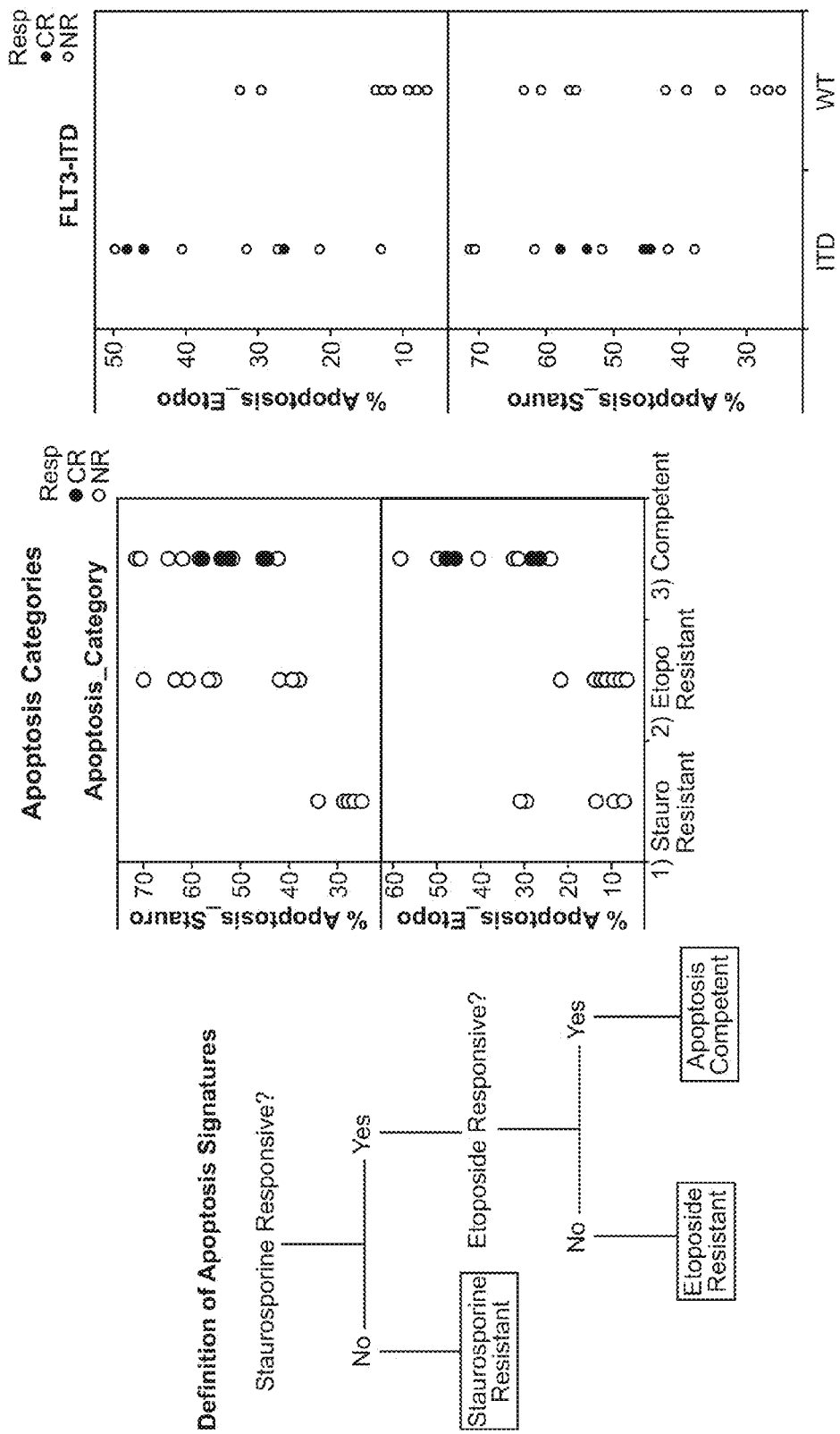
FIG. 28 shows 3 different apoptotic profiles in AML samples revealed after their in vitro exposure to staurosporine and etoposide.
Figure 28C:
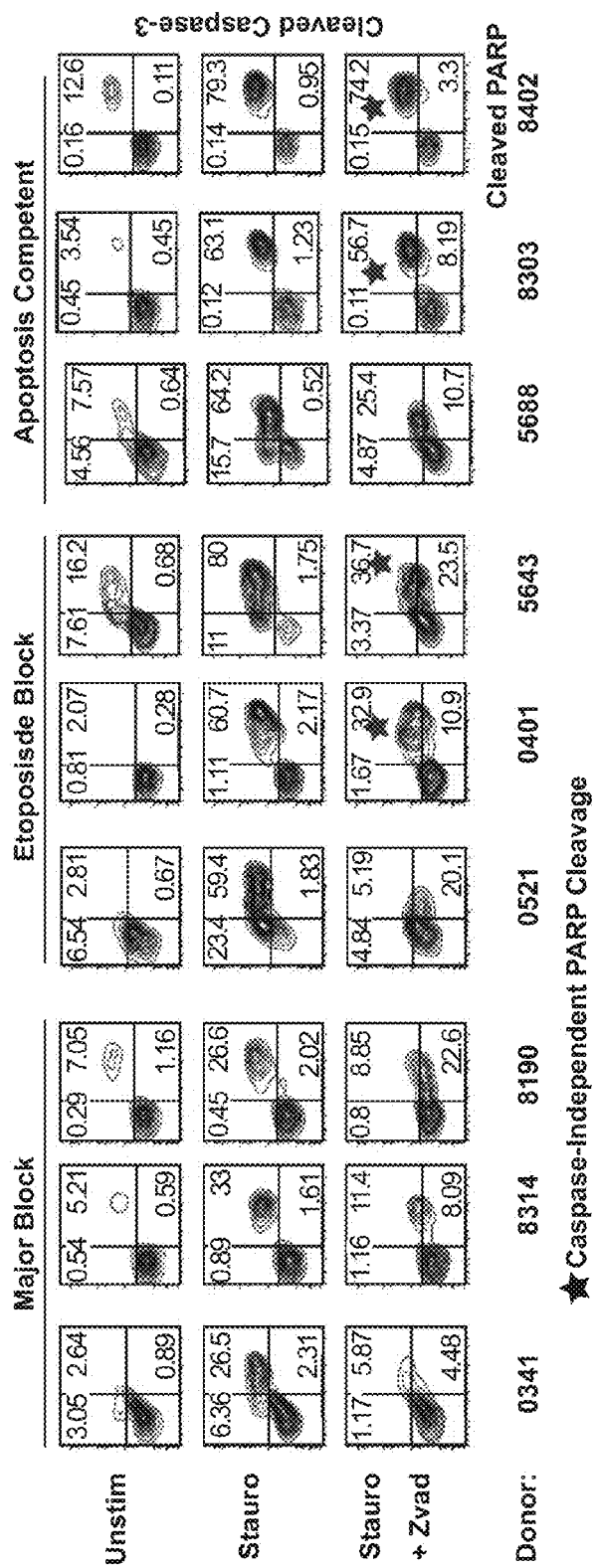
Figure 28D:
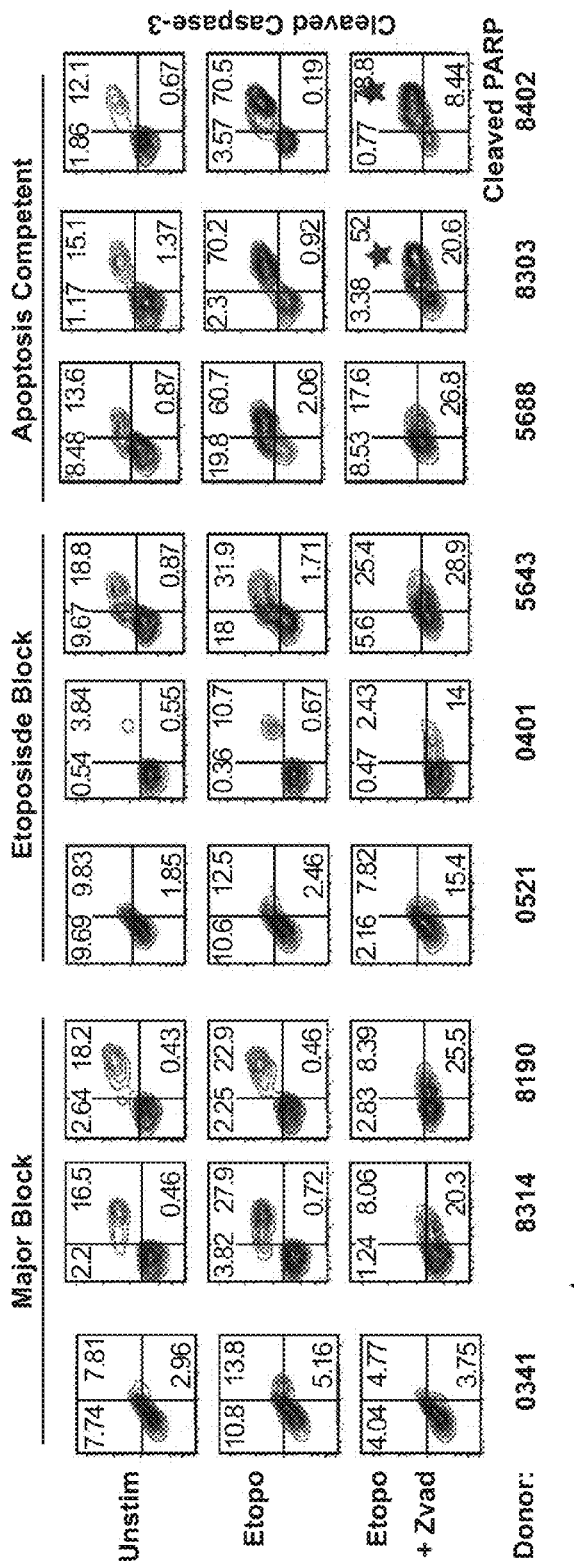

The data showed three distinct apoptosis responses of AML blasts after in vitro exposure to staurosporine and etoposide (FIG. 28). The metric used to analyze this data was "Apoptosis" and is a measure of apoptosis and cell death induced by a drug. A viable cell will be Aqua negative and PARP negative and a measure of cell death is PARP and/or Aqua positivity.

"Apoptosis"=% of PARP$^-$ Aqua$^-_{unstim}$-% of PARP$^-$ Aqua$^-_{Drug}$.

If initially before exposure to a drug a sample has 80% of cells that are PARP$^-$ Aqua$^-$ (live/healthy) and after treatment the sample has 30% of cells that are PARP$^-$ Aqua$^-$ then the drug induced an apoptotic response in 50% of the cells.

In the first profile, staurosporine, a multi-kinase inhibitor and inducer of apoptosis, failed to induce apoptosis (Staurosporine Resistant profile). Samples responsive to staurosporine were then classified by their responses to Etoposide, a topoisomerase II inhibitor which identified a second signature in which AML blasts were competent to undergo an apoptotic response to staurosporine but not to etoposide (Etoposide Resistant Profile). The third profile described AML blasts that were competent to undergo apoptosis in response to both agents (Apoptosis Competent Profile).

Co-incubation of samples with a pan-Caspase inhibitor, Z-VAD, revealed different apoptotic mechanisms among leukemic samples. Various changes in the levels of Cleaved Caspase-3 and PARP were observed upon co-incubation with Z-VAD revealing contributions of both caspase-dependent (Z-VAD sensitive) and caspase-independent (Z-VAD insensitive) pathways of apoptosis, (FIGS. 28 B, C, and D). For example, Z-VAD inhibited cleavage of caspase 3 and PARP to near completion (0341,0521) suggesting that in these samples apoptosis was predominantly caspase-dependent. In other samples (8303, 8402) PARP cleavage was only partially inhibited by Z-VAD treatment suggesting the presence of caspase-independent mechanisms of apoptosis. Samples that were classified by the "Apoptosis Competent profile" were enriched for Z-VAD in sensitive samples, suggesting the presence of both caspase dependent and independent cell death pathways in these samples suggesting that in these samples cells have a choice of cell death pathways (FIGS. 28B, C and D).

Mechanistically, treatment of cells with etoposide (but not staurosporine) will result in DNA damage which will halt the cell cycle through activation of cell cycle checkpoint kinases and give the cell time to repair the damage. If attempts to repair DNA are unsuccessful, cells undergo apoptosis (Huang et al., Molecular Cancer therapeutics 2008 and see references therein). In this study DNA damage was determined by measuring the ATM phosphorylation site, T68, on Chk2. In this AML sample set different DNA Damage and Apoptosis in responses were seen between samples exposed in vitro to Etoposide (FIGS. 28B and D). The spectrum of responses included samples which failed to elicit a DNA damage and apoptosis response (8314), samples in which there was a DNA damage response but no apoptosis (0521, 8390) and samples in which both responses were intact (5688, 8303, 8402). Analysis of the in vitro apoptotic responses in the context of FLT3 mutations revealed a range of apoptosis responses in both molecular classes. Notably, samples in which staurosporine and etoposide induced the greatest apoptotic responses were those that expressed FLT3 ITD (FIG. 28B). As discussed above, given the range of signaling responses within a molecularly classified group, in this case FLT3 ITD mutations, further analysis of networks should be performed to characterize samples and classify patients and their potential response to therapeutic agents.

The apoptosis profile revealed for each AML sample after in vitro exposure to staurosporine and etoposide was compared to the clinical response documented post induction therapy. Strikingly, the "Staurosporine Resistant" and "Etoposide Resistant" apoptosis profiles were completely comprised of AML samples from clinical NR patient samples. In contrast, the "Apoptosis Competent" profile comprised all samples from clinical CR patients. Of note, several samples from NR patients fell into the Apoptosis CompetentProfile". Thus, in vitro apoptosis assays in leukemic samples could potentially model in vivo clinical responsiveness to chemotherapy.

b. Jak/Stat and PI3K Signaling Confer Resistance to Apoptosis in AML Blasts

To understand how proliferation and survival signaling relate to apoptotic potential, JAK/STAT and PI3K/S6 pathway activity in leukemic samples was analyzed in the context of the apoptotic profiles described above. While some differences in the basal unstimulated levels of phosphorylated STAT proteins were observed between apoptotic signature groups, stimulation with cytokines revealed variable JAK/STAT activity among the apoptosis categories described above. Robust Jak/Stat responses were seen upon treatment with G-CSF (p-Stat3, p-Stat5) or GM-CSF (p-Stat5) in all samples from the "Staurosporine Resistant" apoptosis category, consistent with Stat proteins providing a survival function. In the two other apoptotic categories, the G-CSF-mediated increases in p-Stat3 and p-Stat5 were variable suggesting that in these patients, G-CSF signaling provides an apoptosis-independent pathway for analysis and potential patient stratification.

Figure 29A:
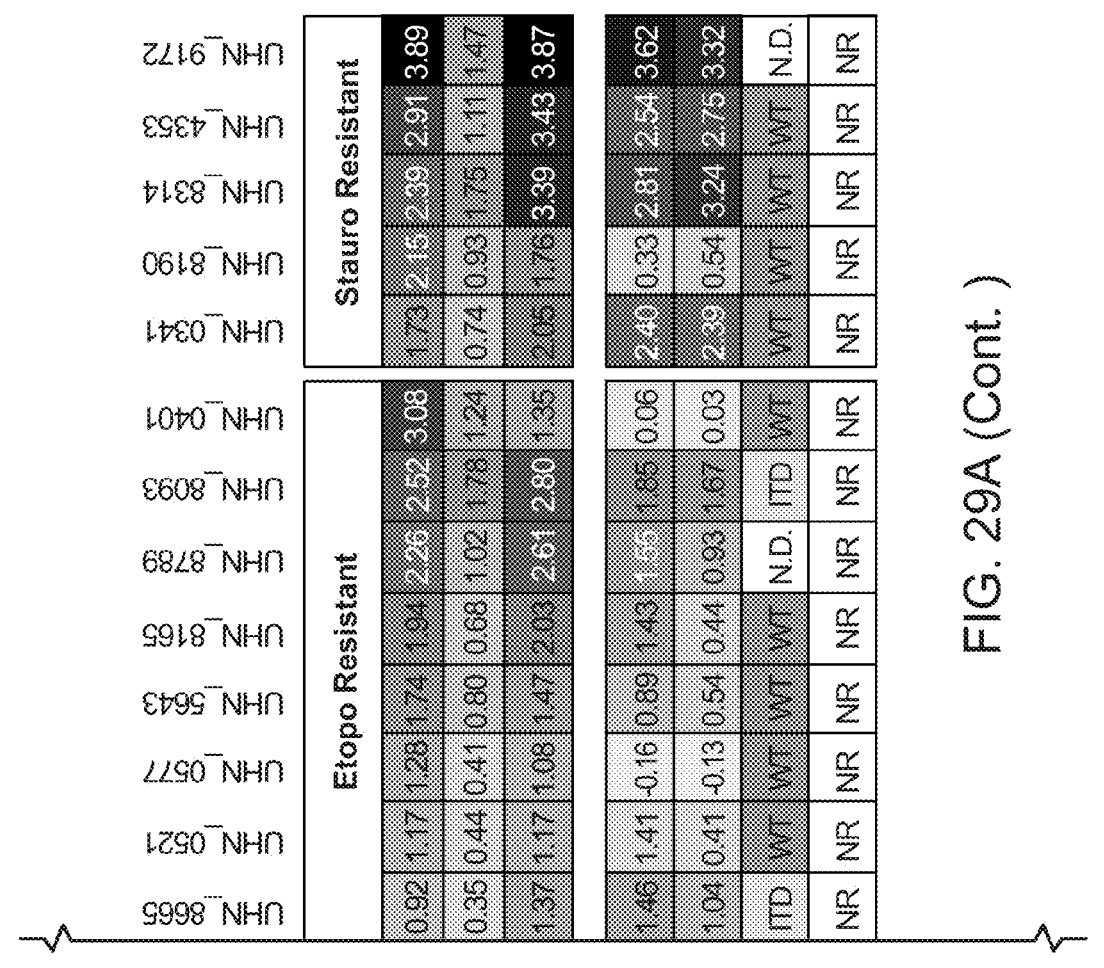
Figure 29B:
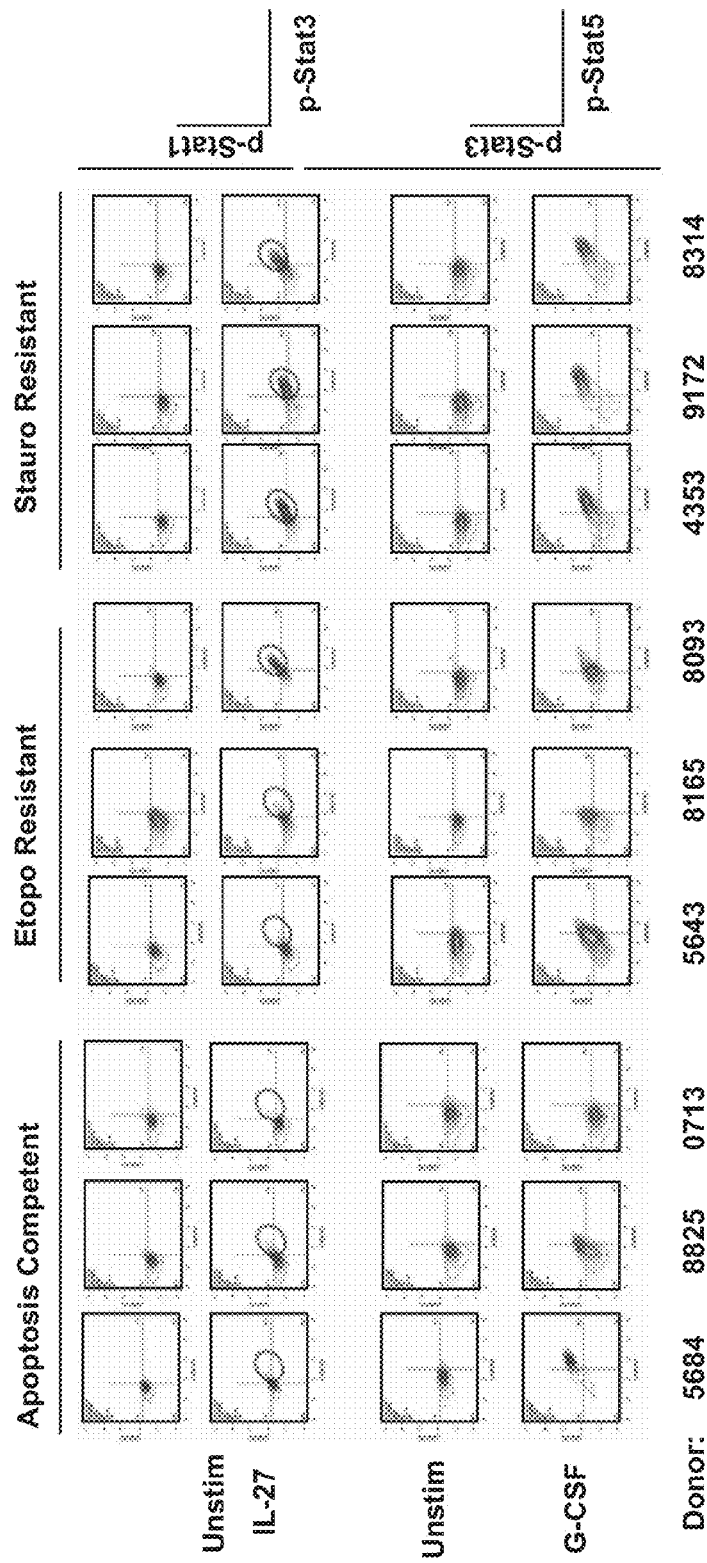
FIG. 29 shows different magnitudes of cytokine and growth factor induced signaling in JAK/STAT and PI3K/S6 pathways within the three apoptotic profiles depicted in FIG. 28.
Figure 29C:
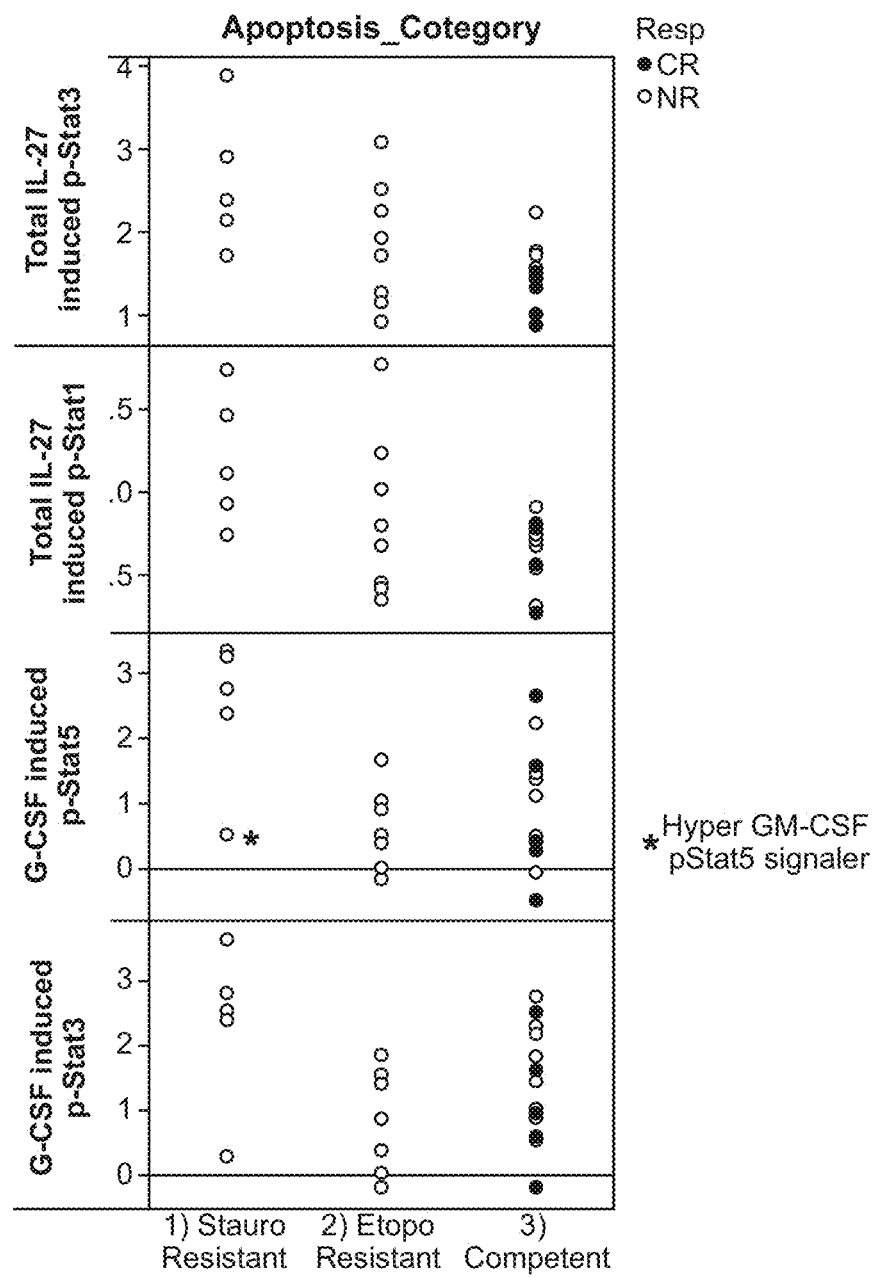

Consistent with the role of augmented Stat signaling in "staurosporine resistant" samples, IL-27-induced levels of total p-Stat1 and p-Stat3 were all greater in this apoptotic sub-category. "Etoposide Resistant" samples had varying levels of IL-27-mediated Stat signaling and the lowest levels of induced Stat phosphorylation were observed in the "Apoptosis Competent" category (FIGS. 29A, B and C).

The NR patients within the "apoptosis Competent" Profile displayed higher IL-27 induced p-Stat than CR patients again emphasizing the need to evaluate multiple pathway in patient samples in order to reach meaningful clinical decisions.

Figure 29D:
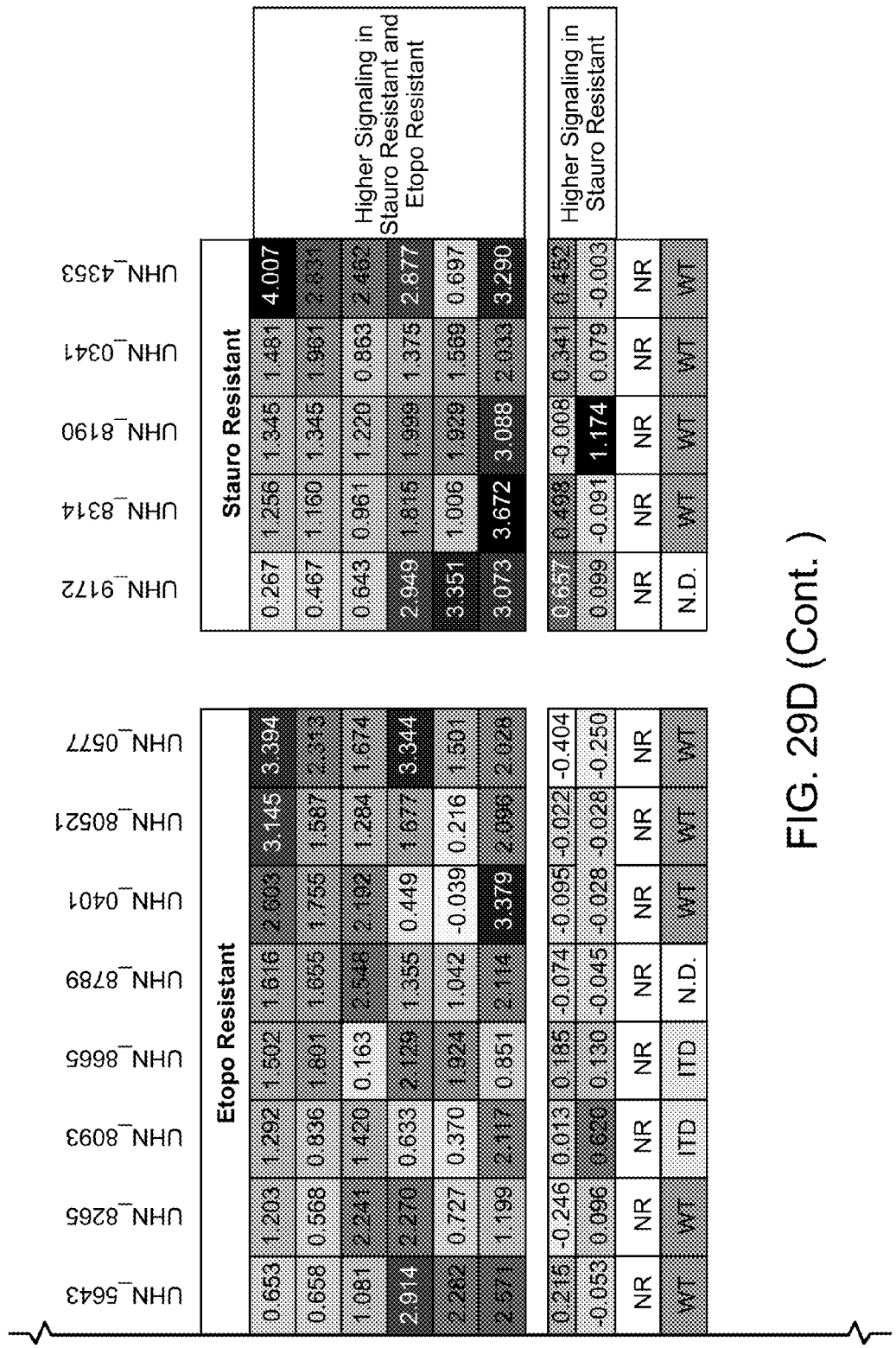
Figure 29E:
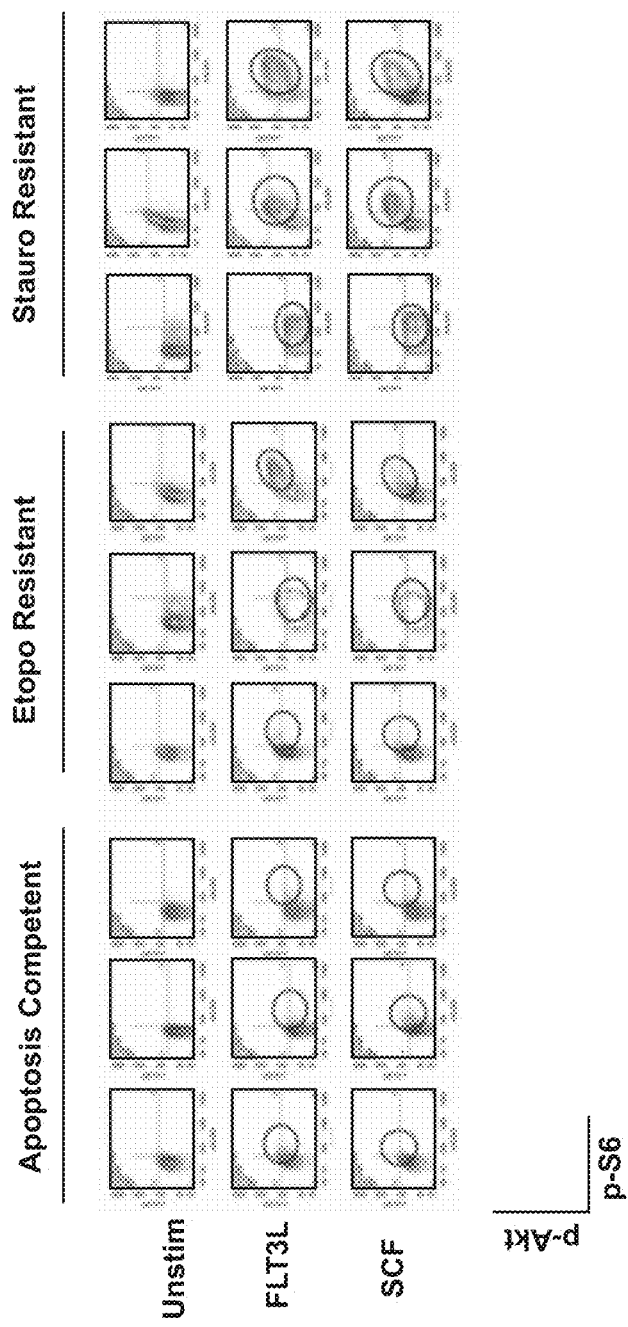
Figure 29F:
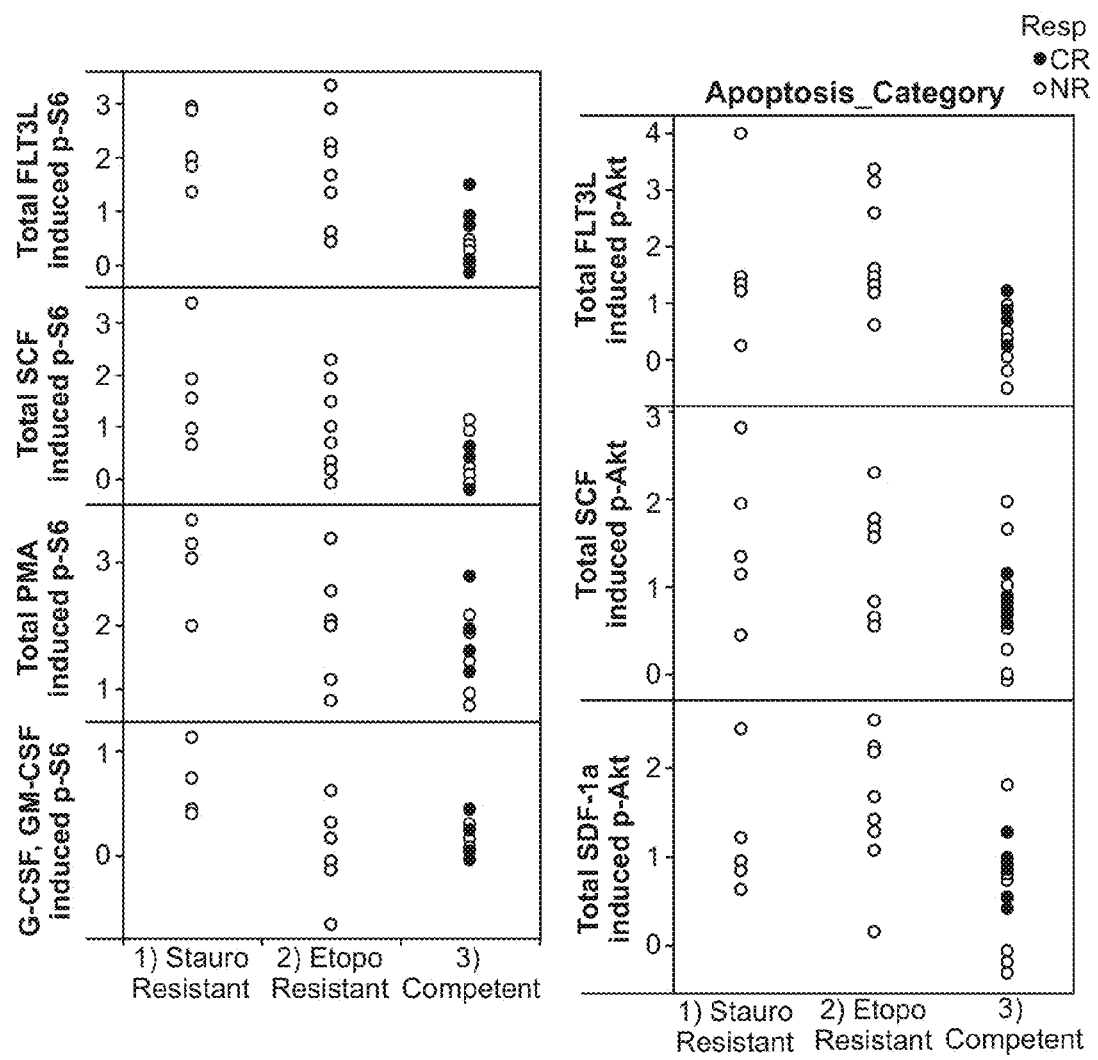

Consistent with their roles in survival, there was an inverse correlation between levels of growth factor-mediated-p-Akt and p-S6 signaling and apoptotic response. Greater induced p-Akt and p-S6 levels were observed in samples where there was a low level of induced apoptosis (Staurosporine and/or Etoposide Resistant categories). In contrast in the "Apoptosis Competent Profile" there were low levels of growth factor-mediated increases in p-Akt and p-S6 (FIGS. 29D, E and F).

Other myeloid cytokines and chemokines known to stimulate the PI3K/S6 and pathway are G-CSF, GM-CSF, and SDF-1α. Overall, these modulators mediated the greatest increase in p-Akt and p-S6 levels in the "Staurosporine Resistant" category consistent with the survival role conferred by the PI3K pathway. Notably, two different cytokines, G-CSF and GM-CSF provided a similar signaling output (p-Stat5, p-S6) in this apoptotic category. Pathway characterization of AML blasts highlights the different signaling mechanisms utilized to evade apoptosis (for example: sample 8093, NR, "Etoposide resistant", induced Jak/Stat signaling elevated, sample 0521, NR, "Etoposide Resistant", induced PI3K/S6 signaling elevated, sample 4353, NR, "Staurosporine Resistant", induced Jak/Stat and PI3K/S6 pathways elevated c. Analysis of Signaling and Apoptosis in the Context of FLT3 Mutations Analysis of the in vitro apoptotic responses in the context of FLT3 mutations revealed that AML samples expressing FLT3 ITD have relatively intact apoptotic machinery compared with AML samples expressing wild type FLT3 (FIG. 28A). However, apoptosis responses to both staurosporine and etoposide varied between samples within FLT3 ITD+ or WT subgroups, demonstrating that molecular characterization alone is not sufficient to classify patients and their potential response to therapeutics. In other analyses FLT3-ITD patients had higher basal p-Stat5 and cytokine induced p-Stat5 levels than FLT3-WT patients although a large spread of responses was seen in either FLT3-ITD or FLT3-WT patients. Also, FLT3-ITD patients had lower basal and FLT3L induced p-S6 than FLT3-WT patients. Again a spread of responses was seen within FLT3 WT or FLT3-ITD subgroups demonstrating how single cell network profiling can further characterize samples within a molecularly-defined patient subgroup Example 7

Scenarios of how this invention might be used to advance the diagnosis or prognosis of disease, or the ability to predict or assess response to therapy are outlined in the following two paragraphs.

A 49 year-old individual presents to their primary medical doctor with the chief complaint of fatigue and bruising. A complete blood count reveals increased white blood cells, decreased hemoglobin and hematocrit, low platelets and circulating blasts. A bone marrow aspirate is obtained and flow cytometry reveals an immature myeloid blast population. The patient is diagnosed with acute myeloid leukemia and the physician and patient must determine the best course of therapy. Using an embodiment of the present invention, the bone marrow or peripheral blood of the patient might be removed and modulators such as GMCSF or PMA added. Activatable elements such asp-Stat3, p-Stat5 and p-Akt might classify this patient as one of the 25% of patients diagnosed with AML less than 60 years old who will not benefit from cytarabine based induction therapy. This invention may also reveal signaling biology within this patient's blasts population that suggests to the physician that the patient should be treated with a DNA methyl transferase inhibitor. With this invention, the patient would then be spared the toxicities associated with cytarabine therapy and could be placed on a clinical trial where he would receive a therapy from which he would likely benefit.

A 52 year-old female presents to her primary medical doctor with the chief complaint of fatigue and bruising. A complete blood count reveals normal numbers of white blood cells, decreased hemoglobin and hematocrit, and low platelets. A bone marrow aspirate and biopsy is obtained and flow cytometry and histology reveals tri-lineage myelodysplasia. The patient is diagnosed with MDS. Using an embodiment of the present invention, the bone marrow or peripheral blood of the patient might be removed and modulators such as GMCSF or PMA added. Activatable elements such as STAT5, STAT5 and AKT might reveal that the biology associated with this patient's MDS is likely of auto-immune origin. The physician promptly places this patient on CSA and ATG. Within 6 weeks she shows complete normalization of her complete blood count.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A kit comprising
   a) at least two modulators selected from the group consisting of Etoposide, Mylotarg, Daunorubicin, AraC, SCF, SDF1a, LPS, Thapsigargin, cyclosporine A, decitibine, azacitadine, Vorinostat, valproic acid, bortezomib, and clofarabine; and
   b) at least three binding elements specific to a compound selected from the group consisting of p-Slp-76, p-Plcg2, p-Creb, cleaved Parp, p-Chk2, p-p65/Rel-A, p-S6, Cleaved Caspase 3, Cleaved Caspase 8, Cytoplasmic Cytochrome C, p-H2AX, p-4EBP-1, and p21.

2. The kit of claim 1 further comprising a binding element specific for a cytokine receptor, growth factor receptor or drug transporter selected from the group consisting of MDR1, ABCG2, MRP, P-Glycoprotein, and c-kit.

3. The kit of claim 1 further comprising a binding element specific for CD 34, CD11, or CD 38.

4. The kit of claim 1 further comprising a binding element specific for CD33, CD45, HLA-DR, or CD11b.

5. The kit of claim 1 further comprising one or more modulators selected from the group consisting of: G-CSF, IFN-gamma, IFN-alpha, IL-27, IL-3, IL-6, IL-10, FLT3L, and PMA.

6. The kit of claim 1 further comprising one or more binding elements specific to a particular activation state of an activatable element selected from the group consisting of: p-Stat3, p-Stat5, p-Stat1, p-Stat6, p-Akt, p-Erk, and p38.

7. The kit of claim 1 further comprising one or more binding elements specific to CXCR4 or FLT3.

8. The kit of claim 1 further comprising one or more antibodies specific for one or more proteins, in their phosphorylated or unphosphorlyated states, selected from the group consisting of PI3-Kinase (p85, p110a, p110b, p110d), Jak1, Jak2, SOCs, Rac, Rho, Cdc42, Ras-GAP, Vav, Tiam, Sos, Dbl, Nck, Gab, PRK, SHP1, SHP2, SHIP1, SHIP2, sSHIP, PTEN, Shc, Grb2, PDK1, SGK, Akt1, Akt2, Akt3, TSC1,2, Rheb, mTor, 4EBP-1, p70S6Kinase, S6, LKB-1, AMPK, PFK, Acetyl-CoAa Carboxylase, DokS, Rafs, Mos, Tpl2, MEK1/2, MLK3, TAK, DLK, MKK3/6, MEKK1,4, MLK3, ASK1, MKK4/7, SAPK/JNK1,2,3, p38s, Erk1/2, Syk, Btk, BLNK, LAT, ZAP70, Lck, Cbl, SLP-76, PLCγ1, PLCγ2, STAT1, STAT 3, STAT 4, STAT 5, STAT 6, FAK, p130CAS, PAKs, LIMK1/2, Hsp90, Hsp70, Hsp27, SMADs, Rel-A (p65-NFKB), CREB, Histone H2B, HATs, HDACs, PKR, Rb, Cyclin D, Cyclin E, Cyclin A, Cyclin B, P16, p14Arf, p27KIP, p21CIP, Cdk4, Cdk6, Cdk7, Cdk1, Cdk2, Cdk9, Cdc25, A/B/C, Abl, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, IAPs, Smac, Fodrin, Actin, Src, Lyn, Fyn, Lck, NIK, IκB, p65(RelA), IKKα, PKA, PKCα, PKCβ, PKCθ, PKCδ, CAMK, Elk, AFT, Myc, Egr-1, NFAT, ATF-2, Mdm2, p53, DNA-PK, Chk1, Chk2, ATM, ATR, βcatenin, CrkL, GSK3α, GSK3β, and FOXO.

9. The kit of claim 1 further comprising a compound selected from the group consisting of aloisine A, alsterpaullone, aminogenistein, API-2, apigenin, arctigenin, AY-22989, BAY 61-3606, Azacitidine bisindolylmaleimide IX, chelerythrine, bevacizumab, 10-[4'-(N,N-Diethylamino)butyl]-2-chlorophenoxazine hydrochloride, dasatinib, 2-Dimethylamino-4,5,6,7-tetrabromo-1H-benzimidazole, 5,7-Dimethoxy-3-(4-pyridinyl)quinoline dihydrochloride, decitibine, edelfosine, ellagic acid, enzastaurin, ER 27319 maleate, erlotinib, ET180CH3, ezatiostat, fasudil, flavopiridol, gefitinib, gemtuzumab ozogamicin, GW 5074, H-7, H-8, H-89, HA-100, HA-1004, HA-1077, HA-1100, hydroxyfasudil, indirubin-3'-oxime, 5-Iodotubercidin, kenpaullone, KN-62, KY12420, LFM-A13, lavendustin A, lonafarnib, luteolin, LY-294002, LY294002, mallotoxin, ML-9, NSC-154020, NSC-226080, NSC-231634, NSC-664704, NSC-680410, NU6102, olomoucine, oxindole I, PD-153035, PD-98059, PD 169316, phloretin, phloridzin, piceatannol, picropodophyllin, PKI, PP1, PP2, purvalanol A, quercetin, R406, R788, rapamune, rapamycin, Ro 31-8220, roscovitine, rottlerin, SB202190, SB203580, sirolimus, sorafenib, SL327, SP600125, staurosporine, STI-571, SU-11274, SU4312, SU6656, 4,5,6,7-Tetrabromotriazole, TG101348, tipifarnib, Triciribine, Tyrphostin AG 490, Tyrphostin AG 825, Tyrphostin AG 957, Tyrphostin AG 1024, Tyrphostin SU1498, U0126, VX-509, VX-667, VX-680, W-7, wortmannin, XL-019, XL-147, XL-184, XL-228, XL-281, XL-518, XL-647, XL-765, XL-820, XL-844, XL-880, Y-27632, ZD-1839, ZM-252868, ZM-447439, H202, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Permolybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, bis(4-Trifluoromethylsulfonamidophenyl)-1,4-diisopropylbenzene, phenyarsine oxide, Pyrrolidine Dithiocarbamate, and Aluminum fluoride.

10. The kit of claim 1, further comprising instructions for diagnosis, prognosis, determining acute myeloid leukemia progression, predicting response to a treatment and/or choosing a treatment for acute myeloid leukemia, myelodysplastic syndrome or myeloproliferative neoplasms in an individual.

* * * * *